US012774336B2

(12) United States Patent
Hsiue et al.

(10) Patent No.: US 12,774,336 B2
(45) Date of Patent: Oct. 27, 2026

(54) MANABODIES AND METHODS OF USING

(71) Applicant: The Johns Hopkins University, Baltimore, MD (US)

(72) Inventors: Emily Han-Chung Hsiue, Baltimore, MD (US); Qing Wang, Owings Mills, MD (US); Bert Vogelstein, Baltimore, MD (US); Kenneth W. Kinzler, Frankford, DE (US); Shibin Zhou, Owings Mills, MD (US); Jacqueline Douglass, Baltimore, MD (US); Michael S. Hwang, Seattle, WA (US); Nickolas Papadopoulos, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 18/473,695

(22) Filed: Sep. 25, 2023

(65) Prior Publication Data

US 2024/0294648 A1 Sep. 5, 2024

Related U.S. Application Data

(63) Continuation of application No. 16/614,005, filed as application No. PCT/US2018/032996 on May 16, 2018, now Pat. No. 11,807,662.

(Continued)

(51) Int. Cl.

| | |
|---|---|
| ***C07K 16/46*** | (2006.01) |
| ***A61K 35/17*** | (2015.01) |

(Continued)

(52) U.S. Cl.

CPC .......... *C07K 16/2833* (2013.01); *A61K 35/17* (2013.01); *A61K 40/11* (2025.01); (Continued)

(58) Field of Classification Search

None

See application file for complete search history.

(56) References Cited

U.S. PATENT DOCUMENTS

| | | | |
|---|---|---|---|
| 6,750,325 | B1 | 6/2004 | Jolliffe et al. |
| 7,655,751 | B2 | 2/2010 | Itoh et al. |

(Continued)

FOREIGN PATENT DOCUMENTS

| | | |
|---|---|---|
| CN | 101228187 | 8/2008 |
| CN | 102675462 | 9/2012 |

(Continued)

OTHER PUBLICATIONS

[No Author Listed], "The problem with neoantigen prediction," Nature Biotechnology, 2017, 35(2):97.

(Continued)

*Primary Examiner* — Claire Kaufman

(74) *Attorney, Agent, or Firm* — Fish & Richardson P.C.

(57) ABSTRACT

This document provides methods and materials for assessing a mammal having or suspected of having cancer and/or for treating a mammal having cancer. For example, molecules including one or more antigen-binding domains (e.g., a single-chain variable fragment (scFv)) that can bind to a modified peptide (e.g., a tumor antigen), as well as method for using such molecules, are provided.

10 Claims, 18 Drawing Sheets

Specification includes a Sequence Listing.

Related U.S. Application Data

(60) Provisional application No. 62/506,674, filed on May 16, 2017.

(51) Int. Cl.

| | |
|---|---|
| ***A61K 40/11*** | (2025.01) |
| ***A61K 40/31*** | (2025.01) |
| ***A61K 40/42*** | (2025.01) |
| ***C07K 14/705*** | (2006.01) |
| ***C07K 16/28*** | (2006.01) |

(52) U.S. Cl.

CPC .......... *A61K 40/31* (2025.01); *A61K 40/4201* (2025.01); *A61K 40/4253* (2025.01); *C07K 14/7051* (2013.01); *C07K 14/70514* (2013.01); *C07K 14/70517* (2013.01); *C07K 14/70521* (2013.01); *C07K 16/2809* (2013.01); *C07K 2317/24* (2013.01); *C07K 2317/31* (2013.01); *C07K 2317/33* (2013.01); *C07K 2317/622* (2013.01); *C07K 2319/03* (2013.01)

(56) References Cited

U.S. PATENT DOCUMENTS

| | | | | |
|---|---|---|---|---|
| 9,718,893 | B2 * | 8/2017 | Jung .................. | C07K 16/2863 |
| 10,118,964 | B2 | 11/2018 | Zhou et al. | |
| 11,111,299 | B2 | 9/2021 | Huang et al. | |
| 11,401,332 | B2 * | 8/2022 | Lim ....................... | A61K 40/32 |
| 11,807,662 | B2 | 11/2023 | Hsiue et al. | |
| 2003/0022244 | A1 | 1/2003 | Solomon et al. | |
| 2005/0042218 | A1 | 2/2005 | Zauderer | |
| 2006/0177896 | A1 | 8/2006 | Mach et al. | |
| 2007/0065437 | A1 | 3/2007 | Elson et al. | |
| 2008/0044413 | A1 | 2/2008 | Hammond et al. | |
| 2013/0287748 | A1 | 10/2013 | June et al. | |
| 2018/0086832 | A1 | 3/2018 | Vogelstein et al. | |
| 2019/0248879 | A1 | 8/2019 | Sabapathy et al. | |
| 2020/0079854 | A1 | 3/2020 | Hsiue et al. | |
| 2020/0368337 | A1 | 11/2020 | Fritsch et al. | |
| 2021/0147572 | A1 | 5/2021 | Weidanz | |
| 2023/0051847 | A1 | 2/2023 | Vogelstein et al. | |
| 2024/0165155 | A1 | 5/2024 | Smith et al. | |
| 2024/0166751 | A1 | 5/2024 | Vogelstein et al. | |
| 2025/0034252 | A1 | 1/2025 | Vogelstein et al. | |

FOREIGN PATENT DOCUMENTS

| | | | |
|---|---|---|---|
| CN | 103635486 | | 3/2014 |
| CN | 108250301 | A | 7/2018 |
| CN | 110382550 | A | 10/2019 |
| JP | 2004187676 | | 7/2004 |
| JP | 2008533986 | | 8/2008 |
| WO | WO 2003070752 | | 8/2003 |
| WO | WO 2005116072 | | 12/2005 |
| WO | WO 2006100681 | | 9/2006 |
| WO | WO 2012162067 | | 11/2012 |
| WO | WO 2014134165 | | 9/2014 |
| WO | WO 2015142675 | | 9/2015 |
| WO | WO 2015150526 | | 10/2015 |
| WO | WO 2016085904 | | 6/2016 |
| WO | WO 2016154047 | | 9/2016 |
| WO | WO 2016154246 | | 9/2016 |
| WO | WO 2016166139 | | 10/2016 |
| WO | WO 2016187508 | | 11/2016 |
| WO | WO 2016199141 | | 12/2016 |
| WO | WO 2016201124 | | 12/2016 |
| WO | WO 2017021527 | | 2/2017 |
| WO | WO 2017048593 | | 3/2017 |
| WO | WO 2017134134 | | 8/2017 |
| WO | WO 2017134158 | | 8/2017 |
| WO | WO 2018071796 | | 4/2018 |
| WO | WO 2018074978 | A1 | 4/2018 |
| WO | WO 2018213467 | | 11/2018 |
| WO | WO 2019067242 | | 4/2019 |
| WO | WO 2019112941 | | 6/2019 |
| WO | WO 2019164451 | A1 | 8/2019 |
| WO | WO 2021127184 | | 6/2021 |
| WO | WO 2021127814 | | 7/2021 |

OTHER PUBLICATIONS

Abelin et al., "Mass spectrometry profiling of HLA-associated peptidomes in mono-allelic cells enables more accurate epitope prediction," Immunity, 2017, 46(2):315-26.

Abrams et al., "Generation of stable CD4+ and CD8+ T cell lines from patients immunized with ras oncogene-derived peptides reflecting codon 12 mutations," Cell Immunol, Dec. 1997, 182(2):137-151.

Abrams et al., "Mutant ras epitopes as targets for cancer vaccines," Feb. 1996, Semin Oncol, 23(1):118-134 (Abstract only).

Adair et al., "Humanization of the murine anti-human CD3 monoclonal antibody OKT3," Human Antibodies, 1994, 5(1-2):41-7.

Adderley et al., "KRAS-mutant non-small cell lung cancer: Converging small molecules and immune checkpoint inhibition, " EBio Medicine, 2019, 41:711-6.

Aldoss et al., "Correlates of resistance and relapse during blinatumomab therapy for relapsed/refractory acute lymphoblastic leukemia," American journal of hematology, 2017, 92(9):858-65.

Anagnostou et al., "Evolution of Neoantigen Landscape during Immune Checkpoint Blockade in Non-Small Cell Lung Cancer", Cancer Discovery, 2017, 7(3):264-276.

Anderson et al., "Intracellular transport of class I Mhc molecules in antigen processing mutant cell lines, " Oct. 1993, J. Immunology, 151(7):3407-3419.

Andreatta et al., "Gapped sequence alignment using artificial neural networks: application to the MHC class I system," Bioinformatics, 2016, 32(4):511-7.

Apps et al., "A critical look at HLA-G," Trends in Immunol, Jul. 2008, 29(7):313-321.

Asano et al., "Rearranging the domain order of a diabody-based IgG-like bispecific antibody enhances its antitumor activity and improves its degradation resistance and pharmacokinetics," MAbs, 2014, 6(5):1243-1254.

Asano et al., "Structural considerations for functional anti-EGFR× anti-CD3 bispecific diabodies in light of domain order and binding affinity," Oncotarget, 2018, 9(17):13884.

Ataie et al., "Structure of a TCR-mimic antibody with target predicts pharmacogenetics," Journal of molecular biology. 2016, 428(1):194-205.

Ayriss et al., "High-throughput screening of single-chain antibodies using multiplexed flow cytometry," Jan. 2007, Journal of Proteome Research, 6(3):1072-1082, 11 pages.

Azriel-Rosenfeld et al., "A Human Synthetic Combinatorial Library of Arrayable Single-chain antibodies based on Shuffling in Vivo Formed CDRs into General Framework Regions," J. Mol. Biol, 2004, 335:177-192.

Baker et al., "Chromosome 17 deletions and p53 gene mutations in colorectal carcinomas, " Science, Apr. 1989, 244(4901):217-21.

Bargou et al., "Tumor regression in cancer patients by very low doses of a T cell-engaging antibody," Science, 2008, 321(5891):974-7.

Barretina et al., "The Cancer Cell Line Encyclopedia enables predictive modelling of anticancer drug sensitivity," Nature, 2012-, 483(7391):603-7.

Bedard et al., "Small molecules, big impact: 20 years of targeted therapy in oncology," The Lancet, 2020, 395(10229):1078-88.

Bernal et al., "Implication of the β2-microglobulin gene in the generation of tumor escape phenotypes," Sep. 2012, Cancer Immunol Immunother, 61(9):1359-71.

Beverley et al., "Distinctive functional characteristics of human „T" lymphocytes defined by E rosetting or a monoclonal anti-T cell antibody, European Journal of Immunology, 1981, 11(4):329-34.

Bluemel et al., "Epitope distance to the target cell membrane and antigen size determine the potency of T cell-mediated lysis by BiTE antibodies specific for a large melanoma surface antigen," Cancer immunology, immunotherapy, 2010, 59(8):1197-209.

(56) References Cited

OTHER PUBLICATIONS

Bondgaard et al., "High specificity but low sensitivity of mutation-specific antibodies against EGFR mutations in non-small-cell cancer," Dec. 2014, Mod Pathol, 27(12):1590-1598, 9 pages.
Borg et al., "A novel interaction between Rab7b and actomyosin reveals a dual role in intracellular transport and cell migration," Journal of Cell Science, 2014, 127(22):4927-39.
Bossi et al., "Examining the presentation of tumor-associated antigens on peptide-pulsed T2 cells," Oncoimmunology, 2013, 2(11):e26840.
Bostrom et al., "Chapter 2: Design and construction of synthetic phage-displayed fab libraries," May 2009, Methods in Molecular Biology, 562:17-35, 19 pages.
Bouvier et al., "Crystal structures of HLA-A*0201 complexed with antigenic peptides with either the amino- or carboxyl-terminal group substituted by a methyl group," May 1998, Proteins, 33(3):97-106, 10 pages.
Bradbury et al., "Beyond natural antibodies: the power of in vitro_display technologies, " Nat Biotechnol, Mar. 2011, 29(3):245-254, 28 pages.
Brickner et al., "The PANE1 gene encodes a novel human minor histocompatibility antigen that is selectively expressed in B-lymphoid cells and B-CLL," May 1, 2006, Blood, 107(9):3779-3786, 24 pages.
Brinkmann et al., "The making of bispecific antibodies," MAbs, 2017, 9(2):182-212.
Brischwein et al., "MT110: A novel bispecific single-chain antibody construct with high efficacy in eradicating established tumors," Mol Immunol., 2006, 43:1129-43.
Buhrman et al., "Analysis of binding site hot spots on the surface of Ras GTPase," Journal of Molecular Biology, 2011, 413(4):773-89.
Cameron et al., "Identification of a Titin-derived HLA-A1-presented peptide as a cross-reactive target for engineered MAGE A3-directed T cells," Science Translational Medicine, 2013, 5(197):197ra103.
Canon et al., "The clinical KRAS (G12C) inhibitor AMG 510 drives anti-tumour immunity," Nature, 2019, 575(7781):217-23.
Carosella et al., "Beyond the increasing complexity of the immunomodulatory HLA-G molecule," Blood, May 2008, 111(10):4862-4870.
Carter et al., "Humanization of an anti-p185HER2 antibody for human cancer therapy," May 1992, Proc. Natl. Acad. Sci., 89(10):4285-4289, 5 pages.
Castle et al., "Exploiting the mutanome for tumor vaccination," Mar. 1, 2012, Cancer Res, 72(5): 1081-1091, 12 pages.
Castle et al., "Mutation-Derived Neoantigens for Cancer Immunotherapy," Frontiers in Immunology, Aug. 7, 2019, 10:1856, 7 pages.
Caushi et al., "Transcriptional programs of neoantigen-specific TIL in anti-PD-1-treated lung cancers, " Nature, Jul. 21, 2021, 596(7870): 126-132.
Chang et al., "A therapeutic T cell receptor mimic antibody targets tumor-associated PRAME peptide/HLA-I antigens," The Journal of Clinical Investigation, 2017, 127(7):2705-18.
Chapuis et al., "T cell receptor gene therapy targeting WT1 prevents acute myeloid leukemia relapse post-transplant," Nature Medicine, 2019, 25(7):1064-72.
Chen et al., "A comprehensive survey of genomic alterations in gastric cancer reveals recurrent neoantigens as potential therapeutic targets," BioMed Research International, 2019.
Choudhuri et al., "T-cell receptor triggering is critically dependent on the dimensions of its peptide-MHC ligand, " Nature, 2005, 436(7050):578-82.
ClinicalTrials.gov [online], "Neoadjuvant Nivolumab, or Nivolumab in Combination With Ipilimumab, in Resectable NSCLC (NA_00092076)," NCT02259621, last updated Nov. 3, 2023, retrieved on Jan. 11, 2024, retrieved from URL<https://clinicaltrials.gov/study/NCT02259621>, 42 pages.
Coles et al., "TCRs with distinct specificity profiles use different binding modes to engage an identical peptide-HLA complex," The Journal of Immunology, 2020, 204(7):1943-53.
Coordinators, "Database resources of the national center for biotechnology information," Nucleic acids research, 2018, 46(Database issue):D8.
Cottrell et al., "Pathologic features of response to neoadjuvant anti-PD-1 in resected non-small-cell lung carcinoma: a proposal for quantitative immune-related pathologic response criteria (irPRC)," Ann. Oncol., Aug. 1, 2018, 29(8):1853-1860.
Curran et al., "Chimeric antigen receptors for T cell immunotherapy: current understanding and future directions," Gene Med, 2012, 14(6):405-415.
D'Angelo et al., "Incidence of EGFR Exon 19 Deletions and L858R in Tumor Specimens From Men and Cigarette Smokers with Lung Adenocarcinomas," May 20, 2011, J. Clin. Oncol., 29(15):2066-2070, 5 pages.
Danilova et al., "The Mutation-Associated Neoantigen Functional Expansion of Specific T Cells (MANAFEST) Assay: A Sensitive Platform for Monitoring Antitumor Immunity," Cancer Immunology Research, Jun. 12, 2018, 6(8):888-899.
Dao et al., "Approaching untargetable tumor-associated antigens with antibodies," Jul. 2013, OncoImmunology, 2(7):e24678, 2 pages.
Dao et al., "Targeting the intracellular WT1 oncogene product with a therapeutic human antibody," Mar. 2013, Science Translational Medicine, 5(176):176ra33, 22 pages.
Dao et al., "Therapeutic bispecific T-cell engager antibody targeting the intracellular oncoprotein WT1," Nat. Biotechnol, Oct. 2015, 33:1079-1086.
De Castro et al., "ScanProsite: detection of PROSITE signature matches and ProRule-associated functional and structural residues in proteins, " Nucleic Acids Research, 2006, 34(suppl_2):W362-5.
De Verteuil et al., "Origin and plasticity of MHC I-associated self peptides," Jul. 2012, Autoimmunity Reviews, 11(9):627-635.
Denkberg et al., "Modification of a tumor-derived peptide at an HLA-A2 anchor residue can alter the conformation of the MHC-peptide complex: probing with TCR-like recombinant antibodies," J. Immunol, 2002, 169:4399-4407.
Digiusto et al., "Preparing clinical grade Ag-specific T cells for adoptive immunotherapy trials," Cytotherapy, 2007, 9(&):613-29.
Dufner et al., "Harnessing phage and ribosome display for antibody optimisation," Trends in Biotechnology, Nov. 2006, 24(11):523-529.
Efremova et al., "Neoantigens Generated by Individual Mutations and Their Role in Cancer Immunity and Immunotherapy," Frontiers in Immunology, 2017, 8(Article 1679):1-8.
Eigenbrot et al., "X-ray structures of the antigen-binding domains from three variants of humanized anti-p185HER2 antibody 4D5 and comparison with molecular modeling, " Feb. 1993, J. Mol. Biol., 229(4):969-995.
Ellis et al., "Frequencies of HLA-A2 alleles in five U.S. population groups: Predominance of A*02011 and identification of HLA-A*0231," Mar. 2000, Human Immunology, 61(3):334-340.
Eshhar et al., "Specific activation and targeting of cytotoxic lymphocytes through chimeric single chains consisting of antibody-binding domains and the gamma or zeta subunits of the immunoglobulin and T-cell receptors," Proc. Natl. Acad. Sci. USA, 1993, 90(2):720-724.
Extended European Search Report in European Application No. 16769561.8, dated Jul. 6, 2018, 9 pages.
Extended European Search Report in European Application No. 18802867.4, dated Dec. 11, 2020, 21 pages.
Extended European Search Report in European Application No. 18802867.4, mailed Mar. 15, 2021, 16 pages.
Extended Search Report in European Appln. No. 20902329.0, mailed on Jan. 26, 2024, 7 pages.
Faroudi et al., "Cutting edge: T lymphocyte activation by repeated immunological synapse formation and intermittent signaling," The Journal of Immunology, 2003, 171(3):1128-32.
Fearon et al., "A Genetic Model for Colorectal Tumorigenesis," Cell Press, Jun. 1, 1990, 61(5):759-767, 9 pages.

(56) References Cited

OTHER PUBLICATIONS

Fellhouse et al., "High-throughput generation of synthetic antibodies from highly functional minimalist phage-displayed libraries," Aug. 2007, J. Mol. Biol., 373(4): 924-940, 17 pages.
Forde et al., "Neoadjuvant PD-1 Blockade in Resectable Lung Cancer," N. Engl. J. Med., May 24, 2018, 378(21):1976-1986.
Gejman et al., "Identification of the Targets of T-cell Receptor Therapeutic Agents and Cells by Use of a High-Throughput Genetic Platform_Identifying T-cell Targets Using a High-Throughput Method," Cancer Immunology Research, 2020, 8(5):672-84.
GenBank Accession No. AAH03596.1, "Tumor protein p53 [*Homo sapiens*]," dated Jun. 9, 2008, 2 pages.
Gerstung et al., "The evolutionary history of 2,658 cancers," Nature, 2020, 578(7793):122-8.
Gomez-Eerland et al., "Manufacture of gene-modified human T-cells with a memory stem/central memory phenotype," Human gene therapy methods, 2014, 25(5):277-87.
Gonzalez-Galarza, et al., "Allele frequency net 2015 update: new features for HLA epitopes, KIR and disease and HLA adverse drug reaction associations," Nucleic Acids Research, 2015, 43(D1):D784-8.
Grossman et al., "Toward a shared vision for cancer genomic data," New England Journal of Medicine, 2016, 375(12):1109-12.
Gubin et al., "Checkpoint Blockade Cancer Immunotherapy Targets Tumour-Specific Mutant Antigens," Nov. 27, 2014, Nature, 515(7528):577-581, 32 pages.
Halilovic et al., "Therapeutic strategies for inhibiting oncogenic BRAF signaling," Curr Opin Pharmacol, Aug. 2008, 8(4):419-426.
Ham et al., "TP53gain-of-function mutation promotes inflammation in glioblastoma," Cell Death & Differentiation, May 2018, 26(3):409-425.
Hammond et al., "Selective targeting and potent control of tumor growth using an EphA2/CD3-Bispecific single-chain antibody construct," Cancer research, 2007, 67(8):3927-35.
Harndahl et al., "Peptide binding to HLA class I molecules: homogenous, high-throughput screening, and affinity assays," J. Biomol. Screen, Feb. 2009, 14(2):173-180.
Harper et al., "An approved in vitro approach to preclinical safety and efficacy evaluation of engineered T cell receptor anti-CD3 bispecific (ImmTAC) molecules," PLoS One, 2018, 13(10):e0205491.
Herold et al., Determinants of the assembly and function of antibody variable domains, Scientific Reports, 7:12276, doi: 10.1038/s41598-017-12519-9, Sep. 2017.
Hexham et al., "Influence of relative binding affinity on efficacy in a panel of anti-CD3 scFv immunotoxins," Molecular immunology, 2001, 38(5):397-408.
hla.alleles.org [online], "HLA Nomenclature," retrieved on Mar. 17, 2015, retrieved from URL<http://hla.alleles.org/nomenclature/stat.html>, 2 pages.
Hobbs et al., "RAS isoforms and mutations in cancer at a glance," Journal of Cell Science, 2016, 129(7):1287-92.
Holliger et al., "Diabodies": small bivalent and bispecific antibody fragments, Proceedings of the National Academy of Sciences, 1993, 90(14):6444-8.
Hoof et al., "Proteome sampling by the HLA class I antigen processing pathway," May 2012, Plos Computational Biology, 8(5):e1002517, 9 pages.
Houghton, et al., "Immune recognition of self in immunity against cancer," J. Clin. Invest., 2004, 114(4):468-471.
Hsiue et al., "Targeting a neoantigen derived from a common TP53 mutation," Science, Mar. 1, 2021, 371(6533): eabc8697.
Huang et al., "CD-HIT Suite: a web server for clustering and comparing biological sequences," Bioinformatics, 2010, 26(5):680-2.
Huehls et al., "Bispecific T-cell engagers for cancer immunotherapy," Immunology and cell biology, 2015, 93(3):290-6.
International Preliminary Report on Patentability in International Application No. PCT/US2016/023673, dated Sep. 26, 2017, 8 pages (with English translation).
International Preliminary Report on Patentability in International Application No. PCT/US2020/065617, dated May 17, 2022, 6 pages.
International Search Report and Written Opinion in International Application No. PCT/US2016/023673, dated Jul. 25, 2016, 13 pages.
International Search Report and Written Opinion in International Application No. PCT/US2020/065617, mailed on Apr. 1, 2021, 8 pages.
International Search Report and Written Opinion in International Appln. No. PCT/US2022/053065, mailed on Mar. 20, 2023, 9 pages.
Janes et al., "Targeting KRAS mutant cancers with a covalent G12C-specific inhibitor," Cell, 2018, 172(3):578-89.
Jena et al., "Redirecting T-cell specificity by introducing a tumor-specific chimeric antigen receptor," Aug. 2010, Blood, 116(7):1035-1044, 17 pages.
Johnson et al., "Effector cell recruitment with novel Fv-based dual-affinity re-targeting protein leads to potent tumor cytolysis and in vivo B-cell depletion. Journal of molecular biology," 2010, 399(3):436-49.
Jones et al., "Core signaling pathways in human pancreatic cancers revealed by global genomic analyses," Science, 2008, 321(5897):1801-6.
Junttila et al., "Antitumor Efficacy of a Bispecific Antibody That Targets HER2 and Activates T Cells," Cancer research, 2014, 74(19):5561-71.
Kato et al., "A monoclonal antibody IMab-1 specifically recognizes IDH1R132H, the most common glioma-derived mutation," Biochemical and Biophysical Research Communications, 2009, 390(3):547-51.
Kato et al., "Effective screening of T cells recognizing neoantigens and construction of T-cell receptor-engineered T cells," Oncotarget, 2018, 9(13):11009.
Kato et al., "Understanding the function-structure and function-mutation relationships of p53 tumor suppressor protein by high-resolution missense mutation analysis," Proceedings of the National Academy of Sciences, 2003, 100(14): 8424-9.
Kershaw et al., "Clinical application of genetically modified T cells in cancer therapy," Apr. 2014, Clinical & Translational Immunology, 3(5):e16, 7 pages.
Kershaw et al.,_ "Supernatural T cells: genetic modification of T cells for cancer therapy," Nature Reviews Immunol., 2005, 5(12):928-940.
Kim et al., "TCR mechanobiology: torques and tunable structures linked to early T cell signaling," Frontiers in immunology, 2012, 3(76):1-8.
Kim et al., "The αβ T cell receptor is an anisotropic mechanosensor," Journal of Biological Chemistry, 2009, 284(45):31028-37.
Kinde et al., "Detection and quantification of rare mutations with massively parallel sequencing," Proceedings of the National Academy of Sciences, 2011, 108(23):9530-5.
Kipriyanov et al., "Effect of domain order on the activity of bacterially produced bispecific single-chain Fv antibodies," Journal of molecular biology, 2003, 330(1):99-111.
Koide et al., "The importance of being tyrosine: lessons in molecular recognition from minimalist synthetic binding proteins," May 2009, ACS Chem. Biol., 4(5):325-334, 16 pages.
Kraemer et al., "-HLA-E: Presentation of a broader peptide repertoire impacts the cellular immune response-implications on HSCT outcome," Stem Cells Inter, 2015, article ID 346714, pp. 1-12.
Kranz et al., Restricted reassociation of heavy and light chains from hapten-specific monoclonal antibodies, Proc. Natl. Acad. Sci., USA, 78(9):5807-5811, 1981.
Krissinel et al., "Inference of macromolecular assemblies from crystalline state," Journal of Molecular Biology, 2007, 372(3):774-97.
Kula et al., "T-Scan: a genome-wide method for the systematic discovery of T cell epitopes," Cell, 2019, 178(4):1016-28.
Kunik et al., "Structural consensus among antibodies defines the antigen binding site," Feb. 2012, PLoS Computational Biology, 8(2):e1002388, 12 pages.

(56) References Cited

OTHER PUBLICATIONS

Kuroda et al., "Structural classification of CDR-H3 revisited: a lesson in antibody modeling," Nov. 2008, Proteins, 73(3):608-620.
Labrijn et al., "Bispecific antibodies: a mechanistic review of the pipeline," Nature reviews Drug discovery, 2019, 18(8):585-608.
Ladner, R.C., Mapping the Epitopes of Antibodies, Biotechnol. Genet. Eng. Rev. 24:1-30, 2007.
Le et al., "Mismatch repair deficiency predicts response of solid tumors to PD-1 blockade," Science, Jul. 2017, 357(6349):409-413.
Li et al., "A model for RAS mutation patterns in cancers: finding the sweet spot," Nature Reviews Cancer, 2018, 18(12):767-77.
Li et al., "Construction and characterization of a humanized anti-human CD3 monoclonal antibody 12F6 with effective immunoregulation functions," Immunology, 2005, 116(4):487-98.
Liddy et al., "Monoclonal TCR-redirected tumor cell killing," Nature Medicine, 2012, 18(6):980-7.
Lin et al., "Enhanced homology-directed human genome engineering by controlled timing of CRISPR/Cas9 delivery," eLife, 2014, 3:e04766.
Link et al., "Anti-CD3-based bispecific antibody designed for therapy of human B-cell malignancy can induce T-cell activation by antigen-dependent and antigen-independent mechanisms," Jul. 1998, Int. J. Cancer, 77(2):251-256, 7 pages.
Lo et al., "Immunologic recognition of a shared p53 mutated neoantigen in a patient with metastatic colorectal cancer," Cancer Immunology Research, 2019, 7(4):534-43.
Low et al., "Targeting mutant p53-expressing tumours with a T cell receptor-like antibody specific for a wild-type antigen," Nature Communications, 2019, 10(1):1-4.
Lowe et al., "TCR-like antibody drug conjugates mediate killing of tumor cells with low peptide/HLA targets," MAbs 2017, 9(4):603-614.
Lu et al., "The effect of variable domain orientation and arrangement on the antigen-binding activity of a recombinant human bispecific diabody," Biochemical and biophysical research communications, 2004, 318(2):507-13.
Luft et al., "Exogenous peptides presented by transporter associated with antigen processing (TAP)-Deficient and TAP-Competent cells: Intracellular loading and kinetics of presentation," Sep. 1, 2017, J. Immunol., 167(5):2529-2537, 10 pages.
Lundegaard et al., "Accurate approximation method for prediction of class I MHC affinities for peptides of length 8, 10 and 11 using prediction tools trained on 9mers," Apr. 2008, Bioinformatics, 24(11): 1397-1398, 2 pages.
Lundegaard et al., "NetMHC-3.0: accurate web accessible predictions of human, mouse and monkey MHC class I affinities for peptides of length 8-11," May 7, 2008, Nucleic Acids Research, 36:W509-512, 4 pages.
Maiers et al., "High-resolution HLA alleles and haplotypes in the United States population," Human Immunology, 2007, 68(9):779-88.
Malekzadeh et al., "Neoantigen screening identifies broad TP53 mutant immunogenicity in patients with epithelial cancers," The Journal of Clinical Investigation, 2021, 129(3).
Martayan et al., "Class I HLA folding and antigen presentation in beta 2-microglobulin-defective Daudi cells," Mar. 2009, The Journal of Immunology, 2009, 182:3609-3617.
Marubashi et al., "Rab7B/42 is functionally involved in protein degradation on melanosomes in keratinocytes," Cell structure and function, 2020, 19039.
Maruyama et al., "Increasing the efficiency of precise genome editing with CRISPR-Cas9 by inhibition of nonhomologous end joining," Nature biotechnology, 2015, 33(5):538-42.
Maude et al., "Chimeric antigen receptor T cells for sustained remissions in leukemia," New England Journal of Medicine, 2014, 371(16):1507-17.
McConnell et al., "An integrated approach to extreme thermostabliliza-tion and affinity maturation of an antibody," Feb. 2013, PEDS, 26(2):151-163, 13 pages.
Merchant et al., "An efficient route to human bispecific IgG," Nature biotechnology, 1998, 16(7):677-81.
Miller et al., "A human monoclonal antibody neutralizes diverse HIV-1 isolates by binding a critical gp41 epitope," Oct. 11, 2005, Proc. Natl. Acad. Sci., 102(41): 14759-14764, 6 pages.
Miller et al., "An engineered antibody fragment targeting mutant β-catenin via major histocompatibility complex I neoantigen presentation," Journal of Biological Chemistry, 2019, 294(50):19322-34.
Miller et al., "High somatic mutation and neoantigen burden are correlated with decreased progression-free survival in multiple myeloma," Blood Cancer Journal, 2017, 7:e612, 1-11.
Miller et al., "T Cell Receptor-Like Recognition of Tumor In Vivo by Synthetic Antibody Fragment," Aug. 2012, PLoS One, 7(8): e43746, 14 pages.
Moore et al., "Application of dual affinity retargeting molecules to achieve optimal redirected T-cell killing of B-cell lymphoma," Blood, The Journal of the American Society of Hematology, 2011, 117(17):4542-51.
Morgan et al., "Cancer regression and neurological toxicity following anti-MAGE-A3 TCR gene therapy," Journal of Immunotherapy, 2013, 36(2):133-51.
Muzumdar et al., "Survival of pancreatic cancer cells lacking KRAS function," Nature communications, 2017, 8(1):1-9.
Myszka, "Improving biosensor analysis" 1999, J. Mol. Recognit, 12:279-284.
NCBI.gov [Online], "HLA-F major histocompatibility complex, class IF [*Homo sapiens*(humans)]," Sep. 4, 2016, retrieved on Sep. 29, 2016, retrieved from URL, <http://www.ncbi.nlm.nih.gov/gene/3134>, 14 pages.
Nielsen et al., "Reliable prediction of T-cell epitopes using neural networks with novel sequence representations," Feb. 2003, Protein Science, 12(5):1007-1017, 11 pages.
Nolan et al., "Flow cytometry: a versatile tool for all phases of drug discovery," Apr. 1999, Drug Discov Today, 4(4):173-180, 8 pages.
Novak et al., "Selective antibody-mediated targeting of class I MHC to EGFR-expressing tumor cells induces potent antitumor CTL activity in vitro and in vivo," Oct. 2006, International Journal of Cancer, 120:329-336, 8 pages.
Ostrem et al., "K-Ras (G12C) inhibitors allosterically control GTP affinity and effector interactions, " Nature, 2013, 503(7477):548-51.
Paix et al., "Precision genome editing using synthesis-dependent repair of Cas9-induced DNA breaks," Proceedings of the National Academy of Sciences, 2017, 114(50):E10745-54.
Park et al., "Long-term follow-up of CD19 CAR therapy in acute lymphoblastic leukemia," New England Journal of Medicine, 2018, 378(5):449-59.
Parkhurst et al., "Unique Neoantigens Arise from Somatic Mutations in Patients with Gastrointestinal Cancers Neoantigens in Patients with Gastrointestinal Cancers," Cancer discovery, 2019, 9(8):1022-35.
PCT International Preliminary Report on Patentability in International Appln. No. PCT/US2018/032996, dated Nov. 19, 2019, 5 pages.
PCT International Preliminary Report on Patentability in International Appln. No. PCT/US2022/022791, mailed on Oct. 12, 2023, 13 pages.
PCT International Search Report and Written Opinion in International Application No. PCT/US2018/032996, mailed on Aug. 27, 2018, 20 pages.
PCT International Search Report and Written Opinion in International Appln. No. PCT/US2022/022791, mailed on Nov. 17, 2022, 21 pages.
Petryszak et al., "Expression Atlas update—an integrated database of gene and protein expression in humans, animals and plants," Nucleic acids research, 2016, 44(D1):D746-52.
Porgador et al., "Localization, quantitation, and in situ detection of specific peptide-MHC class I complexes using a monoclonal antibody," Jun. 1997, Immunity, 6(6):715-726, 12 pages.
Prior et al., "A comprehensive survey of Ras mutations in cancer," Cancer Research, 2012, 72(10):2457-67.
Prior et al., "The Frequency of Ras Mutations in Cancer," Cancer Research, 2020, 80(14):2969-74.

(56) References Cited

OTHER PUBLICATIONS

Purbhoo et al., "T cell killing does not require the formation of a stable mature immunological synapse," Nature Immunology, 2004, 5(5):524-30.
Puri et al., "Highly efficient selection of epitope specific antibody through competitive yeast display library sorting," Aug. 2013, mAbs, 5(4):533-539, 7 pages.
Rafiq et al., "Engineering strategies to overcome the current roadblocks in CAR T cell therapy," Nature Reviews Clinical Oncology, 2020, 17(3):147-67.
Rafiq et al., "Optimized T-cell receptor-mimic chimeric antigen receptor T cells directed toward the intracellular Wilms Tumor 1 antigen," Leukemia, 2017, 31(8):1788-97.
Rahma et al., "The immunological and clinical effects of mutated ras peptide vaccine in combination with IL-2, GM-CSF, or both in patients with solid tumors, " Feb. 2014, Journal of Translational Medicine, 12:55, 12 pages.
Raman et al., "Direct molecular mimicry enables off-target cardiovascular toxicity by an enhanced affinity TCR designed for cancer immunotherapy," Scientific Reports, 2016, 6(1):1-0.
Richardson et al., "Enhancing homology-directed genome editing by catalytically active and inactive CRISPR-Cas9 using asymmetric donor DNA," Nature biotechnology, 2016, 34(3):339-44.
Rizvi et al., "Cancer immunology. Mutational landscape determines sensitivity to PD-1 blockade in non-small cell lung cancer," Science, Apr. 3, 2015, 348(6230):124-128.
Robbins et al., "Mining exomic sequencing data to identify mutated antigens recognized by adoptively transferred tumor-reactive T cells," Jun. 2013, Nat Med, 19(6):747-752, 14 pages.
Roblek et al., "Monoclonal antibodies specific for disease-associated point-mutants: Lamin A/C R453W and R482W," May 2010, PloS One, 5(5):e10604, 14 pages.
Rodrigues et al., "Engineering a humanized bispecific F(ab) 2 fragment for improved binding to T cells," International Journal of Cancer, 1992, 7:45-50.
Rosenberg et al., "Adoptive cell transfer as personalized immunotherapy for human cancer," Science, 2015, 348(6230):62-8.
Rosenberg et al., "Use of tumor-infiltrating lymphocytes and interleukin-2 in the immunotherapy of patients with metastatic melanoma," New England Journal of Medicine, 1988, 319(25):1676-80.
Sadelain et al., "The promise and potential pitfalls of chimeric antigen receptors," Curr. Opin. Immunol., 2009, 21(2):215-223.
Salter et al., "Genes regulating HLA class I antigen expression in T-B lymphoblast hybrids," Mar. 1985, Immunogenetics, 21(3):235-246.
Schmidt et al., "In silico and cell-based analyses reveal strong divergence between prediction and observation of T-cell-recognized tumor antigen T-cell epitopes," Journal of Biological Chemistry, 2017, 292(28):11840-9.
Scholtalbers et al., "TCLP: an online cancer cell line catalogue integrating HLA type, predicted neo-epitopes, virus and gene expression," Genome medicine, 2015, 7(1):1-7.
Schreiber et al., "Cancer Immunoediting: Integrating Immunity's Roles in Cancer Suppression and Promotion," Mar. 2011, Science, 331(6024): 1565-1570, 6 pages.
Schumacher et al., "Neoantigens in cancer immunotherapy," Science, 2015, 348(6230):69-74.
Schuster et al., "Tisagenlecleucel in adult relapsed or refractory diffuse large B-cell lymphoma," New England Journal of Medicine, 2019, 380(1):45-56.
Scott et al., "Monoclonal antibodies in cancer therapy," Cancer Immunity, 2012, 12(1):14.
Segal et al., "Epitope landscape in breast and colorectal cancer," Cancer Research, 2008, 68(3):889-92.
Sela-Culang et al., "The structural basis of antibody-antigen recognition," Oct. 2013, Frontiers in Immunology, 4:302, 13 pages.
Sergeeva et al., "An anti-PR1/HLA-A2 T-cell receptor-like antibody mediates complement-dependent cytotoxicity against acute myeloid leukemia progenitor cells," Blood, 2011, 117(160):4262-4272.
Shalaby et al., "Development of humanized bispecific antibodies reactive with cytotoxic lymphocytes and tumor cells overexpressing the HER2 protooncogene," The Journal of Experimental Medicine, 1992, 175(1):217-25.
Sharma et al., "Epidermal growth factor receptor mutations in lung cancer," Mar. 2007, Nat. Rev. Cancer, 7(3):169-181, 13 pages.
Sharma et al., "Recent advances in T-cell engineering for use in immunotherapy," F1000Research, 2016, 5:F1000 Faculty Rev:2344.
Shtraizent et al., "Hot Spot Mutation in TP53 (R248Q) Causes Oncogenic Gain-of-Function Phenotypes in a Breast Cancer Cell Line Derived from an African American Patient," Int. J. Environ. Res. Public Health, 2016, 13(1):22.
Sidhu et al., Phage-displayed Antibody Libraries of Synthetic Heavy Chain Complementarity Determining Regions, Feb. 2004, J. Mol. Biol., 338(2):299-310, 12 pages.
Skora et al., Generation of MANAbodies specific to HLA-restricted epitopes encoded by somatically mutated genes. Proceedings of the National Academy of Science of the USA.2015, Epub Jul. 27, 2015, 112(32):9967-9972.
Sliwkowski et al., "-Antibody therapeutics in cancer," Science, Sep. 13, 2013, 341(6151):1192-1198.
Smith et al., "Persistent mutant oncogene specific T cells in two patients benefitting from anti-PD-1," Journal for ImmunoTherapy of Cancer, Feb. 11, 2019, 7(1):40, 10 pages.
Snyder et al., "Genetic basis for clinical response to CTLA-4 blockade in melanoma," N. Engl. J. Med., Dec. 4, 2014, 371(23):2189-2199.
Sondek et al., "A general strategy for random insertion and substitution mutagenesis: substoichiometric coupling of trinucleotide phosphoramidites," Proceedings of the National Academy of Sciences, 1992, 89(8):3581-5.
Steinwand et al., "The influence of antibody fragment format on phage display based affinity maturation of IgG," Nov. 26, 2013, mAbs, 6(1):204-218, 16 pages.
Stewart-Jones et al., "Rational development of high-affinity T-cell receptor-like antibodies," Proceedings of the National Academy of Sciences, 2009, 106(14):5784-8.
Stone et al., "A sensitivity scale for targeting T cells with chimeric antigen receptors (CARs) and bispecific T-cell Engagers (BiTEs)," Oncoimmunology, 2012, 1(16):863-73.
Sugiyama et al., "A semi high-throughput method for screening small bispecific antibodies with high cytotoxicity," Scientific reports, 2017, 7(1): 1-2.
Sun et al., "Evolution of CD8+ T Cell Receptor (TCR) Engineered Therapies for the Treatment of Cancer," Cells, Sep. 2021, 10(9):2379.
Sung et al., "Dual-Affinity Re-Targeting proteins direct T cell-mediated cytolysis of latently HIV-infected cells," The Journal of clinical investigation, 2015, 125(11):4077-90.
Taylor et al., "A DNA-based T cell receptor reveals a role for receptor clustering in ligand discrimination," Cell, 2017, 169(1):108-19.
Thakur et al., "Cancer therapy with bispecific antibodies: Clinical experience," Jun. 2010, Curr. Opin. Mol. Ther., 12(3):340-349, 16 pages.
the-scientist.com [online], "Neoantigens Enable Personalized Cancer Immunotherapy," Apr. 2017, [retrieved on May 4, 2018], retrieved from: URL<https://www.the-scientist.com/?articles.view/articleNo/49000/title/Neoantigens-Enable-Personalized-Cancer-Immunotherapy/>, 5 pages.
Thomas et al., "Mesothelin-specific CD8+ T cell responses provide evidence of in vivo cross-priming by antigen-presenting cells in vaccinated pancreatic cancer patients," The Journal of experimental medicine, 2004, 200(3):297-306.
Thomsen et al., "Seq2Logo: a method for construction and visualization of amino acid binding motifs and sequence profiles including sequence weighting, pseudo counts and two-sided representation of amino acid enrichment and depletion," Nucleic acids research, 2012, 40(W1):W281-7.
Tran et al., "Cancer immunotherapy based on mutation-specific CD4+ T cells in a patient with epithelial cancer," Science, 2014, 344(6184):641-5.
Tran et al., "T-cell transfer therapy targeting mutant KRAS in cancer," New England Journal of Medicine, 2016, 375(23):2255-62.

(56) References Cited

OTHER PUBLICATIONS

Tsai et al., "Discovery of a selective inhibitor of oncogenic B-Raf kinase with potent antimelanoma activity," PNAS, Feb. 26, 2008, 105(8):3041-3046, 6 pages.
Tsukahara et al., "Specific targeting of a naturally presented osteosarcoma antigen, papillomavirus binding factor peptide, using an artificial monoclonal antibody," Aug. 2014, Journal of Biological Chemistry, 289(32):22035-22047, 14 pages.
Tumeh et al., "PD-1 blockade induces responses by inhibiting adaptive immune resistance," Nature, Nov. 27, 2014, 515(7528):568-571.
Uhlen et al., "Tissue-based map of the human proteome," Science, 2015, 347(6220):1260419.
Van Allen et al., "Genomic correlates of response to CTLA-4 blockade in metastatic melanoma," Science, Oct. 2015, 350(6257):207-211.
Van Wauwe et al., "OKT3: a monoclonal anti-human T lymphocyte antibody with potent mitogenic properties," The Journal of Immunology, 1980, 124(6):2708-13.
Vauquelin et al., "Exploring avidity: understanding the potential gains in functional affinity and target residence time of bivalent and heterobivalent ligands," British journal of pharmacology, 2013, 168(8):1771-85.
Verma et al., "TCR mimic monoclonal antibody targets a specific peptide/HLA class I complex and significantly impedes tumor growth in vivo using breast cancer models," Feb. 2010, J. Immunol., 184(4):2156-2165, 11 pages.
Vita et al., "The immune epitope database (IEDB): 2018 update," Nucleic acids research, 2019, 47(D1):D339-43.
Vogelstein et al., "Cancer genome landscapes," Science, 2013, 339(6127):1546-58.
Vonderheide et al., "Engineering T cells for cancer: our synthetic future," Jan. 2014, Immunol Rev., 257(1):7-13, 10 pages.
Wang et al., "A naturally processed peptide presented by HLA-A*0201 is expressed at low abundance and recognized by an alloreactive CD8+ cytotoxic T cell with apparent high affinity," Jun. 1997, J. Immunol., 158(12):5797-5804, 8 pages.
Wang et al., "Direct Detection and Quantification of Neoantigens," Cancer Immunology Research, 2019, 7 (11):1748-1754.
Wang et al., "Identification of T-cell Receptors Targeting KRAS-Mutated Human Tumors," Cancer Immunol Res, 2016, 4:204-214.
Ward et al., "The Role of Neoantigens in Naturally Occurring and Therapeutically Induced Immune Responses to Cancer," Adv Immunol, 2016, 130:25-74.
Warren et al., "—A census of predicted mutational epitopes suitable for immunologic cancer control," Human Immunol., 2010, pp. 245-254.
Watanabe et al., "Expanding the therapeutic window for CAR T cell therapy in solid tumors: the knowns and unknowns of CAR T cell biology," Frontiers in Immunology, 2018, 9:2486.
Webb et al., "Functional and structural characteristics of NY-ESO-1-related HLA A2-restricted epitopes and the design of a novel immunogenic analogue," Journal of Biological Chemistry, 2004, 279(22):23438-46.
Weiner et al., "Antibodies and cancer therapy: versatile platforms for cancer immunotherapy," May 2010, Nature Reviews Immunology, 10(5):317-327, 26 pages.
Wu et al., "Kinetic and structural analysis of mutant CD4 receptors that are defective in HIV gp120 binding," Proceedings of the National Academy of Sciences, 1996, 93(26):15030-5.
Wu et al., "T cell engaging bispecific antibody (T-BsAb): from technology to therapeutics," Pharmacology & Therapeutics, 2018, 182:161-75.
Yadav et al., "Predicting immunogenic tumour mutations by combining mass spectrometry and exome sequencing," Nov. 27, 2014, Nature, 515(7528):572-576, 16 pages.
Yang et al., "Rab7b, a novel lysosome-associated small GTPase, is involved in monocytic differentiation of human acute promyelocytic leukemia cells," Biochemical and biophysical research communications, 2004, 318(3):792-9.
Ylera et al., "Off-rate screening for selection of high-affinity anti-drug antibodies," Oct. 2013, Analytical Biochemistry, 441(2):208-213, 6 pages.
Yossef et al., "Enhanced detection of neoantigen-reactive T cells targeting unique and shared oncogenes for personalized cancer immunotherapy," JCI insight, 2018, 3(19):e122467.
Yu et al., "Mutation-specific antibodies for the detection of EGFR mutations in non-small-cell lung cancer," Clinical Cancer Research, 2009, 15(9):3023-8.
Zacharakis et al., "Immune recognition of somatic mutations leading to complete durable regression in metastatic breast cancer," Nature medicine, 2018, 24(6):724-30.
Zhu et al., "Engineering high affinity humanized anti-p185HER2/anti-CD3 bispecific F (ab') 2 for efficient lysis of p185HER2 overexpressing tumor cells," International Journal of Cancer, 1995, 62(3):319-24.
Zhu et al., "Identification of heavy chain residues in a humanized anti-CD3 antibody important for efficient antigen binding and T cell activation," The Journal of Immunology, 1995, 155(4):1903-10.
Zumrut et al., "Integrating ligand-receptor interactions and in vitro evolution for streamlined discovery of artificial nucleic acid ligands," Molecular Therapy-Nucleic Acids, 2019, 17:150-63.
International Preliminary Report on Patentability in International Appln. No. PCT/US2022/053065, mailed on Jun. 27, 2024, 6 pages.
Abrams et al., "Generation of Stable CD4+ and CD8+ T Cell Lines from Patients Immunized withrasOncogene-Derived Peptides Reflecting Codon 12 Mutations," Cellular immunology, Dec. 15, 1997, 182(2):137-51.
Baeuerle et al., "Bispecific T-cell engaging antibodies for cancer therapy," Cancer research, Jun. 15, 2009, 69(12):4941-4.
Edwards et al., "The remarkable flexibility of the human antibody repertoire; isolation of over one thousand different antibodies to a single protein, BLyS," Journal of molecular biology, Nov. 14, 2003, 334(1):103-18.
Gjertsen et al., "HLA-A3 restricted mutant ras specific cytotoxic T-lymphocytes induced by vaccination with T-helper epitopes," Journal of molecular medicine, Jan. 2003, 81(1):43-50.
HLA Alleles Nomenclature, Mar. 2023, 2 pages.
Khan et al., "Adjustable locks and flexible keys: plasticity of epitope-paratope interactions in germline antibodies," The Journal of Immunology, Jun. 2014, 192(11):5398-405.
Liu et al., "Major histocompatibility complex: Interaction with peptides," eLS, Aug. 2011, 1-8.
Lloyd et al., "Modelling the human immune response: performance of a 1011 human antibody repertoire against a broad panel of therapeutically relevant antigens," Protein Engineering, Design & Selection, Mar. 1, 2009, 22(3):159-68.
Poosarla et al., "Computational de novo design of antibodies binding to a peptide with high affinity," Biotechnology and bioengineering, Jun. 2017, 114(6):1331-42.
Wieczorek et al., "Major histocompatibility complex (MHC) class I and MHC class II proteins: conformational plasticity in antigen presentation," Frontiers in immunology, Mar. 17, 2017, 8(292):1-16.
Berglund et al., "The epitope space of the human proteome," Protein Science, Apr. 2008, 17(4):606-13.
Duan et al., "T-cell receptor mimic antibodies for cancer immunotherapy," Molecular Cancer Therapeutics, 20(9):1533-1541.
Extended Search Report in European Appln. No. 22908460.3, mailed on Nov. 13, 2025, 7 pages.
Padlan, "X-ray crystallography of antibodies," Advances in Protein Chemistry, Jan. 1, 1996, 49:57-133.

* cited by examiner

MANABODIES AND METHODS OF USING

CROSS-REFERENCE TO RELATED APPLICATIONS

This application is a continuation of U.S. application Ser. No. 16/614,005, filed on Nov. 15, 2019, which is a National Stage application under 35 U.S.C. § 371 of International Application No. PCT/US2018/032996, having an International Filing Date of May 16, 2018, which claims the benefit of U.S. Patent Application Ser. No. 62/506,674, filed on May 16, 2017. The disclosures of the prior applications are considered part of and are incorporated by reference in the disclosure of this application.

STATEMENT REGARDING FEDERAL FUNDING

This invention was made with government support under grant CA062924 awarded by the National Institutes of Health. The government has certain rights in the invention.

SEQUENCE LISTING

This application contains a Sequence Listing that has been submitted electronically as an XML file named "44807-0146002 SL.xml." The XML file, created on Aug. 19, 2025, is 375,978 bytes in size. The material in the XML file is hereby incorporated by reference in its entirety.

BACKGROUND

1. Technical Field

This document relates to methods and materials for assessing a mammal having or suspected of having cancer and/or for treating a mammal having cancer. For example, this document provides methods and materials for using a molecule including one or more antigen-binding domains (e.g., a single-chain variable fragment (scFv)) that can bind to a modified peptide (e.g., a tumor antigen) to treat a mammal having a cancer.

2. Background Information

Somatic mutations in cancer are ideal targets for cancer therapy as they are uniquely expressed only in tumor cells and not normal cells. In particular, targeting driver gene proteins (broadly subdivided into oncogene proteins and tumor suppressor proteins) have added benefits. First, the tumor's dependence on their oncogenic-endowing capacity makes resistance less likely. Second, these mutations typically occur early during the development of the tumor, thus essentially all daughter cancer cells will contain the mutation. Finally, driver gene proteins tend to have hotspot mutations shared among many patients, thus a therapy targeting a single mutation could be applied to a broad patient population.

Most mutant proteins, including most mutant driver gene proteins, are intracellular. While small molecules can target intracellular proteins, developing small molecules that can specifically inhibit the activity of a mutant driver gene and not its wild-type (wt) counterpart has remained out of reach for the majority of such driver gene proteins. Antibodies, which can have the capacity to distinguish a single amino acid mutation, can typically only target extracellular epitopes.

The immune system samples the intracellular contents of cells through antigen processing and presentation. Following protein proteolysis, a fraction of the resulting peptides are loaded onto human leukocyte antigen (HLA) and sent to the cell surface where they serve as a way for T cells, via their T cell receptor (TCR), to distinguish self from non-self peptides. For example, a virally-infected cell will present viral peptides in its HLA, triggering T cells to kill that cell. Similarly, in cancer, mutant peptides can be presented in HLA on the cancer cell surface, referred to as MANAs, for Mutation-Associated Neo-Antigens. In some cases, and to varying degrees, patients may mount an anti-cancer T cell response against these mutant-peptide-HLA neoantigens, and checkpoint blockade antibodies can further augment this response. However, many patients, particularly those with a low mutational burden, cannot mount a sufficient anti-cancer T cell response. A therapy or diagnostic specifically targeting MANAs could therefore provide a truly tumor-specific method to diagnose or treat cancer.

HLA class I proteins are present on all nucleated cells. There are three classical HLA class I genes, A, B, and C, each of which are highly polymorphic. Each HLA allele has a particular peptide-binding motif, and as a result, only certain peptides will bind to certain HLA alleles.

There is a continuing need in the art to develop new methods to diagnose, monitor, and effectively treat cancers.

SUMMARY

This document provides methods and materials for treating a mammal having cancer. For example, this document provides methods and materials for using one or more molecules including one or more antigen-binding domains (e.g., scFvs) that can bind to a modified peptide (e.g., a modified peptide present in a peptide-HLA-b2M complex) to treat a mammal having a cancer (e.g., a cancer expressing the modified peptide). In some cases, one or more molecules including one or more antigen-binding domains (e.g., scFvs) that can bind to a modified peptide (e.g., a modified peptide present in a peptide-HLA-b2M complex) can be administered to a mammal having a cancer (e.g., a cancer expressing the modified peptide) to treat the mammal.

As demonstrated herein, scFvs were identified that target (e.g., bind to) numerous Mutation-Associated Neo-Antigens (MANAs) present in a peptide-HLA-b2M complex in many acute myeloid leukemia (AML) cases. Also as demonstrated herein, the scFvs were used to design both chimeric antigen receptor (CAR) T cells (CARTs; also abbreviated as CAR Ts or CAR-Ts) and bispecific antibodies capable of recognizing and killing cells expressing MANAs. The ability to specifically target MANAs provides a tumor-specific method to diagnose and/or treat cancer. For example, scFvs specifically targeting MANAs can be used in full-length antibodies or fragments thereof, antibody drug conjugates (ADCs), antibody radionuclide conjugates, CARTs, or bispecific antibodies to diagnose and/or treat a mammal having cancer.

In general, one aspect of this document a molecule comprising an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide. The modified peptide can include from 7 amino acids to 15 amino acids (e.g., 10 amino acids). The modified peptide can be derived from a modified IDH2 polypeptide, a modified EGFR polypeptide, a modified p53 polypeptide, a modified KRAS polypeptide, a modified HRAS polypeptide, a modified NRAS polypeptide, or a modified CTNNB polypeptide. The modified peptide can include an amino acid sequence set forth SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, or SEQ ID NO:32. When the modified peptide includes SEQ ID NO:1, the class I HLA can be an HLA-B7, and the antigen binding fragment can include an amino acid sequence set forth in SEQ ID NO:3, SEQ ID NO:4, SEQ ID NO:5, SEQ ID NO:6, or SEQ ID NO:8. When the modified peptide includes SEQ ID NO: 11, the class I HLA can be an HLA-B7, and the antigen binding fragment can include an amino acid sequence set forth in SEQ ID NO:380, SEQ ID NO:390, SEQ ID NO:391, SEQ ID NO:392, or SEQ ID NO:393. When the modified peptide includes SEQ ID NO: 13, the class I HLA can be an HLA-A2, and the antigen binding fragment can include an amino acid sequence set forth in SEQ ID NO:324, SEQ ID NO:325, SEQ ID NO:326, SEQ ID NO:327, SEQ ID NO:328, SEQ ID NO:329, or SEQ ID NO:330. When the modified peptide includes SEQ ID NO:15, the class I HLA can be an HLA-A2, and the antigen binding fragment can include an amino acid sequence set forth in SEQ ID NO:331, SEQ ID NO:333, SEQ ID NO:336, or SEQ ID NO:337. When the modified peptide includes SEQ ID NO:16, the class I HLA can be an HLA-A2, and the antigen binding fragment can include an amino acid sequence set forth in SEQ ID NO:332, SEQ ID NO:334, SEQ ID NO:335, SEQ ID NO:336, or SEQ ID NO:337. When the modified peptide includes SEQ ID NO: 18, the class I HLA can be an HLA-A2, and the antigen binding fragment can include an amino acid sequence set forth in SEQ ID NO:338, SEQ ID NO:339, or SEQ ID NO:340. When the modified peptide includes SEQ ID NO:20, the class I HLA can be an HLA-A3, and the antigen binding fragment can include an amino acid sequence set forth in SEQ ID NO:341, SEQ ID NO:342, or SEQ ID NO:343. When the modified peptide includes SEQ ID NO:21, the class I HLA can be an HLA-A3, and the antigen binding fragment can include an amino acid sequence set forth in SEQ ID NO:342, SEQ ID NO:343, SEQ ID NO:349, SEQ ID NO:350, SEQ ID NO:351, SEQ ID NO:352, SEQ ID NO:353, SEQ ID NO:354, SEQ ID NO:355, SEQ ID NO:356, or SEQ ID NO:357. When the modified peptide includes SEQ ID NO:22, the class I HLA can be an HLA-A3, and the antigen binding fragment can include an amino acid sequence set forth in SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:369, SEQ ID NO:370, SEQ ID NO:371, SEQ ID NO:372, SEQ ID NO:373, or SEQ ID NO:374. When the modified peptide includes SEQ ID NO:24, the class I HLA can be an HLA-A11, and the antigen binding fragment can include an amino acid sequence set forth in SEQ ID NO:358, SEQ ID NO:359, SEQ ID NO:360, SEQ ID NO:361, SEQ ID NO:362, SEQ ID NO:363, SEQ ID NO:364, SEQ ID NO:365, SEQ ID NO:366, SEQ ID NO:367, or SEQ ID NO:368. When the modified peptide includes SEQ ID NO:26, the class I HLA can be an HLA-A3, and the antigen binding fragment can include an amino acid sequence set forth in SEQ ID NO:375, SEQ ID NO:376, SEQ ID NO:377, SEQ ID NO:378, or SEQ ID NO:379. When the modified peptide includes SEQ ID NO:28, the class I HLA can be an HLA-A1, and the antigen binding fragment can include an amino acid sequence set forth in SEQ ID NO:394. When the modified peptide includes SEQ ID NO:30, the class I HLA can be an HLA-A1, and the antigen binding fragment can include an amino acid sequence set forth in SEQ ID NO:395. When the modified peptide includes SEQ ID NO:31, the class I HLA can be an HLA-A1, and the antigen binding fragment can include an amino acid sequence set forth in SEQ ID NO:396. When the modified peptide includes SEQ ID NO:32, the class I HLA can be an HLA-A1, and the antigen binding fragment can include an amino acid sequence set forth in SEQ ID NO:397, SEQ ID NO: 398, SEQ ID NO:399, SEQ ID NO:400, or SEQ ID NO:401. The molecule can be an antibody, an antibody fragment, a scFv, a CAR, a TCR, a TCR mimic, a tandem scFv, a bispecific T cell engager, a diabody, a single-chain diabody, an scFv-Fc, a bispecific antibody, or a dual-affinity re-targeting antibody (DART). For example, the molecule can be a single-chain diabody. The molecule also can include an antigen-binding domain that can bind to an effector cell receptor (e.g., CD3, CD28, CD4, CD8, CD16a, NKG2D, PD-1, CTLA-4, 4-1BB, OX40, ICOS, or CD27). When the antigen-binding domain that can bind to an effector cell can bind to CD3, the antigen-binding domain can include an amino acid sequence set forth in SEQ ID NO:404, SEQ ID NO:405, SEQ ID NO:406, SEQ ID NO:407, SEQ ID NO:408, SEQ ID NO:409, SEQ ID NO:410, SEQ ID NO:411, SEQ ID NO:412, SEQ ID NO:413, SEQ ID NO:414, SEQ ID NO:415, SEQ ID NO:416, or SEQ ID NO:417.

In another aspect, this document features a CAR. The CAR can include an extracellular domain that includes any antigen-binding domain described herein (e.g., an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide), a transmembrane domain, and an intracellular domain. The transmembrane domain can include a transmembrane domain of CD4, CD8, or CD28. The intracellular domain can include one or more costimulatory domains from CD28, DAP10, ICOS, OX40, and/or 4-1BB. The intracellular domain can include a signaling domain from CD3-zeta.

In another aspect, this document features a T cell expressing any CAR described herein (e.g., a CAR including an extracellular domain that includes any antigen-binding domain described herein, a transmembrane domain, and an intracellular domain). The T cell can express a CAR including an extracellular domain that includes an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide), a transmembrane domain, and an intracellular domain.

In another aspect, this document features methods for treating a mammal having a cancer. The methods can include, or consist essentially of, administering to a mammal one or more molecules that include any antigen-binding domain described herein (e.g., an antigen-binding domain that can bind to a peptide-HLA-beta-2 microglobulin complex, where the peptide includes a modified peptide, where the HLA is a class I HLA, and where the antigen-binding domain does not bind to a complex that includes a wild-type version of the modified peptide), wherein the cancer includes cancer cells expressing a modified peptide. The mammal can be a human. The cancer can be Hodgkin's lymphoma, non-Hodgkin's lymphoma, AML, a lung cancer, a pancreatic cancer, a gastric cancer, a colorectal cancer, an ovarian cancer, an endometrial cancer, a biliary tract cancer, a liver cancer, myeloma, a breast cancer, a prostate cancer, an esophageal cancer, a stomach cancer, a kidney cancer, a bone cancer, a soft tissue cancer, a head and neck cancer, a glioblastoma multiforme, or an astrocytoma.

In another aspect, this document features methods for treating a mammal having a cancer. The methods can include, or consist essentially of, administering to a mammal one or more T cells expressing any one of the CARs described herein (e.g., a CAR including an extracellular domain that includes any antigen-binding domain described herein, a transmembrane domain, and an intracellular domain), where the cancer includes cancer cells expressing a modified peptide. The mammal can be a human. The cancer can be Hodgkin's lymphoma, non-Hodgkin's lymphoma, AML, a lung cancer, a pancreatic cancer, a gastric cancer, a colorectal cancer, an ovarian cancer, an endometrial cancer, a biliary tract cancer, a liver cancer, myeloma, a breast cancer, a prostate cancer, an esophageal cancer, a stomach cancer, a kidney cancer, a bone cancer, a soft tissue cancer, a head and neck cancer, a glioblastoma multiforme, or an astrocytoma.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 15A: IDH2 R140Q(134-143)-B7 cl.1 MANA-CAR-T cells were co-cultured for 4 hours at 37° C. with COS-7 cells co-transfected with plasmids encoding various combinations of HLA-B7, IDH2 (WT), and IDH2(R140Q). Following co-culture, conditioned media was collected and assayed for secreted IFNγ by ELISA. FIG. 15B: KRAS G12V(7-16)-A3 cl.2 MANA-CAR-T cells were co-cultured for 4 hours at 37° C. with COS-7 cells transfected with plasmids encoding various combinations of HLA-A3, KRAS(WT), and KRAS(G12V). Following co-culture, conditioned media was collected and assayed for secreted IFNγ by ELISA.

FIG. 16A: IDH2 R140Q(134-143)-B7 cl.29, cl. 1, and cl.3 scDbs, containing either the anti-CD3 clone mUCHT1 or hUCHT1v9, were incubated at the specified concentrations with T cells and COS-7 cells co-transfected with plasmids encoding various combinations of HLA-B7, IDH2(WT), IDH2(R140Q), and GFP for 24 hours at 37° C. Following co-culture, plates was snap frozen and conditioned media was collected and assayed for secreted IFNγ by ELISA. FIG. 16B: KRAS G12V(7-16)-A3 cl.2 mUCHT1 scDb was incubated at the specified concentrations with or without T cells and either 1) no target cells, 2) COS-7 cells co-transfected with plasmids encoding HLA-A3 and KRAS(WT) or HLA-A3 and KRAS(G12V), or 3) with NCI-H441 parental or HLA-A3 knockout cells for 24 hours at 37° C. Following co-culture, plates was snap frozen and conditioned media was collected and assayed for secreted IFNγ by ELISA.

Figure 1:
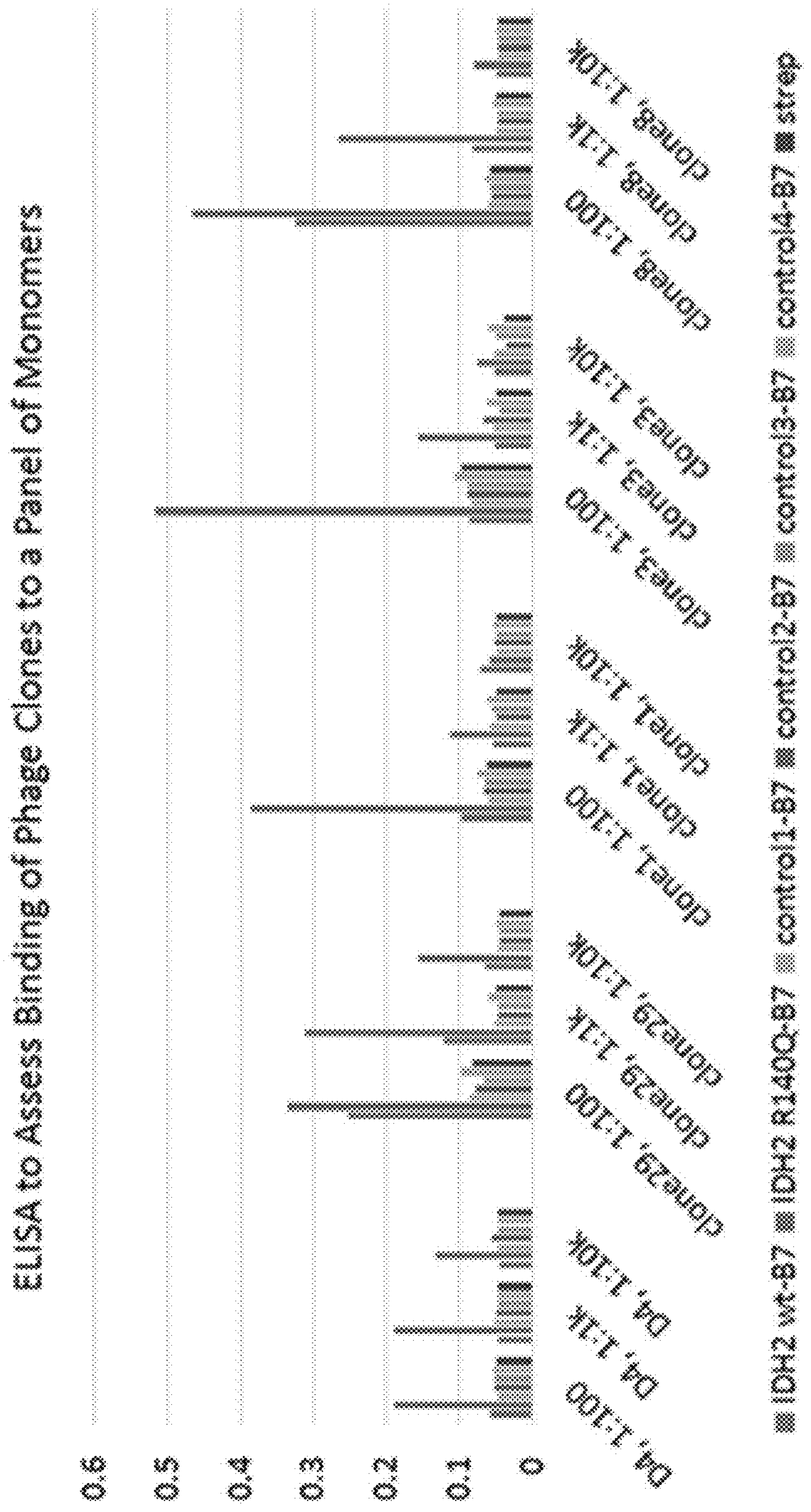
FIG. 1 contains ELISA results showing specificity of IDH2 R140Q HLA-B7 scFvs. Peptide-HLA biotinylated monomers were coated on a streptavidin plate, including the wild type (wt) version of an IDH2 peptide (SPNGTIRNIL; SEQ ID NO:2), an IDH2 peptide containing the R140Q mutation (SPNGTIQNIL; SEQ ID NO:1), and four control HLA-B7 monomers containing the following control peptides: control 1 peptide is SPGAANKRPI (an artificial sequence; SEQ ID NO:418), control 2 peptide is RPIPIKYKAM (from mutant MyD88 L265P; SEQ ID NO:9), control 3 peptide is KPITIGRHAH (from a different peptide from wt IDH2; SEQ ID NO:10), and control 4 peptide is AVGVGKSAL (from mutant KRAS G12V; SEQ ID NO:11). The five clones identified in panning were incubated in the wells at the specified dilutions, followed by a rabbit anti-phage antibody, then anti-Rabbit-HRP antibody.
Figure 2:
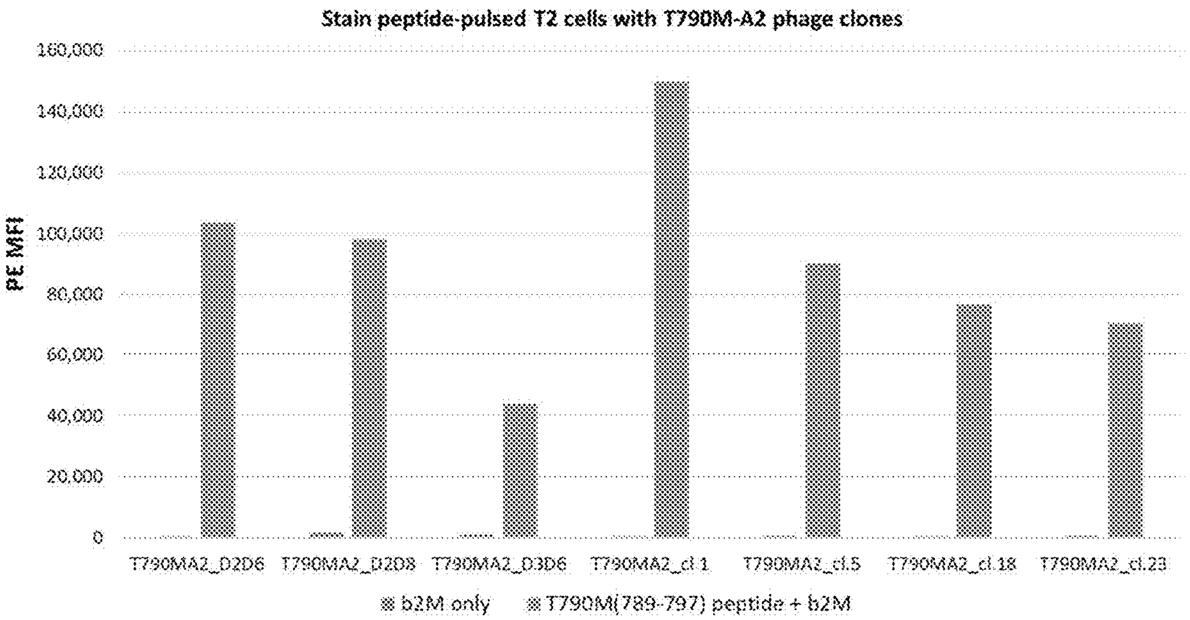
FIG. 2 contains a graph showing flow cytometry on peptide-pulsed A2+ cells. T2 cells were peptide-pulsed overnight at 37° C. in serum-free media with beta-2 microglobulin (b2M) protein only, or b2M with a EGFR T790M (789-797) peptide (IMQLMPFGC; SEQ ID NO:13). The EGFR wt(789-797) peptide (ITQLMPFGC; SEQ ID NO:14) did not bind to HLA-A2. Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 3:
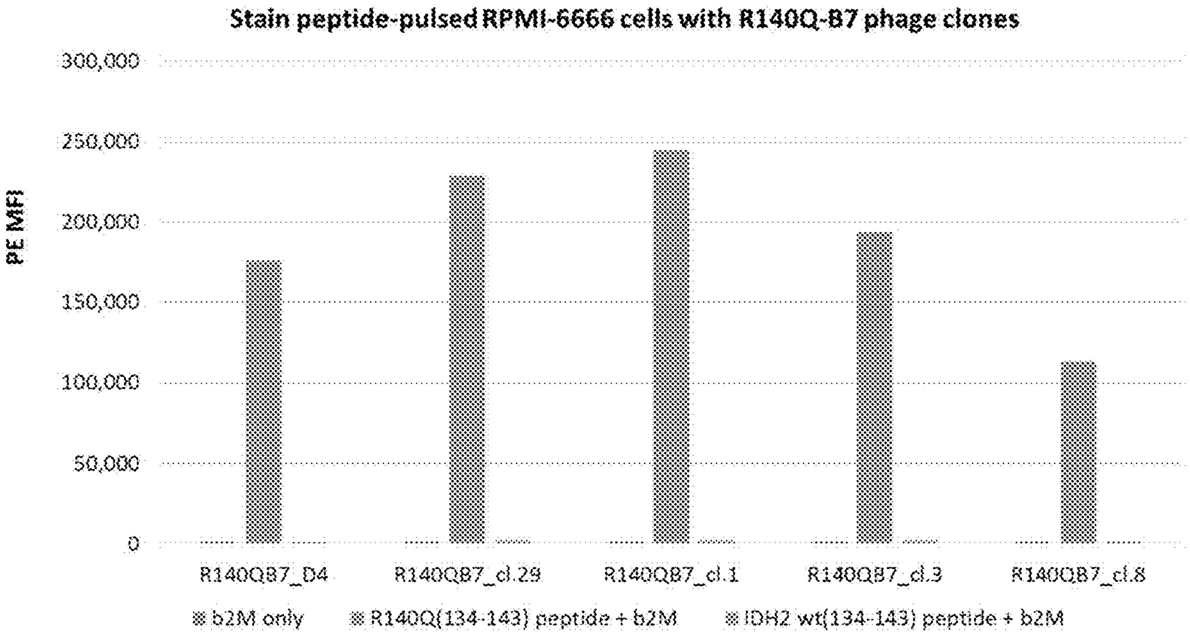
FIG. 3 contains a graph showing flow cytometry on peptide-pulsed B7+ cells. RPMI-6666 cells were peptide pulsed overnight at 37° C. in serum-free media with b2M protein only, b2M protein with an IDH2 mutant R140Q peptide (SPNGTIQNIL; SEQ ID NO:1), or b2M with the IDH2 wt peptide (SPNGTIRNIL; SEQ ID NO:2). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 4:
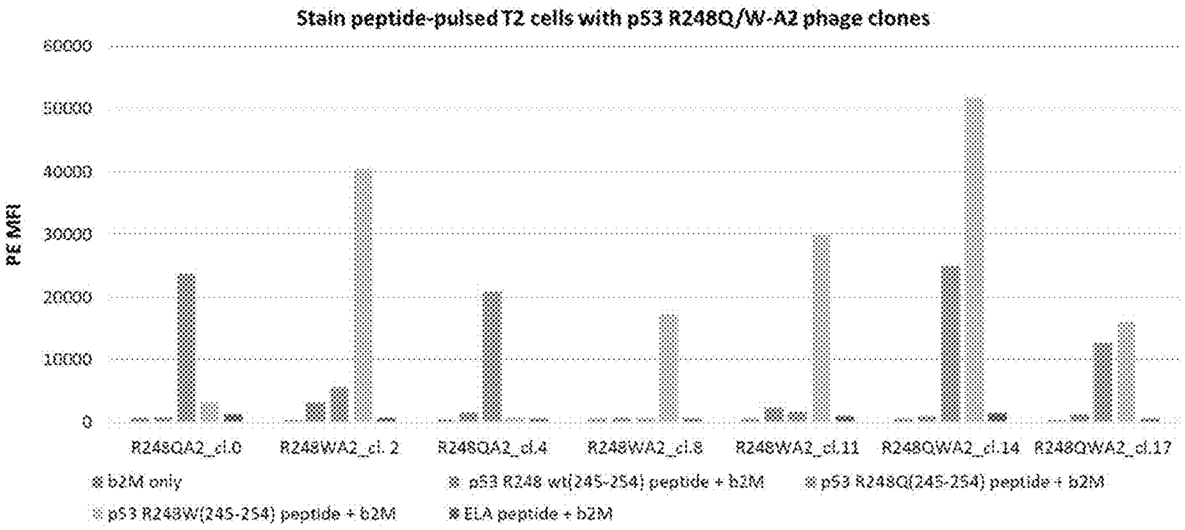
FIG. 4 contains a graph showing flow cytometry on peptide-pulsed A2+ cells. T2 cells were peptide-pulsed overnight at 37° C. in serum-free media with b2M only, b2M with a p53 mutant R248Q(245-254) peptide (GMNQRPILTI; SEQ ID NO:15), b2M with a p53 mutant R248W(245-254) peptide (GMNWRPILTI; SEQ ID NO:16), b2M with the p53 wt(245-254) peptide (GMNRRPILTI; SEQ ID NO:17), or b2M with an HLA-A2 control peptide ELA (ELAGIGILTV; SEQ ID NO:403). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 5:
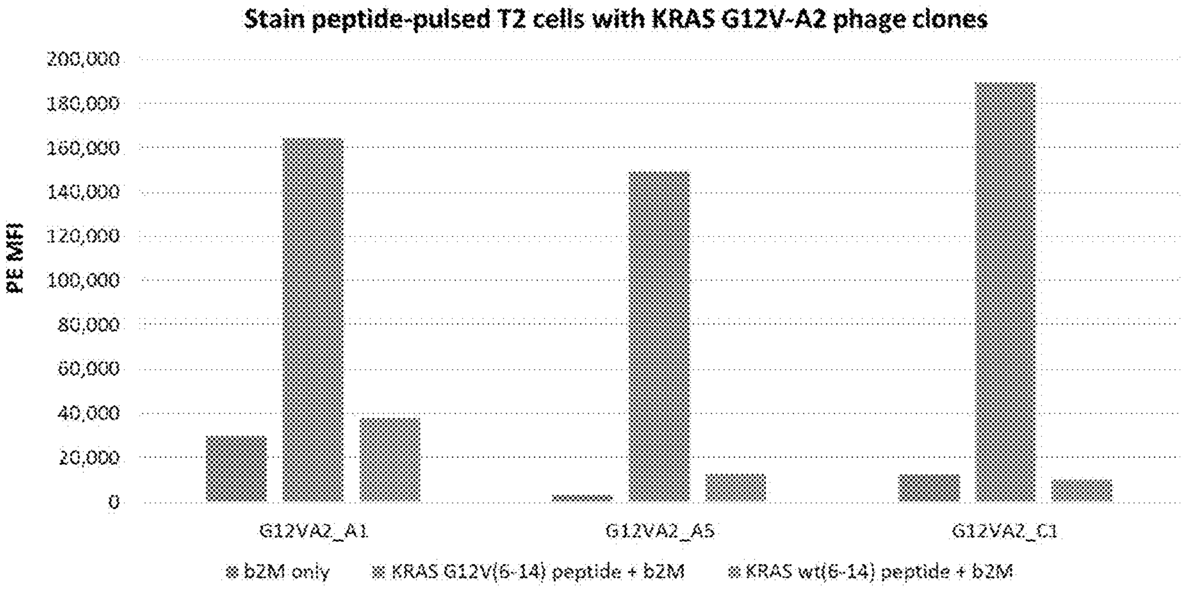
FIG. 5 contains a graph showing flow cytometry on peptide-pulsed A2+ cells. T2 cells were peptide-pulsed overnight at 37° C. in serum-free media with b2M only, b2M with a KRAS mutant G12V(6-14) peptide (LVVVGAVGV; SEQ ID NO:18), or b2M with the KRAS wt(6-14) peptide (LVVVGAGGV; SEQ ID NO:19). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 6:
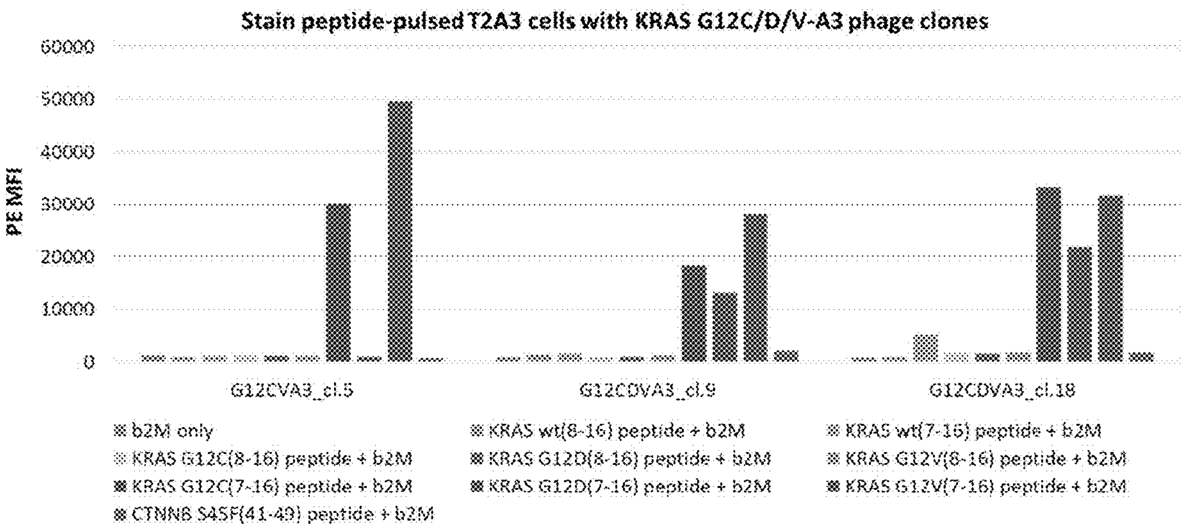
FIG. 6 contains a graph showing flow cytometry on peptide-pulsed A3+ cells. T2A3 cells were peptide-pulsed overnight at 37° C. in serum-free media with b2M only, b2M with a KRAS mutant G12C(8-16) peptide (VVGACGVGK; SEQ ID NO:419), b2M with a KRAS mutant G12D(8-16) peptide (VVGADGVGK; SEQ ID NO:420), b2M with a KRAS mutant G12V(8-16) peptide (VVGAVGVGK; SEQ ID NO:22), b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), b2M with the KRAS wt(8-16) peptide (VVGAGGVGK; SEQ ID NO:25), b2M with the KRAS wt(7-16) peptide (VVVGAGGVGK; SEQ ID NO:23), or the CTNNB S45F(41-49) peptide (TTAPFLSGK; SEQ ID NO:26). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 7:
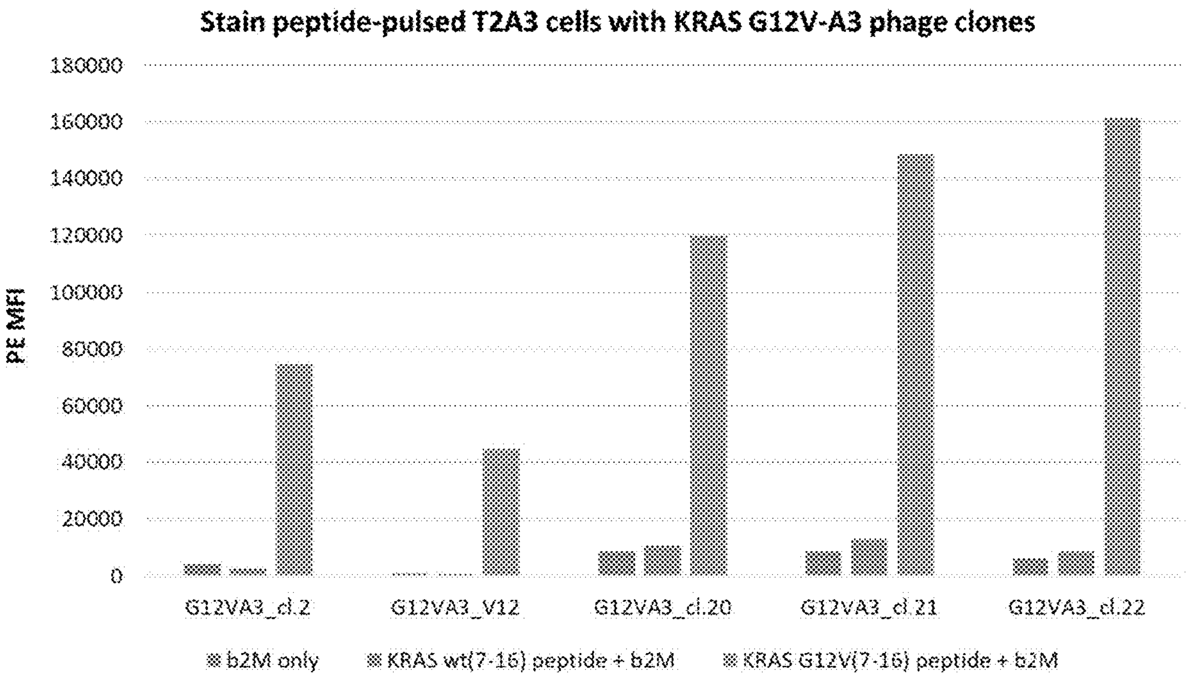
FIG. 7 contains a graph showing flow cytometry on peptide-pulsed A3+ cells. T2A3 cells were peptide-pulsed overnight at 37° C. in serum-free media with b2M only, b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 8:
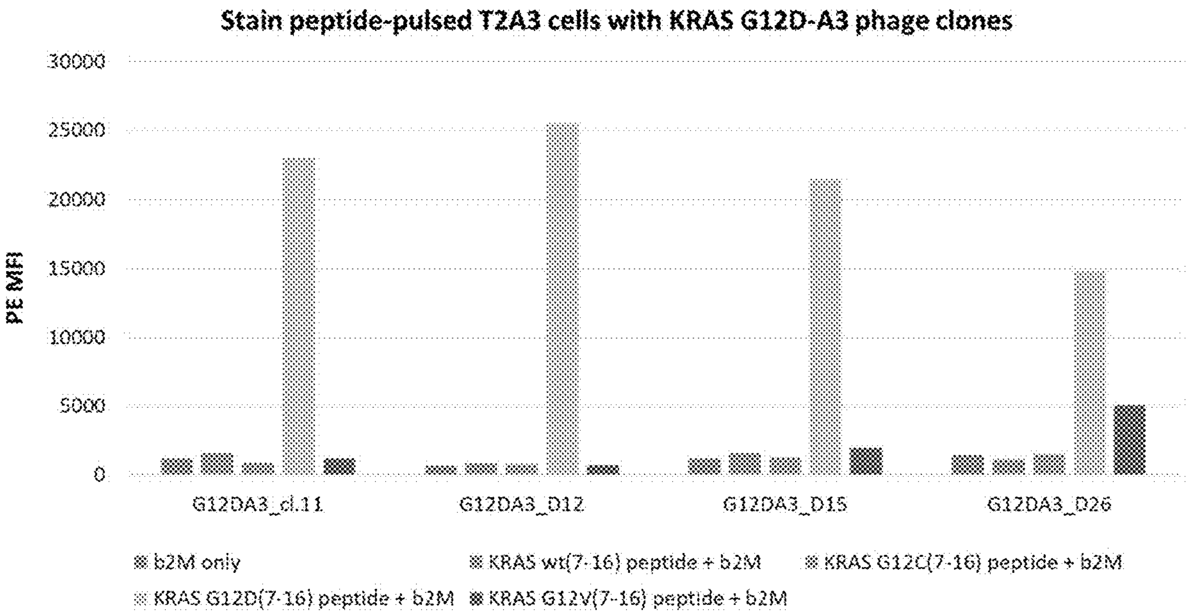
FIG. 8 contains a graph showing flow cytometry on peptide-pulsed A3+ cells. T2A3 cells were peptide-pulsed overnight at 37° C. in serum-free media with b2M only, b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 9:
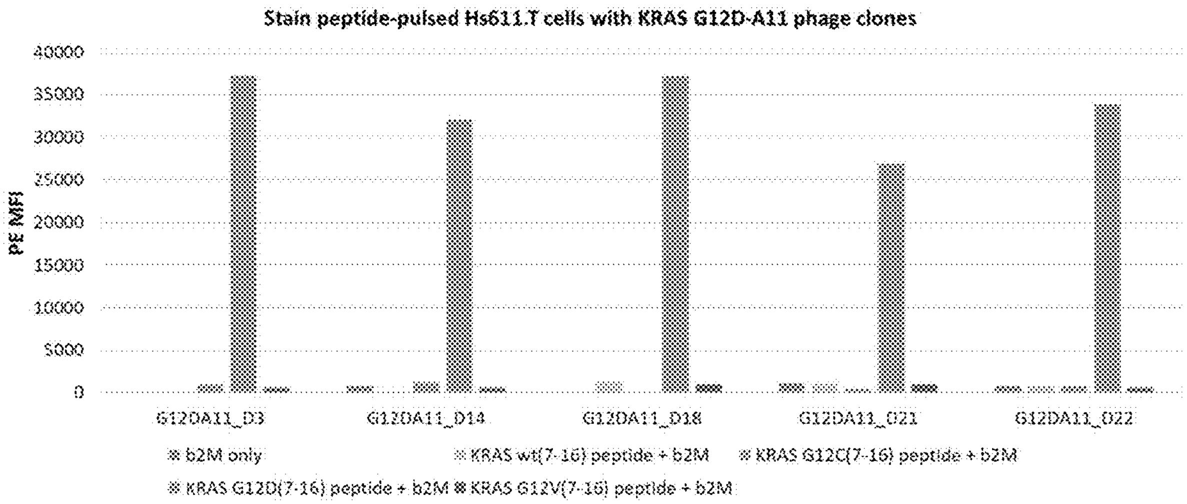
FIG. 9 contains a graph showing flow cytometry on peptide-pulsed A11+ cells. Hs611.T cells were peptide-pulsed overnight at 37° C. in serum-free media with b2M only, b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS mutant G12V(7-16) peptide (VVVGAVGVGK; SEQ ID NO:22), or b2M with the KRAS wt(7-16) peptide (VVVGAGGVGK; SEQ ID NO:23). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 10:
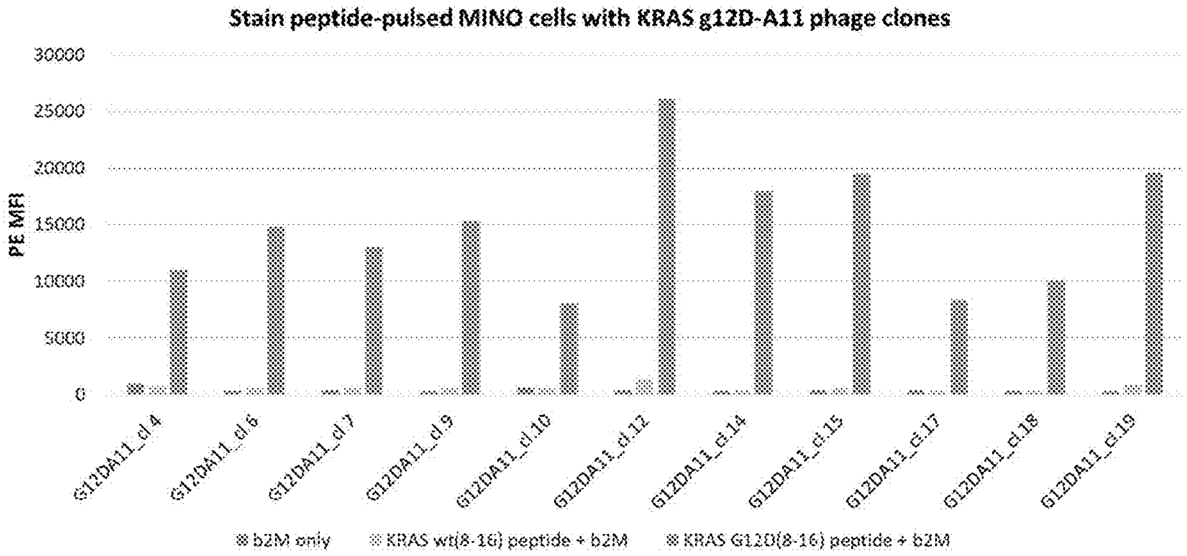
FIG. 10 contains a graph showing flow cytometry on peptide-pulsed A11+ cells. MINO cells were peptide-pulsed overnight at 37° C. in serum-free media with b2M only, b2M with a KRAS mutant G12D(8-16) peptide (VVGADGVGK; SEQ ID NO:24), or b2M with the KRAS wt(8-16) peptide (VVGAGGVGK; SEQ ID NO:25). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 11:
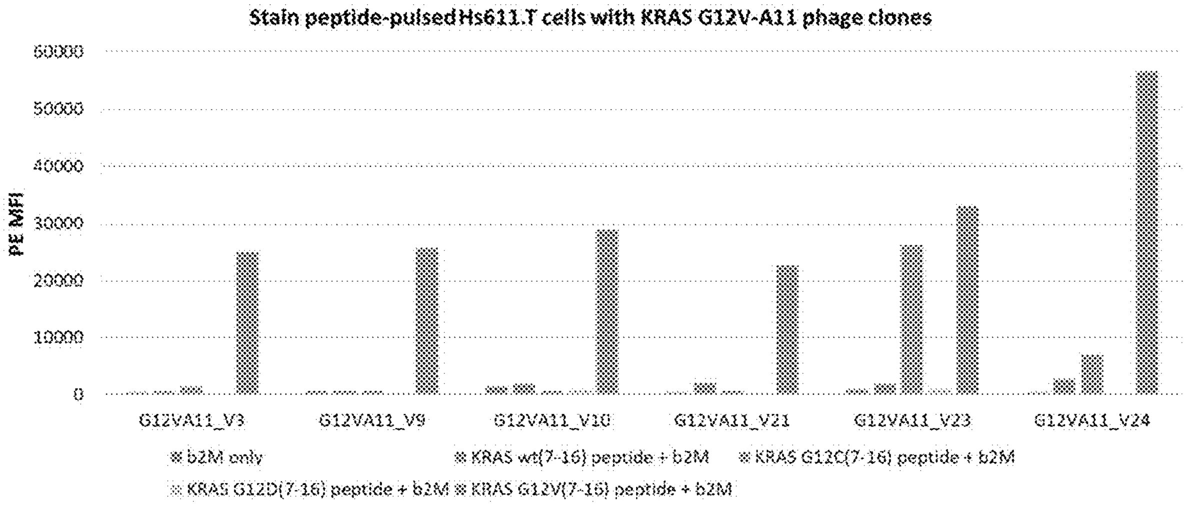
FIG. 11 contains a graph showing flow cytometry on peptide-pulsed A11+ cells. Hs611.T cells were peptide-pulsed overnight at 37° C. in serum-free media with b2M only, b2M with a KRAS mutant G12C(7-16) peptide (VVVGACGVGK; SEQ ID NO:20), b2M with a KRAS mutant G12D(7-16) peptide (VVVGADGVGK; SEQ ID NO:21), b2M with a KRAS G12V(7-16) peptide (VVVGAVGVGK; SEQ ID NO:22), or b2M with the KRAS wt(7-16) peptide (VVVGAGGVGK; SEQ ID NO:23). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 12:
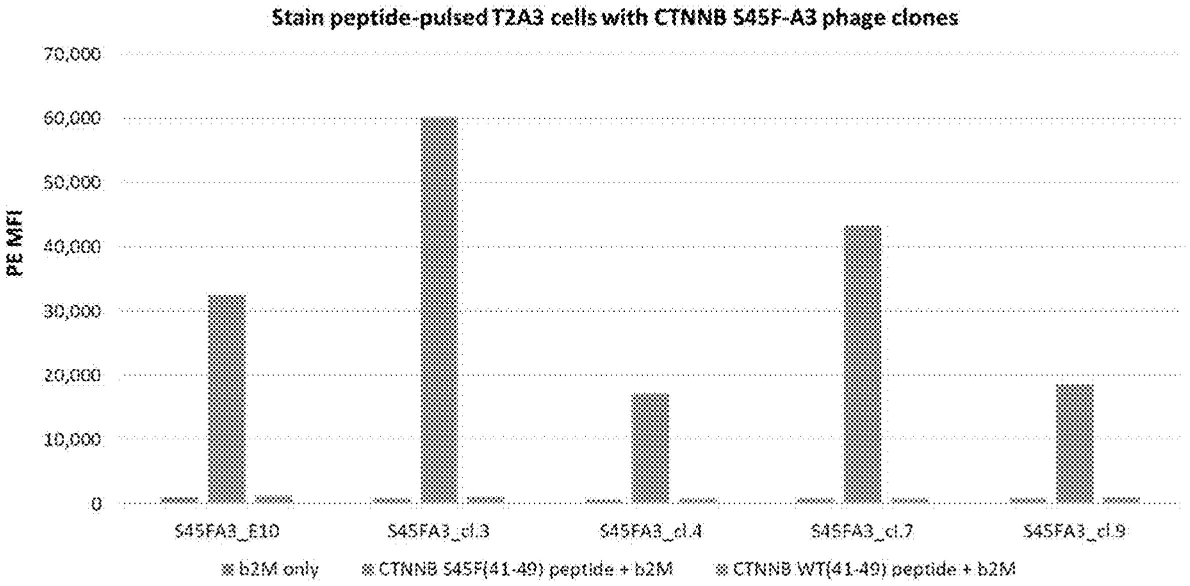
FIG. 12 contains a graph showing flow cytometry on peptide-pulsed A3+ cells. T2A3 cells were peptide-pulsed overnight at 37° C. in serum-free media with b2M only, b2M with a CTNNB mutant S45F(41-49) peptide (TTAPFLSGK; SEQ ID NO:26), or b2M with CTNNB wt(41-49) peptide (TTAPSLSGK; SEQ ID NO:27). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 13:
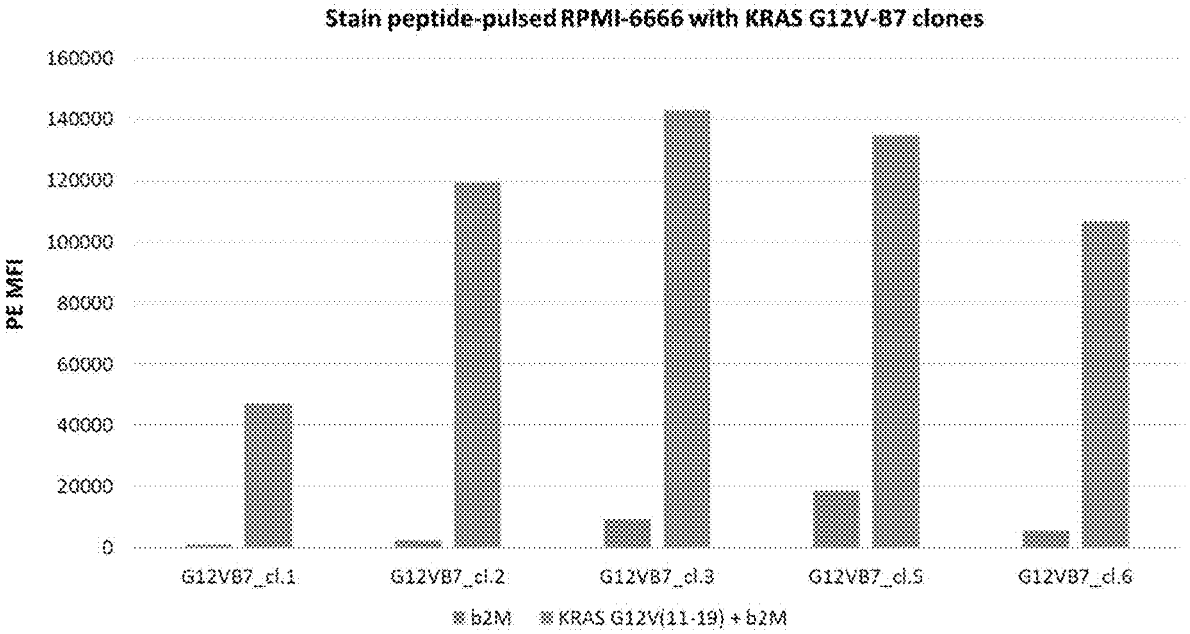
FIG. 13 contains a graph showing flow cytometry on peptide-pulsed B7+ cells. RPMI-6666 cells were peptide-pulsed overnight at 37° C. in serum-free media shows cells pulsed with b2M only, b2M with a KRAS mutant G12V (11-19) peptide (AVGVGKSAL; SEQ ID NO:11). The KRAS wt(11-19) peptide (AGGVGKSAL; SEQ ID NO:12) did not bind to HLA-B7. Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.
Figure 14:
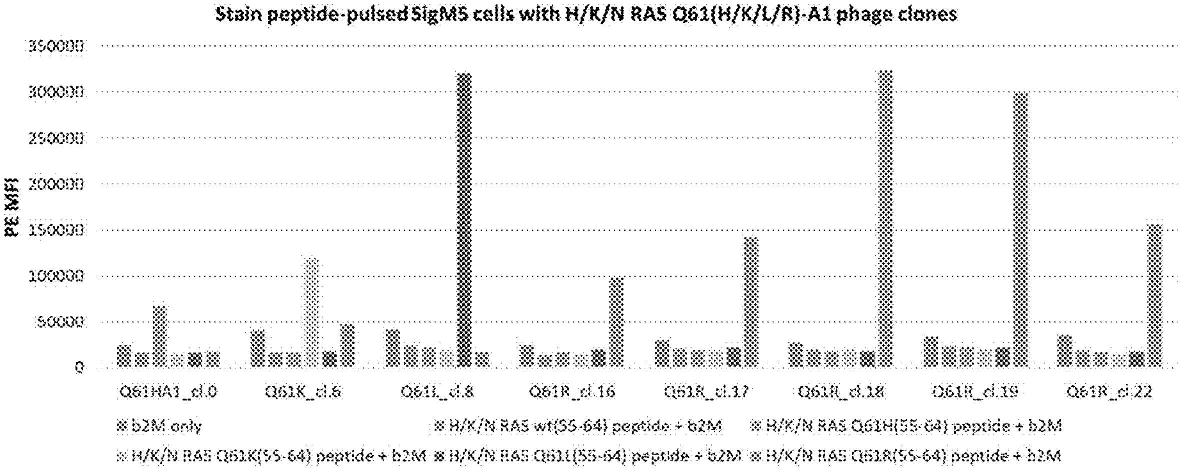
FIG. 14 contains a graph showing flow cytometry on peptide-pulsed A1+ cells. SigM5 cells were peptide-pulsed overnight at 37° C. in serum-free media shows cells pulsed with b2M only, b2M with a H/K/N RAS mutant Q61H(55-64) peptide (ILDTAGHEEY; SEQ ID NO:28), b2M with a H/K/N RAS mutant Q61K(55-64) peptide (ILDTAGKEEY; SEQ ID NO:30), b2M with a H/K/N RAS mutant Q61L(55-64) peptide (ILDTAGLEEY; SEQ ID NO:31), b2M with a H/K/N RAS mutant Q61R(55-64) peptide (ILDTAGREEY; SEQ ID NO:32), or b2M with the H/K/N RAS wt(55-64) peptide (ILDTAGQEEY; SEQ ID NO:29). Cells were stained with 10 μL of precipitated phage per 100 μL of cells, washed and stained with rabbit anti-M13 antibody, then washed and stained with anti-Rabbit-PE antibody. Cells were stained with a live/dead Near-IR dye, washed, and analyzed by an LSRII flow cytometer.

Following co-culture, CellTiter-Glo® was used to assay viable cells in each well. Percent target cell viability was calculated by subtracting the value from T cell only wells and normalizing to the value from target cell only wells.

DETAILED DESCRIPTION

This document provides methods and materials for assessing a mammal having cancer or suspected of having cancer and/or treating a mammal having cancer. For example, one or more molecules including one or more antigen-binding domains (e.g., scFvs) that can target (e.g., bind to) one or more modified peptides (e.g., peptides present in a peptide-HLA complex such as a peptide-HLA-b2M complex) can be used to assess a mammal having cancer or suspected of having cancer and/or to treat a mammal having a cancer (e.g., a cancer expressing one or more modified peptides). In some cases, one or more molecules includes one or more antigen-binding domains that can bind to a modified peptide can be used to detect the presence or absence of one or more modified peptides in a sample obtained from a mammal having cancer or suspected of having cancer. In some cases, one or more molecules including one or more antigen-binding domains that can bind to a modified peptide can be administered to a mammal having a cancer (e.g., a cancer expressing the modified peptide) to treat the mammal.

As used herein, a modified peptide is a peptide derived from a modified polypeptide. A modified polypeptide can be any appropriate modified polypeptide (e.g., a polypeptide having a disease causing mutation such as an oncogenic mutation). A modified peptide can have one or more amino acid modifications (e.g., substitutions) relative to a wild type (wt) peptide (e.g., a peptide derived from a wt polypeptide from which the modified polypeptide is derived). A modified peptide also can be referred to as a mutant peptide. In some cases, a modified peptide can be a tumor antigen. Examples of tumor antigens include, without limitation, mutation-associated neo-antigens (MANAs), tumor-associated antigen, and tumor-specific antigens. A modified peptide can be any appropriate length. In some cases, a modified peptide can be from about 7 amino acids to about 15 amino acids (e.g., from about 8 amino acids to about 15 amino acids, from about 9 amino acids to about 15 amino acids, from about 10 amino acids to about 15 amino acids, from about 11 amino acids to about 15 amino acids, from about 12 amino acids to about 15 amino acids, from about 13 amino acids to about 15 amino acids, from about 7 amino acids to about 14 amino acids, from about 7 amino acids to about 13 amino acids, from about 7 amino acids to about 12 amino acids, from about 7 amino acids to about 11 amino acids, from about 7 amino acids to about 10 amino acids, from about 7 amino acids to about 9 amino acids, or from about 9 amino acids to about 10 amino acids) in length. For example, a modified peptide can be about 9 amino acids in length. For example, a modified peptide can be about 10 amino acids in length. A modified peptide can be derived from any modified (e.g., oncogenic) polypeptide. Examples of modified polypeptides from which modified peptides described herein can be derived include, without limitation, epidermal growth factor receptor (EGFR), isocitrate dehydrogenase 2 (IDH2), p53, RAS (e.g., KRAS, HRAS, and NRAS), and CTNNB. A modified peptide can include any appropriate modification. In some cases, modified peptides described herein can include one or more modifications (e.g., mutations) shown in Table 1.

TABLE 1

Modified peptides.

| Protein of origin | Mutation | Mutant Peptide(s) | SEQ ID NO: | WT Peptide | SEQ ID NO: | Peptide Codons | HLA Allele |
|---|---|---|---|---|---|---|---|
| EGFR | T790M | IMQLMPFGC | 13 | ITQLMPFGC | 14 | 789-797 | A2 |
| IDH2 | R140Q | SPNGTIQNIL | 1 | SPNGTIRNIL | 2 | 134-143 | B7 |
| p53 | R248Q,<br>R248W | GMNQRPILTI,<br>GMNWRPILTI | 15<br>16 | GMNRRPILTI | 17 | 245-254 | A2 |
| KRAS | G12V | LVVVGAVGV | 18 | LVVVGAGGV | 19 | 6-14 | A2 |
| KRAS | G12C,<br>G12D,<br>G12V | VVVGACGVGK,<br>VVVGADGVGK,<br>VVVGAVGVGK | 20<br>21<br>22 | VVVGAGGVGK | 23 | 7-16 | A3 |
| KRAS | G12V | VVVGAVGVGK | 22 | VVVGAGGVGK | 23 | 7-16 | A3 |
| KRAS | G12D | VVVGADGVGK | 21 | VVVGAGGVGK | 23 | 7-16 | A3 |
| KRAS | G12D | VVVGADGVGK | 21 | VVVGAGGVGK | 23 | 7-16 | A11 |
| KRAS | G12D | VVGADGVGK | 24 | VVGAGGVGK | 25 | 8-16 | A11 |
| KRAS | G12V | VVVGAVGVGK | 22 | VVVGAGGVGK | 23 | 7-16 | A11 |
| CTNNB | S45F | TTAPFLSGK | 26 | TTAPSLSGK | 27 | 41-49 | A3 |
| KRAS | G12V | AVGVGKSAL | 11 | AGGVGKSAL | 12 | 11-19 | B7 |
| H/K/N RAS | Q61H | ILDTAGHEEY | 28 | ILDTAGQEEY | 29 | 55-64 | A1 |

TABLE 1-continued

| Modified peptides. | | | | | | | |
|---|---|---|---|---|---|---|---|
| Protein of origin | Mutation | Mutant Peptide(s) | SEQ ID NO: | WT Peptide | SEQ ID NO: | Peptide Codons | HLA Allele |
| H/K/N RAS | Q61K | ILDTAGKEEY | 30 | ILDTAGQEEY | 29 | 55-64 | A1 |
| H/K/N RAS | Q61L | ILDTAGLEEY | 31 | ILDTAGQEEY | 29 | 55-64 | A1 |
| H/K/N RAS | Q61R | ILDTAGREEY | 32 | ILDTAGQEEY | 29 | 55-64 | A1 |

A modified peptide described herein (e.g., a modified peptide including an amino acid sequence set forth in any one of SEQ ID NO:1, SEQ ID NO:11, SEQ ID NO:13, SEQ ID NO:15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be in a complex with any appropriate HLA. An HLA can be any appropriate HLA allele. In some cases, an HLA can be a class I HLA (e.g., HLA-A, HLA-B, and HLA-C) allele. Examples of HLA alleles that a modified peptide described herein can complex with include, without limitation, HLA-A1, HLA-A2, HLA-A3, HLA-11, and HLA-B7. Exemplary HLA alleles for particular modified peptides are shown in Table 1. For example, a modified peptide derived from a modified EGFR polypeptide (e.g., IMQLMPFGC (SEQ ID NO:13)) can be in a complex with HLA-A2 and b2M. For example a modified peptide derived from a modified IDH2 polypeptide (e.g., SPNGTIQNIL (SEQ ID NO:1)) can be in a complex with HLA-B7 and b2M. For example a modified peptide derived from a modified p53 polypeptide (e.g., GMNQRPILTI (SEQ ID NO:15) or GMNWRPILTI 1(SEQ ID NO:16)) can be in a complex with HLA-A2 and b2M. For example a modified peptide derived from a modified KRAS polypeptide (e.g., LVVVGAVGV (SEQ ID NO:18), VVVGACGVGK (SEQ ID NO:20), VVVGADGVGK (SEQ ID NO:21), VVVGAVGVGK (SEQ ID NO:22), and VVGADGVGK (SEQ ID NO:24)) can be in a complex with HLA-A2, HLA-A3, and/or HLA-A11, and b2M. For example a modified peptide derived from a modified CTNNB polypeptide (e.g., TTAPFLSGK (SEQ ID NO:26)) can be in a complex with HLA-A3 and b2M. For example a modified peptide derived from a modified KRAS polypeptide (e.g., AVGVGKSAL (SEQ ID NO:11)) can be in a complex with HLA-B7 and b2M. For example a modified peptide derived from a modified H/K/N RAS polypeptide (e.g., ILDTAGHEEY (SEQ ID NO:28), ILDTAGKEEY (SEQ ID NO:30), ILDTAGLEEY (SEQ ID NO:31), ILDTAGREEY (SEQ ID NO:32)) can be in a complex with HLA-A1 and b2M.

This document provides molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO: 15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32). In some cases, a molecule including one or more antigen-binding domains that can bind to a modified peptide described herein does not target (e.g., does not bind to) a modified peptide described herein that is not present in a complex (e.g., a peptide-HLA-b2M complex). In some cases, a molecule including one or more antigen-binding domains that can bind to a modified peptide described herein does not target (e.g., does not bind to) a wt peptide (e.g., a peptide derived from a wt polypeptide from which the modified polypeptide is derived).

A molecule including one or more antigen-binding domains (e.g., scFvs) that can bind to a modified peptide described herein can be any appropriate type of molecule. In some cases, a molecule can be a monovalent molecule (e.g., containing a single antigen-binding domain). In some cases, a molecule can be a multivalent molecule (e.g., containing two or more antigen-binding domains and simultaneously targeting two or more antigens). For example, a bispecific molecule can include two antigen-binding domains, a trispecific molecule can include three antigen-binding domains, a quadspecific molecule can include four antigen-binding domains, etc. Examples of molecules that contain antigen-binding domains include, without limitation, antibodies, antibody fragments, scFvs, CARs, T cell receptors (TCRs), TCR mimics, tandem scFvs, bispecific T cell engagers, diabodies, scDbs, scFv-Fcs, bispecific antibodies, dual-affinity re-targeting antibodies (DARTs), and any other molecule that includes at least one variable heavy chain (VH) and at least one variable light chain (VL). Any of these molecules can be used in accordance with materials and methods described herein. In some cases, an antigen-binding domain can be a scFv. For example, a molecule including one or more antigen-binding domains (e.g., one or more scFvs) that can bind to a modified peptide described herein can be a CAR. For example, a molecule including two scFvs that can bind to a modified peptide described herein can be a single-chain diabody (scDb).

In some cases, when a molecule including one or more antigen-binding domains (e.g., one or more scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) is a CAR, the CAR can be any appropriate CAR. A CAR provided herein can include an extracellular domain having at least one antigen-binding domain that can bind to a modified peptide described herein, a transmembrane domain, and an intracellular domain (e.g., an intracellular signaling domain such as a costimulatory domain). A CAR can include any appropriate extracellular domain. For example, a CAR can include a molecule (e.g., a scFv) having an antigen binding domain that can bind to a modified peptide including an amino acid sequence set forth in any one of SEQ ID NO:1, SEQ ID NO: 11, SEQ ID NO: 13, SEQ ID NO: 15, SEQ ID NO: 16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32. A CAR can include any appropriate transmembrane domain. A transmembrane domain can be derived from any appropriate polypeptide. Examples of transmembrane domains that can be used in CAR described herein include, without limitation, transmembrane domains of CD4, CD8 (e.g., CD8-alpha and CD8-beta), CD28, CD3 epsilon, CD5, CD6, CD9, CD16, CD22, CD33, CD37, CD45, CD64, CD80, CD86, CD134, 4-1BB, and CD154. In some cases, a CAR described herein can include a CD28 transmembrane domain. A CAR can include any appropriate intracellular domain. An intracellular domain can be derived from any appropriate polypeptide. An intracellular domain can include a costimulatory domain (e.g., a single costimulatory domain or multiple costimulatory domains). In cases where a CAR includes multiple costimulatory domains, the CAR can include multiple costimulatory domains of the same type or multiple costimulatory domains of different types. An intracellular domain can include a signaling domain. Examples of intracellular domains that can be used in CAR described herein include, without limitation, intracellular domains of CD3 (e.g., a CD3-zeta), CD28, DAP10, inducible T-cell costimulator (ICOS), OX40, 4-1BB, CD2, CD4, CD8, CD5, CD22, DAP-12, CD22, and CD79. A CAR can be made using any appropriate method. In some cases, a CAR also can include a hinge sequence (e.g., positioned between the extracellular domain and the transmembrane domain). In some cases, a CAR can be made as described elsewhere (see, Curran et al., 2012 *J. Gene Med* 14:405-415; Kershaw et al., 2005 *Nature Reviews Immunol.* 5(12):928-940; Eshhar et al., 1993 *Proc. Natl. Acad. Sci. U.S.A.* 90(2):720-724; Sadelain et al., 2009 *Curr. Opin. Immunol.* 21(2): 215-223; WO 2015/142675; WO 2015/150526; and WO 2014/134165). Also provided here are CARTs expressing one or more CARs, which CARs can target (e.g., bind to) one or more modified peptides described herein (e.g., CARs having two or more antigen-binding domains). Also provided here are CARTs expressing one or more CARs, which CARTs can target (e.g., bind to) one or more modified peptides described herein.

In some cases, when a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO: 15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) is a multivalent molecule (e.g., a bispecific molecule), a first antigen-binding domain can bind to a modified peptide described herein and a second antigen-binding domain can bind to an effector cell (e.g., an antigen present on an effector cell). Examples of effector cells include, without limitation, T cells, natural killer (NK) cells, natural killer T (NKT) cells, B cells, plasma cells, macrophages, monocytes, microglia, dendritic cells, neutrophils, fibroblasts, and mast cells. Examples of antigens present on effector cells include, without limitation, CD3, CD4, CD8, CD28, CD16a, NKG2D, PD-1, CTLA-4, 4-1BB, OX40, ICOS, CD27, and any other effector cell surface receptors. In some cases, a molecule described herein can include a first antigen-binding domain that can bind to a modified peptide described herein and a second antigen-binding domain that can bind to an antigen present on a T cell (e.g., CD3). In some cases, sequences (e.g., scFv sequences) that can bind to CD3 can be as shown in Table 4. In some cases, sequences (e.g., scFv sequences) that can bind to CD3 can be as described elsewhere (see, e.g., Rodrigues et al., 1992 *Int J Cancer Suppl.* 7:45-50; Shalaby et al., 1992 *J Exp Med.* 175:217-25; Brischwein et al., 2006 *Mol Immunol.* 43:1129-43; Li et al., 2005 *Immunology.* 116:487-98; WO2012162067; US20070065437; US20070065437; US20070065437; US20070065437; US20070065437; and US20070065437). In some cases, a molecule described herein can include a first antigen-binding domain that can bind to a modified peptide described herein and a second antigen-binding domain that can bind to an antigen present on a NK cell (e.g., CD16a or NKG2D). By binding both the modified peptide and the effector cell, the multivalent molecule can bring the cell expressing the modified peptide (e.g., as part of the HLA complex) into proximity with the effector cell, permitting the effector cell to act on the cell expressing the modified peptide.

In some cases, when a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) is a multivalent molecule (e.g., a bispecific molecule), a molecule can be in any appropriate format which includes at least one VH and at least one VL. For example, a VH and a VL can be in any appropriate orientation. In some cases, a VH can be N-terminal to the VL. In some cases, a VH can be C-terminal to the VL. In some cases, a linker amino acid sequence can be positioned between the VH and VL.

In some cases, when a bispecific molecule is a tandem scFv, the tandem scFv can be in any appropriate orientation. Examples of tandem scFv orientations including scFv-A and scFv-B include, without limitation, VLA-LL-VHA-SL-VLB-LL-VHB, VLA-LL-VHA-SL-VHB-LL-VLB, VHA-LL-VLA-SL-VLB-LL-VHB, VHA-LL-VLA-SL-VHB-LL-VLB, VLB-LL-VHB-SL-VLA-LL-VHA, VLB-LL-VHB-SL-VHA-LL-VLA, VHB-LL-VLB-SL-VLA-LL-VHA, and VHB-LL-VLB-SL-VHA-LL-VLA, where SL is a short linker and LL is a long linker. A short linker can be from about 3 amino acids to about 10 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination.

In some cases, when a bispecific molecule is a diabody, the diabody can be in any appropriate orientation. Examples of diabody orientations including scFv-A and scFv-B include, without limitation, VLA-SL-VHB and VLB-SL-VHA, VLA-SL-VLB and VHB-SL-VHA, VHA-SL-VLB and VHB-SL-VLA, VLB-SL-VHA and VLA-SL-VHB, VLB-SL-VLA and VHA-SL-VHB, and VHB-SL-VLA and VHA-SL-VLB, where SL is a short linker. A short linker can be from about 3 amino acids to about 10 amino acids in length. A short linker can include any appropriate amino acids (e.g., glycines and serines) in any appropriate combination.

In some cases, when a bispecific molecule is a scDb, the scDb can be in any appropriate orientation. Examples of scDb orientations including scFv-A and scFv-B include, without limitation, VLA-SL-VHB-LL-VLB-SL-VHA, VHA-SL-VLB-LL-VHB-SL-VLA, VLA-SL-VLB-LL-VHB-SL-VHA, VHA-SL-VHB-LL-VLB-SL-VLA, VLB-SL-VHA-LL-VLA-SL-VHB, VHB-SL-VLA-LL-VHA-SL-VLB, VLB-SL-VLA-LL-VHA-SL-VHB, and VHB-SL- VHA-LL-VLA-SL-VLB, where SL is a short linker and LL is a long linker. A short linker can be from about 3 amino acids to about 10 amino acids in length. A short linker can include any appropriate amino acids (e.g., glycines and serines) in any appropriate combination. A long linker can be from about 10 amino acids to about 25 amino acids in length. A long linker can include any appropriate amino acids (e.g., glycines and serines) in any appropriate combination.

In some cases, when a bispecific molecule is a scFv-Fc, the scFv-Fc can be in any appropriate orientation. Examples of scFv-Fc orientations including scFv-Fc-A, scFv-Fc-B, and an Fc domain include, without limitation, VLA-LL-VHA-hinge-Fc and VLB-LL-VHB-hinge-Fc, VHA-LL-VLA-hinge-Fc and VHB-LL-VLB-hinge-Fc, VLA-LL-VHA-hinge-Fc and VHB-LL-VLB-hinge-Fc, VHA-LL-VLA-hinge-Fc and VLB-LL-VHB-hinge-Fc, where LL is a long linker. A long linker can be from about 10 amino acids to about 25 amino acids in length. A long linker can include any appropriate amino acids (e.g., glycines and serines) in any appropriate combination. In some cases, an Fc domain in a scFv-Fc can include one or more modifications to increase heterodimerization and/or to decrease homodimerization of the scFv-Fc. In some cases, an Fc domain in a scFv-Fc can exclude a hinge domain. In some cases, an Fc domain in a scFv-Fc can be at the N-terminus of the scFv.

A molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can include any appropriate complementarity determining regions (CDRs). For example, a molecule including one or more antigen-binding domains that can bind to a modified peptide described herein can include a variable heavy chain (VH) having three VH complementarity determining regions (CDR-VHs) and a variable light chain (VL) having three VL CDRs (CDR-VLs). For example, a molecule that can bind to a modified peptide derived from a modified EGFR polypeptide (e.g., IMQLMPFGC (SEQ ID NO:13)) can include one of each of the CDRs set forth below:

```
CDR-VL1:
                      (SEQ ID NO: 33)
QDVNTA;

CDR-VL2:
SAS;

CDR-VL3:
                      (SEQ ID NO: 34)
QQYDYAPIT,

                      (SEQ ID NO: 35)
QQSPYYYLPIT,

                      (SEQ ID NO: 36)
QQYYYSPVT,

                      (SEQ ID NO: 37)
QQHYGNPFT,

                      (SEQ ID NO: 38)
QQSYYSPPT,

                      (SEQ ID NO: 39)
QQYYSYPPT,
```

-continued

```
                      (SEQ ID NO: 40)
QQYYYYPPT;

CDR-VH1:
                      (SEQ ID NO: 41)
GFNISWYQ,

                      (SEQ ID NO: 42)
GFNVSWSY,

                      (SEQ ID NO: 43)
GFNISWNQ,

                      (SEQ ID NO: 44)
GFNVGYYG,

                      (SEQ ID NO: 45)
GFNITSSY,

                      (SEQ ID NO: 46)
GFNINSSY,

                      (SEQ ID NO: 47)
GFNISTSY;

CDR-VH2:
                      (SEQ ID NO: 48)
VTPYSGYT,

                      (SEQ ID NO: 49)
IYGDSGYT,

                      (SEQ ID NO: 50)
VSPYSGYT,

                      (SEQ ID NO: 51)
VSGMEGYT,

                      (SEQ ID NO: 52)
ISPADGYN,

                      (SEQ ID NO: 53)
ISPTDGYY,

                      (SEQ ID NO: 54)
IDPNDGYS;
and

CDR-VH3:
                      (SEQ ID NO: 55)
SRSYTDGFDY,

                      (SEQ ID NO: 56)
SRGQWEASYYAMDY,

                      (SEQ ID NO: 57)
SRSDYYAMDY,

                      (SEQ ID NO: 58)
SRDIYGYAMDV,

                      (SEQ ID NO: 59)
SRTDSTAYTAMDV,

                      (SEQ ID NO: 60)
SRTSDTSYAAMDV,

                      (SEQ ID NO: 61)
SRTNNTAADAMDV.
```

For example, a molecule that can bind to a modified peptide derived from a modified IDH2 polypeptide (e.g., SPNG-TIQNIL (SEQ ID NO:1) can include one of each of the CDRs set forth below:

CDR-VL1:
(SEQ ID NO: 33)
QDVNTA;

CDR-VL2:
SAS;

CDR-VL3:
(SEQ ID NO: 62)
QQYSYSPPT, (SEQ ID NO: 63)
QQGKAYWPAT, (SEQ ID NO: 64)
QQVYSSPFT, (SEQ ID NO: 65)
QQYSLYSPMT, (SEQ ID NO: 66)
QQSYYMPFT;

CDR-VH1:
(SEQ ID NO: 67)
GFNISDTY, (SEQ ID NO: 68)
GFNVGHYR, (SEQ ID NO: 69)
GFNVKYYM, (SEQ ID NO: 70)
GFNSFLS, (SEQ ID NO: 71)
GFNIFRGY;

CDR-VH2:
(SEQ ID NO: 72)
ISPRTGYN, (SEQ ID NO: 73)
VSPNGYYT, (SEQ ID NO: 74)
ISPGYDYT, (SEQ ID NO: 75)
IFPSSDYT, (SEQ ID NO: 76)
ISPHSDYT;
and

CDR-VH3:
(SEQ ID NO: 77)
SRAYYSYAYAMDV, (SEQ ID NO: 78)
SRGYSSYAFDY, (SEQ ID NO: 79)
SRSYWRYSVDV, (SEQ ID NO: 80)
SRGKHSSDSNYYMDY, (SEQ ID NO: 81)
SRSYGWAAFDY.

For example, a molecule that can bind to a modified peptide derived from a modified p53 polypeptide (e.g., GMNQRPILTI (SEQ ID NO:15) and GMNWRPILTI (SEQ ID NO:16)) can include one of each of the CDRs set forth below:

CDR-VL1:
(SEQ ID NO: 33)
QDVNTA;

CDR-VL2:
SAS;

CDR-VL3:
(SEQ ID NO: 82)
QQSGYAPIT, (SEQ ID NO: 83)
QQYSYAPIT, (SEQ ID NO: 84)
QQSLYGPFT, (SEQ ID NO: 85)
QQYSYSPIT, (SEQ ID NO: 86)
QQSGYQPDT, (SEQ ID NO: 87)
QQYLYQPWT;

CDR-VH1:
(SEQ ID NO: 89)
GFNISYYS, (SEQ ID NO: 90)
GFNIGYYT, (SEQ ID NO: 91)
GFNIAYEY, (SEQ ID NO: 92)
GFNLFGYG, (SEQ ID NO: 93)
GFNISWYA, (SEQ ID NO: 94)
GFNIDYYG;

CDR-VH2:
(SEQ ID NO: 96)
VDPDSDYT, (SEQ ID NO: 97)
VSPWSYST, (SEQ ID NO: 98)
IGPDSGYT, (SEQ ID NO: 99)
IGPYYYYT, (SEQ ID NO: 100)
IWPDSDWT, (SEQ ID NO: 101)
LYGGSDST;
and

CDR-VH3:
(SEQ ID NO: 103)
SRSWIHMFSMDY, (SEQ ID NO: 104)
SRDHWDEAFDV, (SEQ ID NO: 105)
SRVWYYSTYGMDY,

-continued (SEQ ID NO: 106)
SRENYDMAMDY, (SEQ ID NO: 107)
SRYYYSSAFDV, (SEQ ID NO: 108)
SRQYSAYFDY.

For example, a molecule that can bind to a modified peptide derived from a modified KRAS polypeptide (e.g., LVVVGAVGV (SEQ ID NO:18), VVVGACGVGK (SEQ ID NO:20), VVVGADGVGK (SEQ ID NO:21), VVVGAVGVGK (SEQ ID NO:22), and VVGADGVGK (SEQ ID NO:24)) can include one of each of the CDRs set forth below:

CDR-VL1:
(SEQ ID NO: 33)
QDVNTA;

CDR-VL2:
SAS and SAY;

CDR-VL3:
(SEQ ID NO: 110)
QQWYSSPVT, (SEQ ID NO: 111)
QQYYSRPVT, (SEQ ID NO: 121)
QQSYGSGSPWT, (SEQ ID NO: 122)
QQTYYSPWT, (SEQ ID NO: 123)
QQYYYPPIT, (SEQ ID NO: 132)
QQSYYYFRPIT, (SEQ ID NO: 133)
QQASYYYPLT, (SEQ ID NO: 134)
QQKSEYSPWT, (SEQ ID NO: 135)
QQSGYIPFT, (SEQ ID NO: 136)
QQGAYYRPFT, (SEQ ID NO: 152)
QQYMYSPVT, (SEQ ID NO: 153)
QQSSSSPIT, (SEQ ID NO: 154)
QQSSASPLT, (SEQ ID NO: 155)
QQYAYSPLT, (SEQ ID NO: 168)
QQYSYYPIT, (SEQ ID NO: 169)
QQYSYTPVT, (SEQ ID NO: 170)
QQYSYEPVT,

-continued (SEQ ID NO: 171)
QQYAYYSPVT, (SEQ ID NO: 172)
QQYEYYPMT, (SEQ ID NO: 188)
QQYSFYPFT, (SEQ ID NO: 85)
QQYSYSPIT, (SEQ ID NO: 189)
QQYSAYYQPIT, (SEQ ID NO: 168)
QQYSYYPIT, (SEQ ID NO: 190)
QQYEYVPHT, (SEQ ID NO: 191)
QQYSYMPIT, (SEQ ID NO: 192)
QQYAYYPVT, (SEQ ID NO: 191)
QQYSYMPIT, (SEQ ID NO: 193)
QQYDYRPVT, (SEQ ID NO: 194)
QQYDFTPMT, (SEQ ID NO: 195)
QQYSSSSPVT, (SEQ ID NO: 229)
QQSSYTPIT, (SEQ ID NO: 230)
QQYAYYPIT, (SEQ ID NO: 231)
QQYEYYPIT, (SEQ ID NO: 232)
QQYTYYPIT, (SEQ ID NO: 168)
QQYSYYPIT, (SEQ ID NO: 233)
QQSSVEPWT;

CDR-VH1:
(SEQ ID NO: 112)
GFNINWAN, (SEQ ID NO: 113)
GFNIYLHD, (SEQ ID NO: 114)
GFNIYWSH, (SEQ ID NO: 124)
GFNIVGGG, (SEQ ID NO: 125)
GFNIRSYA, (SEQ ID NO: 126)
GFNVSHTG, (SEQ ID NO: 137)
GFNLSYSD, (SEQ ID NO: 138)
GFNISASG, (SEQ ID NO: 139)
GFNIYRYG, (SEQ ID NO: 140)
GFNIYGTM, (SEQ ID NO: 141)
GFNISYSY, (SEQ ID NO: 156)
GFNVSAYW, (SEQ ID NO: 157)
GFNISGYG, (SEQ ID NO: 158)
GFNVSSVG, (SEQ ID NO: 159)
GFNVSSYG, (SEQ ID NO: 173)
GFNFSYGY, (SEQ ID NO: 174)
GFNVWGPG, (SEQ ID NO: 175)
GFNVSGSQ, (SEQ ID NO: 176)
GFNIYGQM, (SEQ ID NO: 177)
GFNVMYST, (SEQ ID NO: 196)
GFNFGSY, (SEQ ID NO: 197)
GFNISDSY, (SEQ ID NO: 198)
GFNIFSDQ, (SEQ ID NO: 199)
GFNLSYSY, (SEQ ID NO: 200)
GFNISYGY, (SEQ ID NO: 201)
GFNISYQH, (SEQ ID NO: 202)
GFNLSGYY, (SEQ ID NO: 203)
GFNVSGQY, (SEQ ID NO: 204)
GFNVSTSG, (SEQ ID NO: 205)
GFNISYAK, (SEQ ID NO: 206)
GFNFSSYV, (SEQ ID NO: 234)
GFNISQGG, (SEQ ID NO: 235)
GFNISSTG, (SEQ ID NO: 236)
GFNFFSTV, (SEQ ID NO: 237)
GFNLHGYL, (SEQ ID NO: 238)
GFNLSTHV, (SEQ ID NO: 239)
GFNVSYYS;

CDR-VH2:

(SEQ ID NO: 115)
ISPPYDYT, (SEQ ID NO: 116)
IIPAIDYT, (SEQ ID NO: 117)
ISSFEGYT, (SEQ ID NO: 127)
IYPQGDYT, (SEQ ID NO: 128)
VGPGKGYT, (SEQ ID NO: 128)
VGPGKGYT, (SEQ ID NO: 142)
VMPDSGHT, (SEQ ID NO: 143)
IHPLKPYT, (SEQ ID NO: 144)
LYPYGYST, (SEQ ID NO: 145)
FKPDSYNT, (SEQ ID NO: 146)
LLPYDGNT, (SEQ ID NO: 160)
IYGGSGYT, (SEQ ID NO: 161)
LYGGSDYT, (SEQ ID NO: 162)
IYGTSDYT, (SEQ ID NO: 163)
IAPRRDYT, (SEQ ID NO: 178)
ISGYTGNT, (SEQ ID NO: 179)
IHPFSGNT, (SEQ ID NO: 180)
IPGWSGYT, (SEQ ID NO: 181)
LSPFSGNT, (SEQ ID NO: 182)
IYSWSDYT, (SEQ ID NO: 207)
ISGYSGNT, (SEQ ID NO: 208)
FSPYSSNT, (SEQ ID NO: 209)
FNIPYDSYYT, (SEQ ID NO: 210)
ISGFSGNT,

-continued

FHYGSGNT, (SEQ ID NO: 211)

FMPYQGST, (SEQ ID NO: 212)

FSPYSGYT, (SEQ ID NO: 213)

ISPVSGNT, (SEQ ID NO: 214)

IYGAYSGT, (SEQ ID NO: 215)

LTYWGGYT, (SEQ ID NO: 216)

VYPDSGGT, (SEQ ID NO: 217)

VYPGGGQT, (SEQ ID NO: 240)

LLGGSGNT, (SEQ ID NO: 241)

IYPWSGST, (SEQ ID NO: 242)

IYPPNGYT, (SEQ ID NO: 243)

FYPYVGYT, (SEQ ID NO: 244)

IYPWNDYT; (SEQ ID NO: 245)
and

CDR-VH3:

SRSYSYYFDY, (SEQ ID NO: 118)

SRRDGYYFDY, (SEQ ID NO: 119)

SRSYSYYMDY, (SEQ ID NO: 120)

SRDSSYLAFDY, (SEQ ID NO: 129)

SRNFQSTSHAFDY, (SEQ ID NO: 130)

SRKTYYAFDY, (SEQ ID NO: 131)

SRATNIPVYAFDY, (SEQ ID NO: 147)

SRYSSMYYYYFDY, (SEQ ID NO: 148)

SRSYAYGYFAY, (SEQ ID NO: 149)

SRGEVYHYYAFDY, (SEQ ID NO: 150)

SRAAYSSMDV, (SEQ ID NO: 151)

SRTHSYWSAFDY, (SEQ ID NO: 164)

SRTVRYAFDY, (SEQ ID NO: 165)

-continued

SRSSRYSMDY, (SEQ ID NO: 166)

SRKSSYYFDY, (SEQ ID NO: 167)

SRAASLSSSYYSAFDV, (SEQ ID NO: 183)

SRGYSYSAMDY, (SEQ ID NO: 184)

SRGYSYFAMDY, (SEQ ID NO: 185)

SRNISYEQSSAFDY, (SEQ ID NO: 186)

SRGYAHNSFDY, (SEQ ID NO: 187)

SRSNQSAYSYMDY, (SEQ ID NO: 218)

SRSQFTFYQYFDY, (SEQ ID NO: 219)

SRMSVRNAFDY, (SEQ ID NO: 220)

SRSDSYYTAMDY, (SEQ ID NO: 221)

SRSNYYYLDY, (SEQ ID NO: 222)

SRANIYSSHSFFDY, (SEQ ID NO: 223)

SRTHSSIYHSFDY, (SEQ ID NO: 224)

SRPMKTSYYGAFDY, (SEQ ID NO: 225)

SRSQSYTYWSAMDY, (SEQ ID NO: 226)

SRGEYGTYMDY, (SEQ ID NO: 227)

SRTSSYYAFDY, (SEQ ID NO: 228)

SRGYDYSAFDY, (SEQ ID NO: 246)

SRGLQYSAMDY, (SEQ ID NO: 247)

SRSRSSNYYFDV, (SEQ ID NO: 248)

SRGVDYAYLDY, (SEQ ID NO: 249)

SRGYRYQYMDV, (SEQ ID NO: 250)

SRGSYYSFDY. (SEQ ID NO: 251)

For example, a molecule that can bind to a modified peptide derived from a modified CTNNB polypeptide (e.g., TTAP-FLSGK (SEQ ID NO:26)) can include one of each of the CDRs set forth below:

CDR-VL1:
QDVNTA; (SEQ ID NO: 33)

CDR-VL2:
SAS and SAY;

CDR-VL3:
QQSYYSPPT, (SEQ ID NO: 38)
QQIYTSPIT, (SEQ ID NO: 252)
QQRAYFPIT, (SEQ ID NO: 253)
QQQYAYTPIT, (SEQ ID NO: 254)
QQIHYKPLT; (SEQ ID NO: 255)

CDR-VH1:
GFNINNTY, (SEQ ID NO: 256)
GFNFITTG, (SEQ ID NO: 257)
GFNFSDYG, (SEQ ID NO: 258)
GFNVWSYG, (SEQ ID NO: 259)
GFNVAWYS; (SEQ ID NO: 260)

CDR-VH2:
IYPTDGYT, (SEQ ID NO: 260)
IGPGSDYT, (SEQ ID NO: 261)
LIPASGYT, (SEQ ID NO: 262)
VTPDGSYT, (SEQ ID NO: 263)
VYGGSSYT; (SEQ ID NO: 264)
and CDR-VH3:
SRTYYSYYSAMDV, (SEQ ID NO: 265)
SRYYYASALDY, (SEQ ID NO: 266)
SRGWSYYMDY, (SEQ ID NO: 267)
SRSYGWAMDY, (SEQ ID NO: 268)
SRDFYSSGMDY. (SEQ ID NO: 269)

For example, a molecule that can bind to a modified peptide derived from a modified KRAS polypeptide (e.g., AVGVGKSAL (SEQ ID NO:11)) can include one of each of the CDRs set forth below:

CDR-VL1:
QDVNTA; (SEQ ID NO: 33)

CDR-VL2:
SAS;

CDR-VL3:
QQEWRLPIT, (SEQ ID NO: 270)
QQGTSTPFT, (SEQ ID NO: 271)
QQSWRYPMT, (SEQ ID NO: 272)
QQSYSYPVT, (SEQ ID NO: 273)
QQGWLYSPFT; (SEQ ID NO: 274)

CDR-VH1:
GFNVYGNQ, (SEQ ID NO: 275),
GFNLSYYG, (SEQ ID NO: 402)
GFNISRYG, (SEQ ID NO: 276)
GFNIYSSW, (SEQ ID NO: 277)
GFNISGYG; (SEQ ID NO: 157)

CDR-VH2:
IYPYSGST, (SEQ ID NO: 278)
IYPDSGYT, (SEQ ID NO: 279)
FYPSSSYT, (SEQ ID NO: 280)
FQPYSGYT, (SEQ ID NO: 281)
VYGGSGYT; (SEQ ID NO: 282)
and CDR-VH3:
SRSAYVAYSYFDY, (SEQ ID NO: 283)
SRAYLYYYLAY, (SEQ ID NO: 284)
SRKYYEAMDY, (SEQ ID NO: 285)
SREYTYYFDY, (SEQ ID NO: 286)
SRAHSSYYVDY. (SEQ ID NO: 287)

For example, a molecule that can bind to a modified peptide derived from a modified H/K/N RAS polypeptide (e.g., ILDTAGHEEY (SEQ ID NO:28), ILDTAGKEEY (SEQ ID NO:30), ILDTAGLEEY (SEQ ID NO:31), ILDTAGREEY (SEQ ID NO:32)) can include one of each of the CDRs set forth below:

```
CDR-VL1:
                                  (SEQ ID NO: 33)
QDVNTA;

CDR-VL2:
SAS;

CDR-VL3:
                                 (SEQ ID NO: 292)
QQHYYSPVT,

                                 (SEQ ID NO: 296)
QQYAYAPFT,

                                 (SEQ ID NO: 300)
QQAHMIPIT,

                                 (SEQ ID NO: 301)
QQSVYDPIT,

                                 (SEQ ID NO: 302)
QQSYTSPLT,

                                 (SEQ ID NO: 303)
QQGQYSPFT,

                                 (SEQ ID NO: 320)
QQYWYLPTT;

CDR-VH1:
                                 (SEQ ID NO: 289)
GFNIGYYG,

                                 (SEQ ID NO: 293)
GFNIFYQD,

                                 (SEQ ID NO: 297)
GFNVSYSM,

                                 (SEQ ID NO: 305)
GFNFSFPG,

                                 (SEQ ID NO: 306)
GFNISGSW,

                                (SEQ ID NO: 307),
GFNIYYGV,

                                 (SEQ ID NO: 308)
GFNVSYEY,

                                 (SEQ ID NO: 321)
GFNISWYD;

CDR-VH2:
                                 (SEQ ID NO: 290)
VYPGGGYT,

                                 (SEQ ID NO: 294)
IYPDYDYT,

                                 (SEQ ID NO: 298)
VWGDGGVT,

                                 (SEQ ID NO: 310)
FVGYDGYT,

                                 (SEQ ID NO: 311)
LYPDSDYT,

                                 (SEQ ID NO: 312)
IYPDSSWT,

                                 (SEQ ID NO: 313)
IYGGSDNT,
```

-continued

```
                                 (SEQ ID NO: 322)
IEPSVGYT;
and

CDR-VH3:
                                 (SEQ ID NO: 291)
SRYYYYGFDY,

                                 (SEQ ID NO: 295)
SRTYSVYMDY,

                                 (SEQ ID NO: 299)
SRGSYYAFDY,

                                 (SEQ ID NO: 316)
SRDYYSFSMDY,

                                 (SEQ ID NO: 317)
SRAHTYAFDY,

                                 (SEQ ID NO: 318)
SRDQDFHYMNYYLSYALDY,

                                 (SEQ ID NO: 319)
SRPLGSYFDY,

                                 (SEQ ID NO: 323)
SRSYPYYYFDY.
```

Examples of CDRs (e.g., particular combinations of a CDR-VL1, a CDR-VL2, a CDR-VL3, a CDR-VH1, a CDR-VH2, and a CDR-VH3) that can bind to particular modified peptides are shown in Table 2. In some cases, a molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can include any appropriate set of CDR sequences (e.g., any of the CDR sequence sets described herein).

A molecule including one or more antigen-binding domains (e.g., scFvs) that can bind to a modified peptide described herein (e.g., a modified peptide including an amino acid sequence set forth in any one of SEQ ID NO:1, SEQ ID NO: 11, SEQ ID NO: 13, SEQ ID NO:15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can include any appropriate sequence. For example, a molecule that can bind to a modified peptide derived from a modified EGFR polypeptide (e.g., IMQLMPFGC (SEQ ID NO:13)) can include, without limitation, the scFv sequence set forth in any one of SEQ ID NO:324, SEQ ID NO:325, SEQ ID NO:326, SEQ ID NO:327, SEQ ID NO:328, SEQ ID NO:329, and SEQ ID NO:330. For example, a molecule that can bind to a modified peptide derived from a modified IDH2 polypeptide (e.g., SPNGTIQNIL (SEQ ID NO:1)) can include, without limitation, the scFv sequence set forth in any one of SEQ ID NO:3, SEQ ID NO:4, SEQ ID NO:5, SEQ ID NO:6, and SEQ ID NO:8. For example, a molecule that can bind to a modified peptide derived from a modified p53 polypeptide (e.g., GMNQRPILTI (SEQ ID NO:15) and GMNWRPILTI 1(SEQ ID NO:16)) can include, without limitation, the scFv sequence set forth in any one of SEQ ID NO:331, SEQ ID NO:332, SEQ ID NO:333, SEQ ID NO:334, SEQ ID NO:335, SEQ ID NO:336, and SEQ ID NO:337. For example, a molecule that can bind to a modified peptide derived from a modified KRAS polypeptide (e.g., LVVVGAVGV (SEQ ID NO:18), VVVGACGVGK (SEQ ID NO:20), VVVGADGVGK (SEQ ID NO:21), VVVGAVGVGK (SEQ ID NO:22), and VVGADGVGK (SEQ ID NO:24)) can include, without limitation, the scFv sequence set forth in any one of SEQ ID NO:338, SEQ ID NO:339, SEQ ID NO:340, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:350, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:361, SEQ ID NO:362, SEQ ID NO:363, SEQ ID NO:364, SEQ ID NO:365, SEQ ID NO:366, SEQ ID NO:367, SEQ ID NO:368, SEQ ID NO:369, SEQ ID NO:370, SEQ ID NO:371, SEQ ID NO:372, SEQ ID NO:373, and SEQ ID NO:374. For example, a molecule that can bind to a modified peptide derived from a modified CTNNB polypeptide (e.g., TTAPFLSGK (SEQ ID NO:26)) can include, without limitation, the scFv sequence set forth in any one of SEQ ID NO:375, SEQ ID NO:376, SEQ ID NO:377, SEQ ID NO:378, SEQ ID NO:379. For example, a molecule that can bind to a modified peptide derived from a modified KRAS polypeptide (e.g., AVGVGKSAL (SEQ ID NO:11)) can include, without limitation, the scFv sequence set forth in any one of SEQ ID NO:380, SEQ ID NO:390, SEQ ID NO:391, SEQ ID NO:392, and SEQ ID NO:393. For example, a molecule that can bind to a modified peptide derived from a modified H/K/N RAS polypeptide (e.g., ILDTAGHEEY (SEQ ID NO:28), ILDTAGKEEY (SEQ ID NO:30), ILDTAGLEEY (SEQ ID NO:31), ILDTAGREEY (SEQ ID NO:32)) can include, without limitation, the scFv sequence set forth in any one of SEQ ID NO:394, SEQ ID NO:395, SEQ ID NO:396, SEQ ID NO:397, SEQ ID NO:398, SEQ ID NO:399, and SEQ ID NO:400. Examples of sequences (e.g., scFv sequences) that can bind to particular modified peptides are shown in Table 3. In some cases, a molecule including one or more antigen-binding domains (e.g., scFvs) that can bind to a modified peptide described herein (e.g., a modified peptide including an amino acid sequence set forth in any one of SEQ ID NO: 1, SEQ ID NO: 11, SEQ ID NO: 13, SEQ ID NO: 15, SEQ ID NO:16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can have a sequence that deviates from a sequence shown in Table 3, sometimes referred to as a variant sequence. For example, a molecule including one or more antigen-binding domains that can bind to a modified peptide described herein can have at least 75% sequence identity (e.g., at least 80% sequence identity, at least 85% sequence identity, at least 90% sequence identity, at least 95% sequence identity, at least 96% sequence identity, at least 97% sequence identity, at least 98% sequence identity, at least 99% sequence identity, or more) to any of the sequences shown in Table 3, provided the variant sequence maintains the ability to bind to a modified peptide described herein. In some cases, a molecule including one or more antigen-binding domains that can bind to a modified peptide described herein can include any appropriate set of CDR sequences described herein, and any sequence deviations from a sequence shown in Table 3 can be in the scaffold sequence(s).

A molecule including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO: 16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be attached (e.g., covalently or non-covalently attached) to a label (e.g., a detectable label). A detectable label can be any appropriate label. In some cases, a label can be used to assist in detecting the presence or absence of one or more modified peptides described herein. For example, a molecule described herein that is labelled can be used in vitro to detect cancer cells (e.g., cancer cells expressing a modified peptide described herein) in a sample obtained from a mammal. In some cases, a label (e.g., a detectable label) can be used to assist in determining the location of one or more modified peptides described herein. For example, molecule described herein that is labelled can be used in vivo to monitor anti-tumor therapy and/or to detect cancer cells (e.g., cancer cells expressing a modified peptide described herein) in a mammal. Examples of labels that can be attached to a molecule described herein include, without limitation, radionuclides, chromophores, enzymes, and fluorescent molecules (e.g., green fluorescent protein).

A molecule including one or more antigen-binding domains (e.g., scFvs) that can bind to a modified peptide described herein (e.g., a modified peptide including an amino acid sequence set forth in any one of SEQ ID NO:1, SEQ ID NO: 11, SEQ ID NO: 13, SEQ ID NO:15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be attached (e.g., covalently or non-covalently attached) to a therapeutic agent. A therapeutic agent can be any therapeutic agent. In some cases, a therapeutic agent can be an anti-cancer agent. Examples of therapeutic agents that can be attached to a molecule described herein include, without limitation, anti-cancer agents such as monomethyl auristatin E (MMAE), monomethyl auristatin F (MMAF), maytansine, mertansine/emtansine (DM1), ravtansine/soravtansine (DM4), SN-38, calicheamicin, D6.5, dimeric pyrrolobenzodiazepines (PBDs), ricin, pseudomonas exotoxin A, diphtheria toxin, and gelonin.

This document also provides methods for using one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO: 13, SEQ ID NO: 15, SEQ ID NO: 16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32). For example, one or more molecules including one or more antigen-binding domains (e.g., scFvs) that can target (e.g., bind to) one or more modified peptides can be used to assess a mammal having cancer or suspected of having cancer and/or to treat a mammal having a cancer (e.g., a cancer expressing one or more modified peptides). In some cases, one or more molecules includes one or more antigen-binding domains that can bind to a modified peptide can be used to detect the presence or absence of one or more modified peptides in a sample obtained from a mammal having cancer or suspected of having cancer. In some cases, one or more molecules including one or more antigen-binding domains that can bind to a modified peptide can be administered to a mammal having a cancer (e.g., a cancer expressing the modified peptide) to treat the mammal. Administration of one or more molecules including one or more antigen-binding domains that can bind to a modified peptide described herein to a mammal (e.g., human) having a cancer can be effective to treat the mammal.

Any type of mammal can be assessed and/or treated as described herein. Examples of mammals that can be assessed and/or treated as described herein include, without limitation, primates (e.g., humans and non-human primates such as chimpanzees, baboons, or monkeys), dogs, cats, pigs, sheep, rabbits, mice, and rats. In some cases, a mammal can be a human.

A mammal can be assessed and/or treated for any appropriate cancer. In some cases, a cancer can express one or more modified peptides (e.g., one or more MANAs) described herein. A cancer can be a primary cancer. A cancer can be a metastatic cancer. A cancer can include one or more solid tumors. A cancer can include one or more non-solid tumors. Examples of cancers that can be assessed as described herein (e.g., based at least in part on the presence of one or more modified peptides described herein) and/or treated as described herein (e.g, by administering one or more molecules including one or more antigen-binding domains (e.g., scFvs) that can bind to a modified peptide described herein) include, without limitation, blood cancers (e.g., Hodgkin's lymphoma, non-Hodgkin's lymphoma, leukemia such as acute myeloid leukemia (AML), and myeloma), lung cancers, pancreatic cancers, gastric cancers, colon cancers (e.g., colorectal cancers), ovarian cancers, endometrial cancers, biliary tract cancers, liver cancers, bone and soft tissue cancers, breast cancers, prostate cancers, esophageal cancers, stomach cancers, kidney cancers, head and neck cancers, and brain cancers (e.g., glioblastoma multiforme and astrocytomas).

When assessing a mammal having cancer or suspected of having cancer, one or more molecules including one or more antigen-binding domains (e.g., scFvs) that can bind to a modified peptide described herein (e.g., a modified peptide including an amino acid sequence set forth in any one of SEQ ID NO:1, SEQ ID NO: 11, SEQ ID NO: 13, SEQ ID NO: 15, SEQ ID NO:16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be used to assess for the presence or absence of one or more modified peptides described herein. For example, the presence, absence, or level of one or more modified peptides described herein in a sample obtained from a human can be used to determine whether or not the human has a cancer. In some cases, the presence of one or more modified peptides described herein in a sample obtained from a mammal can be used to identify the mammal as having a cancer. For example, a mammal can be identified as having a cancer when a sample obtained from the mammal has one or more modified peptides described herein.

Any appropriate sample obtained from a mammal can be assessed for the presence, absence, or level of one or more modified peptides described herein. For example, biological samples such as tissue samples (e.g., breast tissue), and fluid samples (e.g., blood, serum, plasma, or urine) can be obtained from a mammal and assessed for the presence, absence, or level of one or more modified peptides described herein. Any appropriate method can be used to detect the presence, absence, or level of one or more modified peptides described herein. For example, sequencing techniques including, but not limited to, Sanger sequencing, chemical sequencing, nanopore sequencing, sequencing by ligation (SOLID sequencing), and sequencing with mass spectrometry can be used to determine the presence, absence, or level of one or more modified peptides described herein in a sample obtained from a mammal.

When treating a mammal having cancer, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO: 15, SEQ ID NO: 16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered to a mammal having cancer to treat the mammal. In some cases, a mammal can have a cancer expressing one or more modified peptides described herein. For example, one or more molecules including one or more antigen-binding domains that can bind to a modified peptide described herein can be administered to a mammal having a cancer expressing that modified peptide to treat the mammal. For example, one or more molecules including one or more scFvs that can bind to a modified peptide described herein (e.g., one or more CARs and/or one or more scDbs) can be administered to a mammal having a cancer expressing that modified peptide to treat the mammal.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered to a mammal (e.g., a mammal having a cancer) once or multiple times over a period of time ranging from days to weeks. In some cases, one or more molecules including one or more antigen-binding domains (e.g., scFvs) that can bind to a modified peptide described herein can be formulated into a pharmaceutically acceptable composition for administration to a mammal. For example, an effective amount of one or more molecules including one or more antigen-binding domains (e.g., scFvs) that can bind to a modified peptide described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO: 13, SEQ ID NO:15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be designed for oral, parenteral (including subcutaneous, intramuscular, intravenous, and intradermal), or intratumoral administration. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

A composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered using any appropriate technique and to any appropriate location. A composition including one or more molecules including one or more antigen-binding domains (e.g., scFvs) that can bind to a modified peptide described herein can be administered locally (e.g., intratumorally) or systemically. For example, a composition provided herein can be administered locally by intratumoral administration (e.g., injection into tumors) or by administration into biological spaces infiltrated by tumors (e.g. intraspinal administration, intracelebellar administration, intraperitoneal administration and/or pleural administration). For example, a composition provided herein can be administered systemically by oral administration or by intravenous administration (e.g., injection or infusion) to a mammal (e.g., a human).

Effective doses can vary depending on the risk and/or the severity of the cancer, the route of administration, the age and general health condition of the subject, excipient usage, the possibility of co-usage with other therapeutic treatments such as use of other agents, and the judgment of the treating physician. An effective amount of a composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO: 13, SEQ ID NO:15, SEQ ID NO:16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be any amount that treats a cancer present within the subject without producing significant toxicity to the subject. If a particular subject fails to respond to a particular amount, then the amount of one or more molecules including one or more antigen-binding domains (e.g., scFvs) that can bind to a modified peptide described herein can be increased (e.g., by two-fold, three-fold, four-fold, or more). After receiving this higher amount, the mammal can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO: 13, SEQ ID NO: 15, SEQ ID NO: 16, SEQ ID NO: 18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be any frequency that effectively treats a mammal having a cancer without producing significant toxicity to the mammal. For example, the frequency of administration of one or more molecules including one or more antigen-binding domains (e.g., scFvs) that can bind to a modified peptide described herein can be from about two to about three times a week to about two to about three times a year. In some cases, a subject having cancer can receive a single administration of one or more antibodies described herein. The frequency of administration of one or more molecules including one or more antigen-binding domains (e.g., scFvs) that can bind to a modified peptide described herein can remain constant or can be variable during the duration of treatment. A course of treatment with a composition containing one or more molecules including one or more antigen-binding domains (e.g., scFvs) that can bind to a modified peptide described herein can include rest periods. For example, a composition containing one or more molecules including one or more antigen-binding domains (e.g., scFvs) that can bind to a modified peptide described herein can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO: 13, SEQ ID NO: 15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be any duration that effectively treats a cancer present within the mammal without producing significant toxicity to the mammal. In some cases, the effective duration can vary from several months to several years. In general, the effective duration for treating a mammal having a cancer can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, a cancer within a mammal can be monitored to evaluate the effectiveness of the cancer treatment. Any appropriate method can be used to determine whether or not a mammal having cancer is treated. For example, imaging techniques or laboratory assays can be used to assess the number of cancer cells and/or the size of a tumor present within a mammal. For example, imaging techniques or laboratory assays can be used to assess the location of cancer cells and/or a tumor present within a mammal.

In some cases, one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32) can be administered to a mammal having a cancer as a combination therapy with one or more additional cancer treatments (e.g., anti-cancer agents). A cancer treatment can include any appropriate cancer treatments. In some cases, a cancer treatment can include surgery. In some cases, a cancer treatment can include radiation therapy. In some cases, a cancer treatment can include administration of one or more therapeutic agents (e.g., one or more anti-cancer agents). Examples of anti-cancer agents include, without limitation, platinum compounds (e.g., a cisplatin or carboplatin), taxanes (e.g., paclitaxel, docetaxel, or an albumin bound paclitaxel such as nab-paclitaxel), altretamine, capecitabine, cyclophosphamide, etoposide (vp-16), gemcitabine, ifosfamide, irinotecan (cpt-11), liposomal doxorubicin, melphalan, pemetrexed, topotecan, vinorelbine, luteinizing-hormone-releasing hormone (LHRH) agonists (e.g., goserelin and leuprolide), anti-estrogens (e.g., tamoxifen), aromatase inhibitors (e.g., letrozole, anastrozole, and exemestane), angiogenesis inhibitors (e.g., bevacizumab), poly(ADP)-ribose polymerase (PARP) inhibitors (e.g., olaparib, rucaparib, and niraparib), radioactive phosphorus, anti-CTLA-4 antibodies, anti-PD-1 antibodies, anti-PD-L1 antibodies, IL-2 and other cytokines, and any combinations thereof. In cases where one or more molecules including one or more antigen-binding domains (e.g., scFvs) that can bind to a modified peptide described herein are used in combination with one or more additional cancer treatments, the one or more additional cancer treatments can be administered at the same time or independently. For example, a composition including one or more molecules including one or more antigen-binding domains (e.g., scFvs) that can bind to a modified peptide described herein can be administered first, and the one or more additional cancer treatments administered second, or vice versa.

Also provided herein are kits that include one or more molecules including one or more antigen-binding domains (e.g., scFvs) that can bind to a modified peptide described herein (e.g., a modified peptide including an amino acid sequence set forth in any one of SEQ ID NO:1, SEQ ID NO:11, SEQ ID NO:13, SEQ ID NO:15, SEQ ID NO:16, SEQ ID NO:18, SEQ ID NO:20, SEQ ID NO:21, SEQ ID NO:22, SEQ ID NO:24, SEQ ID NO:26, SEQ ID NO:28, SEQ ID NO:30, SEQ ID NO:31, and SEQ ID NO:32). For example, a kit can include a composition (e.g., a pharmaceutically acceptable composition) containing one or more molecules including one or more antigen-binding domains (e.g., scFvs) that can bind to a modified peptide described herein. In some cases, a kit can include instructions for performing any of the methods described herein. In some cases, a kit can include at least one dose of any of the compositions (e.g., pharmaceutical compositions) described herein. In some cases, a kit can provide a means (e.g., a syringe) for administering any of the compositions (e.g., pharmaceutical compositions) described herein.

The invention is further described in the following examples, which do not limit the scope of the invention described in the claims.

EXAMPLES

Example 1: Identification of Additional MANAbody Clones and Conversion of MANAbody Clones into T Cell-Based Therapeutic Formats In this study, two phage display libraries were designed and built, both of which displayed a single chain variable fragment (scFv) on the phage surface. The scFvs present in both libraries were based on the humanized 4D5 (trastuzumab) framework with amino acid variability introduced at key positions of the scFv's complementarity determining regions (CDRs).

Phage display libraries were used to identify scFvs that specifically recognized mutation-containing peptides folded into a complex with a recombinant HLA allele alpha chain and beta-2 microglobulin (b2M). These complexes, also referred to herein as monomers, mimic the natural peptide/HLA complexes on a cancer cell surface.

Peptide-HLA targets can include mutant peptides (e.g., Mutation-Associated Neo-Antigens (MANAs)) shown in Table 1. Complementarity-determining regions (CDRs) that can specifically bind to peptide-HLA targets in Table 1 are shown in Table 2. scFvs that can specifically bind to peptide-HLA targets in Table 1 are shown in Table 3. These scFvs can also be referred to as MANAbodies for their ability to bind to Mutation-Associated Neo-Antigens.

TABLE 2

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| 1) EGFR T790M(789-797)-A2 | | | | | | | |
| IMQLMPFGC (SEQ ID NO: 13) | HLA-A2 | QDVNTA (SEQ ID NO: 33) | SAS | QQYDYAPIT (SEQ ID NO: 34) | GFNISWYQ (SEQ ID NO: 41) | VTPYSGYT (SEQ ID NO: 48) | SRSYTDGFDY (SEQ ID NO: 55) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| IMQLMPFGC (SEQ ID NO: 13) | HLA-A2 | QDVNTA (SEQ ID NO: 33) | SAS | QQSPYYYLPIT (SEQ ID NO: 35) | GFNVSWSY (SEQ ID NO: 42) | IYGDSGYT (SEQ ID NO: 49) | SRGQWEASYYAMDY (SEQ ID NO: 56) |
| IMQLMPFGC (SEQ ID NO: 13) | HLA-A2 | QDVNTA (SEQ ID NO: 33) | SAS | QQYYYSPVT (SEQ ID NO: 36) | GFNISWNQ (SEQ ID NO: 43) | VSPYSGYT (SEQ ID NO: 50) | SRSDYYAMDY (SEQ ID NO: 57) |
| IMQLMPFGC (SEQ ID NO: 13) | HLA-A2 | QDVNTA (SEQ ID NO: 33) | SAS | QQHYGNPFT (SEQ ID NO: 37) | GFNVGYYG (SEQ ID NO: 44) | VSGMEGYT (SEQ ID NO: 51) | SRDIYGYAMDV (SEQ ID NO: 58) |
| IMQLMPFGC (SEQ ID NO: 13) | HLA-A2 | QDVNTA (SEQ ID NO: 33) | SAS | QQSYYSPPT (SEQ ID NO: 38) | GFNITSSY (SEQ ID NO: 45) | ISPADGYN (SEQ ID NO: 52) | SRTDSTAYTAMDV (SEQ ID NO: 59) |
| IMQLMPFGC (SEQ ID NO: 13) | HLA-A2 | QDVNTA (SEQ ID NO: 33) | SAS | QQYYSYPPT (SEQ ID NO: 39) | GFNINSSY (SEQ ID NO: 46) | ISPTDGYY (SEQ ID NO: 53) | SRTSDTSYAAMDV (SEQ ID NO: 60) |
| IMQLMPFGC (SEQ ID NO: 13) | HLA-A2 | QDVNTA (SEQ ID NO: 33) | SAS | QQYYYYPPT (SEQ ID NO: 40) | GFNISTSY (SEQ ID NO: 47) | IDPNDGYS (SEQ ID NO: 54) | SRTNNTAADAMDV (SEQ ID NO: 61) |
| 2) IDH2 R140Q(134-143)-B7 | | | | | | | |
| SPNGTIQNIL (SEQ ID NO: 1) | HLA-B7 | QDVNTA (SEQ ID NO: 33) | SAS | QQYSYSPPT (SEQ ID NO: 62) | GFNISDTY (SEQ ID NO: 67) | ISPRTGYN (SEQ ID NO: 72) | SRAYYSYAYAMDV (SEQ ID NO: 77) |
| SPNGTIQNIL (SEQ ID NO: 1) | HLA-B7 | QDVNTA (SEQ ID NO: 33) | SAS | QQGKAYWPAT (SEQ ID NO: 63) | GFNVGHYR (SEQ ID NO: 68) | VSPNGYYT (SEQ ID NO: 73) | SRGYSSYAFDY (SEQ ID NO: 78) |
| SPNGTIQNIL (SEQ ID NO: 1) | HLA-B7 | QDVNTA (SEQ ID NO: 33) | SAS | QQVYSSPFT (SEQ ID NO: 64) | GFNVKYYM (SEQ ID NO: 69) | ISPGYDYT (SEQ ID NO: 74) | SRSYWRYSVDV (SEQ ID NO: 79) |
| SPNGTIQNIL (SEQ ID NO: 1) | HLA-B7 | QDVNTA (SEQ ID NO: 33) | SAS | QQYSLYSPMT (SEQ ID NO: 65) | GFNSFLS (SEQ ID NO: 70) | IFPSSDYT (SEQ ID NO: 75) | SRGKHSSDSNYYMDY (SEQ ID NO: 80) |
| SPNGTIQNIL (SEQ ID NO: 1) | HLA-B7 | QDVNTA (SEQ ID NO: 33) | SAS | QQSYYMPFT (SEQ ID NO: 66) | GFNIFRGY (SEQ ID NO: 71) | ISPHSDYT (SEQ ID NO: 76) | SRSYGWAAFDY (SEQ ID NO: 81) |
| 3) p53 R248Q/W(245-254)-A2 | | | | | | | |
| GMNQRPILTI (SEQ ID NO: 15) | HLA-A2 | QDVNTA (SEQ ID NO: 33) | SAS | QQSGYAPIT (SEQ ID NO: 82) | GFNISYYS (SEQ ID NO: 89) | VDPDSDYT (SEQ ID NO: 96) | SRSWIHMFSMDY (SEQ ID NO: 103) |
| GMNWRPILTI (SEQ ID NO: 16) | HLA-A2 | QDVNTA (SEQ ID NO: 33) | SAS | QQYSYAPIT (SEQ ID NO: 83) | GFNIGYYT (SEQ ID NO: 90) | VSPWSYST (SEQ ID NO: 97) | SRDHWDEAFDV (SEQ ID NO: 104) |
| GMNQRPILTI (SEQ ID NO: 15) | HLA-A2 | QDVNTA (SEQ ID NO: 33) | SAS | QQSLYGPFT (SEQ ID NO: 84) | GFNIAYEY (SEQ ID NO: 91) | IGPDSGYT (SEQ ID NO: 98) | SRVWYYSTYGMDY (SEQ ID NO: 105) |
| GMNWRPILTI (SEQ ID NO: 16) | HLA-A2 | QDVNTA (SEQ ID NO: 33) | SAS | QQYSYSPIT (SEQ ID NO: 85) | GFNLFGYG (SEQ ID NO: 92) | IGPYYYYT (SEQ ID NO: 99) | SRENYDMAMDY (SEQ ID NO: 106) |
| GMNWRPILTI (SEQ ID NO: 16) | HLA-A2 | QDVNTA (SEQ ID NO: 33) | SAS | QQSGYQPDT (SEQ ID NO: 86) | GFNISWYA (SEQ ID NO: 93) | IWPDSDWT (SEQ ID NO: 100) | SRYYYSSAFDV (SEQ ID NO: 107) |
| GMNQRPILTI (SEQ ID NO: 15), GMNWRPILTI (SEQ ID NO: 16) | HLA-A2 | QDVNTA (SEQ ID NO: 33) | SAS | QQYLYQPWT (SEQ ID NO: 87) | GFNIDYYG (SEQ ID NO: 94) | LYGGSDST (SEQ ID NO: 101) | SRQYSAYFDY (SEQ ID NO: 108) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| GMNQRPILTI (SEQ ID NO: 15), GMNWRPILTI (SEQ ID NO: 16) | HLA-A2 | QDVNTA (SEQ ID NO: 33) | SAS | QQGLYYPWT (SEQ ID NO: 88) | GFNV SYS S (SEQ ID NO: 95) | IWPD SGQT (SEQ ID NO: 102) | SRSSYFDAMDY (SEQ ID NO: 109) |
| 4) KRAS G12V(6-14)-A2 | | | | | | | |
| LVVVGAVGV (SEQ ID NO: 18) | HLA-A2 | QDVNTA (SEQ ID NO: 33) | SAS | QQWYSSPVT (SEQ ID NO: 110) | GFNINWAN (SEQ ID NO: 112) | ISPPYDYT (SEQ ID NO: 115) | SRSYSYYFDY (SEQ ID NO: 118) |
| LVVVGAVGV (SEQ ID NO: 18) | HLA-A2 | QDVNTA (SEQ ID NO: 33) | SAS | QQYYSRPVT (SEQ ID NO: 111) | GFNIYLHD (SEQ ID NO: 113) | IIPAIDYT (SEQ ID NO: 116) | SRRDGYYFDY (SEQ ID NO: 119) |
| LVVVGAVGV (SEQ ID NO: 18) | HLA-A2 | QDVNTA (SEQ ID NO: 33) | SAS | QQWYSSPVT (SEQ ID NO: 110) | GFNIYWSH (SEQ ID NO: 114) | ISSFEGYT (SEQ ID NO: 117) | SRSYSYYMDY (SEQ ID NO: 120) |
| 5) KRAS G12C/D/V(7-16)-A3 | | | | | | | |
| VVVGACGVGK (SEQ ID NO: 20), VVVGAVGVGK (SEQ ID NO: 22) | HLA-A3 | QDVNTA (SEQ ID NO: 33) | SAS | QQSYGSGSPWT (SEQ ID NO: 121) | GFNIVGGG (SEQ ID NO: 124) | IYPQGDYT (SEQ ID NO: 127) | SRDSSYLAFDY (SEQ ID NO: 129) |
| VVVGACGVGK (SEQ ID NO: 20), VVVGADGVGK (SEQ ID NO: 21), VVVGAVGVGK (SEQ ID NO: 22) | HLA-A3 | QDVNTA (SEQ ID NO: 33) | SAS | QQTYYSPWT (SEQ ID NO: 122) | GFNIRSYA (SEQ ID NO: 125) | VGPGKGYT (SEQ ID NO: 128) | SRNFQSTSHAFDY (SEQ ID NO: 130) |
| VVVGACGVGK (SEQ ID NO: 20), VVVGADGVGK (SEQ ID NO: 21), VVVGAVGVGK (SEQ ID NO: 22) | HLA-A3 | QDVNTA (SEQ ID NO: 33) | SAS | QQYYYPPIT (SEQ ID NO: 123) | GFNVSHTG (SEQ ID NO: 126) | VGPGKGYT (SEQ ID NO: 128) | SRKTYYAFDY (SEQ ID NO: 131) |
| 6) KRAS G12V(7-16)-A3 | | | | | | | |
| VVVGAVGVGK (SEQ ID NO: 22) | HLA-A3 | QDVNTA (SEQ ID NO: 33) | SAS | QQSYYYFRPIT (SEQ ID NO: 132) | GFNLSYSD (SEQ ID NO: 137) | VMPDSGHT (SEQ ID NO: 142) | SRATNIPVYAFDY (SEQ ID NO: 147) |
| VVVGAVGVGK (SEQ ID NO: 22) | HLA-A3 | QDVNTA (SEQ ID NO: 33) | SAS | QQASYYYPLT (SEQ ID NO: 133) | GFNISASG (SEQ ID NO: 138) | IHPLKPYT (SEQ ID NO: 143) | SRYSSMYYYYFDY (SEQ ID NO: 148) |
| VVVGAVGVGK (SEQ ID NO: 22) | HLA-A3 | QDVNTA (SEQ ID NO: 33) | SAS | QQKSEYSPWT (SEQ ID NO: 134) | GFNIYRYG (SEQ ID NO: 139) | LYPYGYST (SEQ ID NO: 144) | SRSYAYGYFAY (SEQ ID NO: 149) |
| VVVGAVGVGK (SEQ ID NO: 22) | HLA-A3 | QDVNTA (SEQ ID NO: 33) | SAS | QQSGYIPFT (SEQ ID NO: 135) | GFNIYGTM (SEQ ID NO: 140) | FKPDSYNT (SEQ ID NO: 145) | SRGEVYHYYAFDY (SEQ ID NO: 150) |
| VVVGAVGVGK (SEQ ID NO: 22) | HLA-A3 | QDVNTA (SEQ ID NO: 33) | SAS | QQGAYYRPFT (SEQ ID NO: 136) | GFNISYSY (SEQ ID NO: 141) | LLPYDGNT (SEQ ID NO: 146) | SRAAYSSMDV (SEQ ID NO: 151) |
| 7) KRAS G12D(7-16)-A3 | | | | | | | |
| VVVGADGVGK (SEQ ID NO: 21) | HLA-A3 | QDVNTA (SEQ ID NO: 33) | SAS | QQYMYSPVT (SEQ ID NO: 152) | GFNVSAYW (SEQ ID NO: 156) | IYGGSGYT (SEQ ID NO: 160) | SRTHSYWSAFDY (SEQ ID NO: 164) |
| VVVGADGVGK (SEQ ID NO: 21) | HLA-A3 | QDVNTA (SEQ ID NO: 33) | SAS | QQSSSSPIT (SEQ ID NO: 153) | GFNISGYG (SEQ ID NO: 157) | LYGGSDYT (SEQ ID NO: 161) | SRTVRYAFDY (SEQ ID NO: 165) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| VVVGADGVGK (SEQ ID NO: 21) | HLA-A3 | QDVNTA (SEQ ID NO: 33) | SAS | QQSSASPLT (SEQ ID NO: 154) | GFNVSSVG (SEQ ID NO: 158) | IYGTSDYT (SEQ ID NO: 162) | SRSSRYSMDY (SEQ ID NO: 166) |
| VVVGADGVGK (SEQ ID NO: 21) | HLA-A3 | QDVNTA (SEQ ID NO: 33) | SAS | QQYAYSPLT (SEQ ID NO: 155) | GFNVSSYG (SEQ ID NO: 159) | IAPRRDYT (SEQ ID NO: 163) | SRKSSYYFDY (SEQ ID NO: 167) |
| 8) KRAS G12D(7-16)-A11 | | | | | | | |
| VVVGADGVGK (SEQ ID NO: 21) | HLA-A11 | QDVNTA (SEQ ID NO: 33) | SAS | QQYSYYPIT (SEQ ID NO: 168) | GFNFSYGY (SEQ ID NO: 173) | ISGYTGNT (SEQ ID NO: 178) | SRAASLSSSYYSAFDV (SEQ ID NO: 183) |
| VVVGADGVGK (SEQ ID NO: 21) | HLA-A11 | QDVNTA (SEQ ID NO: 33) | SAS | QQYSYTPVT (SEQ ID NO: 169) | GFNVWGPG (SEQ ID NO: 174) | IHPFSGNT (SEQ ID NO: 179) | SRGYSYSAMDY (SEQ ID NO: 184) |
| VVVGADGVGK (SEQ ID NO: 21) | HLA-A11 | QDVNTA (SEQ ID NO: 33) | SAS | QQYSYEPVT (SEQ ID NO: 170) | GFNVSGSQ (SEQ ID NO: 175) | IPGWSGYT (SEQ ID NO: 180) | SRGYSYFAMDY (SEQ ID NO: 185) |
| VVVGADGVGK (SEQ ID NO: 21) | HLA-A11 | QDVNTA (SEQ ID NO: 33) | SAS | QQYAYYSPVT (SEQ ID NO: 171) | GFNIYGQM (SEQ ID NO: 176) | LSPFSGNT (SEQ ID NO: 181) | SRNISYEQSSAFDY (SEQ ID NO: 186) |
| VVVGADGVGK (SEQ ID NO: 21) | HLA-A11 | QDVNTA (SEQ ID NO: 33) | SAS | QQYEYYPMT (SEQ ID NO: 172) | GFNVMYST (SEQ ID NO: 177) | IYSWSDYT (SEQ ID NO: 182) | SRGYAHNSFDY (SEQ ID NO: 187) |
| 9) KRAS G12D(8-16)-A11 | | | | | | | |
| VVGADGVGK (SEQ ID NO: 24) | HLA-A11 | QDVNTA (SEQ ID NO: 33) | SAS | QQYSFYPFT (SEQ ID NO: 188) | GFNFGSY (SEQ ID NO: 196) | ISGYSGNT (SEQ ID NO: 207) | SRSNQSAYSYMDY (SEQ ID NO: 218) |
| VVGADGVGK (SEQ ID NO: 24) | HLA-A11 | QDVNTA (SEQ ID NO: 33) | SAS | QQYSYSPIT (SEQ ID NO: 85) | GFNISDSY (SEQ ID NO: 197) | FSPYSSNT (SEQ ID NO: 208) | SRSQFTFYQYFDY (SEQ ID NO: 219) |
| VVGADGVGK (SEQ ID NO: 24) | HLA-A11 | QDVNTA (SEQ ID NO: 33) | SAY | QQYSAYYQPIT (SEQ ID NO: 189) | GFNIFSDQ (SEQ ID NO: 198) | FMPYDSYYT (SEQ ID NO: 209) | SRMSVRNAFDY (SEQ ID NO: 220) |
| VVGADGVGK (SEQ ID NO: 24) | HLA-A11 | QDVNTA (SEQ ID NO: 33) | SAS | QQYSYYPIT (SEQ ID NO: 168) | GFNLSYSY (SEQ ID NO: 199) | ISGFSGNT (SEQ ID NO: 210) | SRSDSYYTAMDY (SEQ ID NO: 221) |
| VVGADGVGK (SEQ ID NO: 24) | HLA-A11 | QDVNTA (SEQ ID NO: 33) | SAS | QQYEYVPHT (SEQ ID NO: 190) | GFNISYGY (SEQ ID NO: 200) | FHYGSGNT (SEQ ID NO: 211) | SRSNYYYLDY (SEQ ID NO: 222) |
| VVGADGVGK (SEQ ID NO: 24) | HLA-A11 | QDVNTA (SEQ ID NO: 33) | SAS | QQYSYMPIT (SEQ ID NO: 191) | GFNISYQH (SEQ ID NO: 201) | FMPYQGST (SEQ ID NO: 212) | SRANIYSSHSFFDY (SEQ ID NO: 223) |
| VVGADGVGK (SEQ ID NO: 24) | HLA-A11 | QDVNTA (SEQ ID NO: 33) | SAS | QQYAYYPVT (SEQ ID NO: 192) | GFNLSGYY (SEQ ID NO: 202) | FSPYSGYT (SEQ ID NO: 213) | SRTHSSIYHSFDY (SEQ ID NO: 224) |
| VVGADGVGK (SEQ ID NO: 24) | HLA-A11 | QDVNTA (SEQ ID NO: 33) | SAS | QQYSYMPIT (SEQ ID NO: 191) | GFNVSGQY (SEQ ID NO: 203) | ISPVSGNT (SEQ ID NO: 214) | SRPMKTSYYGAFDY (SEQ ID NO: 225) |
| VVGADGVGK (SEQ ID NO: 24) | HLA-A11 | QDVNTA (SEQ ID NO: 33) | SAS | QQYDYRPVT (SEQ ID NO: 193) | GFNVSTSG (SEQ ID NO: 204) | IYGAYSGT (SEQ ID NO: 215) | SRSQSYTYWSAMDY (SEQ ID NO: 226) |
| VVGADGVGK (SEQ ID NO: 24) | HLA-A11 | QDVNTA (SEQ ID NO: 33) | SAS | QQYDFTPMT (SEQ ID NO: 194) | GFNISYAK (SEQ ID NO: 205) | LTYWGGYT (SEQ ID NO: 216) | SRGEYGTYMDY (SEQ ID NO: 227) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| VVGADGVGK (SEQ ID NO: 24) | HLA-A11 | QDVNTA (SEQ ID NO: 33) | SAS | QQYSSSSPVT (SEQ ID NO: 195) | GFNFSSYV (SEQ ID NO: 206) | VYPDSGGT (SEQ ID NO: 217) | SRTSSYYAFDY (SEQ ID NO: 228) |
| 10) KRAS G12V(7-16)-A11 | | | | | | | |
| VVVGAVGVGK (SEQ ID NO: 22) | HLA-A11 | QDVNTA (SEQ ID NO: 33) | SAS | QQSSYTPIT (SEQ ID NO: 229) | GFNISQGG (SEQ ID NO: 234) | VYPGGGQT (SEQ ID NO: 240) | SRGYDYSAFDY (SEQ ID NO: 246) |
| VVVGAVGVGK (SEQ ID NO: 22) | HLA-A11 | QDVNTA (SEQ ID NO: 33) | SAS | QQYAYYPIT (SEQ ID NO: 230) | GFNISSTG (SEQ ID NO: 235) | LLGGSGNT (SEQ ID NO: 241) | SRGLQYSAMDY (SEQ ID NO: 247) |
| VVVGAVGVGK (SEQ ID NO: 22) | HLA-A11 | QDVNTA | SAS | QQYEYYPIT (SEQ ID NO: 231) | GFNFFSTV (SEQ ID NO: 236) | IYPWSGST (SEQ ID NO: 242) | SRSRSSNYYFDV (SEQ ID NO: 248) |
| VVVGAVGVGK (SEQ ID NO: 22) | HLA-A11 | QDVNTA (SEQ ID NO: 33) | SAS | QQYTYYPIT (SEQ ID NO: 232) | GFNLHGYL (SEQ ID NO: 237) | IYPPNGYT (SEQ ID NO: 243) | SRGVDYAYLDY (SEQ ID NO: 249) |
| VVVGAVGVGK (SEQ ID NO: 22) | HLA-A11 | QDVNTA (SEQ ID NO: 33) | SAS | QQYSYYPIT (SEQ ID NO: 168) | GFNLSTHV (SEQ ID NO: 238) | FYPYVGYT (SEQ ID NO: 244) | SRGYRYQYMDV (SEQ ID NO: 250) |
| VVVGAVGVGK (SEQ ID NO: 22) | HLA-A11 | QDVNTA (SEQ ID NO: 33) | SAS | QQSSVEPWT (SEQ ID NO: 233) | GFNVSYYS (SEQ ID NO: 239) | IYPWNDYT (SEQ ID NO: 245) | SRGSYYSFDY (SEQ ID NO: 251) |
| 11) CTNNB S45F(41-49)-A3 | | | | | | | |
| TTAPFLSGK (SEQ ID NO: 26) | HLA-A3 | QDVNTA (SEQ ID NO: 33) | SAS | QQSYYSPPT (SEQ ID NO: 38) | GFNINNTY (SEQ ID NO: 256) | IYPTDGYT (SEQ ID NO: 260) | SRTYYSYYSAMDV (SEQ ID NO: 265) |
| TTAPFLSGK (SEQ ID NO: 26) | HLA-A3 | QDVNTA (SEQ ID NO: 33) | SAY | QQIYTSPIT (SEQ ID NO: 252) | GFNFITTG (SEQ ID NO: 257) | IGPGSDYT (SEQ ID NO: 261) | SRYYYASALDY (SEQ ID NO: 266) |
| TTAPFLSGK (SEQ ID NO: 26) | HLA-A3 | QDVNTA (SEQ ID NO: 33) | SAS | QQRAYFPIT (SEQ ID NO: 253) | GFNFSDYG (SEQ ID NO: 258) | LIPASGYT (SEQ ID NO: 262) | SRGWSYYMDY (SEQ ID NO: 267) |
| TTAPFLSGK (SEQ ID NO: 26) | HLA-A3 | QDVNTA (SEQ ID NO: 33) | SAS | QQQYAYTPIT (SEQ ID NO: 254) | GFNVWSYG (SEQ ID NO: 259) | VTPDGSYT (SEQ ID NO: 263) | SRSYGWAMDY (SEQ ID NO: 268) |
| TTAPFLSGK (SEQ ID NO: 26) | HLA-A3 | QDVNTA (SEQ ID NO: 33) | SAY | QQIHYKPLT (SEQ ID NO: 255) | GFNVAWYS (SEQ ID NO: 260) | VYGGSSYT (SEQ ID NO: 264) | SRDFYSSGMDY (SEQ ID NO: 269) |
| 12) KRAS G12V(11-19)-B7 | | | | | | | |
| AVGVGKSAL (SEQ ID NO: 11) | HLA-B7 | QDVNTA (SEQ ID NO: 33) | SAS | QQEWRLPIT (SEQ ID NO: 270) | GFNVYGNQ (SEQ ID NO: 275) | IYPYSGST (SEQ ID NO: 278) | SRSAYVAYSYFDY (SEQ ID NO: 283) |
| AVGVGKSAL (SEQ ID NO: 11) | HLA-B7 | QDVNTA (SEQ ID NO: 33) | SAS | QQGTSTPFT (SEQ ID NO: 271) | GFNLSYYG (SEQ ID NO: 402) | IYPDSGYT (SEQ ID NO: 279) | SRAYLYYYLAY (SEQ ID NO: 284) |
| AVGVGKSAL (SEQ ID NO: 11) | HLA-B7 | QDVNTA (SEQ ID NO: 33) | SAS | QQSWRYPMT (SEQ ID NO: 272) | GFNISRYG (SEQ ID NO: 276) | FYPSSSYT (SEQ ID NO: 280) | SRKYYEAMDY (SEQ ID NO: 285) |
| AVGVGKSAL (SEQ ID NO: 11) | HLA-B7 | QDVNTA (SEQ ID NO: 33) | SAS | QQSYSYPVT (SEQ ID NO: 273) | GFNIYSSW (SEQ ID NO: 277) | FQPYSGYT (SEQ ID NO: 281) | SREYTYYFDY (SEQ ID NO: 286) |
| AVGVGKSAL (SEQ ID NO: 11) | HLA-B7 | QDVNTA (SEQ ID NO: 33) | SAS | QQGWLYSPFT (SEQ ID NO: 274) | GFNISGYG (SEQ ID NO: 157) | VYGGSGYT (SEQ ID NO: 282) | SRAHSSYYVDY (SEQ ID NO: 287) |

TABLE 2-continued

MANAbody complementarity-determining region (CDR) sequences of light (L) chains and heavy (H) chains.

| Target Peptide(s) | Target HLA Allele | CDR L1 | CDR L2 | CDR L3 | CDR H1 | CDR H2 | CDR H3 |
|---|---|---|---|---|---|---|---|
| 13) H/K/N RAS Q61H(55-64)-A1 | | | | | | | |
| ILDTAGHEEY (SEQ ID NO: 28) | HLA-A1 | QDVNTA (SEQ ID NO: 33) | SAS | QQGYFYYPNT (SEQ ID NO: 288) | GFNIGYYG (SEQ ID NO: 289) | VYPGGGYT (SEQ ID NO: 290) | SRYYYYGFDY (SEQ ID NO: 291) |
| 14) H/K/N RAS Q61K(55-64)-A1 | | | | | | | |
| ILDTAGKEEY (SEQ ID NO: 30) | HLA-A1 | QDVNTA (SEQ ID NO: 33) | SAS | QQHYYSPVT (SEQ ID NO: 292) | GFNIFYQD (SEQ ID NO: 293) | IYPDYDYT (SEQ ID NO: 294) | SRTYSVYMDY (SEQ ID NO: 295) |
| 15) H/K/N Q61L(55-64)-A1 | | | | | | | |
| ILDTAGLEEY (SEQ ID NO: 31) | HLA-A1 | QDVNTA (SEQ ID NO: 33) | SAS | QQYAYAPFT (SEQ ID NO: 296) | GFNVSYSM (SEQ ID NO: 297) | VWGDGGVT (SEQ ID NO: 298) | SRGSYYAFDY (SEQ ID NO: 299) |
| 16) H/K/N RAS Q61R(55-64)-A1 | | | | | | | |
| ILDTAGREEY (SEQ ID NO: 32) | HLA-A1 | QDVNTA (SEQ ID NO: 33) | SAS | QQAHMIPIT (SEQ ID NO: 300) | GFNFSFPG (SEQ ID NO: 305) | FVGYDGYT (SEQ ID NO: 310) | SRDYYSFSMDY (SEQ ID NO: 316) |
| ILDTAGREEY (SEQ ID NO: 32) | HLA-A1 | QDVNTA (SEQ ID NO: 33) | SAS | QQSVYDPIT (SEQ ID NO: 301) | GFNISGSW (SEQ ID NO: 306) | LYPDSDYT (SEQ ID NO: 311) | SRAHTYAFDY (SEQ ID NO: 317) |
| ILDTAGREEY (SEQ ID NO: 32) | HLA-A1 | QDVNTA (SEQ ID NO: 33) | SAS | QQSYTSPLT (SEQ ID NO: 302) | GFNIYYGV (SEQ ID NO: 307) | IYPDSSWT (SEQ ID NO: 312) | SRDQDFHYMNYYLSYALDY (SEQ ID NO: 318) |
| ILDTAGREEY (SEQ ID NO: 32) | HLA-A1 | QDVNTA (SEQ ID NO: 33) | SAS | QQGQYSPFT (SEQ ID NO: 303) | GFNVSYEY (SEQ ID NO: 308) | IYGGSDNT (SEQ ID NO: 313) | SRPLGSYFDY (SEQ ID NO: 319) |
| ILDTAGREEY (SEQ ID NO: 32) | HLA-A1 | QDVNTA (SEQ ID NO: 33) | SAS | QQYWYLPTT (SEQ ID NO: 320) | GFNISWYD (SEQ ID NO: 321) | IEPSVGYT (SEQ ID NO: 322) | SRSYPYYYFDY (SEQ ID NO: 323) |

TABLE 3

MANAbody scFv sequences.

| Target Peptide(s) | Target HLA Allele | ScFc clone name | scFv sequence | SEQ ID NO: |
|---|---|---|---|---|
| 1) EGFR T790M(789-797)-A2 | | | | |
| IMQLMPFGC (SEQ ID NO: 13) | HLA-A2 | EGFR_T790M_A2_cl1 | DIQMTQSPSSLSASVGDRVTITCRASQDVNTAVAWYQQKPGKAPKLLIYSASFLYSGVPSRFSGSRSGTDFTLTISSLQPEDFATYYCQQYDYAPITFGQGTKVEIKRTGGGSGGGGSGGGASEVQLVESGGGLVQPGGSLRLSCAASGFNISWYQMHWVRQAPGKGLEWVALVTPYSGYTYYADSVKGRFTISADTSKNTAYLQMNSLRAEDTAVYYCSRSYTDGFDYWGQGTLVTVSS | 324 |
| IMQLMPFGC (SEQ ID NO: 13) | HLA-A2 | EGFR_T790M_A2_cl5 | DIQMTQSPSSLSASVGDRVTITCRASQDVNTAVAWYQQKPGKAPKLLIYSASFLYSGVPSRFSGSRSGTDFTLTISSLQPEDFATYYCQQSPYYYLPITFGQGTKVEIKRTGGGSGGGGSGGGASEVQLVESGGGLVQPGGSLRLSCAASGFNVSWSYMHWVRQAPGKGLEWVANIYGDSGYTHYADSVKGRFTISADTSKNTAYLQMNSLRAEDTAVYYCSRGQWEASYYAMDYWGQGTLVTVSS | 325 |
| IMQLMPFGC (SEQ ID NO: 13) | HLA-A2 | EGFR_T790M_A2_cl18 | DIQMTQSPSSLSASVGDRVTITCRASQDVNTAVAWYQQKPGKAPKLLIYSASFLYSGVPSRFSGSRSGTDFTLTISSLQPEDFATYYCQQYYYSPVTFGQGTKVEIKRTGGGSGGGGSGGGASEVQLVESGGGLVQPGGSLRLSCAASGFNI | 326 |

TABLE 3-continued

MANAbody scFv sequences.

| Target Peptide(s) | Target HLA Allele | ScFc clone name | scFv sequence | SEQ ID NO: |
|---|---|---|---|---|
| | | | SWNQMHWVRQAPGKGLEWVALVSPYSGYTYYADSVKGR FTISADTSKNTAYLQMNSLRAEDTAVYYCSRSDYYAMD YWGQGTLVTVSS | |
| IMQLMPFGC (SEQ ID NO: 13) | HLA-A2 | EGFR_T790M_A2_cl23 | DIQMTQSPSSLSASVGDRVTITCRASQDVNTAVAWYQQ KPGKAPKLLIYSASFLYSGVPSRFSGSRSGTDFTLTIS SLQPEDFATYYCQQHYGNPFTFGQGTKVEIKRTGGGSG GGGSGGGASEVQLVESGGGLVQPGGSLRLSCAASGFNV GYYGMHWVRQAPGKGLEWVAFVSGMEGYTSYADSVKGR FTISADTSKNTAYLQMNSLRAEDTAVYYCSRDIYGYAM DVWGQGTLVTVSS | 327 |
| IMQLMPFGC (SEQ ID NO: 13) | HLA-A2 | EGFR_T790M_A2_D2D6 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYYSPPTFGQGTKVEIKRTGGGSG GGGSGGGASEVQLVESGGGLVQPGGSLRLSCAASGFNI TSSYIHWVRQAPGKGLEWVAYISPADGYNRYADSVKGR FTISADTSKNTAYLQMNSLRAEDTAVYYCSRTDSTAYT AMDVWGQGTLVTVSS | 328 |
| IMQLMPFGC (SEQ ID NO: 13) | HLA-A2 | EGFR_T790M_A2_D2D8 | DIQMTQSPSSLSASVGDRVTITCRASQDVNTAVAWYQQ KPGKAPKLLIYSASFLYSGVPSRFSGSRSGTDFTLTIS SLQPEDFATYYCQQYYSYPPTFGQGTKVEIKRTGGGSG GGGSGGGASEVQLVESGGGLVQPGGSLRLSCAASGFNI NSSYIHWVRQAPGKGLEWVAYISPTDGYYRYADSVKGR FTISADTSKNTAYLQMNSLRAEDTAVYYCSRTSDTSYA AMDVWGQGTLVTVSS | 329 |
| IMQLMPFGC (SEQ ID NO: 13) | HLA-A2 | EGFR_T790M_A2_D3E6 | DIQMTQSPSSLSASVGDRVTITCRASQDVNTAVAWYQQ KPGKAPKLLIYSASFLYSGVPSRFSGSRSGTDFTLTIS SLQPEDFATYYCQQYYYYPPTFGQGTKVEIKRTGGGSG GGGSGGGASEVQLVESGGGLVQPGGSLRLSCAASGFNI STSYIHWVRQAPGKGLEWVATIDPNDGYSRYADSVKGR FTISADTSKNTAYLQMNSLRAEDTAVYYCSRTNNTAAD AMDVWGQGTLVTVSS | 330 |
| | | 2) IDH2 R140Q(134-143)-B7 | | |
| SPNGTIQNIL (SEQ ID NO: 1) | HLA-B7 | IDH2_R140Q_B7_D4 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYSPPTFGQGTKVEIKRTGGGSG GGGSGGGASEVQLVESGGGLVQPGGSLRLSCAASGFNI SDTYIHWVRQAPGKGLEWVASISPRTGYNRYADSVKGR FTISADTSKNTAYLQMNSLRAEDTAVYYCSRAYYSYAY AMDVWGQGTLVTVSS | 3 |
| SPNGTIQNIL (SEQ ID NO: 1) | HLA-B7 | IDH2_R140Q_B7_cl29 | DIQMTQSPSSLSASVGDRVTITCRASQDVNTAVAWYQQ KPGKAPKLLIYSASFLYSGVPSRFSGSRSGTDFTLTIS SLQPEDFATYYCQQGKAYWPATFGQGTKVEIKRTGGGS GGGGSGGGASEVQLVESGGGLVQPGGSLRLSCAASGFN VGHYRMHWVRQAPGKGLEWVAMVSPNGYYTYYADSVKG RFTISADTSKNTAYLQMNSLRAEDTAVYYCSRGYSSYA FDYWGQGTLVTVSS | 4 |
| SPNGTIQNIL (SEQ ID NO: 1) | HLA-B7 | IDH2_R140Q_B7_cl1 | DIQMTQSPSSLSASVGDRVTITCRASQDVNTAVAWYQQ KPGKAPKLLIYSASFLYSGVPSRFSGSRSGTDFTLTIS SLQPEDFATYYCQQVYSSPFTFGQGTKVEIKRTGGGSG GGGSGGGASEVQLVESGGGLVQPGGSLRLSCAASGFNV KYYMMHWVRQAPGKGLEWVAAISPGYDYTYYADSVKGR FTISADTSKNTAYLQMNSLRAEDTAVYYCSRSYWRYSV DVWGQGTLVTVSS | 5 |
| SPNGTIQNIL (SEQ ID NO: 1) | HLA-B7 | IDH2_R140Q_B7_cl3 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSLYSPMTFGQGTKVEIKRTGGGS GGGGSGGGASEVQLVESGGGLVQPGGSLRLSCAASGFN SFLSIHWVRQAPGKGLEWVAHIFPSSDYTSYADSVKGR FTISADTSKNTAYLQMNSLRAEDTAVYYCSRGKHSSDS NYYMDYWGQGTLVTVSS | 6 |
| SPNGTIQNIL (SEQ ID NO: 1) | HLA-B7 | IDH2_R140Q_B7_cl8 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYYMPFTFGQGTKVEIKRTGGGSG | 8 |

TABLE 3-continued

MANAbody scFv sequences.

| Target Peptide(s) | Target HLA Allele | ScFc clone name | scFv sequence | SEQ ID NO: |
|---|---|---|---|---|
| | | | GGGSGGGASEVQLVESGGGLVQPGGSLRLSCAASGFNI FRGYMHWVRQAPGKGLEWVAMISPHSDYTSYADSVKGR FTISADTSKNTAYLQMNSLRAEDTAVYYCSRSYGWAAF DYWGQGTLVTVSS | |
| 3) p53 R248Q/W(245-254)-A2 | | | | |
| GMNQRPILTI (SEQ ID NO: 15) | HLA-A2 | p53_R248Q_A2_cl0 | DIQMTQSPSSLSASVGDRVTITCRASQDVNTAVAWYQQ KPGKAPKLLIYSASFLYSGVPSRFSGSRSGTDFTLTIS SLQPEDFATYYCQQSGYAPITFGQGTKVEIKRTGGGSG GGGSGGGASEVQLVESGGGLVQPGGSLRLSCAASGFNI SYYSMHWVRQAPGKGLEWVADVDPDSDYTEYADSVKGR FTISADTSKNTAYLQMNSLRAEDTAVYYCSRSWIHMFS MDYWGQGTLVTVSS | 331 |
| GMNWRPILTI (SEQ ID NO: 16) | HLA-A2 | p53_R248W_A2_cl2 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYAPITFGQGTKVEIKRTGGGSG GGGSGGGASEVQLVESGGGLVQPGGSLRLSCAASGFNI GYYTMHWVRQAPGKGLEWVAEVSPWSYSTSYADSVKGR FTISADTSKNTAYLQMNSLRAEDTAVYYCSRDHWDEAF DVWGQGTLVTVSS | 332 |
| GMNQRPILTI (SEQ ID NO: 15) | HLA-A2 | p53_R248Q_A2_cl4 | DIQMTQSPSSLSASVGDRVTITCRASQDVNTAVAWYQQ KPGKAPKLLIYSASFLYSGVPSRFSGSRSGTDFTLTIS SLQPEDFATYYCQQSLYGPFTFGQGTKVEIKRTGGGSG GGGSGGGASEVQLVESGGGLVQPGGSLRLSCAASGFNI AYEYMHWVRQAPGKGLEWVALIGPDSGYTYYADSVKGR FTISADTSKNTAYLQMNSLRAEDTAVYYCSRVWYYSTY GMDYWGQGTLVTVSS | 333 |
| GMNWRPILTI (SEQ ID NO: 16) | HLA-A2 | p53_R248W_A2_cl8 | DIQMTQSPSSLSASVGDRVTITCRASQDVNTAVAWYQQ KPGKAPKLLIYSASFLYSGVPSRFSGSRSGTDFTLTIS SLQPEDFATYYCQQYSYSPITFGQGTKVEIKRTGGGSG GGGSGGGASEVQLVESGGGLVQPGGSLRLSCAASGFNL FGYGMHWVRQAPGKGLEWVAEIGPYYYYTSYADSVKGR FTISADTSKNTAYLQMNSLRAEDTAVYYCSRENYDMAM DYWGQGTLVTVSS | 334 |
| GMNWRPILTI (SEQ ID NO: 16) | HLA-A2 | p53_R248W_A2_cl11 | DIQMTQSPSSLSASVGDRVTITCRASQDVNTAVAWYQQ KPGKAPKLLIYSASFLYSGVPSRFSGSRSGTDFTLTIS SLQPEDFATYYCQQSGYQPDTFGQGTKVEIKRTGGGSG GGGSGGGASEVQLVESGGGLVQPGGSLRLSCAASGFNI SWYAMHWVRQAPGKGLEWVAEIWPDSDWTYYADSVKGR FTISADTSKNTAYLQMNSLRAEDTAVYYCSRYYYSSAF DVWGQGTLVTVSS | 335 |
| GMNQRPILTI (SEQ ID NO: 15), GMNWRPILTI (SEQ ID NO: 16) | HLA-A2 | p53_R248QW_A2_cl14 | DIQMTQSPSSLSASVGDRVTITCRASQDVNTAVAWYQQ KPGKAPKLLIYSASFLYSGVPSRFSGSRSGTDFTLTIS SLQPEDFATYYCQQYLYQPWTFGQGTKVEIKRTGGGSG GGGSGGGASEVQLVESGGGLVQPGGSLRLSCAASGFNI DYYGMHWVRQAPGKGLEWVASLYGGSDSTDYADSVKGR FTISADTSKNTAYLQMNSLRAEDTAVYYCSRQYSAYFD YWGQGTLVTVSS | 336 |
| GMNQRPILTI (SEQ ID NO: 15), GMNWRPILTI (SEQ ID NO: 16) | HLA-A2 | p53_R248QW_A2_cl17 | DIQMTQSPSSLSASVGDRVTITCRASQDVNTAVAWYQQ KPGKAPKLLIYSASFLYSGVPSRFSGSRSGTDFTLTIS SLQPEDFATYYCQQGLYYPWTFGQGTKVEIKRTGGGSG GGGSGGGASEVQLVESGGGLVQPGGSLRLSCAASGFNV SYSSIHWVRQAPGKGLEWVAEIWPDSGQTWYADSVKGR FTISADTSKNTAYLQMNSLRAEDTAVYYCSRSSYFDAM DYWGQGTLVTVSS | 337 |
| 4) KRAS G12V(6-14)-A2 | | | | |
| LVVVGAVGV (SEQ ID NO: 18) | HLA-A2 | KRAS_G12V_A2_A1 | DIQMTQSPSSLSASVGDRVTITCRASQDVNTAVAWYQQ KPGKAPKLLIYSASFLYSGVPSRFSGSRSGTDFTLTIS SLQPEDFATYYCQQWYSSPVTFGQGTKVEIKRTGGGSG GGGSGGGASEVQLVESGGGLVQPGGSLRLSCAASGFNI NWANMHWVRQAPGKGLEWVAQISPPYDYTNYADSVKGR FTISADTSKNTAYLQMNSLRAEDTAVYYCSRSYSYYFD YWGQGTLVTVSS | 338 |

TABLE 3-continued

| MANAbody scFv sequences. | | | | |
|---|---|---|---|---|
| Target Peptide(s) | Target HLA Allele | ScFc clone name | scFv sequence | SEQ ID NO: |
| LVVVGAVGV (SEQ ID NO: 18) | HLA-A2 | KRAS_G12V_A2_C1 | DIQMTQSPSSLSASVGDRVTITCRASQDVNTAVAWYQQKPGKAPKLLIYSASFLYSGVPSRFSGSRSGTDFTLTISSLQPEDFATYYCQQYYSRPVTFGQGTKVEIKRTGGGSGGGGSGGGASEVQLVESGGGLVQPGGSLRLSCAASGFNIYLHDMHWVRQAPGKGLEWVAQIIPAIDYTNYADSVKGRFTISADTSKNTAYLQMNSLRAEDTAVYYCSRRDGYYFDYWGQGTLVTVSS | 339 |
| LVVVGAVGV (SEQ ID NO: 18) | HLA-A2 | KRAS_G12V_A2_A5 | DIQMTQSPSSLSASVGDRVTITCRASQDVNTAVAWYQQKPGKAPKLLIYSASFLYSGVPSRFSGSRSGTDFTLTISSLQPEDFATYYCQQWYSSPVTFGQGTKVEIKRTGGGSGGGGSGGGASEVQLVESGGGLVQPGGSLRLSCAASGFNIYWSHMHWVRQAPGKGLEWVAIISSFEGYTYYADSVKGRFTISADTSKNTAYLQMNSLRAEDTAVYYCSRSYSYYMDYWGQGTLVTVSS | 340 |
| 5) KRAS G12C/D/V(7-16)-A3 | | | | |
| VVVGACGVGK (SEQ ID NO: 20), VVVGAVGVGK (SEQ ID NO: 22) | HLA-A3 | KRAS_G12CV_A3_cl5 | DIQMTQSPSSLSASVGDRVTITCRASQDVNTAVAWYQQKPGKAPKLLIYSASFLYSGVPSRFSGSRSGTDFTLTISSLQPEDFATYYCQQSYGSGSPWTFGQGTKVEIKRTGGGSGGGGSGGGASEVQLVESGGGLVQPGGSLRLSCAASGFNIVGGGIHWVRQAPGKGLEWVAKIYPQGDYTYYADSVKGRFTISADTSKNTAYLQMNSLRAEDTAVYYCSRDSSYLAFDYWGQGTLVTVSS | 341 |
| VVVGACGVGK (SEQ ID NO: 20), VVVGADGVGK (SEQ ID NO: 21), VVVGAVGVGK (SEQ ID NO: 22) | HLA-A3 | KRAS_G12CDV_A3_cl9 | DIQMTQSPSSLSASVGDRVTITCRASQDVNTAVAWYQQKPGKAPKLLIYSASFLYSGVPSRFSGSRSGTDFTLTISSLQPEDFATYYCQQTYYSPWTFGQGTKVEIKRTGGGSGGGGSGGGASEVQLVESGGGLVQPGGSLRLSCAASGFNIRSYAMHWVRQAPGKGLEWVAQVGPGKGYTYYADSVKGRFTISADTSKNTAYLQMNSLRAEDTAVYYCSRNFQSTSHAFDYWGQGTLVTVSS | 342 |
| VVVGACGVGK (SEQ ID NO: 20), VVVGADGVGK (SEQ ID NO: 21), VVVGAVGVGK (SEQ ID NO: 22) | HLA-A3 | KRAS_G12CDV_A3_cl18 | DIQMTQSPSSLSASVGDRVTITCRASQDVNTAVAWYQQKPGKAPKLLIYSASFLYSGVPSRFSGSRSGTDFTLTISSLQPEDFATYYCQQYYYPPITFGQGTKVEIKRTGGGSGGGGSGGGASEVQLVESGGGLVQPGGSLRLSCAASGFNVSHTGMHWVRQAPGKGLEWVAVVGPGKGYTYYADSVKGRFTISADTSKNTAYLQMNSLRAEDTAVYYCSRKTYYAFDYWGQGTLVTVSS | 343 |
| 6) KRAS G12V(7-16)-A3 | | | | |
| VVVGAVGVGK (SEQ ID NO: 22) | HLA-A3 | KRAS_G12VA3_cl2 | DIQMTQSPSSLSASVGDRVTITCRASQDVNTAVAWYQQKPGKAPKLLIYSASFLYSGVPSRFSGSRSGTDFTLTISSLQPEDFATYYCQQSYYYFRPITFGQGTKVEIKRTGGGSGGGGSGGGASEVQLVESGGGLVQPGGSLRLSCAASGFNLSYSDIHWVRQAPGKGLEWVAVVMPDSGHTNYADSVKGRFTISADTSKNTAYLQMNSLRAEDTAVYYCSRATNIPVYAFDYWGQGTLVTVSS | 344 |
| VVVGAVGVGK (SEQ ID NO: 22) | HLA-A3 | KRAS G12V_A3_V12 | DIQMTQSPSSLSASVGDRVTITCRASQDVNTAVAWYQQKPGKAPKLLIYSASFLYSGVPSRFSGSRSGTDFTLTISSLQPEDFATYYCQQASYYYPLTFGQGTKVEIKRTGGGSGGGGSGGGASEVQLVESGGGLVQPGGSLRLSCAASGFNISASGMHWVRQAPGKGLEWVADIHPLKPYTNYADSVKGRFTISADTSKNTAYLQMNSLRAEDTAVYYCSRYSSMYYYFDYWGQGTLVTVSS | 345 |
| VVVGAVGVGK (SEQ ID NO: 22) | HLA-A3 | KRAS G12V_A3_cl20 | DIQMTQSPSSLSASVGDRVTITCRASQDVNTAVAWYQQKPGKAPKLLIYSASFLYSGVPSRFSGSRSGTDFTLTISSLQPEDFATYYCQQKSEYSPWTFGQGTKVEIKRTGGGSGGGGSGGGASEVQLVESGGGLVQPGGSLRLSCAASGFNIYRYGIHWVRQAPGKGLEWVAVLYPYGYSTSYADSVKGRFTISADTSKNTAYLQMNSLRAEDTAVYYCSRSYAYGYFAYWGQGTLVTVSS | 346 |

TABLE 3-continued

MANAbody scFv sequences.

| Target Peptide(s) | Target HLA Allele | ScFc clone name | scFv sequence | SEQ ID NO: |
|---|---|---|---|---|
| VVVGAVGVGK (SEQ ID NO: 22) | HLA-A3 | KRAS G12V_A3_cl21 | DIQMTQSPSSLSASVGDRVTITCRASQDVNTAVAWYQQKPGKAPKLLIYSASFLYSGVPSRFSGSRSGTDFTLTISSLQPEDFATYYCQQSGYIPFTFGQGTKVEIKRTGGGSGGGGSGGGASEVQLVESGGGLVQPGGSLRLSCAASGFNIYGTMMHWVRQAPGKGLEWVAQFKPDSYNTYYADSVKGRFTISADTSKNTAYLQMNSLRAEDTAVYYCSRGEVYHYYAFDYWGQGTLVTVSS | 347 |
| VVVGAVGVGK (SEQ ID NO: 22) | HLA-A3 | KRAS G12V_A3_cl22 | DIQMTQSPSSLSASVGDRVTITCRASQDVNTAVAWYQQKPGKAPKLLIYSASFLYSGVPSRFSGSRSGTDFTLTISSLQPEDFATYYCQQGAYYRPFTFGQGTKVEIKRTGGGSGGGGSGGGASEVQLVESGGGLVQPGGSLRLSCAASGFNISYSYMHWVRQAPGKGLEWVATLLPYDGNTYYADSVKGRFTISADTSKNTAYLQMNSLRAEDTAVYYCSRAAYSSMDVWGQGTLVTVSS | 348 |
| | | 7) KRAS G12D(7-16)-A3 | | |
| VVVGADGVGK (SEQ ID NO: 21) | HLA-A3 | KRAS_G12D_A3_cl11 | DIQMTQSPSSLSASVGDRVTITCRASQDVNTAVAWYQQKPGKAPKLLIYSASFLYSGVPSRFSGSRSGTDFTLTISSLQPEDFATYYCQQYMYSPVTFGQGTKVEIKRTGGGSGGGGSGGGASEVQLVESGGGLVQPGGSLRLSCAASGFNVSAYWNIHWVRQAPGKGLEWVAQIYGGSGYTMYADSVKGRFTISADTSKNTAYLQMNSLRAEDTAVYYCSRTHSYWSAFDYWGQGTLVTVSS | 349 |
| VVVGADGVGK (SEQ ID NO: 21) | HLA-A3 | KRAS_G12D_A3_D12 | DIQMTQSPSSLSASVGDRVTITCRASQDVNTAVAWYQQKPGKAPKLLIYSASFLYSGVPSRFSGSRSGTDFTLTISSLQPEDFATYYCQQSSSSPITFGQGTKVEIKRTGGGSGGGGSGGGASEVQLVESGGGLVQPGGSLRLSCAASGFNISGYGMHWVRQAPGKGLEWVAYLYGGSDYTNYADSVKGRFTISADTSKNTAYLQMNSLRAEDTAVYYCSRTVRYAFDYWGQGTLVTVSS | 350 |
| VVVGADGVGK (SEQ ID NO: 21) | HLA-A3 | KRAS_G12D_A3_D15 | DIQMTQSPSSLSASVGDRVTITCRASQDVNTAVAWYQQKPGKAPKLLIYSASFLYSGVPSRFSGSRSGTDFTLTISSLQPEDFATYYCQQSSASPLTFGQGTKVEIKRTGGGSGGGGSGGGASEVQLVESGGGLVQPGGSLRLSCAASGFNVSSVGNIHWVRQAPGKGLEWVAYIYGTSDYTYYADSVKGRFTISADTSKNTAYLQMNSLRAEDTAVYYCSRSSRYSMDYWGQGTLVTVSS | 351 |
| VVVGADGVGK (SEQ ID NO: 21) | HLA-A3 | KRAS_G12D_A3_D26 | DIQMTQSPSSLSASVGDRVTITCRASQDVNTAVAWYQQKPGKAPKLLIYSASFLYSGVPSRFSGSRSGTDFTLTISSLQPEDFATYYCQQYAYSPLTFGQGTKVEIKRTGGGSGGGGSGGGASEVQLVESGGGLVQPGGSLRLSCAASGFNVSSYGMHWVRQAPGKGLEWVAFIAPRRDYTSYADSVKGRFTISADTSKNTAYLQMNSLRAEDTAVYYCSRKSSYYFDYWGQGTLVTVSS | 352 |
| | | 8) KRAS G12D(7-16)-A11 | | |
| VVVGADGVGK (SEQ ID NO: 21) | HLA-A11 | KRAS_G12D_A11_D3 | DIQMTQSPSSLSASVGDRVTITCRASQDVNTAVAWYQQKPGKAPKLLIYSASFLYSGVPSRFSGSRSGTDFTLTISSLQPEDFATYYCQQYSYYPITFGQGTKVEIKRTGGGSGGGGSGGGASEVQLVESGGGLVQPGGSLRLSCAASGFNFSYGYMHWVRQAPGKGLEWVAWISGYTGNTYYADSVKGRFTISADTSKNTAYLQMNSLRAEDTAVYYCSRAASLSSSYYSAFDVWGQGTLVTVSS | 353 |
| VVVGADGVGK (SEQ ID NO: 21) | HLA-A11 | KRAS_G12D_A11_D14 | DIQMTQSPSSLSASVGDRVTITCRASQDVNTAVAWYQQKPGKAPKLLIYSASFLYSGVPSRFSGSRSGTDFTLTISSLQPEDFATYYCQQYSYTPVTFGQGTKVEIKRTGGGSGGGGSGGGASEVQLVESGGGLVQPGGSLRLSCAASGFNVWGPGMHWVRQAPGKGLEWVARIHPFSGNTYYADSVKGRFTISADTSKNTAYLQMNSLRAEDTAVYYCSRGYSYSAMDYWGQGTLVTVSS | 354 |
| VVVGADGVGK (SEQ ID NO: 21) | HLA-A11 | KRAS_G12D_A11_D18 | DIQMTQSPSSLSASVGDRVTITCRASQDVNTAVAWYQQKPGKAPKLLIYSASFLYSGVPSRFSGSRSGTDFTLTISSLQPEDFATYYCQQYSYEPVTFGQGTKVEIKRTGGGSGGGGSGGGASEVQLVESGGGLVQPGGSLRLSCAASGFNV | 355 |

TABLE 3-continued

MANAbody scFv sequences.

| Target Peptide(s) | Target HLA Allele | ScFc clone name | scFv sequence | SEQ ID NO: |
|---|---|---|---|---|
| | | | SGSQMHWVRQAPGKGLEWVARIPGWSGYTYYADSVKGR<br>FTISADTSKNTAYLQMNSLRAEDTAVYYCSRGYSYFAM<br>DYWGQGTLVTVSS | |
| VVVGADGVGK (SEQ ID NO: 21) | HLA-A11 | KRAS_G12D_A11_D21 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYAYYSPVTFGQGTKVEIKRTGGGS<br>GGGGSGGGASEVQLVESGGGLVQPGGSLRLSCAASGFN<br>IYGQMMHWVRQAPGKGLEWVAFLSPFSGNTYYADSVKG<br>RFTISADTSKNTAYLQMNSLRAEDTAVYYCSRNISYEQ<br>SSAFDYWGQGTLVTVSS | 356 |
| VVVGADGVGK (SEQ ID NO: 21) | HLA-A11 | KRAS_G12D_A11_D22 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYEYYPMTFGQGTKVEIKRTGGGSG<br>GGGSGGGASEVQLVESGGGLVQPGGSLRLSCAASGFNV<br>MYSTMHWVRQAPGKGLEWVASIYSWSDYTYYADSVKGR<br>FTISADTSKNTAYLQMNSLRAEDTAVYYCSRGYAHNSF<br>DYWGQGTLVTVSS | 357 |
| 9) KRAS G12D(8-16)-A11 | | | | |
| VVGADGVGK (SEQ ID NO: 24) | HLA-A11 | KRAS_G12D_A11_cl4 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYSFYPFTFGQGTKVEIKRTGGGSG<br>GGGSGGGASEVQLVESGGGLVQPGGSLRLSCAASGFNF<br>GSYIHWVRQAPGKGLEWVAIISGYSGNTYYADSVKGRF<br>TISADTSKNTAYLQMNSLRAEDTAVYYCSRSNQSAYSY<br>MDYWGQGTLVTVSS | 358 |
| VVGADGVGK (SEQ ID NO: 24) | HLA-A11 | KRAS_G12D_A11_cl6 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYSYSPITFGQGTKVEIKRTGGGSG<br>GGGSGGGASEVQLVESGGGLVQPGGSLRLSCAASGFNI<br>SDSYMHWVRQAPGKGLEWVATFSPYSSNTWYADSVKGR<br>FTISADTSKNTAYLQMNSLRAEDTAVYYCSRSQFTFYQ<br>YFDYWGQGTLVTVSS | 359 |
| VVGADGVGK (SEQ ID NO: 24) | HLA-A11 | KRAS_G12D_A11_cl7 | DIQMTQSPSSLSASVGDRVTITCRASQDVNTAVAWYQQ<br>KPGKAPKLLIYSAYFLYSGVPSRFSGSRSGTDFTLTIS<br>SLQPEDFATYYCQQYSAYYQPITFGQGTKVEIKRTGGG<br>SGGGGSGGGASEVQLVESGGGLVQPGGSLRLSCAASGF<br>NIFSDQMHWVRQAPGKGLEWVAGFMPYDSYYTNYADSV<br>KGRFTISADTSKNTAYLQMNSLRAEDTAVYYCSRMSVR<br>NAFDYWGQGTLVTVSS | 360 |
| VVGADGVGK (SEQ ID NO: 24) | HLA-A11 | KRAS_G12D_A11_cl9 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYSYYPITFGQGTKVEIKRTGGGSG<br>GGGSGGGASEVQLVESGGGLVQPGGSLRLSCAASGFNL<br>SYSYNIHWVRQAPGKGLEWVAVISGFSGNTYYADSVKG<br>RFTISADTSKNTAYLQMNSLRAEDTAVYYCSRSDSYYT<br>AMDYWGQGTLVTVSS | 361 |
| VVGADGVGK (SEQ ID NO: 24) | HLA-A11 | KRAS_G12D_A11_cl10 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYEYVPHTFGQGTKVEIKRTGGGSG<br>GGGSGGGASEVQLVESGGGLVQPGGSLRLSCAASGFNI<br>SYGYMHWVRQAPGKGLEWVAKFHYGSGNTYYADSVKGR<br>FTISADTSKNTAYLQMNSLRAEDTAVYYCSRSNYYYLD<br>YWGQGTLVTVSS | 362 |
| VVGADGVGK (SEQ ID NO: 24) | HLA-A11 | KRAS_G12D_A11_cl12 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYSYMPITFGQGTKVEIKRTGGGSG<br>GGGSGGGASEVQLVESGGGLVQPGGSLRLSCAASGFNI<br>SYQHIHWVRQAPGKGLEWVAVFMPYQGSTYYADSVKGR<br>FTISADTSKNTAYLQMNSLRAEDTAVYYCSRANIYSSH<br>SFFDYWGQGTLVTVSS | 363 |
| VVGADGVGK (SEQ ID NO: 24) | HLA-A11 | KRAS_G12D_A11_cl14 | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQYAYYPVTFGQGTKVEIKRTGGGSG<br>GGGSGGGASEVQLVESGGGLVQPGGSLRLSCAASGFNL | 364 |

TABLE 3-continued

MANAbody scFv sequences.

| Target Peptide(s) | Target HLA Allele | ScFc clone name | scFv sequence | SEQ ID NO: |
|---|---|---|---|---|
| | | | SGYYMHWVRQAPGKGLEWVAWFSPYSGYTYYADSVKGRFTISADTSKNTAYLQMNSLRAEDTAVYYCSRTHSSIYHSFDYWGQGTLVTVSS | |
| VVGADGVGK (SEQ ID NO: 24) | HLA-A11 | KRAS_G12D_A11_cl15 | DIQMTQSPSSLSASVGDRVTITCRASQDVNTAVAWYQQKPGKAPKLLIYSASFLYSGVPSRFSGSRSGTDFTLTISSLQPEDFATYYCQQYSYMPITFGQGTKVEIKRTGGGSGGGGSGGGASEVQLVESGGGLVQPGGSLRLSCAASGFNVSGQYMHWVRQAPGKGLEWVAVISPVSGNTYYADSVKGRFTISADTSKNTAYLQMNSLRAEDTAVYYCSRPMKTSYYGAFDYWGQGTLVTVSS | 365 |
| VVGADGVGK (SEQ ID NO: 24) | HLA-A11 | KRAS_G12D_A11_cl17 | DIQMTQSPSSLSASVGDRVTITCRASQDVNTAVAWYQQKPGKAPKLLIYSASFLYSGVPSRFSGSRSGTDFTLTISSLQPEDFATYYCQQYDYRPVTFGQGTKVEIKRTGGGSGGGGSGGGASEVQLVESGGGLVQPGGSLRLSCAASGFNVSTSGMHWVRQAPGKGLEWVAFIYGAYSGTYYADSVKGRFTISADTSKNTAYLQMNSLRAEDTAVYYCSRSQSYTYWSAMDYWGQGTLVTVSS | 366 |
| VVGADGVGK (SEQ ID NO: 24) | HLA-A11 | KRAS_G12D_A11_cl18 | DIQMTQSPSSLSASVGDRVTITCRASQDVNTAVAWYQQKPGKAPKLLIYSASFLYSGVPSRFSGSRSGTDFTLTISSLQPEDFATYYCQQYDFTPMTFGQGTKVEIKRTGGGSGGGGSGGGASEVQLVESGGGLVQPGGSLRLSCAASGFNISYAKMHWVRQAPGKGLEWVAYLTYWGGYTNYADSVKGRFTISADTSKNTAYLQMNSLRAEDTAVYYCSRGEYGTYMDYWGQGTLVTVSS | 367 |
| VVGADGVGK (SEQ ID NO: 24) | HLA-A11 | KRAS_G12D_A11_cl19 | DIQMTQSPSSLSASVGDRVTITCRASQDVNTAVAWYQQKPGKAPKLLIYSASFLYSGVPSRFSGSRSGTDFTLTISSLQPEDFATYYCQQYSSSSPVTFGQGTKVEIKRTGGGSGGGGSGGGASEVQLVESGGGLVQPGGSLRLSCAASGFNFSSYVMHWVRQAPGKGLEWVAVVYPDSGGTYYADSVKGRFTISADTSKNTAYLQMNSLRAEDTAVYYCSRTSSYYAFDYWGQGTLVTVSS | 368 |
| 10) KRAS G12V(7-16)-A11 | | | | |
| VVVGAVGVGK (SEQ ID NO: 22) | HLA-A11 | KRAS_G12V_A11_V3 | DIQMTQSPSSLSASVGDRVTITCRASQDVNTAVAWYQQKPGKAPKLLIYSASFLYSGVPSRFSGSRSGTDFTLTISSLQPEDFATYYCQQSSYTPITFGQGTKVEIKRTGGGSGGGGSGGGASEVQLVESGGGLVQPGGSLRLSCAASGFNISQGGIHWVRQAPGKGLEWVAYVYPGGGQTNYADSVKGRFTISADTSKNTAYLQMNSLRAEDTAVYYCSRGYDYSAFDYWGQGTLVTVSS | 369 |
| VVVGAVGVGK (SEQ ID NO: 22) | HLA-A11 | KRAS_G12_VA11_V9 | DIQMTQSPSSLSASVGDRVTITCRASQDVNTAVAWYQQKPGKAPKLLIYSASFLYSGVPSRFSGSRSGTDFTLTISSLQPEDFATYYCQQYAYYPITFGQGTKVEIKRTGGGSGGGGSGGGASEVQLVESGGGLVQPGGSLRLSCAASGFNISSTGMHWVRQAPGKGLEWVAELLGGSGNTNYADSVKGRFTISADTSKNTAYLQMNSLRAEDTAVYYCSRGLQYSAMDYWGQGTLVTVSS | 370 |
| VVVGAVGVGK (SEQ ID NO: 22) | HLA-A11 | KRAS_G12V_A11V10 | DIQMTQSPSSLSASVGDRVTITCRASQDVNTAVAWYQQKPGKAPKLLIYSASFLYSGVPSRFSGSRSGTDFTLTISSLQPEDFATYYCQQYEYYPITFGQGTKVEIKRTGGGSGGGGSGGGASEVQLVESGGGLVQPGGSLRLSCAASGFNFFSTVIHWVRQAPGKGLEWVAEIYPWSGSTYYADSVKGRFTISADTSKNTAYLQMNSLRAEDTAVYYCSRSRSSNYYFDVWGQGTLVTVSS | 371 |
| VVVGAVGVGK (SEQ ID NO: 22) | HLA-A11 | KRAS_G12V_A11_V21 | DIQMTQSPSSLSASVGDRVTITCRASQDVNTAVAWYQQKPGKAPKLLIYSASFLYSGVPSRFSGSRSGTDFTLTISSLQPEDFATYYCQQYTYYPITFGQGTKVEIKRTGGGSGGGGSGGGASEVQLVESGGGLVQPGGSLRLSCAASGFNLHGYLMHWVRQAPGKGLEWVAFIYPPNGYTYYADSVKGRFTISADTSKNTAYLQMNSLRAEDTAVYYCSRGVDYAYLDYWGQGTLVTVSS | 372 |
| VVVGAVGVGK (SEQ ID NO: 22) | HLA-A11 | KRAS_G12V_A11_V23 | DIQMTQSPSSLSASVGDRVTITCRASQDVNTAVAWYQQKPGKAPKLLIYSASFLYSGVPSRFSGSRSGTDFTLTISSLQPEDFATYYCQQYSYYPITFGQGTKVEIKRTGGGSGGGGSGGGASEVQLVESGGGLVQPGGSLRLSCAASGFNL | 373 |

TABLE 3-continued

MANAbody scFv sequences.

| Target Peptide(s) | Target HLA Allele | ScFc clone name | scFv sequence | SEQ ID NO: |
|---|---|---|---|---|
| | | | STHVMHWVRQAPGKGLEWVAEFYPYVGYTYYADSVKGRFTISADTSKNTAYLQMNSLRAEDTAVYYCSRGYRYQYMDVWGQGTLVTVSS | |
| VVVGAVGVGK (SEQ ID NO: 22) | HLA-A11 | KRAS_G12V_A11_V24 | DIQMTQSPSSLSASVGDRVTITCRASQDVNTAVAWYQQKPGKAPKLLIYSASFLYSGVPSRFSGSRSGTDFTLTISSLQPEDFATYYCQQSSVEPWTFGQGTKVEIKRTGGGSGGGGSGGGASEVQLVESGGGLVQPGGSLRLSCAASGFNVSYYSIHWVRQAPGKGLEWVAYIYPWNDYTYYADSVKGRFTISADTSKNTAYLQMNSLRAEDTAVYYCSRGSYYSFDYWGQGTLVTVSS | 374 |
| 11) CTNNB S45F(41-49)-A3 | | | | |
| TTAPFLSGK (SEQ ID NO: 26) | HLA-A3 | CTNNB_S45F_A3_E10 | DIQMTQSPSSLSASVGDRVTITCRASQDVNTAVAWYQQKPGKAPKLLIYSASFLYSGVPSRFSGSRSGTDFTLTISSLQPEDFATYYCQQSYYSPPTFGQGTKVEIKRTGGGSGGGASEVQLVESGGGLVQPGGSLRLSCAASGFNINNTYIHWVRQAPGKGLEWVASIYPTDGYTRYADSVKGRFTISADTSKNTAYLQMNSLRAEDTAVYYCSRTYYSYYSAMDVWGQGTLVTVSS | 375 |
| TTAPFLSGK (SEQ ID NO: 26) | HLA-A3 | CTNNB_S45_FA3_cl3 | DIQMTQSPSSLSASVGDRVTITCRASQDVNTAVAWYQQKPGKAPKLLIYSAYFLYSGVPSRFSGSRSGTDFTLTISSLQPEDFATYYCQQIYTSPITFGQGTKVEIKRTGGGSGGGGSGGGASEVQLVESGGGLVQPGGSLRLSCAASGFNFITTGMHWVRQAPGKGLEWVARIGPGSDYTNYADSVKGRFTISADTSKNTAYLQMNSLRAEDTAVYYCSRYYYASALDYWGQGTLVTVSS | 376 |
| TTAPFLSGK (SEQ ID NO: 26) | HLA-A3 | CTNNB_S45_FA3_cl4 | DIQMTQSPSSLSASVGDRVTITCRASQDVNTAVAWYQQKPGKAPKLLIYSASFLYSGVPSRFSGSRSGTDFTLTISSLQPEDFATYYCQQRAYFPITFGQGTKVEIKRTGGGSGGGGSGGGASEVQLVESGGGLVQPGGSLRLSCAASGFNFSDYGMHWVRQAPGKGLEWVAMLIPASGYTNYADSVKGRFTISADTSKNTAYLQMNSLRAEDTAVYYCSRGWSYYMDYWGQGTLVTVSS | 377 |
| TTAPFLSGK (SEQ ID NO: 26) | HLA-A3 | CTNNB_S45_FA3 cl7 | DIQMTQSPSSLSASVGDRVTITCRASQDVNTAVAWYQQKPGKAPKLLIYSASFLYSGVPSRFSGSRSGTDFTLTISSLQPEDFATYYCQQQYAYTPITFGQGTKVEIKRTGGGSGGGGSGGGASEVQLVESGGGLVQPGGSLRLSCAASGFNVWSYGIHWVRQAPGKGLEWVAGVTPDGSYTYYADSVKGRFTISADTSKNTAYLQMNSLRAEDTAVYYCSRSYGWAMDYWGQGTLVTVSS | 378 |
| TTAPFLSGK (SEQ ID NO: 26) | HLA-A3 | CTNNB_S45_FA3 cl9 | DIQMTQSPSSLSASVGDRVTITCRASQDVNTAVAWYQQKPGKAPKLLIYSAYFLYSGVPSRFSGSRSGTDFTLTISSLQPEDFATYYCQQIHYKPLTFGQGTKVEIKRTGGGSGGGGSGGGASEVQLVESGGGLVQPGGSLRLSCAASGFNVAWYSIHWVRQAPGKGLEWVAQVYGGSSYTYYADSVKGRFTISADTSKNTAYLQMNSLRAEDTAVYYCSRDFYSSGMDYWGQGTLVTVSS | 379 |
| 12) KRAS G12V(11-19)-B7 | | | | |
| AVGVGKSAL (SEQ ID NO: 11) | HLA-B7 | KRAS_G12VB7_cl1 | DIQMTQSPSSLSASVGDRVTITCRASQDVNTAVAWYQQKPGKAPKLLIYSASFLYSGVPSRFSGSRSGTDFTLTISSLQPEDFATYYCQQEWRLPITFGQGTKVEIKRTGGGSGGGGSGGGASEVQLVESGGGLVQPGGSLRLSCAASGFNVYGNQIHWVRQAPGKGLEWVARIYPYSGSTYYADSVKGRFTISADTSKNTAYLQMNSLRAEDTAVYYCSRSAYVAYSYFDYWGQGTLVTVSS | 380 |
| AVGVGKSAL (SEQ ID NO: 11) | HLA-B7 | KRAS_G12VB7_cl2 | DIQMTQSPSSLSASVGDRVTITCRASQDVNTAVAWYQQKPGKAPKLLIYSASFLYSGVPSRFSGSRSGTDFTLTISSLQPEDFATYYCQQGTSTPFTFGQGTKVEIKRTGGGSGGGGSGGGASEVQLVESGGGLVQPGGSLRLSCAASGFNLSYYGMHWVRQAPGKGLEWVATIYPDSGYTKYADSVKGRFTISADTSKNTAYLQMNSLRAEDTAVYYCSRAYLYYYLAYWGQGTLVTVSS | 390 |
| AVGVGKSAL (SEQ ID NO: 11) | HLA-B7 | KRAS_G12VB7_cl3 | DIQMTQSPSSLSASVGDRVTITCRASQDVNTAVAWYQQKPGKAPKLLIYSASFLYSGVPSRFSGSRSGTDFTLTIS | 391 |

TABLE 3-continued

MANAbody scFv sequences.

| Target Peptide(s) | Target HLA Allele | ScFc clone name | scFv sequence | SEQ ID NO: |
|---|---|---|---|---|
| | | | SLQPEDFATYYCQQSWRYPMTFGQGTKVEIKRTGGGSG GGGSGGGASEVQLVESGGGLVQPGGSLRLSCAASGFNI SRYGMHWVRQAPGKGLEWVAVFYPSSSYTYYADSVKGR FTISADTSKNTAYLQMNSLRAEDTAVYYCSRKYYEAMD YWGQGTLVTVSS | |
| AVGVGKSAL (SEQ ID NO: 11) | HLA-B7 | KRAS_G12VB7_c15 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYSYPVTFGHGTKVEIKRTGGGSG GGGSGGGASEVQLVESGGGLVQPGGSLRLSCAASGFNI YSSWMHWVRQAPGKGLEWVAYFQPYSGYTKYADSVKGR FTISADTSKNTAYLQMNSLRAEDTAVYYCSREYTYYFD YWGQGTLVTVSS | 392 |
| AVGVGKSAL (SEQ ID NO: 11) | HLA-B7 | KRAS_G12VB7_c16 | DIQMTQSPSSLSASVGDRVTITCRASQDVNTAVAWYQQ KPGKAPKLLIYSASFLYSGVPSRFSGSRSGTDFTLTIS SLQPEDFATYYCQQGWLYSPFTFGQGTKVEIKRTGGGS GGGGSGGGASEVQLVESGGGLVQPGGSLRLSCAASGFN ISGYGMHWVRQAPGKGLEWVARVYGGSGYTYYADSVKG RFTISADTSKNTAYLQMNSLRAEDTAVYYCSRAHSSYY VDYWGQGTLVTVSS | 393 |
| | | 13) H/K/N RAS Q61H(55-64)-A1 | | |
| ILDTAGHEEY (SEQ ID NO: 28) | HLA-A1 | H/K/N RAS Q61H_A1_c10 | DIQMTQSPSSLSASVGDRVTITCRASQDVNTAVAWYQQ KPGKAPKLLIYSASFLYSGVPSRFSGSRSGTDFTLTIS SLQPEDFATYYCQQGYFYYPNTFGQGTKVEIKRTGGGS GGGGSGGGASEVQLVESGGGLVQPGGSLRLSCAASGFN IGYYGMHWVRQAPGKGLEWVATVYPGGGYTSYADSVKG RFTISADTSKNTAYLQMNSLRAEDTAVYYCSRYYYYGF DYWGQGTLVTVSS | 394 |
| | | 14) H/K/N RAS Q61K(55-64)-A1 | | |
| ILDTAGKEEY (SEQ ID NO: 30) | HLA-A1 | H/K/N RAS Q61K_A1_c16 | DIQMTQSPSSLSASVGDRVTITCRASQDVNTAVAWYQQ KPGKAPKLLIYSASFLYSGVPSRFSGSRSGTDFTLTIS SLQPEDFATYYCQQHYYSPVTFGQGTKVEIKRTGGGSG GGGSGGGASEVQLVESGGGLVQPGGSLRLSCAASGFNI FYQDMHWVRQAPGKGLEWVAMIYPDYDYTYYADSVKGR FTISADTSKNTAYLQMNSLRAEDTAVYYCSRTYSVYMD YWGQGTLVTVSS | 395 |
| | | 15) H/K/N RAS Q61L(55-64)-A1 | | |
| ILDTAGLEEY (SEQ ID NO: 31) | HLA-A1 | H/K/N RAS Q61K_A1_c18 | DIQMTQSPSSLSASVGDRVTITCRASQDVNTAVAWYQQ KPGKAPKLLIYSASFLYSGVPSRFSGSRSGTDFTLTIS SLQPEDFATYYCQQYAYAPFTFGQGTKVEIKRTGGGSG GGGSGGGASEVQLVESGGGLVQPGGSLRLSCAASGFNV SYSMIHWVRQAPGKGLEWVARVWGDGGVTYYADSVKGR FTISADTSKNTAYLQMNSLRAEDTAVYYCSRGSYYAFD YWGQGTLVTVSS | 396 |
| | | 16) H/K/N RAS Q61R(55-64)-A1 | | |
| ILDTAGREEY (SEQ ID NO: 32) | HLA-A1 | H/R/N RAS Q61R_A1_c116 | DIQMTQSPSSLSASVGDRVTITCRASQDVNTAVAWYQQ KPGKAPKLLIYSASFLYSGVPSRFSGSRSGTDFTLTIS SLQPEDFATYYCQQAHMIPITFGQGTKVEIKRTGGGSG GGGSGGGASEVQLVESGGGLVQPGGSLRLSCAASGFNF SFPGMEIWVRQAPGKGLEWVAWFVGYDGYTYYADSVKG RFTISADTSKNTAYLQMNSLRAEDTAVYYCSRDYYSFS MDYWGQGTLVTVSS | 397 |
| ILDTAGREEY (SEQ ID NO: 32) | HLA-A1 | H/R/N RAS Q61R_A1_c117 | DIQMTQSPSSLSASVGDRVTITCRASQDVNTAVAWYQQ KPGKAPKLLIYSASFLYSGVPSRFSGSRSGTDFTLTIS SLQPEDFATYYCQQSVYDPITFGQGTKVEIKRTGGGSG GGGSGGGASEVQLVESGGGLVQPGGSLRLSCAASGFNI SGSWIHWVRQAPGKGLEWVAWLYPDSDYTYYADSVKGR FTISADTSKNTAYLQMNSLRAEDTAVYYCSRAHTYAFD YWGQGTLVTVSS | 398 |
| ILDTAGREEY (SEQ ID NO: 32) | HLA-A1 | H/R/N RAS Q61R_A1_c118 | DIQMTQSPSSLSASVGDRVTITCRASQDVNTAVAWYQQ KPGKAPKLLIYSASFLYSGVPSRFSGSRSGTDFTLTIS SLQPEDFATYYCQQSYTSPLTFGQGTKVEIKRTGGGSG GGGSGGGASEVQLVESGGGLVQPGGSLRLSCAASGFNI | 399 |

TABLE 3-continued

MANAbody scFv sequences.

| Target Peptide(s) | Target HLA Allele | ScFc clone name | scFv sequence | SEQ ID NO: |
|---|---|---|---|---|
| | | | YYGVMHWVRQAPGKGLEWVAMIYPDSSWTYYADSVKGRFTISADTSKNTAYLQMNSLRAEDTAVYYCSRDQDFHYMNYYLSYALDYWGQGTLVTVSS | |
| ILDTAGREEY (SEQ ID NO: 32) | HLA-A1 | H/R/N RAS Q61R_A1_cl19 | DIQMTQSPSSLSASVGDRVTITCRASQDVNTAVAWYQQKPGKAPKLLIYSASFLYSGVPSRFSGSRSGTDFTLTISSLQPEDFATYYCQQGQYSPFTFGQGTKVEIKRTGGGSGGGGSGGGASEVQLVESGGGLVQPGGSLRLSCAASGFNVSYEYMHWVRQAPGKGLEWVAEIYGGSDNTYYADSVKGRFTISADTSKNTAYLQMNSLRAEDTAVYYCSRPLGSYFDYWGQGTLVTVSS | 400 |
| ILDTAGREEY (SEQ ID NO: 32) | HLA-A1 | H/R/N RAS Q61R_A1_cl22 | DIQMTQSPSSLSASVGDRVTITCRASQDVNTAVAWYQQKPGKAPKLLIYSASFLYSGVPSRFSGSRSGTDFTLTISSLQPEDFATYYCQQYWYLPTTFGQGTKVEIKRTGGGSGGGGSGGGASEVQLVESGGGLVQPGGSLRLSCAASGFNISWYDIHWVRQAPGKGLEWVADIEPSVGYTYYADSVKGRFTISADTSKNTAYLQMNSLRAEDTAVYYCSRSYPYYYFDYWGQGTLVTVSS | 401 |

Representative ELISA data for a scFvs that specifically recognized an IDH2 peptide containing the R140Q mutation in complex with HLA-B7 (SPNGTIQNIL; SEQ ID NO: 1) are shown in FIG. 1. The scFvs did not recognize the wt version of the peptide of interest in complex with the same HLA allele. The scFvs did not recognize other control peptides in complex with the HLA allele when tested for binding to a monomer-coated ELISA plate.

Further flow cytometry using showed that MANAbody scFv clones specifically stain the HLA allele-matched cell lines when these cells are pulsed with the mutant peptide, but not the wt peptide or other control peptides (FIGS. 2-14).

Figure 15A:
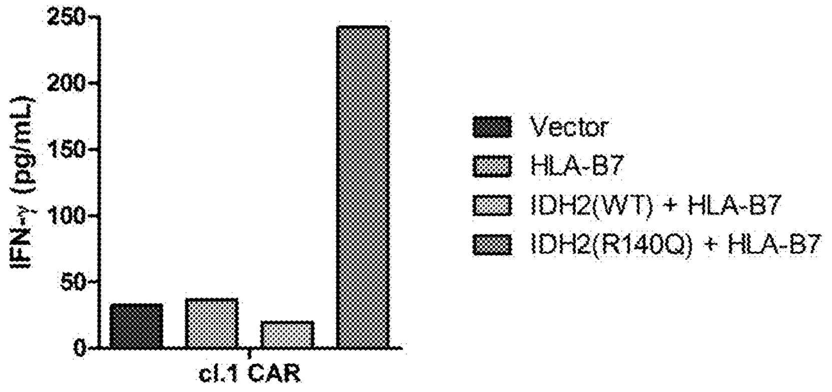
FIGS. 15A-15B show that MANAbody clones can be converted into CAR-T cells.
Figure 15B:
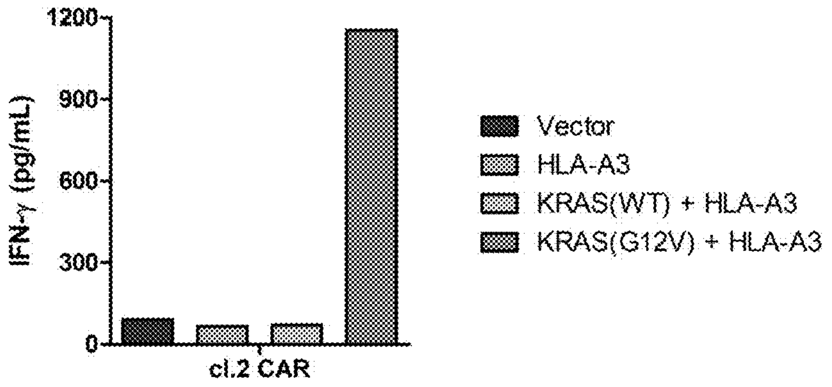

To demonstrate that MANAbody clones can be utilized as a therapeutic modality, selected MANAbody clones were engineered into CAR-T cells. Chimeric antigen receptor (CAR) T cells (CARTs) capable of recognizing and killing cells expressing oncogenic mutation-containing peptides in the context of HLA molecules via their endogenous processing and presentation machinery were engineered. Specifically, CARTs targeting a mutant KRAS G12V peptide presented in the context of HLA-A3 were engineered, and CARTs targeting a mutant IDH2 R140Q peptide presented in the context of HLA-B7 were engineered. MANAbody scFvs targeting either mutant peptide were grafted onto a 3rd Generation CAR construct, and CAR receptors were expressed in CD3+ T cells by mRNA electroporation. CAR-T cells were subsequently co-cultured with COS-7 cells co-transfected with plasmids encoding KRAS/IDH2 mutant and wt proteins in combination with their respective HLA. As T cells, including CAR-T cells, produce cytokines following activation by cognate antigen on target cells, the release of IFNγ in the co-culture media supernatant was measured by ELISA. Only when COS-7 cells were co-transfected with the mutant and cognate HLA plasmids was there significant release of IFNγ over background (FIG. 15). CAR-T cells co-cultured with COS-7 cells co-transfected with the wt and cognate HLA released only background levels of IFNγ. Together, these findings suggest that CAR-T cells expressing MANAbody clones can target tumor cells expressing MANAs presented in the context of HLA molecules.

To demonstrate that MANAbody clones can be utilized as a therapeutic modality, selected MANAbody clones were engineered into bispecific antibodies. A bispecific antibody having one antibody-fragment binding to a target cancer cell and having one antibody-fragment binding to a CD3 protein on the T cell surface was engineered. There are a number of different anti-CD3 scFv clones targeting human CD3 epsilon, delta, and/or gamma molecules. Examples of such clones are listed in Table 4.

Bispecific antibodies having one antibody-fragment binding to a mutant KRAS G12V peptide presented in the context of HLA-A3 and having one antibody-fragment binding to a CD3 protein on the T cell surface were engineered. Specifically, bispecific antibodies targeting a mutant KRAS G12V peptide presented in the context of HLA-A3 and CD3 were engineered, and bispecific antibodies targeting a mutant IDH2 R140Q peptide presented in the context of HLA-B7 and CD3 were engineered.

TABLE 4

Anti-human CD3 scFv sequences.

| Clone Name | Clone scFv Sequence | SEQ ID NO: |
|---|---|---|
| humanized UCHT1 (hUCHT1v9) | DIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIKGGGGSGGGGSGGGGSEVQLVESGGGLVQPGGSLRLSCAASGYSFTGYTMNWVRQAPGKGLEWVALINPYKGVSTYNQKFKDRFTISVDKSKNTAYLQMNSLRAEDTAVYYCARSGYYGDSDWYFDVWGQGTLVTVSS | 404 |
| murine UCHT1 (mUCHT1) | DIQMTQTTSSLSASLGDRVTISCRASQDIRNYLNWYQQKPDGTVKLLIYYTSRLHSGVPSKFSGSGSGTDYSLTISNLEQEDIATYFCQQGNTLPWTFAGGTKLEIKGGGGSGGGGSGGGGSEVQLQQSGPELVKPGASMKISC | 405 |

TABLE 4-continued

Anti-human CD3 scFv sequences.

| Clone Name | Clone scFv Sequence | SEQ ID NO: |
|---|---|---|
| | KASGYSFTGYTMNWVKQSHGKNLEWMGLINPYKGVSTYNQKFKDKATLTVDKSSSTAYMELLSLTSEDSAVY YCARSGYYGDSDWYFDVWGAGTTVTVSS | |
| diL2K | DIVLTQSPATLSLSPGERATLSCRASQSVSYMNWYQQKPGKAPKRWIYDTSKVASGVPARFSGSGSGTDYSL TINSLEAEDAATYYCQQWSSNPLTFGGGTKVEIKGGGGSGGGGSGGGGSDVQLVQSGAEVKKPGASVKVSCK ASGYTFTRYTMHWVRQAPGQGLEWIGYINPSRGYTNYADSVKGRFTITTDKSTSTAYMELSSLRSEDTATYY CARYYDDHYCLDYWGQGTTVTVSS | 406 |
| hXR32 | QAVVTQEPSLTVSPGGTVTLTCRSSTGAVTTSNYANWVQQKPGQAPRGLIGGTNKRAPWTPARFSGSLLGGK AALTITGAQAEDEADYYCALWYSNLWVFGGGTKLTVLGGGGSGGGGSGGGGSEVQLVESGGGLVQPGGSLRL SCAASGFTFNTYAMNWVRQAPGKGLEWVARIRSKYNNYATYYADSVKDRFTISRDDSKNSLYLQMNSLKTED TAVYYCVRHGNFGNSYVSWFAYWGQGTLVTVSS | 407 |
| L2K-07 | DIQLTQSPAIMSASPGEKVTMTCRASSSVSYMNWYQQKSGTSPKRWIYDTSKVASGVPYRFSGSGSGTSYSL TISSMEAEDAATYYCQQWSSNPLTFGAGTKLELKGGGGSGGGGSGGGGSDIKLQQSGAELARPGASVKMSCK TSGYTFTRYTMHWVKQRPGQGLEWIGYINPSRGYTNYNQKFKDKATLTTDKSSSTAYMQLSSLTSEDSAVYY CARYYDDHYCLDYWGQGTTLTVSS | 408 |
| OKT3 | QIVLTQSPAIMSASPGEKVTMTCSASSSVSYMNWYQQKSGTSPKRWIYDTSKLASGVPAHFRGSGSGTSYSL TISGMEAEDAATYYCQQWSSNPFTFGSGTKLEINGGGGSGGGGSGGGGSQVQLQQSGAELARPGASVKMSCK ASGYTFTRYTMHWVKQRPGQGLEWIGYINPSRGYTNYNQKFKDKATLTTDKSSSTAYMQLSSLTSEDSAVYY CARYYDDHYCLDYWGQGTTLTVSS | 409 |
| PSMA-CD3 | QTVVTQEPSLTVSPGGTVTLTCGSSTGAVTSGNYPNWVQQKPGQAPRGLIGGTKFLAPGTPARFSGSLLGGK AALTLSGVQPEDEAEYYCVLWYSNRWVFGGGTKLTVLGGGGSGGGGSGGGGSEVQLVESGGGLVQPGGSLKL SCAASGFTFNKYAMNWVRQAPGKGLEWVARIRSKYNNYATYYADSVKDRFTISRDDSKNTAYLQMNNLKTED TAVYYCVRHGNFGNSYISYWAYWGQGTLVTVSS | 410 |
| 28F11 | EIVLTQSPATLSLSPGERATLSCRASQSVSSYLAWYQQKPGQAPRLLIYDASNRATGIPARFSGSGSGTDFT LTISSLEPEDFAVYYCQQRSNWPPLTFGGGTKVEIKGGGGSGGGGSGGGGSQVQLVESGGGVVQPGRSLRLS CAASGFKFSGYGMHWVRQAPGKGLEWVAVIWYDGSKKYYVDSVKGRFTISRDNSKNTLYLQMNSLRAEDTAV YYCARQMGYWHFDLWGRGTLVTVSS | 411 |
| 27H5-VL1 | EIVLTQSPRTLSLSPGERATLSCRASQSVSSSYLAWYQQKPGQAPRLLIYGASSRATGIPDRFSGSGSGTDF TLTISRLDPEDFAVYYCQQYGSSPITFGQGTRLEIKGGGGSGGGGSGGGGSQVQLVESGGGVVQPGRSLRLS CAASGFTFRSYGMHWVRQAPGKGLEWVAIIWYDGSKKNYADSVKGRFTISRDNSKNTLYLQMNSLRAEDTAV YYCARGTGYNWFDPWGQGTLVTVSS | 412 |
| 27H5-VL2 | DILMTQSPSSLSASVGDRVTITCRASQGISSALAWYQQKPGKAPKLLIYYASSLQSGVPSRFSGSGSGTDYT LTISSLQPEDFATYYCQQYYSTLTFGGGTKVEIKGGGGSGGGGSGGGGSQVQLVESGGGVVQPGRSLRLSCA ASGFTFRSYGMHWVRQAPGKGLEWVAIIWYDGSKKNYADSVKGRFTISRDNSKNTLYLQMNSLRAEDTAVYY CARGTGYNWFDPWGQGTLVTVSS | 413 |
| 23F10 | EIVLTQSPATLSLSPGERATLSCRASQSVSSYLAWYQQKPGQAPRLLIYDASNRATGIPARFSGSGSGTDFT LTISSLEPEDFAVYYCQQRSNWPPLTFGGGTKVEIKGGGGSGGGGSGGGGSQVQLVQSGGGVVQSGRSLRLS CAASGFKFSGYGMHWVRQAPGKGLEWVAVIWYDGSKKYYVDSVKGRFTISRDNSKNTLYLQMNSLRGEDTAV YYCARQMGYWHFDLWGRGTLVTVSS | 414 |
| 15C3-VL1 | EIVLTQSPATLSLSPGERATLSCRASQSVSSYLAWYQQKPGQAPRLLIYDASNRATGIPARFSGSGSGTDFT LTISSLEPEDFAVYYCQQRSNWPWTFGQGTKVEIKGGGGSGGGGSGGGGSQVQLVQSGGGVVQPGRSLRLSC VASGFTFSSYGMHWVRQAPGKGLEWVAAIWYNGRKQDYADSVKGRFTISRDNSKNTLYLQMNSLRAEDTAVY YCTRGTGYNWFDPWGQGTLVTVSS | 415 |
| 15C3-VL2 | AIQLTQSPSSLSASVGDRVTITCRASQGISSALAWYQQKPGKAPKLLIYDASSLESGVPSRFSGSGSGTDFT LTISSLQPEDFATYYCQQFNSYPITFGQGTRLEIKGGGGSGGGGSGGGGSQVQLVQSGGGVVQPGRSLRLSC VASGFTFSSYGMHWVRQAPGKGLEWVAAIWYNGRKQDYADSVKGRFTISRDNSKNTLYLQMNSLRAEDTAVY YCTRGTGYNWFDPWGQGTLVTVSS | 416 |
| hu 12F6 | QIVLSQSPAILSASPGEKVTMTCRASSSVSYMHWYQQKPGSSPKPWIYATSNLASGVPARFSGSGSGTSYSL TISRVEAEDAATYYCQQWSSNPPTFGGGTKLETKRGGGGSGGGGSGGGGSQVQLQQSGAELARPGASVKMSC KASGYTFTSYTMHWVKQRPGQGLEWIGYINPSSGYTKYNQKFKDKATLTADKSSSTAYMQLSSLTSEDSAVY YCARWQDYDVYFDYWGQGTTLTVSS | 417 |

Figure 16A:
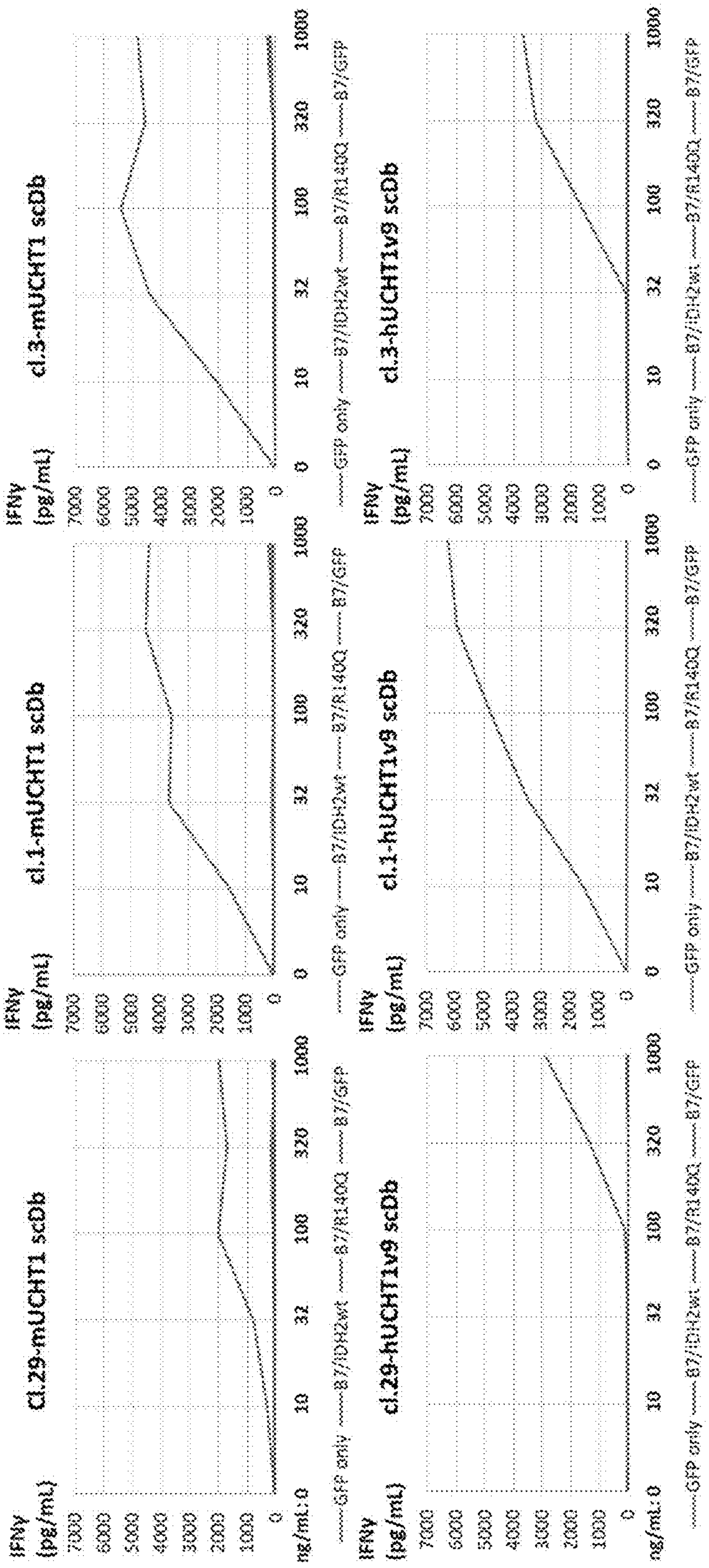
FIGS. 16A-16B show that MANAbody clones can be converted into single-chain diabodies (scDbs).
Figure 16B:
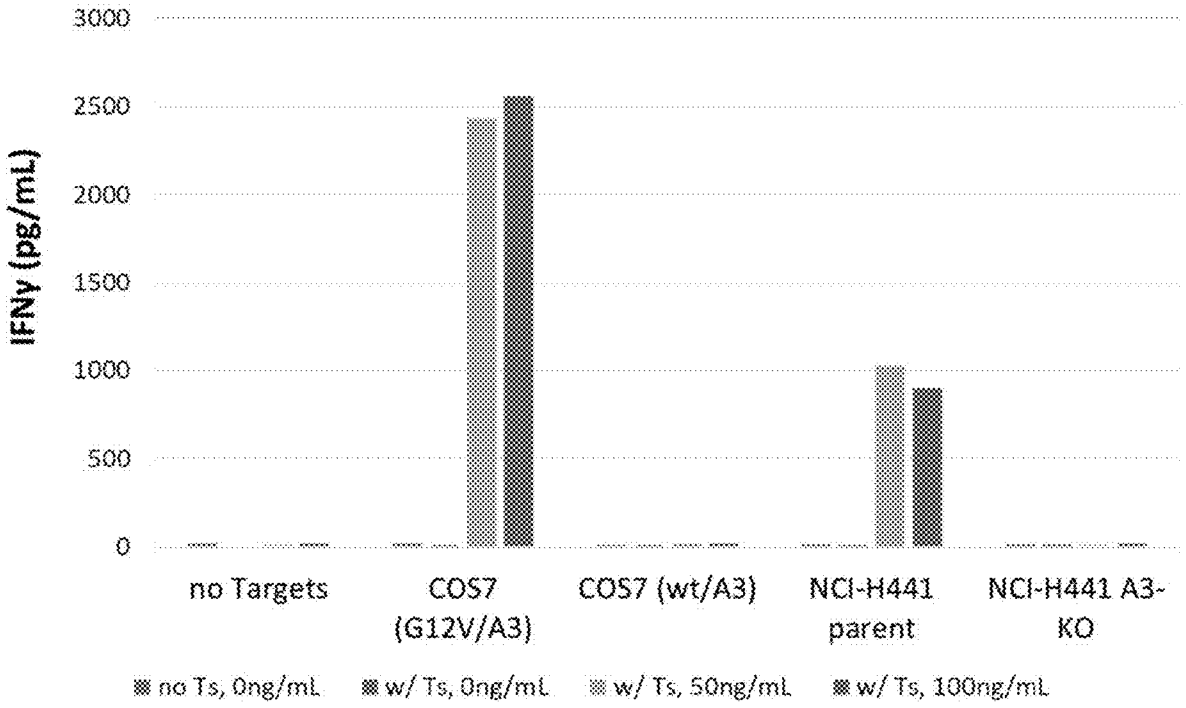

Representative scDb co-culture results are shown in FIG. 16A for three IDH2 R140Q HLA-B7 MANAbody scFv clones combined with two different anti-CD3 scFv clones. T cells were co-cultured with COS-7 cells co-transfected with plasmids encoding HLA-B7, full-length IDH2 variants, and/or GFP in the presence of the specified concentration of scDb. As a read out of T cell activation by cognate antigen on target cells, the release of IFNγ in the co-culture media supernatant was measured by ELISA. Only when COS-7 cells were co-transfected with HLA-B7 and mutant IDH2 R140Q plasmids was there significant T cell release of IFNγ over background, with the level of IFNγ dependent on the concentration of scDb included in the well. T cells co-cultured with COS-7 cells co-transfected with HLA-B7 and wt IDH2 released only background levels of IFNγ. Representative scDb co-culture results are shown in FIG. 16B for a KRAS G12V HLA-A3 MANAbody scFv clone combined with an anti-CD3 clone into a single chain diabody. In this co-culture, the single chain diabody was tested at concentrations of 0, 50, and 100 ng/mL. Only when COS-7 cells were co-transfected with HLA-A3 and mutant KRAS G12V plasmids was there significant T cell release of IFNγ over background. T cells co-cultured with COS-7 cells co-transfected with HLA-A3 and wt KRAS released only background levels of IFNγ, similar to the levels of IFNγ seen in no T cell, no target cell, and no scDb wells. An endogenous KRAS G12V HLA-A3 positive cell line NCI-H441 as a target cell line along with its isogenic HLA-A3 knockout control. IFNγ release was only seen against the parental NCI-H441 cell line but not the HLA-A3 knockout NCI-H441. Together, these findings suggest that bispecific antibodies containing MANAbody clones that target tumor cells expressing MANAs presented in the context of HLA molecules.

Figure 17:
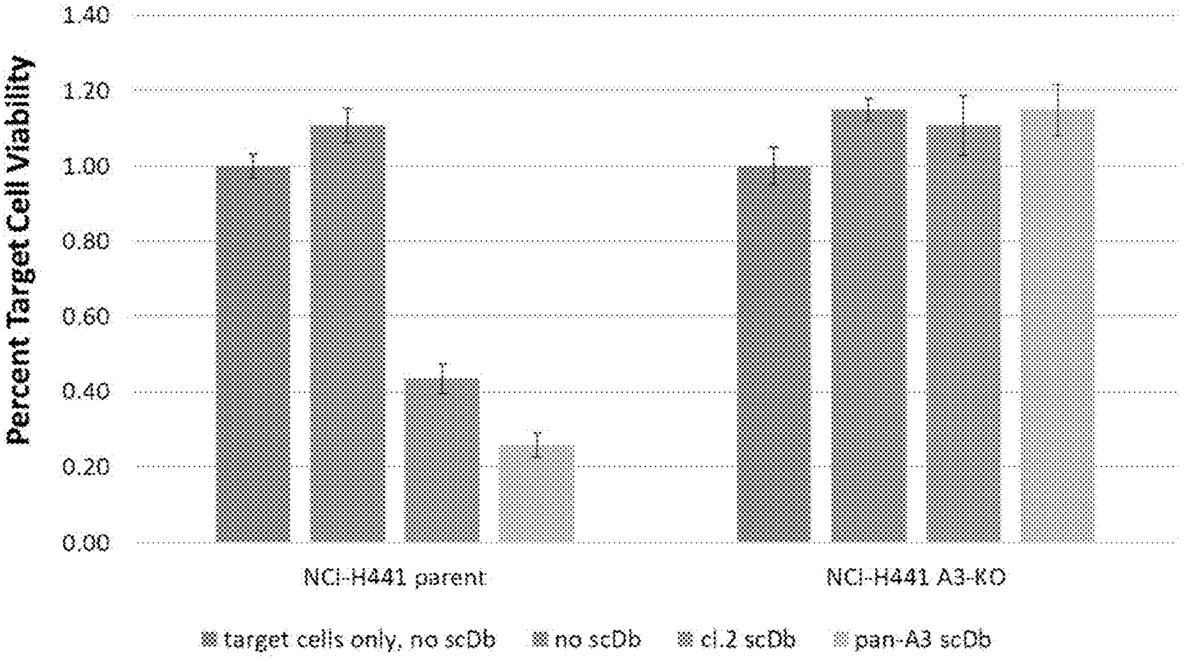
FIG. 17 shows that a MANAbody clone converted into a scDb can kill target cells. KRAS G12V(7-16)-A3 cl.2 mUCHT1 scDb and a pan-HLA-A3 scDb were incubated at 0 or 50 ng/mL with or without T cells and with NCI-H441 parental or HLA-A3 knockout cells for 24 hours at 37° C.

To evaluate the efficacy of using MANAbody clones as a therapeutic modality, target cell viability of a KRAS G12V HLA-A3 single-chain diabody was assayed using PROMEGA® CellTiter-Glo® reagent (FIG. 17). CellTiter-Glo® measures ATP concentration in a well, which is proportional to the number of viable cells. Percent target cell viability was measured by subtracting the CellTiter-Glo® value from T cell only wells and normalizing to target cell only wells. Only when NCI-H441 parent cells were incubated with T cells in the presence of the KRAS G12V-A3 scDb or a pan-HLA-A3 scDb positive control, was there significant target cell death. No target cell death was observed in the absence of scDb or among the NCI-H441 HLA-A3 knockout wells.

Together, these findings demonstrate that MANAbodies can be used to redirect and activate T cells to kill tumor cells expressing particular mutant protein and HLA allele pairs (e.g., IDH2 R140Q with HLA-B7 and KRAS G12V with HLA-A3).

Materials and Methods

Cells and Cell Lines.

RPMI-6666 cells (ATCC, Manassas, VA) was cultured in RPMI-1640 (ATCC) with 20% FBS (GE Hyclone, Logan, Utah, USA), and 1% penicillin streptomycin (Life Technologies). T2 cells (ATCC) and MINO cells (ATCC) were cultured in RPMI-1640 (ATCC) with 10% FBS (GE Hyclone), and 1% penicillin streptomycin (Thermo Fisher). T2A3 cells (gifted from Dr. Eric Lutz) were cultured in RPMI-1640 (ATCC) with 10% FBS (GE Hyclone), 1% penicillin streptomycin (Thermo Fisher), 0.1 mM MEM Non-Essential Amino Acids (NEAA, Thermo Fisher), and 500 μg/mL geneticin (Thermo Fisher). SigM5 cells (DSMZ, Brunswick, Germany) were cultured in Iscove's MDM (ATCC) with 20% FBS (GE Hyclone), and 1% penicillin streptomycin (Thermo Fisher). Hs611.T cells (ATCC) was cultured in Dulbecco's Modified Eagle's Medium (ATCC) with 10% FBS (GE Hyclone), and 1% penicillin streptomycin (Thermo Fisher). NCI-H441 cells (ATCC) and COS-7 cells (ATCC) was cultured in McCoy's 5A (Modified) Medium (Thermo Fisher) with 10% FBS (GE Hyclone), and 1% penicillin streptomycin (Thermo Fisher). COS-7 cells (ATCC, CRL-1651™) were cultured in DMEM (high glucose, pyruvate; Thermo Fisher) with 10% FBS (GE Hyclone), and 1% Penicillin-Streptomycin (Thermo Fisher). 293FT cells (Thermo Fisher) were cultured in high-glucose D-MEM (Thermo Fisher), with 10% FBS (GE Hyclone), 0.1 mM MEM Non-Essential Amino Acids (NEAA, Thermo Fisher), 6 mM L-glutamine (Thermo Fisher), 1 mM MEM Sodium Pyruvate (Thermo Fisher), 500 μg/ml geneticin (Thermo Fisher), and 1% Penicillin-Streptomycin (Thermo Fisher). All cell lines were maintained at 37° C. under 5% $CO_2$.

PBMCs were obtained by Ficoll-Paque PLUS (GE Healthcare) gradient centrifugation of whole blood from healthy volunteer donors. CD3+ cells were positively selected with CD3 MicroBeads (Miltenyi Biotec) from PBMCs, and were activated and expanded with Dynabeads® Human T-Activator CD3/CD28 (Life Technologies). Unless otherwise noted, primary CD3+ T cells were cultured in RPMI-1640 (ATCC) with 10% FBS (GE Hyclone), 1% Penicillin-Streptomycin (Life Technologies), and 100 IU/mL recombinant human interleukin-2 (Proleukin®) at 37° C. under 5% $CO_2$.

Phage Display Library Construction.

For the 1st generation phage library, oligonucleotides were synthesized at DNA 2.0 (Menlo Park, CA) using mixed and split pool degenerate oligonucleotide syntheses. For the 2nd generation phage library, oligonucleotides were synthesized at GeneArt® (Thermo Fisher, Halethorpe, MD) using trinucleotide mutagenesis (TRIM) technology. For both libraries, the oligonucleotides were incorporated into the pADL-10b phagemid (Antibody Design Labs, San Diego, CA). This phagemid contains an Fl origin, a transcriptional repressor to limit uninduced expression, a lac operator, and a lac repressor. The scFv was synthesized with a pelB periplasmic secretion signal and was subcloned downstream of the lac operator. For the 1st generation library, a myc epitope tag followed by a TEV protease cleavage recognition sequence was placed immediately downstream of the variable heavy chain, while in the 2nd generation library, the scFv was followed by a FLAG tag. Following the scFv, tag, and cleavage site, was the full length, in-frame M13 pIII coat protein sequence.

To transform the phagemid DNA into bacteria, 10-20 ng of the ligation product was mixed on ice with 10 μL of electrocompetent SS320 cells (Lucigen, Middleton, WI) and 14 μL of double-distilled water. This mixture was electroporated using a Gene Pulser electroporation system (Bio-Rad, Hercules, CA) and allowed to recover in Recovery Media (Lucigen) for 60 min at 37° C. Cells transformed with 60 ng of ligation product were pooled and plated on a 24-cm×24-cm plate containing 2×YT medium supplemented with carbenicillin (100 μg/mL) and 2% glucose. Cells were grown at 37° C. for 6 hours and placed at 4° C. overnight. To determine the transformation efficiency for each series of electroporations, aliquots were taken and titered by serial dilution. Cells grown on plates were scraped into 850 mL of 2×YT medium with carbenicillin (100 μg/mL) plus 2% glucose for a final OD600 of 5-15. Two mL of the 850 mL culture were taken and diluted ~1:200 to reach a final OD600 of 0.05-0.07. To the remaining culture, 150 mL of sterile glycerol were added before snap freezing to produce glycerol stocks. The diluted bacteria were grown to an OD600 of 0.2-0.4, infected with M13K07 Helper phage (Antibody Design Labs, San Diego, CA) and allowed to shake at 37° C. for 1 hour. The culture was centrifuged and the cells were resuspended in 2×YT medium with carbenicillin (100 μg/mL) and kanamycin (50 g/mL) and grown overnight at 30° C. for phage production. The following morning, the bacterial culture was aliquoted into 50 mL Falcon tubes and pelleted twice at high speed to obtain clarified supernatant. The phage-laden supernatant was precipitated on ice for 40 min with a 20% PEG-8000/2.5M NaCl solution at a 4:1 ratio of PEG/NaCl to supernatant. After precipitation, phage was centrifuged at 12,000 g for 40 minutes and resuspended in a 1 mL vol 1×TBS, 2 mM EDTA. Phage from multiple tubes was pooled, re-precipitated, and resuspended to an average titer of $1\times10^{13}$ cfu/mL. For the 1st generation library, the total number of transformants obtained was $5.5\times10^{9}$. For the 2nd generation library, the total number of transformants obtained was $3.6\times10^{10}$. Each library was aliquoted and stored in 15% glycerol at −80° C.

Next-Generation Sequencing of the Complete Phage Library.

DNA from the libraries was amplified using primers that flank the CDR-H3 region. The sequences at the 5'-ends of these primers incorporated molecular barcodes to facilitate unambiguous enumeration of distinct phage sequences. The protocols for PCR-amplification and sequencing are described in Kinde et al. Sequences processed and translated using a custom SQL database and both the nucleotide sequences and amino acid translations were analyzed using Microsoft Excel.

Peptides and HLA-Monomers.

Mutant, wt, and control peptides (listed in Table 1) were predicted to bind to HLA alleles using NetMHC version 4.0. All peptides were synthesized at a purity of >90% by Peptide 2.0 (Chantilly, VA). Peptides were resuspended in DMSO or DMF at 10 mg/mL and stored at −20° C. HLA monomers were synthesized by refolding recombinant HLA with peptide and beta-2 microglobulin, purified by gel-filtration, and biotinylated (Fred Hutchinson Immune Monitoring Lab, Seattle, WA). Monomers were confirmed to be folded prior to selection by performing an ELISA using W6/32 antibody (BioLegend, San Diego, CA).

Selection for Phage Binding to Mutant Peptide-HLA Monomers.

Biotinylated monomers containing HLA and beta-2-microglobulin proteins were conjugated to MyOne™ T1 streptavidin magnetic beads (Life Technologies, Carlsbad, CA). The biotinylated monomers were incubated with 30 μL of MyOne™ T1 beads (per 1 μg of monomer) in blocking buffer (PBS, 0.5% BSA, 0.1% Na-azide) for 1 hour at room temperature (RT). After the initial incubation, the complexes were washed 3 times with 1 ml blocking buffer and resuspended in 1 ml blocking buffer.

Enrichment Phase.

In the enrichment phase of selection (round 1), phage representing 1000-fold coverage of the library was incubated with naked, washed MyOne™ T1 beads and heat-denatured, bead-conjugated HLA monomer overnight at 4° C. on a rotator. This step was necessary to remove any phage recognizing either streptavidin or denatured monomer, present to a small extent in every preparation of biotinylated monomer. After negative selection, beads were isolated with a DynaMag-2 magnet (Life Technologies) and the supernatant containing unbound phage was transferred for positive selection against 1 μg of the mutant peptide-HLA monomer conjugated to MyOne™ T1 streptavidin magnetic beads. Prior to elution, beads were washed 10 times with 1 ml, 1×TBS containing 0.5% Tween®-20 using a magnet. Phage was eluted by resuspending the beads in 1 mL of 0.2 M glycine, pH 2.2. After a 10-minute incubation, the solution was neutralized by the addition of 150 μL of 1 M Tris, pH 9.0. Neutralized phage was used to infect 10 ml cultures of mid-log-phage SS320s, with the addition of M13K07 helper phage (MOI of 4) and 2% glucose. After shaking for 1 hour at 37° C., bacteria was resuspended in 2×YT medium with carbenicillin (100 μg/mL), kanamycin (50 μg/mL), and 50 uM of IPTG and grown overnight at 30° C. for phage production. Phage was precipitated the next morning with PEG/NaCl as previously described.

Final Selection Phase.

Three to five rounds of final selection were performed with phage resulting from the enrichment phase. For each round of final selection, the first negative selection was performed using 10-0.1% of the precipitated phage against HLA-allele matched cells lacking the mutated protein of interest. The unbound phage was then negatively selected against native wt peptide-HLA monomer and unrelated HLA-allele matched monomer. After negative selection, beads were isolated with a Dynamag 2 magnet (Life Technologies) and the supernatant containing unbound phage was transferred for positive selection with 250 ng to 1 μg of mutant peptide-HLA monomer, as described for the enrichment phase above.

ELISA.

Streptavidin-coated, 96-well plates (R&D Systems, Minneapolis, MN) were coated with 50 ng (in 50 uL) of biotinylated mutant or wt peptide-HLA monomers in blocking buffer (PBS with 0.5% BSA, 2 mM EDTA, and 0.1% sodium azide) at 4° C. overnight. Plates were briefly washed with 1×TBST (TBS+0.05% Trition-X 100). Phage was serially diluted to the specified concentrations in blocking buffer and 50 uL was added to each well. Phage were incubated for 2 hrs at RT, followed by washing (6 washes with 1×TBS-0.05% Tween®-20 (TBST) using an ELISA plate washer (BioTek, Winooski, VT). The bound phage were incubated with 50 μL of rabbit anti-M13 antibody (Pierce, Rockford, IL) diluted 1:3000 in 1×TBST for 1 hr at room temperature, followed by washing an additional 6× times and incubation with 50 μL of anti-Rabbit HRP (Thermo Fisher) diluted 1:10,000 in 1×TBST for 1 hour at room temperature. After a final 6 washes with 1×TBST, 50 L of TMB substrate (BioLegend, San Diego, CA) was added to the well and the reaction was quenched with IN sulfuric acid. Absorbance at 450 nm was measured with a Synergy H1 Multi-Mode Reader (BioTek, Winooski, VT).

Monoclonal phage ELISA was performed by selecting individual colonies of SS320 cells transformed with a limiting dilution of phage obtained from the final selection. Individual colonies were inoculated into 200 μl of 2×YT medium containing 100 μg/mL carbenicillin and 2% glucose and grown for three hours at 37° C. The cells were then infected with $1.6\times10^{7}$ M13K07 helper phage (Antibody Design Labs, San Diego, CA) and incubated for at 37° C. with shaking. The cells were pelleted, resuspended in 300 μL of 2×YT medium containing carbenicillin (100 μg/mL), kanamycin (50 μg/mL), and 50 μM IPTG, and grown overnight at 30° C. Cells were pelleted and the phage-laden supernatant was used for ELISA as described above.

Peptide Pulsing and Flow Cytometry.

For peptide pulsing, HLA-matched cells were washed once with PBS and once with serum-free RPMI-1640 before incubation at $10^{6}$ cells per mL in serum-free RPMI-1640 containing 50 μg/mL peptide and 10 μg/mL human beta-2 microglobulin (ProSpec, East Brunswick, NJ) overnight at 37° C. The pulsed cells were pelleted, washed once in cold stain buffer (PBS containing 0.5% BSA, 2 mM EDTA, and 0.1% sodium azide), and resuspended in 100 μL of stain buffer. Phage staining was performed on ice with 10 uL (approximately $1\times10^{9}$) phage for 1 hour in 100 uL total volume, followed by one 4 mL wash in cold stain buffer. Cells were then stained with 1 uL of rabbit anti-M13 antibody (Pierce, Rockford, IL) in 100 uL total volume on ice for 1 hour and washed once with 4 mL of cold stain buffer. Cells were stained with anti-rabbit-PE (Biolegend) on ice for 1 hour in 100 uL total volume, followed by incubation with LIVE/DEAD Fixable Near-IR Dead Cell Stain (Thermo Fisher) for 10 min at room temperature per manufacturer's instructions. Cells were washed once in 4 mL of stain buffer followed by resuspension in 300 uL of stain buffer before analysis. Stained cells were analyzed using an LSRII flow cytometer (Becton Dickinson, Mansfield, MA).

CAR Construction and Generation.

A third-generation Chimeric Antigen Receptor (CAR) construct, containing the MANAbody scFv, a CD28 transmembrane domain, and 4-1BB and CD3ζ intracellular domains, was synthesized (GeneArt®) and cloned into the mammalian expression vector pCI (PROMEGA®). mRNA was synthesized with the T7 mScript™ Standard mRNA Production System Kit (CellScript™) per manufacturer's instructions. CAR mRNA was electroporated into primary CD3+ T cells with the BTX ECM 2001 Electro Cell Manipulator (Harvard Apparatus) to generate CAR-T cells.

CAR-T Activation Co-Culture Assay.

COS-7 cells were transfected with various combinations of pcDNA3.1 (Life Technologies) plasmids encoding HLA-A3, HLA-B7, IDH2(WT), IDH2(R140Q), KRAS(WT), and KRAS(G12V) with Lipofectamine 3000 (Life Technologies) per manufacturer's instructions in 96-well plate format. 100,000 electroporated CAR-T cells were overlaid over the transfected COS-7 cells, and the co-culture was allowed to incubate for 4 hours at 37° C. under 5% $CO_2$. Following co-culture, conditioned media was collected and assayed for secreted IFNγ by ELISA (Quantikine®, R&D Systems).

Bispecific Antibody Production.

gBLOCKs encoding bispecific antibodies were ordered from IDT (Skokie, Illinois). gBLOCKs were topo-cloned into the pcDNA3.4 plasmid (Thermo Fisher) following the manufacturer's protocol. 293FT cells (Thermo Fisher) were transfected with the bispecific antibody pcDNA3.4 plasmids using Lipofectamine 3000 (Life Technologies) per manufacturer's instructions in a T75 flask. Following a 5-7 day incubation, media was harvest and centrifuged at 3,000 g for 10 min at 4 C. Bispecific antibody protein was purified using a Clontech Capturem™ His-Tagged Purification Miniprep Kit (Takara, Mountain View, CA) per manufacturer's instructions. Bispecific antibody protein was desalted into PBS using Zeba spin 7 k MWCO desalting columns per manufacturer's instructions. Bispecific antibody concentration was quantified using Mini-PROTEAN® TGX Stain-Free™ Precast Gels (Biorad, Hercules, California) using a standard curve of protein of known concentration. Stain-free gels were imaged using the ChemiDoc XRS+ Imager (Biorad).

Bispecific Antibody Co-Culture Assay.

COS-7 cells were transfected with various combinations of pcDNA3.1 (Life Technologies) plasmids encoding HLA-A3, HLA-B7, IDH2(WT), IDH2(R140Q), KRAS(WT), and KRAS(G12V) with Lipofectamine 3000 (Life Technologies) per manufacturer's instructions in a T75 flask. 50,000 T cells were combined with transfected 30,000 COS-7 cells or 10,000 NCI-H441 cells and the specified concentration of bispecific antibody in a 96-well plate, and the co-culture was allowed to incubate for 24 hours at 37° C. under 5% $CO_2$. Following co-culture, the 96-well plate was snap frozen and conditioned media lysate was collected and assayed for secreted IFNγ by ELISA (Quantikine®, R&D Systems). Alternatively, following coculture, target cell viability was measured using CellTiter-Glo® (PROMEGA®).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 420
SEQ ID NO: 1            moltype = AA  length = 10
FEATURE                 Location/Qualifiers
source                  1..10
                        mol_type = protein
                        organism = synthetic construct
SEQUENCE: 1
SPNGTIQNIL                                                        10

SEQ ID NO: 2            moltype = AA  length = 10
FEATURE                 Location/Qualifiers
source                  1..10
                        mol_type = protein
                        organism = synthetic construct
SEQUENCE: 2
SPNGTIRNIL                                                        10

SEQ ID NO: 3            moltype = AA  length = 243
FEATURE                 Location/Qualifiers
source                  1..243
                        mol_type = protein
                        organism = synthetic construct
SEQUENCE: 3
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYSPPTFGQ GTKVEIKRTG GGSGGGGSGG  120
GASEVQLVES GGGLVQPGGS LRLSCAASGF NISDTYIHWV RQAPGKGLEW VASISPRTGY  180
NRYADSVKGR FTISADTSKN TAYLQMNSLR AEDTAVYYCS RAYYSYAYAM DVWGQGTLVT  240
VSS                                                               243

SEQ ID NO: 4            moltype = AA  length = 242
FEATURE                 Location/Qualifiers
source                  1..242
```

```
                        mol_type = protein
                        organism = synthetic construct
SEQUENCE: 4
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GKAYWPATFG QGTKVEIKRT GGGSGGGGSG  120
GGASEVQLVE SGGGLVQPGG SLRLSCAASG FNVGHYRMHW VRQAPGKGLE WVAMVSPNGY  180
YTYYADSVKG RFTISADTSK NTAYLQMNSL RAEDTAVYYC SRGYSSYAFD YWGQGTLVTV  240
SS                                                                 242

SEQ ID NO: 5            moltype = AA  length = 241
FEATURE                 Location/Qualifiers
source                  1..241
                        mol_type = protein
                        organism = synthetic construct
SEQUENCE: 5
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ VYSSPFTFGQ GTKVEIKRTG GGSGGGGSGG  120
GASEVQLVES GGGLVQPGGS LRLSCAASGF NVKYYMMHWV RQAPGKGLEW VAAISPGYDY  180
TYYADSVKGR FTISADTSKN TAYLQMNSLR AEDTAVYYCS RSYWRYSVDV WGQGTLVTVS  240
S                                                                  241

SEQ ID NO: 6            moltype = AA  length = 245
FEATURE                 Location/Qualifiers
source                  1..245
                        mol_type = protein
                        organism = synthetic construct
SEQUENCE: 6
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSLYSPMTFG QGTKVEIKRT GGGSGGGGSG  120
GGASEVQLVE SGGGLVQPGG SLRLSCAASG FNSFLSIHWV RQAPGKGLEW VAHIFPSSDY  180
TSYADSVKGR FTISADTSKN TAYLQMNSLR AEDTAVYYCS RGKHSSDSNY YMDYWGQGTL  240
VTVSS                                                              245

SEQ ID NO: 7            moltype =   length =
SEQUENCE: 7
000

SEQ ID NO: 8            moltype = AA  length = 241
FEATURE                 Location/Qualifiers
source                  1..241
                        mol_type = protein
                        organism = synthetic construct
SEQUENCE: 8
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SYYMPFTFGQ GTKVEIKRTG GGSGGGGSGG  120
GASEVQLVES GGGLVQPGGS LRLSCAASGF NIFRGYMHWV RQAPGKGLEW VAMISPHSDY  180
TSYADSVKGR FTISADTSKN TAYLQMNSLR AEDTAVYYCS RSYGWAAFDY WGQGTLVTVS  240
S                                                                  241

SEQ ID NO: 9            moltype = AA  length = 10
FEATURE                 Location/Qualifiers
source                  1..10
                        mol_type = protein
                        organism = synthetic construct
SEQUENCE: 9
RPIPIKYKAM                                                         10

SEQ ID NO: 10           moltype = AA  length = 10
FEATURE                 Location/Qualifiers
source                  1..10
                        mol_type = protein
                        organism = synthetic construct
SEQUENCE: 10
KPITIGRHAH                                                         10

SEQ ID NO: 11           moltype = AA  length = 9
FEATURE                 Location/Qualifiers
source                  1..9
                        mol_type = protein
                        organism = synthetic construct
SEQUENCE: 11
AVGVGKSAL                                                          9

SEQ ID NO: 12           moltype = AA  length = 9
FEATURE                 Location/Qualifiers
source                  1..9
                        mol_type = protein
                        organism = synthetic construct
SEQUENCE: 12
```

```
AGGVGKSAL                                                          9

SEQ ID NO: 13            moltype = AA  length = 9
FEATURE                  Location/Qualifiers
source                   1..9
                         mol_type = protein
                         organism = synthetic construct
SEQUENCE: 13
IMQLMPFGC                                                          9

SEQ ID NO: 14            moltype = AA  length = 9
FEATURE                  Location/Qualifiers
source                   1..9
                         mol_type = protein
                         organism = synthetic construct
SEQUENCE: 14
ITQLMPFGC                                                          9

SEQ ID NO: 15            moltype = AA  length = 10
FEATURE                  Location/Qualifiers
source                   1..10
                         mol_type = protein
                         organism = synthetic construct
SEQUENCE: 15
GMNQRPILTI                                                         10

SEQ ID NO: 16            moltype = AA  length = 10
FEATURE                  Location/Qualifiers
source                   1..10
                         mol_type = protein
                         organism = synthetic construct
SEQUENCE: 16
GMNWRPILTI                                                         10

SEQ ID NO: 17            moltype = AA  length = 10
FEATURE                  Location/Qualifiers
source                   1..10
                         mol_type = protein
                         organism = synthetic construct
SEQUENCE: 17
GMNRRPILTI                                                         10

SEQ ID NO: 18            moltype = AA  length = 9
FEATURE                  Location/Qualifiers
source                   1..9
                         mol_type = protein
                         organism = synthetic construct
SEQUENCE: 18
LVVVGAVGV                                                          9

SEQ ID NO: 19            moltype = AA  length = 9
FEATURE                  Location/Qualifiers
source                   1..9
                         mol_type = protein
                         organism = synthetic construct
SEQUENCE: 19
LVVVGAGGV                                                          9

SEQ ID NO: 20            moltype = AA  length = 10
FEATURE                  Location/Qualifiers
source                   1..10
                         mol_type = protein
                         organism = synthetic construct
SEQUENCE: 20
VVVGACGVGK                                                         10

SEQ ID NO: 21            moltype = AA  length = 10
FEATURE                  Location/Qualifiers
source                   1..10
                         mol_type = protein
                         organism = synthetic construct
SEQUENCE: 21
VVVGADGVGK                                                         10

SEQ ID NO: 22            moltype = AA  length = 9
FEATURE                  Location/Qualifiers
source                   1..9
                         mol_type = protein
                         organism = synthetic construct
```

```
SEQUENCE: 22
VVGAVGVGK                                                    9

SEQ ID NO: 23          moltype = AA  length = 10
FEATURE                Location/Qualifiers
source                 1..10
                       mol_type = protein
                       organism = synthetic construct
SEQUENCE: 23
VVVGAGGVGK                                                   10

SEQ ID NO: 24          moltype = AA  length = 9
FEATURE                Location/Qualifiers
source                 1..9
                       mol_type = protein
                       organism = synthetic construct
SEQUENCE: 24
VVGADGVGK                                                    9

SEQ ID NO: 25          moltype = AA  length = 9
FEATURE                Location/Qualifiers
source                 1..9
                       mol_type = protein
                       organism = synthetic construct
SEQUENCE: 25
VVGAGGVGK                                                    9

SEQ ID NO: 26          moltype = AA  length = 9
FEATURE                Location/Qualifiers
source                 1..9
                       mol_type = protein
                       organism = synthetic construct
SEQUENCE: 26
TTAPFLSGK                                                    9

SEQ ID NO: 27          moltype = AA  length = 9
FEATURE                Location/Qualifiers
source                 1..9
                       mol_type = protein
                       organism = synthetic construct
SEQUENCE: 27
TTAPSLSGK                                                    9

SEQ ID NO: 28          moltype = AA  length = 10
FEATURE                Location/Qualifiers
source                 1..10
                       mol_type = protein
                       organism = synthetic construct
SEQUENCE: 28
ILDTAGHEEY                                                   10

SEQ ID NO: 29          moltype = AA  length = 10
FEATURE                Location/Qualifiers
source                 1..10
                       mol_type = protein
                       organism = synthetic construct
SEQUENCE: 29
ILDTAGQEEY                                                   10

SEQ ID NO: 30          moltype = AA  length = 10
FEATURE                Location/Qualifiers
source                 1..10
                       mol_type = protein
                       organism = synthetic construct
SEQUENCE: 30
ILDTAGKEEY                                                   10

SEQ ID NO: 31          moltype = AA  length = 10
FEATURE                Location/Qualifiers
source                 1..10
                       mol_type = protein
                       organism = synthetic construct
SEQUENCE: 31
ILDTAGLEEY                                                   10

SEQ ID NO: 32          moltype = AA  length = 10
FEATURE                Location/Qualifiers
source                 1..10
                       mol_type = protein
```

```
                        organism = synthetic construct
SEQUENCE: 32
ILDTAGREEY                                                                10

SEQ ID NO: 33           moltype = AA  length = 6
FEATURE                 Location/Qualifiers
source                  1..6
                        mol_type = protein
                        organism = synthetic construct
SEQUENCE: 33
QDVNTA                                                                    6

SEQ ID NO: 34           moltype = AA  length = 9
FEATURE                 Location/Qualifiers
source                  1..9
                        mol_type = protein
                        organism = synthetic construct
SEQUENCE: 34
QQYDYAPIT                                                                 9

SEQ ID NO: 35           moltype = AA  length = 11
FEATURE                 Location/Qualifiers
source                  1..11
                        mol_type = protein
                        organism = synthetic construct
SEQUENCE: 35
QQSPYYYLPI T                                                              11

SEQ ID NO: 36           moltype = AA  length = 9
FEATURE                 Location/Qualifiers
source                  1..9
                        mol_type = protein
                        organism = synthetic construct
SEQUENCE: 36
QQYYYSPVT                                                                 9

SEQ ID NO: 37           moltype = AA  length = 9
FEATURE                 Location/Qualifiers
source                  1..9
                        mol_type = protein
                        organism = synthetic construct
SEQUENCE: 37
QQHYGNPFT                                                                 9

SEQ ID NO: 38           moltype = AA  length = 9
FEATURE                 Location/Qualifiers
source                  1..9
                        mol_type = protein
                        organism = synthetic construct
SEQUENCE: 38
QQSYYSPPT                                                                 9

SEQ ID NO: 39           moltype = AA  length = 9
FEATURE                 Location/Qualifiers
source                  1..9
                        mol_type = protein
                        organism = synthetic construct
SEQUENCE: 39
QQYYSYPPT                                                                 9

SEQ ID NO: 40           moltype = AA  length = 9
FEATURE                 Location/Qualifiers
source                  1..9
                        mol_type = protein
                        organism = synthetic construct
SEQUENCE: 40
QQYYYYPPT                                                                 9

SEQ ID NO: 41           moltype = AA  length = 8
FEATURE                 Location/Qualifiers
source                  1..8
                        mol_type = protein
                        organism = synthetic construct
SEQUENCE: 41
GFNISWYQ                                                                  8

SEQ ID NO: 42           moltype = AA  length = 8
FEATURE                 Location/Qualifiers
source                  1..8
```

```
                        mol_type = protein
                        organism = synthetic construct
SEQUENCE: 42
GFNVSWSY                                                                  8

SEQ ID NO: 43           moltype = AA  length = 8
FEATURE                 Location/Qualifiers
source                  1..8
                        mol_type = protein
                        organism = synthetic construct
SEQUENCE: 43
GFNISWNQ                                                                  8

SEQ ID NO: 44           moltype = AA  length = 8
FEATURE                 Location/Qualifiers
source                  1..8
                        mol_type = protein
                        organism = synthetic construct
SEQUENCE: 44
GFNVGYYG                                                                  8

SEQ ID NO: 45           moltype = AA  length = 8
FEATURE                 Location/Qualifiers
source                  1..8
                        mol_type = protein
                        organism = synthetic construct
SEQUENCE: 45
GFNITSSY                                                                  8

SEQ ID NO: 46           moltype = AA  length = 8
FEATURE                 Location/Qualifiers
source                  1..8
                        mol_type = protein
                        organism = synthetic construct
SEQUENCE: 46
GFNINSSY                                                                  8

SEQ ID NO: 47           moltype = AA  length = 8
FEATURE                 Location/Qualifiers
source                  1..8
                        mol_type = protein
                        organism = synthetic construct
SEQUENCE: 47
GFNISTSY                                                                  8

SEQ ID NO: 48           moltype = AA  length = 8
FEATURE                 Location/Qualifiers
source                  1..8
                        mol_type = protein
                        organism = synthetic construct
SEQUENCE: 48
VTPYSGYT                                                                  8

SEQ ID NO: 49           moltype = AA  length = 8
FEATURE                 Location/Qualifiers
source                  1..8
                        mol_type = protein
                        organism = synthetic construct
SEQUENCE: 49
IYGDSGYT                                                                  8

SEQ ID NO: 50           moltype = AA  length = 8
FEATURE                 Location/Qualifiers
source                  1..8
                        mol_type = protein
                        organism = synthetic construct
SEQUENCE: 50
VSPYSGYT                                                                  8

SEQ ID NO: 51           moltype = AA  length = 8
FEATURE                 Location/Qualifiers
source                  1..8
                        mol_type = protein
                        organism = synthetic construct
SEQUENCE: 51
VSGMEGYT                                                                  8

SEQ ID NO: 52           moltype = AA  length = 8
FEATURE                 Location/Qualifiers
```

```
source                  1..8
                        mol_type = protein
                        organism = synthetic construct
SEQUENCE: 52
ISPADGYN                                                                    8

SEQ ID NO: 53           moltype = AA  length = 8
FEATURE                 Location/Qualifiers
source                  1..8
                        mol_type = protein
                        organism = synthetic construct
SEQUENCE: 53
ISPTDGYY                                                                    8

SEQ ID NO: 54           moltype = AA  length = 8
FEATURE                 Location/Qualifiers
source                  1..8
                        mol_type = protein
                        organism = synthetic construct
SEQUENCE: 54
IDPNDGYS                                                                    8

SEQ ID NO: 55           moltype = AA  length = 10
FEATURE                 Location/Qualifiers
source                  1..10
                        mol_type = protein
                        organism = synthetic construct
SEQUENCE: 55
SRSYTDGFDY                                                                  10

SEQ ID NO: 56           moltype = AA  length = 14
FEATURE                 Location/Qualifiers
source                  1..14
                        mol_type = protein
                        organism = synthetic construct
SEQUENCE: 56
SRGQWEASYY AMDY                                                             14

SEQ ID NO: 57           moltype = AA  length = 10
FEATURE                 Location/Qualifiers
source                  1..10
                        mol_type = protein
                        organism = synthetic construct
SEQUENCE: 57
SRSDYYAMDY                                                                  10

SEQ ID NO: 58           moltype = AA  length = 11
FEATURE                 Location/Qualifiers
source                  1..11
                        mol_type = protein
                        organism = synthetic construct
SEQUENCE: 58
SRDIYGYAMD V                                                                11

SEQ ID NO: 59           moltype = AA  length = 13
FEATURE                 Location/Qualifiers
source                  1..13
                        mol_type = protein
                        organism = synthetic construct
SEQUENCE: 59
SRTDSTAYTA MDV                                                              13

SEQ ID NO: 60           moltype = AA  length = 13
FEATURE                 Location/Qualifiers
source                  1..13
                        mol_type = protein
                        organism = synthetic construct
SEQUENCE: 60
SRTSDTSYAA MDV                                                              13

SEQ ID NO: 61           moltype = AA  length = 13
FEATURE                 Location/Qualifiers
source                  1..13
                        mol_type = protein
                        organism = synthetic construct
SEQUENCE: 61
SRTNNTAADA MDV                                                              13

SEQ ID NO: 62           moltype = AA  length = 9
```

```
FEATURE                Location/Qualifiers
source                 1..9
                       mol_type = protein
                       organism = synthetic construct
SEQUENCE: 62
QQYSYSPPT                                                      9

SEQ ID NO: 63          moltype = AA  length = 10
FEATURE                Location/Qualifiers
source                 1..10
                       mol_type = protein
                       organism = synthetic construct
SEQUENCE: 63
QQGKAYWPAT                                                     10

SEQ ID NO: 64          moltype = AA  length = 9
FEATURE                Location/Qualifiers
source                 1..9
                       mol_type = protein
                       organism = synthetic construct
SEQUENCE: 64
QQVYSSPFT                                                      9

SEQ ID NO: 65          moltype = AA  length = 10
FEATURE                Location/Qualifiers
source                 1..10
                       mol_type = protein
                       organism = synthetic construct
SEQUENCE: 65
QQYSLYSPMT                                                     10

SEQ ID NO: 66          moltype = AA  length = 9
FEATURE                Location/Qualifiers
source                 1..9
                       mol_type = protein
                       organism = synthetic construct
SEQUENCE: 66
QQSYYMPFT                                                      9

SEQ ID NO: 67          moltype = AA  length = 8
FEATURE                Location/Qualifiers
source                 1..8
                       mol_type = protein
                       organism = synthetic construct
SEQUENCE: 67
GFNISDTY                                                       8

SEQ ID NO: 68          moltype = AA  length = 8
FEATURE                Location/Qualifiers
source                 1..8
                       mol_type = protein
                       organism = synthetic construct
SEQUENCE: 68
GFNVGHYR                                                       8

SEQ ID NO: 69          moltype = AA  length = 8
FEATURE                Location/Qualifiers
source                 1..8
                       mol_type = protein
                       organism = synthetic construct
SEQUENCE: 69
GFNVKYYM                                                       8

SEQ ID NO: 70          moltype = AA  length = 7
FEATURE                Location/Qualifiers
source                 1..7
                       mol_type = protein
                       organism = synthetic construct
SEQUENCE: 70
GFNSFLS                                                        7

SEQ ID NO: 71          moltype = AA  length = 8
FEATURE                Location/Qualifiers
source                 1..8
                       mol_type = protein
                       organism = synthetic construct
SEQUENCE: 71
GFNIFRGY                                                       8
```

```
SEQ ID NO: 72           moltype = AA  length = 8
FEATURE                 Location/Qualifiers
source                  1..8
                        mol_type = protein
                        organism = synthetic construct
SEQUENCE: 72
ISPRTGYN                                                    8

SEQ ID NO: 73           moltype = AA  length = 8
FEATURE                 Location/Qualifiers
source                  1..8
                        mol_type = protein
                        organism = synthetic construct
SEQUENCE: 73
VSPNGYYT                                                    8

SEQ ID NO: 74           moltype = AA  length = 8
FEATURE                 Location/Qualifiers
source                  1..8
                        mol_type = protein
                        organism = synthetic construct
SEQUENCE: 74
ISPGYDYT                                                    8

SEQ ID NO: 75           moltype = AA  length = 8
FEATURE                 Location/Qualifiers
source                  1..8
                        mol_type = protein
                        organism = synthetic construct
SEQUENCE: 75
IFPSSDYT                                                    8

SEQ ID NO: 76           moltype = AA  length = 8
FEATURE                 Location/Qualifiers
source                  1..8
                        mol_type = protein
                        organism = synthetic construct
SEQUENCE: 76
ISPHSDYT                                                    8

SEQ ID NO: 77           moltype = AA  length = 13
FEATURE                 Location/Qualifiers
source                  1..13
                        mol_type = protein
                        organism = synthetic construct
SEQUENCE: 77
SRAYYSYAYA MDV                                              13

SEQ ID NO: 78           moltype = AA  length = 11
FEATURE                 Location/Qualifiers
source                  1..11
                        mol_type = protein
                        organism = synthetic construct
SEQUENCE: 78
SRGYSSYAFD Y                                                11

SEQ ID NO: 79           moltype = AA  length = 11
FEATURE                 Location/Qualifiers
source                  1..11
                        mol_type = protein
                        organism = synthetic construct
SEQUENCE: 79
SRSYWRYSVD V                                                11

SEQ ID NO: 80           moltype = AA  length = 15
FEATURE                 Location/Qualifiers
source                  1..15
                        mol_type = protein
                        organism = synthetic construct
SEQUENCE: 80
SRGKHSSDSN YYMDY                                            15

SEQ ID NO: 81           moltype = AA  length = 11
FEATURE                 Location/Qualifiers
source                  1..11
                        mol_type = protein
                        organism = synthetic construct
SEQUENCE: 81
SRSYGWAAFD Y                                                11
```

```
SEQ ID NO: 82           moltype = AA  length = 9
FEATURE                 Location/Qualifiers
source                  1..9
                        mol_type = protein
                        organism = synthetic construct
SEQUENCE: 82
QQSGYAPIT                                                              9

SEQ ID NO: 83           moltype = AA  length = 9
FEATURE                 Location/Qualifiers
source                  1..9
                        mol_type = protein
                        organism = synthetic construct
SEQUENCE: 83
QQYSYAPIT                                                              9

SEQ ID NO: 84           moltype = AA  length = 9
FEATURE                 Location/Qualifiers
source                  1..9
                        mol_type = protein
                        organism = synthetic construct
SEQUENCE: 84
QQSLYGPFT                                                              9

SEQ ID NO: 85           moltype = AA  length = 9
FEATURE                 Location/Qualifiers
source                  1..9
                        mol_type = protein
                        organism = synthetic construct
SEQUENCE: 85
QQYSYSPIT                                                              9

SEQ ID NO: 86           moltype = AA  length = 9
FEATURE                 Location/Qualifiers
source                  1..9
                        mol_type = protein
                        organism = synthetic construct
SEQUENCE: 86
QQSGYQPDT                                                              9

SEQ ID NO: 87           moltype = AA  length = 9
FEATURE                 Location/Qualifiers
source                  1..9
                        mol_type = protein
                        organism = synthetic construct
SEQUENCE: 87
QQYLYQPWT                                                              9

SEQ ID NO: 88           moltype = AA  length = 9
FEATURE                 Location/Qualifiers
source                  1..9
                        mol_type = protein
                        organism = synthetic construct
SEQUENCE: 88
QQGLYYPWT                                                              9

SEQ ID NO: 89           moltype = AA  length = 8
FEATURE                 Location/Qualifiers
source                  1..8
                        mol_type = protein
                        organism = synthetic construct
SEQUENCE: 89
GFNISYYS                                                               8

SEQ ID NO: 90           moltype = AA  length = 8
FEATURE                 Location/Qualifiers
source                  1..8
                        mol_type = protein
                        organism = synthetic construct
SEQUENCE: 90
GFNIGYYT                                                               8

SEQ ID NO: 91           moltype = AA  length = 8
FEATURE                 Location/Qualifiers
source                  1..8
                        mol_type = protein
                        organism = synthetic construct
SEQUENCE: 91
```

-continued

```
GFNIAYEY                                                                  8

SEQ ID NO: 92           moltype = AA  length = 8
FEATURE                 Location/Qualifiers
source                  1..8
                        mol_type = protein
                        organism = synthetic construct
SEQUENCE: 92
GFNLFGYG                                                                  8

SEQ ID NO: 93           moltype = AA  length = 8
FEATURE                 Location/Qualifiers
source                  1..8
                        mol_type = protein
                        organism = synthetic construct
SEQUENCE: 93
GFNISWYA                                                                  8

SEQ ID NO: 94           moltype = AA  length = 8
FEATURE                 Location/Qualifiers
source                  1..8
                        mol_type = protein
                        organism = synthetic construct
SEQUENCE: 94
GFNIDYYG                                                                  8

SEQ ID NO: 95           moltype = AA  length = 8
FEATURE                 Location/Qualifiers
source                  1..8
                        mol_type = protein
                        organism = synthetic construct
SEQUENCE: 95
GFNVSYSS                                                                  8

SEQ ID NO: 96           moltype = AA  length = 8
FEATURE                 Location/Qualifiers
source                  1..8
                        mol_type = protein
                        organism = synthetic construct
SEQUENCE: 96
VDPDSDYT                                                                  8

SEQ ID NO: 97           moltype = AA  length = 8
FEATURE                 Location/Qualifiers
source                  1..8
                        mol_type = protein
                        organism = synthetic construct
SEQUENCE: 97
VSPWSYST                                                                  8

SEQ ID NO: 98           moltype = AA  length = 8
FEATURE                 Location/Qualifiers
source                  1..8
                        mol_type = protein
                        organism = synthetic construct
SEQUENCE: 98
IGPDSGYT                                                                  8

SEQ ID NO: 99           moltype = AA  length = 8
FEATURE                 Location/Qualifiers
source                  1..8
                        mol_type = protein
                        organism = synthetic construct
SEQUENCE: 99
IGPYYYYT                                                                  8

SEQ ID NO: 100          moltype = AA  length = 8
FEATURE                 Location/Qualifiers
source                  1..8
                        mol_type = protein
                        organism = synthetic construct
SEQUENCE: 100
IWPDSDWT                                                                  8

SEQ ID NO: 101          moltype = AA  length = 8
FEATURE                 Location/Qualifiers
source                  1..8
                        mol_type = protein
                        organism = synthetic construct
```

```
SEQUENCE: 101
LYGGSDST                                                      8

SEQ ID NO: 102          moltype = AA  length = 8
FEATURE                 Location/Qualifiers
source                  1..8
                        mol_type = protein
                        organism = synthetic construct
SEQUENCE: 102
IWPDSGQT                                                      8

SEQ ID NO: 103          moltype = AA  length = 12
FEATURE                 Location/Qualifiers
source                  1..12
                        mol_type = protein
                        organism = synthetic construct
SEQUENCE: 103
SRSWIHMFSM DY                                                 12

SEQ ID NO: 104          moltype = AA  length = 11
FEATURE                 Location/Qualifiers
source                  1..11
                        mol_type = protein
                        organism = synthetic construct
SEQUENCE: 104
SRDHWDEAFD V                                                  11

SEQ ID NO: 105          moltype = AA  length = 13
FEATURE                 Location/Qualifiers
source                  1..13
                        mol_type = protein
                        organism = synthetic construct
SEQUENCE: 105
SRVWYYSTYG MDY                                                13

SEQ ID NO: 106          moltype = AA  length = 11
FEATURE                 Location/Qualifiers
source                  1..11
                        mol_type = protein
                        organism = synthetic construct
SEQUENCE: 106
SRENYDMAMD Y                                                  11

SEQ ID NO: 107          moltype = AA  length = 11
FEATURE                 Location/Qualifiers
source                  1..11
                        mol_type = protein
                        organism = synthetic construct
SEQUENCE: 107
SRYYYSSAFD V                                                  11

SEQ ID NO: 108          moltype = AA  length = 10
FEATURE                 Location/Qualifiers
source                  1..10
                        mol_type = protein
                        organism = synthetic construct
SEQUENCE: 108
SRQYSAYFDY                                                    10

SEQ ID NO: 109          moltype = AA  length = 11
FEATURE                 Location/Qualifiers
source                  1..11
                        mol_type = protein
                        organism = synthetic construct
SEQUENCE: 109
SRSSYFDAMD Y                                                  11

SEQ ID NO: 110          moltype = AA  length = 9
FEATURE                 Location/Qualifiers
source                  1..9
                        mol_type = protein
                        organism = synthetic construct
SEQUENCE: 110
QQWYSSPVT                                                     9

SEQ ID NO: 111          moltype = AA  length = 8
FEATURE                 Location/Qualifiers
source                  1..8
                        mol_type = protein
```

```
                        organism = synthetic construct
SEQUENCE: 111
GFNINWAN                                                                8

SEQ ID NO: 112          moltype = AA  length = 8
FEATURE                 Location/Qualifiers
source                  1..8
                        mol_type = protein
                        organism = synthetic construct
SEQUENCE: 112
GFNINWAN                                                                8

SEQ ID NO: 113          moltype = AA  length = 8
FEATURE                 Location/Qualifiers
source                  1..8
                        mol_type = protein
                        organism = synthetic construct
SEQUENCE: 113
GFNIYLHD                                                                8

SEQ ID NO: 114          moltype = AA  length = 8
FEATURE                 Location/Qualifiers
source                  1..8
                        mol_type = protein
                        organism = synthetic construct
SEQUENCE: 114
GFNIYWSH                                                                8

SEQ ID NO: 115          moltype = AA  length = 8
FEATURE                 Location/Qualifiers
source                  1..8
                        mol_type = protein
                        organism = synthetic construct
SEQUENCE: 115
ISPPYDYT                                                                8

SEQ ID NO: 116          moltype = AA  length = 8
FEATURE                 Location/Qualifiers
source                  1..8
                        mol_type = protein
                        organism = synthetic construct
SEQUENCE: 116
IIPAIDYT                                                                8

SEQ ID NO: 117          moltype = AA  length = 8
FEATURE                 Location/Qualifiers
source                  1..8
                        mol_type = protein
                        organism = synthetic construct
SEQUENCE: 117
ISSFEGYT                                                                8

SEQ ID NO: 118          moltype = AA  length = 10
FEATURE                 Location/Qualifiers
source                  1..10
                        mol_type = protein
                        organism = synthetic construct
SEQUENCE: 118
SRSYSYYFDY                                                              10

SEQ ID NO: 119          moltype = AA  length = 10
FEATURE                 Location/Qualifiers
source                  1..10
                        mol_type = protein
                        organism = synthetic construct
SEQUENCE: 119
SRRDGYYFDY                                                              10

SEQ ID NO: 120          moltype = AA  length = 10
FEATURE                 Location/Qualifiers
source                  1..10
                        mol_type = protein
                        organism = synthetic construct
SEQUENCE: 120
SRSYSYYMDY                                                              10

SEQ ID NO: 121          moltype = AA  length = 11
FEATURE                 Location/Qualifiers
source                  1..11
```

```
                        mol_type = protein
                        organism = synthetic construct
SEQUENCE: 121
QQSYGSGSPW T                                                    11

SEQ ID NO: 122          moltype = AA  length = 9
FEATURE                 Location/Qualifiers
source                  1..9
                        mol_type = protein
                        organism = synthetic construct
SEQUENCE: 122
QQTYYSPWT                                                       9

SEQ ID NO: 123          moltype = AA  length = 9
FEATURE                 Location/Qualifiers
source                  1..9
                        mol_type = protein
                        organism = synthetic construct
SEQUENCE: 123
QQYYYPPIT                                                       9

SEQ ID NO: 124          moltype = AA  length = 8
FEATURE                 Location/Qualifiers
source                  1..8
                        mol_type = protein
                        organism = synthetic construct
SEQUENCE: 124
GFNIVGGG                                                        8

SEQ ID NO: 125          moltype = AA  length = 8
FEATURE                 Location/Qualifiers
source                  1..8
                        mol_type = protein
                        organism = synthetic construct
SEQUENCE: 125
GFNIRSYA                                                        8

SEQ ID NO: 126          moltype = AA  length = 8
FEATURE                 Location/Qualifiers
source                  1..8
                        mol_type = protein
                        organism = synthetic construct
SEQUENCE: 126
GFNVSHTG                                                        8

SEQ ID NO: 127          moltype = AA  length = 8
FEATURE                 Location/Qualifiers
source                  1..8
                        mol_type = protein
                        organism = synthetic construct
SEQUENCE: 127
IYPQGDYT                                                        8

SEQ ID NO: 128          moltype = AA  length = 8
FEATURE                 Location/Qualifiers
source                  1..8
                        mol_type = protein
                        organism = synthetic construct
SEQUENCE: 128
VGPGKGYT                                                        8

SEQ ID NO: 129          moltype = AA  length = 11
FEATURE                 Location/Qualifiers
source                  1..11
                        mol_type = protein
                        organism = synthetic construct
SEQUENCE: 129
SRDSSYLAFD Y                                                    11

SEQ ID NO: 130          moltype = AA  length = 13
FEATURE                 Location/Qualifiers
source                  1..13
                        mol_type = protein
                        organism = synthetic construct
SEQUENCE: 130
SRNFQSTSHA FDY                                                  13

SEQ ID NO: 131          moltype = AA  length = 10
FEATURE                 Location/Qualifiers
```

```
source                  1..10
                        mol_type = protein
                        organism = synthetic construct
SEQUENCE: 131
SRKTYYAFDY                                                    10

SEQ ID NO: 132          moltype = AA  length = 11
FEATURE                 Location/Qualifiers
source                  1..11
                        mol_type = protein
                        organism = synthetic construct
SEQUENCE: 132
QQSYYYFRPI T                                                  11

SEQ ID NO: 133          moltype = AA  length = 10
FEATURE                 Location/Qualifiers
source                  1..10
                        mol_type = protein
                        organism = synthetic construct
SEQUENCE: 133
QQASYYYPLT                                                    10

SEQ ID NO: 134          moltype = AA  length = 10
FEATURE                 Location/Qualifiers
source                  1..10
                        mol_type = protein
                        organism = synthetic construct
SEQUENCE: 134
QQKSEYSPWT                                                    10

SEQ ID NO: 135          moltype = AA  length = 9
FEATURE                 Location/Qualifiers
source                  1..9
                        mol_type = protein
                        organism = synthetic construct
SEQUENCE: 135
QQSGYIPFT                                                     9

SEQ ID NO: 136          moltype = AA  length = 10
FEATURE                 Location/Qualifiers
source                  1..10
                        mol_type = protein
                        organism = synthetic construct
SEQUENCE: 136
QQGAYYRPFT                                                    10

SEQ ID NO: 137          moltype = AA  length = 8
FEATURE                 Location/Qualifiers
source                  1..8
                        mol_type = protein
                        organism = synthetic construct
SEQUENCE: 137
GFNLSYSD                                                      8

SEQ ID NO: 138          moltype = AA  length = 8
FEATURE                 Location/Qualifiers
source                  1..8
                        mol_type = protein
                        organism = synthetic construct
SEQUENCE: 138
GFNISASG                                                      8

SEQ ID NO: 139          moltype = AA  length = 8
FEATURE                 Location/Qualifiers
source                  1..8
                        mol_type = protein
                        organism = synthetic construct
SEQUENCE: 139
GFNIYRYG                                                      8

SEQ ID NO: 140          moltype = AA  length = 8
FEATURE                 Location/Qualifiers
source                  1..8
                        mol_type = protein
                        organism = synthetic construct
SEQUENCE: 140
GFNIYGTM                                                      8

SEQ ID NO: 141          moltype = AA  length = 8
```

```
FEATURE                Location/Qualifiers
source                 1..8
                       mol_type = protein
                       organism = synthetic construct
SEQUENCE: 141
GFNISYSY                                                      8

SEQ ID NO: 142         moltype = AA  length = 8
FEATURE                Location/Qualifiers
source                 1..8
                       mol_type = protein
                       organism = synthetic construct
SEQUENCE: 142
VMPDSGHT                                                      8

SEQ ID NO: 143         moltype = AA  length = 8
FEATURE                Location/Qualifiers
source                 1..8
                       mol_type = protein
                       organism = synthetic construct
SEQUENCE: 143
IHPLKPYT                                                      8

SEQ ID NO: 144         moltype = AA  length = 8
FEATURE                Location/Qualifiers
source                 1..8
                       mol_type = protein
                       organism = synthetic construct
SEQUENCE: 144
LYPYGYST                                                      8

SEQ ID NO: 145         moltype = AA  length = 8
FEATURE                Location/Qualifiers
source                 1..8
                       mol_type = protein
                       organism = synthetic construct
SEQUENCE: 145
FKPDSYNT                                                      8

SEQ ID NO: 146         moltype = AA  length = 8
FEATURE                Location/Qualifiers
source                 1..8
                       mol_type = protein
                       organism = synthetic construct
SEQUENCE: 146
LLPYDGNT                                                      8

SEQ ID NO: 147         moltype = AA  length = 13
FEATURE                Location/Qualifiers
source                 1..13
                       mol_type = protein
                       organism = synthetic construct
SEQUENCE: 147
SRATNIPVYA FDY                                                13

SEQ ID NO: 148         moltype = AA  length = 13
FEATURE                Location/Qualifiers
source                 1..13
                       mol_type = protein
                       organism = synthetic construct
SEQUENCE: 148
SRYSSMYYYY FDY                                                13

SEQ ID NO: 149         moltype = AA  length = 11
FEATURE                Location/Qualifiers
source                 1..11
                       mol_type = protein
                       organism = synthetic construct
SEQUENCE: 149
SRSYAYGYFA Y                                                  11

SEQ ID NO: 150         moltype = AA  length = 13
FEATURE                Location/Qualifiers
source                 1..13
                       mol_type = protein
                       organism = synthetic construct
SEQUENCE: 150
SRGEVYHYYA FDY                                                13
```

```
SEQ ID NO: 151          moltype = AA  length = 10
FEATURE                 Location/Qualifiers
source                  1..10
                        mol_type = protein
                        organism = synthetic construct
SEQUENCE: 151
SRAAYSSMDV                                                    10

SEQ ID NO: 152          moltype = AA  length = 9
FEATURE                 Location/Qualifiers
source                  1..9
                        mol_type = protein
                        organism = synthetic construct
SEQUENCE: 152
QQYMYSPVT                                                     9

SEQ ID NO: 153          moltype = AA  length = 9
FEATURE                 Location/Qualifiers
source                  1..9
                        mol_type = protein
                        organism = synthetic construct
SEQUENCE: 153
QQSSSSPIT                                                     9

SEQ ID NO: 154          moltype = AA  length = 9
FEATURE                 Location/Qualifiers
source                  1..9
                        mol_type = protein
                        organism = synthetic construct
SEQUENCE: 154
QQSSASPLT                                                     9

SEQ ID NO: 155          moltype = AA  length = 9
FEATURE                 Location/Qualifiers
source                  1..9
                        mol_type = protein
                        organism = synthetic construct
SEQUENCE: 155
QQYAYSPLT                                                     9

SEQ ID NO: 156          moltype = AA  length = 8
FEATURE                 Location/Qualifiers
source                  1..8
                        mol_type = protein
                        organism = synthetic construct
SEQUENCE: 156
GFNVSAYW                                                      8

SEQ ID NO: 157          moltype = AA  length = 8
FEATURE                 Location/Qualifiers
source                  1..8
                        mol_type = protein
                        organism = synthetic construct
SEQUENCE: 157
GFNISGYG                                                      8

SEQ ID NO: 158          moltype = AA  length = 8
FEATURE                 Location/Qualifiers
source                  1..8
                        mol_type = protein
                        organism = synthetic construct
SEQUENCE: 158
GFNVSSVG                                                      8

SEQ ID NO: 159          moltype = AA  length = 8
FEATURE                 Location/Qualifiers
source                  1..8
                        mol_type = protein
                        organism = synthetic construct
SEQUENCE: 159
GFNVSSYG                                                      8

SEQ ID NO: 160          moltype = AA  length = 8
FEATURE                 Location/Qualifiers
source                  1..8
                        mol_type = protein
                        organism = synthetic construct
SEQUENCE: 160
IYGGSGYT                                                      8
```

```
SEQ ID NO: 161          moltype = AA  length = 8
FEATURE                 Location/Qualifiers
source                  1..8
                        mol_type = protein
                        organism = synthetic construct
SEQUENCE: 161
LYGGSDYT                                                    8

SEQ ID NO: 162          moltype = AA  length = 8
FEATURE                 Location/Qualifiers
source                  1..8
                        mol_type = protein
                        organism = synthetic construct
SEQUENCE: 162
IYGTSDYT                                                    8

SEQ ID NO: 163          moltype = AA  length = 8
FEATURE                 Location/Qualifiers
source                  1..8
                        mol_type = protein
                        organism = synthetic construct
SEQUENCE: 163
IAPRRDYT                                                    8

SEQ ID NO: 164          moltype = AA  length = 12
FEATURE                 Location/Qualifiers
source                  1..12
                        mol_type = protein
                        organism = synthetic construct
SEQUENCE: 164
SRTHSYWSAF DY                                               12

SEQ ID NO: 165          moltype = AA  length = 10
FEATURE                 Location/Qualifiers
source                  1..10
                        mol_type = protein
                        organism = synthetic construct
SEQUENCE: 165
SRTVRYAFDY                                                  10

SEQ ID NO: 166          moltype = AA  length = 10
FEATURE                 Location/Qualifiers
source                  1..10
                        mol_type = protein
                        organism = synthetic construct
SEQUENCE: 166
SRSSRYSMDY                                                  10

SEQ ID NO: 167          moltype = AA  length = 10
FEATURE                 Location/Qualifiers
source                  1..10
                        mol_type = protein
                        organism = synthetic construct
SEQUENCE: 167
SRKSSYYFDY                                                  10

SEQ ID NO: 168          moltype = AA  length = 9
FEATURE                 Location/Qualifiers
source                  1..9
                        mol_type = protein
                        organism = synthetic construct
SEQUENCE: 168
QQYSYYPIT                                                   9

SEQ ID NO: 169          moltype = AA  length = 9
FEATURE                 Location/Qualifiers
source                  1..9
                        mol_type = protein
                        organism = synthetic construct
SEQUENCE: 169
QQYSYTPVT                                                   9

SEQ ID NO: 170          moltype = AA  length = 9
FEATURE                 Location/Qualifiers
source                  1..9
                        mol_type = protein
                        organism = synthetic construct
SEQUENCE: 170
```

```
QQYSYEPVT                                                                  9

SEQ ID NO: 171          moltype = AA  length = 10
FEATURE                 Location/Qualifiers
source                  1..10
                        mol_type = protein
                        organism = synthetic construct
SEQUENCE: 171
QQYAYYSPVT                                                                 10

SEQ ID NO: 172          moltype = AA  length = 9
FEATURE                 Location/Qualifiers
source                  1..9
                        mol_type = protein
                        organism = synthetic construct
SEQUENCE: 172
QQYEYYPMT                                                                  9

SEQ ID NO: 173          moltype = AA  length = 8
FEATURE                 Location/Qualifiers
source                  1..8
                        mol_type = protein
                        organism = synthetic construct
SEQUENCE: 173
GFNFSYGY                                                                   8

SEQ ID NO: 174          moltype = AA  length = 8
FEATURE                 Location/Qualifiers
source                  1..8
                        mol_type = protein
                        organism = synthetic construct
SEQUENCE: 174
GFNVWGPG                                                                   8

SEQ ID NO: 175          moltype = AA  length = 8
FEATURE                 Location/Qualifiers
source                  1..8
                        mol_type = protein
                        organism = synthetic construct
SEQUENCE: 175
GFNVSGSQ                                                                   8

SEQ ID NO: 176          moltype = AA  length = 8
FEATURE                 Location/Qualifiers
source                  1..8
                        mol_type = protein
                        organism = synthetic construct
SEQUENCE: 176
GFNIYGQM                                                                   8

SEQ ID NO: 177          moltype = AA  length = 8
FEATURE                 Location/Qualifiers
source                  1..8
                        mol_type = protein
                        organism = synthetic construct
SEQUENCE: 177
GFNVMYST                                                                   8

SEQ ID NO: 178          moltype = AA  length = 8
FEATURE                 Location/Qualifiers
source                  1..8
                        mol_type = protein
                        organism = synthetic construct
SEQUENCE: 178
ISGYTGNT                                                                   8

SEQ ID NO: 179          moltype = AA  length = 8
FEATURE                 Location/Qualifiers
source                  1..8
                        mol_type = protein
                        organism = synthetic construct
SEQUENCE: 179
IHPFSGNT                                                                   8

SEQ ID NO: 180          moltype = AA  length = 8
FEATURE                 Location/Qualifiers
source                  1..8
                        mol_type = protein
                        organism = synthetic construct
```

```
SEQUENCE: 180
IPGWSGYT                                                          8

SEQ ID NO: 181          moltype = AA  length = 8
FEATURE                 Location/Qualifiers
source                  1..8
                        mol_type = protein
                        organism = synthetic construct
SEQUENCE: 181
LSPFSGNT                                                          8

SEQ ID NO: 182          moltype = AA  length = 8
FEATURE                 Location/Qualifiers
source                  1..8
                        mol_type = protein
                        organism = synthetic construct
SEQUENCE: 182
IYSWSDYT                                                          8

SEQ ID NO: 183          moltype = AA  length = 16
FEATURE                 Location/Qualifiers
source                  1..16
                        mol_type = protein
                        organism = synthetic construct
SEQUENCE: 183
SRAASLSSSY YSAFDV                                                 16

SEQ ID NO: 184          moltype = AA  length = 11
FEATURE                 Location/Qualifiers
source                  1..11
                        mol_type = protein
                        organism = synthetic construct
SEQUENCE: 184
SRGYSYSAMD Y                                                      11

SEQ ID NO: 185          moltype = AA  length = 11
FEATURE                 Location/Qualifiers
source                  1..11
                        mol_type = protein
                        organism = synthetic construct
SEQUENCE: 185
SRGYSYFAMD Y                                                      11

SEQ ID NO: 186          moltype = AA  length = 14
FEATURE                 Location/Qualifiers
source                  1..14
                        mol_type = protein
                        organism = synthetic construct
SEQUENCE: 186
SRNISYEQSS AFDY                                                   14

SEQ ID NO: 187          moltype = AA  length = 11
FEATURE                 Location/Qualifiers
source                  1..11
                        mol_type = protein
                        organism = synthetic construct
SEQUENCE: 187
SRGYAHNSFD Y                                                      11

SEQ ID NO: 188          moltype = AA  length = 9
FEATURE                 Location/Qualifiers
source                  1..9
                        mol_type = protein
                        organism = synthetic construct
SEQUENCE: 188
QQYSFYPFT                                                         9

SEQ ID NO: 189          moltype = AA  length = 11
FEATURE                 Location/Qualifiers
source                  1..11
                        mol_type = protein
                        organism = synthetic construct
SEQUENCE: 189
QQYSAYYQPI T                                                      11

SEQ ID NO: 190          moltype = AA  length = 9
FEATURE                 Location/Qualifiers
source                  1..9
                        mol_type = protein
```

```
                        organism = synthetic construct
SEQUENCE: 190
QQYEYVPHT                                                                  9

SEQ ID NO: 191          moltype = AA  length = 9
FEATURE                 Location/Qualifiers
source                  1..9
                        mol_type = protein
                        organism = synthetic construct
SEQUENCE: 191
QQYSYMPIT                                                                  9

SEQ ID NO: 192          moltype = AA  length = 9
FEATURE                 Location/Qualifiers
source                  1..9
                        mol_type = protein
                        organism = synthetic construct
SEQUENCE: 192
QQYAYYPVT                                                                  9

SEQ ID NO: 193          moltype = AA  length = 9
FEATURE                 Location/Qualifiers
source                  1..9
                        mol_type = protein
                        organism = synthetic construct
SEQUENCE: 193
QQYDYRPVT                                                                  9

SEQ ID NO: 194          moltype = AA  length = 9
FEATURE                 Location/Qualifiers
source                  1..9
                        mol_type = protein
                        organism = synthetic construct
SEQUENCE: 194
QQYDFTPMT                                                                  9

SEQ ID NO: 195          moltype = AA  length = 10
FEATURE                 Location/Qualifiers
source                  1..10
                        mol_type = protein
                        organism = synthetic construct
SEQUENCE: 195
QQYSSSSPVT                                                                 10

SEQ ID NO: 196          moltype = AA  length = 7
FEATURE                 Location/Qualifiers
source                  1..7
                        mol_type = protein
                        organism = synthetic construct
SEQUENCE: 196
GFNFGSY                                                                    7

SEQ ID NO: 197          moltype = AA  length = 8
FEATURE                 Location/Qualifiers
source                  1..8
                        mol_type = protein
                        organism = synthetic construct
SEQUENCE: 197
GFNISDSY                                                                   8

SEQ ID NO: 198          moltype = AA  length = 8
FEATURE                 Location/Qualifiers
source                  1..8
                        mol_type = protein
                        organism = synthetic construct
SEQUENCE: 198
GFNIFSDQ                                                                   8

SEQ ID NO: 199          moltype = AA  length = 8
FEATURE                 Location/Qualifiers
source                  1..8
                        mol_type = protein
                        organism = synthetic construct
SEQUENCE: 199
GFNLSYSY                                                                   8

SEQ ID NO: 200          moltype = AA  length = 8
FEATURE                 Location/Qualifiers
source                  1..8
```

```
                        mol_type = protein
                        organism = synthetic construct
SEQUENCE: 200
GFNISYGY                                                          8

SEQ ID NO: 201          moltype = AA  length = 8
FEATURE                 Location/Qualifiers
source                  1..8
                        mol_type = protein
                        organism = synthetic construct
SEQUENCE: 201
GFNISYQH                                                          8

SEQ ID NO: 202          moltype = AA  length = 8
FEATURE                 Location/Qualifiers
source                  1..8
                        mol_type = protein
                        organism = synthetic construct
SEQUENCE: 202
GFNLSGYY                                                          8

SEQ ID NO: 203          moltype = AA  length = 8
FEATURE                 Location/Qualifiers
source                  1..8
                        mol_type = protein
                        organism = synthetic construct
SEQUENCE: 203
GFNVSGQY                                                          8

SEQ ID NO: 204          moltype = AA  length = 8
FEATURE                 Location/Qualifiers
source                  1..8
                        mol_type = protein
                        organism = synthetic construct
SEQUENCE: 204
GFNVSTSG                                                          8

SEQ ID NO: 205          moltype = AA  length = 8
FEATURE                 Location/Qualifiers
source                  1..8
                        mol_type = protein
                        organism = synthetic construct
SEQUENCE: 205
GFNISYAK                                                          8

SEQ ID NO: 206          moltype = AA  length = 8
FEATURE                 Location/Qualifiers
source                  1..8
                        mol_type = protein
                        organism = synthetic construct
SEQUENCE: 206
GFNFSSYV                                                          8

SEQ ID NO: 207          moltype = AA  length = 8
FEATURE                 Location/Qualifiers
source                  1..8
                        mol_type = protein
                        organism = synthetic construct
SEQUENCE: 207
ISGYSGNT                                                          8

SEQ ID NO: 208          moltype = AA  length = 8
FEATURE                 Location/Qualifiers
source                  1..8
                        mol_type = protein
                        organism = synthetic construct
SEQUENCE: 208
FSPYSSNT                                                          8

SEQ ID NO: 209          moltype = AA  length = 9
FEATURE                 Location/Qualifiers
source                  1..9
                        mol_type = protein
                        organism = synthetic construct
SEQUENCE: 209
FMPYDSYYT                                                         9

SEQ ID NO: 210          moltype = AA  length = 8
FEATURE                 Location/Qualifiers
```

```
source                  1..8
                        mol_type = protein
                        organism = synthetic construct
SEQUENCE: 210
ISGFSGNT                                                       8

SEQ ID NO: 211          moltype = AA  length = 8
FEATURE                 Location/Qualifiers
source                  1..8
                        mol_type = protein
                        organism = synthetic construct
SEQUENCE: 211
FHYGSGNT                                                       8

SEQ ID NO: 212          moltype = AA  length = 8
FEATURE                 Location/Qualifiers
source                  1..8
                        mol_type = protein
                        organism = synthetic construct
SEQUENCE: 212
FMPYQGST                                                       8

SEQ ID NO: 213          moltype = AA  length = 8
FEATURE                 Location/Qualifiers
source                  1..8
                        mol_type = protein
                        organism = synthetic construct
SEQUENCE: 213
FSPYSGYT                                                       8

SEQ ID NO: 214          moltype = AA  length = 8
FEATURE                 Location/Qualifiers
source                  1..8
                        mol_type = protein
                        organism = synthetic construct
SEQUENCE: 214
ISPVSGNT                                                       8

SEQ ID NO: 215          moltype = AA  length = 8
FEATURE                 Location/Qualifiers
source                  1..8
                        mol_type = protein
                        organism = synthetic construct
SEQUENCE: 215
IYGAYSGT                                                       8

SEQ ID NO: 216          moltype = AA  length = 8
FEATURE                 Location/Qualifiers
source                  1..8
                        mol_type = protein
                        organism = synthetic construct
SEQUENCE: 216
LTYWGGYT                                                       8

SEQ ID NO: 217          moltype = AA  length = 8
FEATURE                 Location/Qualifiers
source                  1..8
                        mol_type = protein
                        organism = synthetic construct
SEQUENCE: 217
VYPDSGGT                                                       8

SEQ ID NO: 218          moltype = AA  length = 13
FEATURE                 Location/Qualifiers
source                  1..13
                        mol_type = protein
                        organism = synthetic construct
SEQUENCE: 218
SRSNQSAYSY MDY                                                 13

SEQ ID NO: 219          moltype = AA  length = 13
FEATURE                 Location/Qualifiers
source                  1..13
                        mol_type = protein
                        organism = synthetic construct
SEQUENCE: 219
SRSQFTFYQY FDY                                                 13

SEQ ID NO: 220          moltype = AA  length = 11
```

```
FEATURE                Location/Qualifiers
source                 1..11
                       mol_type = protein
                       organism = synthetic construct
SEQUENCE: 220
SRMSVRNAFD Y                                                      11

SEQ ID NO: 221         moltype = AA  length = 12
FEATURE                Location/Qualifiers
source                 1..12
                       mol_type = protein
                       organism = synthetic construct
SEQUENCE: 221
SRSDSYYTAM DY                                                     12

SEQ ID NO: 222         moltype = AA  length = 10
FEATURE                Location/Qualifiers
source                 1..10
                       mol_type = protein
                       organism = synthetic construct
SEQUENCE: 222
SRSNYYYLDY                                                        10

SEQ ID NO: 223         moltype = AA  length = 14
FEATURE                Location/Qualifiers
source                 1..14
                       mol_type = protein
                       organism = synthetic construct
SEQUENCE: 223
SRANIYSSHS FFDY                                                   14

SEQ ID NO: 224         moltype = AA  length = 13
FEATURE                Location/Qualifiers
source                 1..13
                       mol_type = protein
                       organism = synthetic construct
SEQUENCE: 224
SRTHSSIYHS FDY                                                    13

SEQ ID NO: 225         moltype = AA  length = 14
FEATURE                Location/Qualifiers
source                 1..14
                       mol_type = protein
                       organism = synthetic construct
SEQUENCE: 225
SRPMKTSYYG AFDY                                                   14

SEQ ID NO: 226         moltype = AA  length = 14
FEATURE                Location/Qualifiers
source                 1..14
                       mol_type = protein
                       organism = synthetic construct
SEQUENCE: 226
SRSQSYTYWS AMDY                                                   14

SEQ ID NO: 227         moltype = AA  length = 11
FEATURE                Location/Qualifiers
source                 1..11
                       mol_type = protein
                       organism = synthetic construct
SEQUENCE: 227
SRGEYGTYMD Y                                                      11

SEQ ID NO: 228         moltype = AA  length = 11
FEATURE                Location/Qualifiers
source                 1..11
                       mol_type = protein
                       organism = synthetic construct
SEQUENCE: 228
SRTSSYYAFD Y                                                      11

SEQ ID NO: 229         moltype = AA  length = 8
FEATURE                Location/Qualifiers
source                 1..8
                       mol_type = protein
                       organism = synthetic construct
SEQUENCE: 229
QQSSYTPI                                                          8
```

```
SEQ ID NO: 230          moltype = AA  length = 9
FEATURE                 Location/Qualifiers
source                  1..9
                        mol_type = protein
                        organism = synthetic construct
SEQUENCE: 230
QQYAYYPIT                                                                9

SEQ ID NO: 231          moltype = AA  length = 9
FEATURE                 Location/Qualifiers
source                  1..9
                        mol_type = protein
                        organism = synthetic construct
SEQUENCE: 231
QQYEYYPIT                                                                9

SEQ ID NO: 232          moltype = AA  length = 9
FEATURE                 Location/Qualifiers
source                  1..9
                        mol_type = protein
                        organism = synthetic construct
SEQUENCE: 232
QQYTYYPIT                                                                9

SEQ ID NO: 233          moltype = AA  length = 9
FEATURE                 Location/Qualifiers
source                  1..9
                        mol_type = protein
                        organism = synthetic construct
SEQUENCE: 233
QQSSVEPWT                                                                9

SEQ ID NO: 234          moltype = AA  length = 8
FEATURE                 Location/Qualifiers
source                  1..8
                        mol_type = protein
                        organism = synthetic construct
SEQUENCE: 234
GFNISQGG                                                                 8

SEQ ID NO: 235          moltype = AA  length = 8
FEATURE                 Location/Qualifiers
source                  1..8
                        mol_type = protein
                        organism = synthetic construct
SEQUENCE: 235
GFNISSTG                                                                 8

SEQ ID NO: 236          moltype = AA  length = 8
FEATURE                 Location/Qualifiers
source                  1..8
                        mol_type = protein
                        organism = synthetic construct
SEQUENCE: 236
GFNFFSTV                                                                 8

SEQ ID NO: 237          moltype = AA  length = 8
FEATURE                 Location/Qualifiers
source                  1..8
                        mol_type = protein
                        organism = synthetic construct
SEQUENCE: 237
GFNLHGYL                                                                 8

SEQ ID NO: 238          moltype = AA  length = 8
FEATURE                 Location/Qualifiers
source                  1..8
                        mol_type = protein
                        organism = synthetic construct
SEQUENCE: 238
GFNLSTHV                                                                 8

SEQ ID NO: 239          moltype = AA  length = 8
FEATURE                 Location/Qualifiers
source                  1..8
                        mol_type = protein
                        organism = synthetic construct
SEQUENCE: 239
GFNVSYYS                                                                 8
```

```
SEQ ID NO: 240          moltype = AA  length = 8
FEATURE                 Location/Qualifiers
source                  1..8
                        mol_type = protein
                        organism = synthetic construct
SEQUENCE: 240
VYPGGGQT                                                                  8

SEQ ID NO: 241          moltype = AA  length = 8
FEATURE                 Location/Qualifiers
source                  1..8
                        mol_type = protein
                        organism = synthetic construct
SEQUENCE: 241
LLGGSGNT                                                                  8

SEQ ID NO: 242          moltype = AA  length = 8
FEATURE                 Location/Qualifiers
source                  1..8
                        mol_type = protein
                        organism = synthetic construct
SEQUENCE: 242
IYPWSGST                                                                  8

SEQ ID NO: 243          moltype = AA  length = 8
FEATURE                 Location/Qualifiers
source                  1..8
                        mol_type = protein
                        organism = synthetic construct
SEQUENCE: 243
IYPPNGYT                                                                  8

SEQ ID NO: 244          moltype = AA  length = 8
FEATURE                 Location/Qualifiers
source                  1..8
                        mol_type = protein
                        organism = synthetic construct
SEQUENCE: 244
FYPYVGYT                                                                  8

SEQ ID NO: 245          moltype = AA  length = 8
FEATURE                 Location/Qualifiers
source                  1..8
                        mol_type = protein
                        organism = synthetic construct
SEQUENCE: 245
IYPWNDYT                                                                  8

SEQ ID NO: 246          moltype = AA  length = 11
FEATURE                 Location/Qualifiers
source                  1..11
                        mol_type = protein
                        organism = synthetic construct
SEQUENCE: 246
SRGYDYSAFD Y                                                              11

SEQ ID NO: 247          moltype = AA  length = 11
FEATURE                 Location/Qualifiers
source                  1..11
                        mol_type = protein
                        organism = synthetic construct
SEQUENCE: 247
SRGLQYSAMD Y                                                              11

SEQ ID NO: 248          moltype = AA  length = 12
FEATURE                 Location/Qualifiers
source                  1..12
                        mol_type = protein
                        organism = synthetic construct
SEQUENCE: 248
SRSRSSNYYF DV                                                             12

SEQ ID NO: 249          moltype = AA  length = 11
FEATURE                 Location/Qualifiers
source                  1..11
                        mol_type = protein
                        organism = synthetic construct
SEQUENCE: 249
```

```
SRGVDYAYLD Y                                                        11

SEQ ID NO: 250          moltype = AA  length = 11
FEATURE                 Location/Qualifiers
source                  1..11
                        mol_type = protein
                        organism = synthetic construct
SEQUENCE: 250
SRGYRYQYMD V                                                        11

SEQ ID NO: 251          moltype = AA  length = 10
FEATURE                 Location/Qualifiers
source                  1..10
                        mol_type = protein
                        organism = synthetic construct
SEQUENCE: 251
SRGSYYSFDY                                                          10

SEQ ID NO: 252          moltype = AA  length = 9
FEATURE                 Location/Qualifiers
source                  1..9
                        mol_type = protein
                        organism = synthetic construct
SEQUENCE: 252
QQIYTSPIT                                                           9

SEQ ID NO: 253          moltype = AA  length = 9
FEATURE                 Location/Qualifiers
source                  1..9
                        mol_type = protein
                        organism = synthetic construct
SEQUENCE: 253
QQRAYFPIT                                                           9

SEQ ID NO: 254          moltype = AA  length = 10
FEATURE                 Location/Qualifiers
source                  1..10
                        mol_type = protein
                        organism = synthetic construct
SEQUENCE: 254
QQQYAYTPIT                                                          10

SEQ ID NO: 255          moltype = AA  length = 9
FEATURE                 Location/Qualifiers
source                  1..9
                        mol_type = protein
                        organism = synthetic construct
SEQUENCE: 255
QQIHYKPLT                                                           9

SEQ ID NO: 256          moltype = AA  length = 8
FEATURE                 Location/Qualifiers
source                  1..8
                        mol_type = protein
                        organism = synthetic construct
SEQUENCE: 256
GFNINNTY                                                            8

SEQ ID NO: 257          moltype = AA  length = 8
FEATURE                 Location/Qualifiers
source                  1..8
                        mol_type = protein
                        organism = synthetic construct
SEQUENCE: 257
GFNFITTG                                                            8

SEQ ID NO: 258          moltype = AA  length = 8
FEATURE                 Location/Qualifiers
source                  1..8
                        mol_type = protein
                        organism = synthetic construct
SEQUENCE: 258
GFNFSDYG                                                            8

SEQ ID NO: 259          moltype = AA  length = 8
FEATURE                 Location/Qualifiers
source                  1..8
                        mol_type = protein
                        organism = synthetic construct
```

```
SEQUENCE: 259
GFNVWSYG                                                        8

SEQ ID NO: 260          moltype = AA  length = 8
FEATURE                 Location/Qualifiers
source                  1..8
                        mol_type = protein
                        organism = synthetic construct
SEQUENCE: 260
GFNVAWYS                                                        8

SEQ ID NO: 261          moltype = AA  length = 8
FEATURE                 Location/Qualifiers
source                  1..8
                        mol_type = protein
                        organism = synthetic construct
SEQUENCE: 261
IGPGSDYT                                                        8

SEQ ID NO: 262          moltype = AA  length = 8
FEATURE                 Location/Qualifiers
source                  1..8
                        mol_type = protein
                        organism = synthetic construct
SEQUENCE: 262
LIPASGYT                                                        8

SEQ ID NO: 263          moltype = AA  length = 8
FEATURE                 Location/Qualifiers
source                  1..8
                        mol_type = protein
                        organism = synthetic construct
SEQUENCE: 263
VTPDGSYT                                                        8

SEQ ID NO: 264          moltype = AA  length = 8
FEATURE                 Location/Qualifiers
source                  1..8
                        mol_type = protein
                        organism = synthetic construct
SEQUENCE: 264
VYGGSSYT                                                        8

SEQ ID NO: 265          moltype = AA  length = 13
FEATURE                 Location/Qualifiers
source                  1..13
                        mol_type = protein
                        organism = synthetic construct
SEQUENCE: 265
SRTYYSYYSA MDV                                                  13

SEQ ID NO: 266          moltype = AA  length = 11
FEATURE                 Location/Qualifiers
source                  1..11
                        mol_type = protein
                        organism = synthetic construct
SEQUENCE: 266
SRYYYASALD Y                                                    11

SEQ ID NO: 267          moltype = AA  length = 10
FEATURE                 Location/Qualifiers
source                  1..10
                        mol_type = protein
                        organism = synthetic construct
SEQUENCE: 267
SRGWSYYMDY                                                      10

SEQ ID NO: 268          moltype = AA  length = 10
FEATURE                 Location/Qualifiers
source                  1..10
                        mol_type = protein
                        organism = synthetic construct
SEQUENCE: 268
SRSYGWAMDY                                                      10

SEQ ID NO: 269          moltype = AA  length = 11
FEATURE                 Location/Qualifiers
source                  1..11
                        mol_type = protein
```

```
                        organism = synthetic construct
SEQUENCE: 269
SRDFYSSGMD Y                                                    11

SEQ ID NO: 270          moltype = AA  length = 9
FEATURE                 Location/Qualifiers
source                  1..9
                        mol_type = protein
                        organism = synthetic construct
SEQUENCE: 270
QQEWRLPIT                                                       9

SEQ ID NO: 271          moltype = AA  length = 9
FEATURE                 Location/Qualifiers
source                  1..9
                        mol_type = protein
                        organism = synthetic construct
SEQUENCE: 271
QQGTSTPFT                                                       9

SEQ ID NO: 272          moltype = AA  length = 9
FEATURE                 Location/Qualifiers
source                  1..9
                        mol_type = protein
                        organism = synthetic construct
SEQUENCE: 272
QQSWRYPMT                                                       9

SEQ ID NO: 273          moltype = AA  length = 9
FEATURE                 Location/Qualifiers
source                  1..9
                        mol_type = protein
                        organism = synthetic construct
SEQUENCE: 273
QQSYSYPVT                                                       9

SEQ ID NO: 274          moltype = AA  length = 10
FEATURE                 Location/Qualifiers
source                  1..10
                        mol_type = protein
                        organism = synthetic construct
SEQUENCE: 274
QQGWLYSPFT                                                      10

SEQ ID NO: 275          moltype = AA  length = 8
FEATURE                 Location/Qualifiers
source                  1..8
                        mol_type = protein
                        organism = synthetic construct
SEQUENCE: 275
GFNVYGNQ                                                        8

SEQ ID NO: 276          moltype = AA  length = 8
FEATURE                 Location/Qualifiers
source                  1..8
                        mol_type = protein
                        organism = synthetic construct
SEQUENCE: 276
GFNISRYG                                                        8

SEQ ID NO: 277          moltype = AA  length = 8
FEATURE                 Location/Qualifiers
source                  1..8
                        mol_type = protein
                        organism = synthetic construct
SEQUENCE: 277
GFNIYSSW                                                        8

SEQ ID NO: 278          moltype = AA  length = 8
FEATURE                 Location/Qualifiers
source                  1..8
                        mol_type = protein
                        organism = synthetic construct
SEQUENCE: 278
IYPYSGST                                                        8

SEQ ID NO: 279          moltype = AA  length = 8
FEATURE                 Location/Qualifiers
source                  1..8
```

```
                        mol_type = protein
                        organism = synthetic construct
SEQUENCE: 279
IYPDSGYT                                                                8

SEQ ID NO: 280          moltype = AA  length = 8
FEATURE                 Location/Qualifiers
source                  1..8
                        mol_type = protein
                        organism = synthetic construct
SEQUENCE: 280
FYPSSSYT                                                                8

SEQ ID NO: 281          moltype = AA  length = 8
FEATURE                 Location/Qualifiers
source                  1..8
                        mol_type = protein
                        organism = synthetic construct
SEQUENCE: 281
FQPYSGYT                                                                8

SEQ ID NO: 282          moltype = AA  length = 8
FEATURE                 Location/Qualifiers
source                  1..8
                        mol_type = protein
                        organism = synthetic construct
SEQUENCE: 282
VYGGSGYT                                                                8

SEQ ID NO: 283          moltype = AA  length = 13
FEATURE                 Location/Qualifiers
source                  1..13
                        mol_type = protein
                        organism = synthetic construct
SEQUENCE: 283
SRSAYVAYSY FDY                                                          13

SEQ ID NO: 284          moltype = AA  length = 11
FEATURE                 Location/Qualifiers
source                  1..11
                        mol_type = protein
                        organism = synthetic construct
SEQUENCE: 284
SRAYLYYYLA Y                                                            11

SEQ ID NO: 285          moltype = AA  length = 10
FEATURE                 Location/Qualifiers
source                  1..10
                        mol_type = protein
                        organism = synthetic construct
SEQUENCE: 285
SRKYYEAMDY                                                              10

SEQ ID NO: 286          moltype = AA  length = 10
FEATURE                 Location/Qualifiers
source                  1..10
                        mol_type = protein
                        organism = synthetic construct
SEQUENCE: 286
SREYTYYFDY                                                              10

SEQ ID NO: 287          moltype = AA  length = 11
FEATURE                 Location/Qualifiers
source                  1..11
                        mol_type = protein
                        organism = synthetic construct
SEQUENCE: 287
SRAHSSYYVD Y                                                            11

SEQ ID NO: 288          moltype = AA  length = 10
FEATURE                 Location/Qualifiers
source                  1..10
                        mol_type = protein
                        organism = synthetic construct
SEQUENCE: 288
QQGYFYYPNT                                                              10

SEQ ID NO: 289          moltype = AA  length = 8
FEATURE                 Location/Qualifiers
```

```
source                1..8
                      mol_type = protein
                      organism = synthetic construct
SEQUENCE: 289
GFNIGYYG                                                      8

SEQ ID NO: 290        moltype = AA  length = 8
FEATURE               Location/Qualifiers
source                1..8
                      mol_type = protein
                      organism = synthetic construct
SEQUENCE: 290
VYPGGGYT                                                      8

SEQ ID NO: 291        moltype = AA  length = 10
FEATURE               Location/Qualifiers
source                1..10
                      mol_type = protein
                      organism = synthetic construct
SEQUENCE: 291
SRYYYYGFDY                                                    10

SEQ ID NO: 292        moltype = AA  length = 9
FEATURE               Location/Qualifiers
source                1..9
                      mol_type = protein
                      organism = synthetic construct
SEQUENCE: 292
QQHYYSPVT                                                     9

SEQ ID NO: 293        moltype = AA  length = 9
FEATURE               Location/Qualifiers
source                1..9
                      mol_type = protein
                      organism = synthetic construct
SEQUENCE: 293
QQHYYSPVT                                                     9

SEQ ID NO: 294        moltype = AA  length = 8
FEATURE               Location/Qualifiers
source                1..8
                      mol_type = protein
                      organism = synthetic construct
SEQUENCE: 294
IYPDYDYT                                                      8

SEQ ID NO: 295        moltype = AA  length = 10
FEATURE               Location/Qualifiers
source                1..10
                      mol_type = protein
                      organism = synthetic construct
SEQUENCE: 295
SRTYSVYMDY                                                    10

SEQ ID NO: 296        moltype = AA  length = 9
FEATURE               Location/Qualifiers
source                1..9
                      mol_type = protein
                      organism = synthetic construct
SEQUENCE: 296
QQYAYAPFT                                                     9

SEQ ID NO: 297        moltype = AA  length = 8
FEATURE               Location/Qualifiers
source                1..8
                      mol_type = protein
                      organism = synthetic construct
SEQUENCE: 297
GFNVSYSM                                                      8

SEQ ID NO: 298        moltype = AA  length = 8
FEATURE               Location/Qualifiers
source                1..8
                      mol_type = protein
                      organism = synthetic construct
SEQUENCE: 298
VWGDGGVT                                                      8

SEQ ID NO: 299        moltype = AA  length = 10
```

```
FEATURE                 Location/Qualifiers
source                  1..10
                        mol_type = protein
                        organism = synthetic construct
SEQUENCE: 299
SRGSYYAFDY                                                     10

SEQ ID NO: 300          moltype = AA  length = 9
FEATURE                 Location/Qualifiers
source                  1..9
                        mol_type = protein
                        organism = synthetic construct
SEQUENCE: 300
QQAHMIPIT                                                      9

SEQ ID NO: 301          moltype = AA  length = 9
FEATURE                 Location/Qualifiers
source                  1..9
                        mol_type = protein
                        organism = synthetic construct
SEQUENCE: 301
QQSVYDPIT                                                      9

SEQ ID NO: 302          moltype = AA  length = 9
FEATURE                 Location/Qualifiers
source                  1..9
                        mol_type = protein
                        organism = synthetic construct
SEQUENCE: 302
QQSYTSPLT                                                      9

SEQ ID NO: 303          moltype = AA  length = 9
FEATURE                 Location/Qualifiers
source                  1..9
                        mol_type = protein
                        organism = synthetic construct
SEQUENCE: 303
QQGQYSPFT                                                      9

SEQ ID NO: 304          moltype =   length =
SEQUENCE: 304
000

SEQ ID NO: 305          moltype = AA  length = 8
FEATURE                 Location/Qualifiers
source                  1..8
                        mol_type = protein
                        organism = synthetic construct
SEQUENCE: 305
GFNFSFPG                                                       8

SEQ ID NO: 306          moltype = AA  length = 8
FEATURE                 Location/Qualifiers
source                  1..8
                        mol_type = protein
                        organism = synthetic construct
SEQUENCE: 306
GFNISGSW                                                       8

SEQ ID NO: 307          moltype = AA  length = 8
FEATURE                 Location/Qualifiers
source                  1..8
                        mol_type = protein
                        organism = synthetic construct
SEQUENCE: 307
GFNIYYGV                                                       8

SEQ ID NO: 308          moltype = AA  length = 8
FEATURE                 Location/Qualifiers
source                  1..8
                        mol_type = protein
                        organism = synthetic construct
SEQUENCE: 308
GFNVSYEY                                                       8

SEQ ID NO: 309          moltype =   length =
SEQUENCE: 309
000
```

```
SEQ ID NO: 310          moltype = AA  length = 8
FEATURE                 Location/Qualifiers
source                  1..8
                        mol_type = protein
                        organism = synthetic construct
SEQUENCE: 310
FVGYDGYT                                                                  8

SEQ ID NO: 311          moltype = AA  length = 8
FEATURE                 Location/Qualifiers
source                  1..8
                        mol_type = protein
                        organism = synthetic construct
SEQUENCE: 311
LYPDSDYT                                                                  8

SEQ ID NO: 312          moltype = AA  length = 8
FEATURE                 Location/Qualifiers
source                  1..8
                        mol_type = protein
                        organism = synthetic construct
SEQUENCE: 312
IYPDSSWT                                                                  8

SEQ ID NO: 313          moltype = AA  length = 8
FEATURE                 Location/Qualifiers
source                  1..8
                        mol_type = protein
                        organism = synthetic construct
SEQUENCE: 313
IYGGSDNT                                                                  8

SEQ ID NO: 314          moltype =   length =
SEQUENCE: 314
000

SEQ ID NO: 315          moltype =   length =
SEQUENCE: 315
000

SEQ ID NO: 316          moltype = AA  length = 11
FEATURE                 Location/Qualifiers
source                  1..11
                        mol_type = protein
                        organism = synthetic construct
SEQUENCE: 316
SRDYYSFSMD Y                                                              11

SEQ ID NO: 317          moltype = AA  length = 10
FEATURE                 Location/Qualifiers
source                  1..10
                        mol_type = protein
                        organism = synthetic construct
SEQUENCE: 317
SRAHTYAFDY                                                                10

SEQ ID NO: 318          moltype = AA  length = 19
FEATURE                 Location/Qualifiers
source                  1..19
                        mol_type = protein
                        organism = synthetic construct
SEQUENCE: 318
SRDQDFHYMN YYLSYALDY                                                      19

SEQ ID NO: 319          moltype = AA  length = 10
FEATURE                 Location/Qualifiers
source                  1..10
                        mol_type = protein
                        organism = synthetic construct
SEQUENCE: 319
SRPLGSYFDY                                                                10

SEQ ID NO: 320          moltype = AA  length = 9
FEATURE                 Location/Qualifiers
source                  1..9
                        mol_type = protein
                        organism = synthetic construct
SEQUENCE: 320
QQYWYLPTT                                                                 9
```

```
SEQ ID NO: 321          moltype = AA  length = 8
FEATURE                 Location/Qualifiers
source                  1..8
                        mol_type = protein
                        organism = synthetic construct
SEQUENCE: 321
GFNISWYD                                                    8

SEQ ID NO: 322          moltype = AA  length = 8
FEATURE                 Location/Qualifiers
source                  1..8
                        mol_type = protein
                        organism = synthetic construct
SEQUENCE: 322
IEPSVGYT                                                    8

SEQ ID NO: 323          moltype = AA  length = 11
FEATURE                 Location/Qualifiers
source                  1..11
                        mol_type = protein
                        organism = synthetic construct
SEQUENCE: 323
SRSYPYYYFD Y                                                11

SEQ ID NO: 324          moltype = AA  length = 240
FEATURE                 Location/Qualifiers
source                  1..240
                        mol_type = protein
                        organism = synthetic construct
SEQUENCE: 324
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YDYAPITFGQ GTKVEIKRTG GGSGGGGSGG  120
GASEVQLVES GGGLVQPGGS LRLSCAASGF NISWYQMHWV RQAPGKGLEW VALVTPYSGY  180
TYYADSVKGR FTISADTSKN TAYLQMNSLR AEDTAVYYCS RSYTDGFDYW GQGTLVTVSS  240

SEQ ID NO: 325          moltype = AA  length = 246
FEATURE                 Location/Qualifiers
source                  1..246
                        mol_type = protein
                        organism = synthetic construct
SEQUENCE: 325
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SPYYYLPITF GQGTKVEIKR TGGGSGGGGS  120
GGGASEVQLV ESGGGLVQPG GSLRLSCAAS GFNVSWSYMH WVRQAPGKGL EWVANIYGDS  180
GYTHYADSVK GRFTISADTS KNTAYLQMNS LRAEDTAVYY CSRGQWEASY YAMDYWGQGT  240
LVTVSS                                                      246

SEQ ID NO: 326          moltype = AA  length = 240
FEATURE                 Location/Qualifiers
source                  1..240
                        mol_type = protein
                        organism = synthetic construct
SEQUENCE: 326
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YYYSPVTFGQ GTKVEIKRTG GGSGGGGSGG  120
GASEVQLVES GGGLVQPGGS LRLSCAASGF NISWNQMHWV RQAPGKGLEW VALVSPYSGY  180
TYYADSVKGR FTISADTSKN TAYLQMNSLR AEDTAVYYCS RSDYYAMDYW GQGTLVTVSS  240

SEQ ID NO: 327          moltype = AA  length = 241
FEATURE                 Location/Qualifiers
source                  1..241
                        mol_type = protein
                        organism = synthetic construct
SEQUENCE: 327
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYGNPFTFGQ GTKVEIKRTG GGSGGGGSGG  120
GASEVQLVES GGGLVQPGGS LRLSCAASGF NVGYYGMHWV RQAPGKGLEW VAFVSGMEGY  180
TSYADSVKGR FTISADTSKN TAYLQMNSLR AEDTAVYYCS RDIYGYAMDV WGQGTLVTVS  240
S                                                           241

SEQ ID NO: 328          moltype = AA  length = 243
FEATURE                 Location/Qualifiers
source                  1..243
                        mol_type = protein
                        organism = synthetic construct
SEQUENCE: 328
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SYYSPPTFGQ GTKVEIKRTG GGSGGGGSGG  120
```

```
GASEVQLVES GGGLVQPGGS LRLSCAASGF NITSSYIHWV RQAPGKGLEW VAYISPADGY  180
NRYADSVKGR FTISADTSKN TAYLQMNSLR AEDTAVYYCS RTDSTAYTAM DVWGQGTLVT  240
VSS                                                                243

SEQ ID NO: 329          moltype = AA  length = 243
FEATURE                 Location/Qualifiers
source                  1..243
                        mol_type = protein
                        organism = synthetic construct
SEQUENCE: 329
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YYSYPPTFGQ GTKVEIKRTG GGSGGGGSGG  120
GASEVQLVES GGGLVQPGGS LRLSCAASGF NINSSYIHWV RQAPGKGLEW VAYISPTDGY  180
YRYADSVKGR FTISADTSKN TAYLQMNSLR AEDTAVYYCS RTSDTSYAAM DVWGQGTLVT  240
VSS                                                                243

SEQ ID NO: 330          moltype = AA  length = 243
FEATURE                 Location/Qualifiers
source                  1..243
                        mol_type = protein
                        organism = synthetic construct
SEQUENCE: 330
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YYYYPPTFGQ GTKVEIKRTG GGSGGGGSGG  120
GASEVQLVES GGGLVQPGGS LRLSCAASGF NISTSYIHWV RQAPGKGLEW VATIDPNDGY  180
SRYADSVKGR FTISADTSKN TAYLQMNSLR AEDTAVYYCS RTNNTAADAM DVWGQGTLVT  240
VSS                                                                243

SEQ ID NO: 331          moltype = AA  length = 242
FEATURE                 Location/Qualifiers
source                  1..242
                        mol_type = protein
                        organism = synthetic construct
SEQUENCE: 331
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SGYAPITFGQ GTKVEIKRTG GGSGGGGSGG  120
GASEVQLVES GGGLVQPGGS LRLSCAASGF NISYYSMHWV RQAPGKGLEW VADVDPDSDY  180
TEYADSVKGR FTISADTSKN TAYLQMNSLR AEDTAVYYCS RSWIHMFSMD YWGQGTLVTV  240
SS                                                                 242

SEQ ID NO: 332          moltype = AA  length = 241
FEATURE                 Location/Qualifiers
source                  1..241
                        mol_type = protein
                        organism = synthetic construct
SEQUENCE: 332
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYAPITFGQ GTKVEIKRTG GGSGGGGSGG  120
GASEVQLVES GGGLVQPGGS LRLSCAASGF NIGYYTMHWV RQAPGKGLEW VAEVSPWSYS  180
TSYADSVKGR FTISADTSKN TAYLQMNSLR AEDTAVYYCS RDHWDEAFDV WGQGTLVTVS  240
S                                                                  241

SEQ ID NO: 333          moltype = AA  length = 243
FEATURE                 Location/Qualifiers
source                  1..243
                        mol_type = protein
                        organism = synthetic construct
SEQUENCE: 333
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SLYGPFTFGQ GTKVEIKRTG GGSGGGGSGG  120
GASEVQLVES GGGLVQPGGS LRLSCAASGF NIAYEYMHWV RQAPGKGLEW VALIGPDSGY  180
TYYADSVKGR FTISADTSKN TAYLQMNSLR AEDTAVYYCS RVWYYSTYGM DYWGQGTLVT  240
VSS                                                                243

SEQ ID NO: 334          moltype = AA  length = 241
FEATURE                 Location/Qualifiers
source                  1..241
                        mol_type = protein
                        organism = synthetic construct
SEQUENCE: 334
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYSPITFGQ GTKVEIKRTG GGSGGGGSGG  120
GASEVQLVES GGGLVQPGGS LRLSCAASGF NLFGYGMHWV RQAPGKGLEW VAEIGPYYYY  180
TSYADSVKGR FTISADTSKN TAYLQMNSLR AEDTAVYYCS RENYDMAMDY WGQGTLVTVS  240
S                                                                  241

SEQ ID NO: 335          moltype = AA  length = 241
FEATURE                 Location/Qualifiers
source                  1..241
```

```
                         mol_type = protein
                         organism = synthetic construct
SEQUENCE: 335
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SGYQPDTFGQ GTKVEIKRTG GGSGGGGSGG  120
GASEVQLVES GGGLVQPGGS LRLSCAASGF NISWYAMHWV RQAPGKGLEW VAEIWPDSDW  180
TYYADSVKGR FTISADTSKN TAYLQMNSLR AEDTAVYYCS RYYYSSAFDV WGQGTLVTVS  240
S                                                                  241

SEQ ID NO: 336           moltype = AA  length = 240
FEATURE                  Location/Qualifiers
source                   1..240
                         mol_type = protein
                         organism = synthetic construct
SEQUENCE: 336
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YLYQPWTFGQ GTKVEIKRTG GGSGGGGSGG  120
GASEVQLVES GGGLVQPGGS LRLSCAASGF NIDYYGMHWV RQAPGKGLEW VASLYGGSDS  180
TDYADSVKGR FTISADTSKN TAYLQMNSLR AEDTAVYYCS RQYSAYFDYW GQGTLVTVSS  240

SEQ ID NO: 337           moltype = AA  length = 241
FEATURE                  Location/Qualifiers
source                   1..241
                         mol_type = protein
                         organism = synthetic construct
SEQUENCE: 337
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GLYYPWTFGQ GTKVEIKRTG GGSGGGGSGG  120
GASEVQLVES GGGLVQPGGS LRLSCAASGF NVSYSSIHWV RQAPGKGLEW VAEIWPDSGQ  180
TWYADSVKGR FTISADTSKN TAYLQMNSLR AEDTAVYYCS RSSYFDAMDY WGQGTLVTVS  240
S                                                                  241

SEQ ID NO: 338           moltype = AA  length = 240
FEATURE                  Location/Qualifiers
source                   1..240
                         mol_type = protein
                         organism = synthetic construct
SEQUENCE: 338
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ WYSSPVTFGQ GTKVEIKRTG GGSGGGGSGG  120
GASEVQLVES GGGLVQPGGS LRLSCAASGF NINWANMHWV RQAPGKGLEW VAQISPPYDY  180
TNYADSVKGR FTISADTSKN TAYLQMNSLR AEDTAVYYCS RSYSYYFDYW GQGTLVTVSS  240

SEQ ID NO: 339           moltype = AA  length = 240
FEATURE                  Location/Qualifiers
source                   1..240
                         mol_type = protein
                         organism = synthetic construct
SEQUENCE: 339
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YYSRPVTFGQ GTKVEIKRTG GGSGGGGSGG  120
GASEVQLVES GGGLVQPGGS LRLSCAASGF NIYLHDMHWV RQAPGKGLEW VAQIIPAIDY  180
TNYADSVKGR FTISADTSKN TAYLQMNSLR AEDTAVYYCS RRDGYYFDYW GQGTLVTVSS  240

SEQ ID NO: 340           moltype = AA  length = 240
FEATURE                  Location/Qualifiers
source                   1..240
                         mol_type = protein
                         organism = synthetic construct
SEQUENCE: 340
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ WYSSPVTFGQ GTKVEIKRTG GGSGGGGSGG  120
GASEVQLVES GGGLVQPGGS LRLSCAASGF NIYWSHMHWV RQAPGKGLEW VAIISSFEGY  180
TYYADSVKGR FTISADTSKN TAYLQMNSLR AEDTAVYYCS RSYSYYMDYW GQGTLVTVSS  240

SEQ ID NO: 341           moltype = AA  length = 243
FEATURE                  Location/Qualifiers
source                   1..243
                         mol_type = protein
                         organism = synthetic construct
SEQUENCE: 341
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SYGSGSPWTF GQGTKVEIKR TGGGSGGGGS  120
GGGASEVQLV ESGGGLVQPG GSLRLSCAAS GFNIVGGGIH WVRQAPGKGL EWVAKIYPQG  180
DYTYYADSVK GRFTISADTS KNTAYLQMNS LRAEDTAVYY CSRDSSYLAF DYWGQGTLVT  240
VSS                                                                243

SEQ ID NO: 342           moltype = AA  length = 243
FEATURE                  Location/Qualifiers
```

```
source                 1..243
                       mol_type = protein
                       organism = synthetic construct
SEQUENCE: 342
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ TYYSPWTFGQ GTKVEIKRTG GGSGGGGSGG  120
GASEVQLVES GGGLVQPGGS LRLSCAASGF NIRSYAMHWV RQAPGKGLEW VAQVGPGKGY  180
TYYADSVKGR FTISADTSKN TAYLQMNSLR AEDTAVYYCS RNFQSTSHAF DYWGQGTLVT  240
VSS                                                                243

SEQ ID NO: 343         moltype = AA  length = 240
FEATURE                Location/Qualifiers
source                 1..240
                       mol_type = protein
                       organism = synthetic construct
SEQUENCE: 343
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YYYPPITFGQ GTKVEIKRTG GGSGGGGSGG  120
GASEVQLVES GGGLVQPGGS LRLSCAASGF NVSHTGMHWV RQAPGKGLEW VAVVGPGKGY  180
TYYADSVKGR FTISADTSKN TAYLQMNSLR AEDTAVYYCS RKTYYAFDYW GQGTLVTVSS  240

SEQ ID NO: 344         moltype = AA  length = 245
FEATURE                Location/Qualifiers
source                 1..245
                       mol_type = protein
                       organism = synthetic construct
SEQUENCE: 344
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SYYYFRPITF GQGTKVEIKR TGGGSGGGGS  120
GGGASEVQLV ESGGGLVQPG GSLRLSCAAS GFNLSYSDIH WVRQAPGKGL EWVAVVMPDS  180
GHTNYADSVK GRFTISADTS KNTAYLQMNS LRAEDTAVYY CSRATNIPVY AFDYWGQGTL  240
VTVSS                                                              245

SEQ ID NO: 345         moltype = AA  length = 244
FEATURE                Location/Qualifiers
source                 1..244
                       mol_type = protein
                       organism = synthetic construct
SEQUENCE: 345
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ ASYYYPLTFG QGTKVEIKRT GGGSGGGGSG  120
GGASEVQLVE SGGGLVQPGG SLRLSCAASG FNISASGMHW VRQAPGKGLE WVADIHPLKP  180
YTNYADSVKG RFTISADTSK NTAYLQMNSL RAEDTAVYYC SRYSSMYYYY FDYWGQGTLV  240
TVSS                                                               244

SEQ ID NO: 346         moltype = AA  length = 242
FEATURE                Location/Qualifiers
source                 1..242
                       mol_type = protein
                       organism = synthetic construct
SEQUENCE: 346
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ KSEYSPWTFG QGTKVEIKRT GGGSGGGGSG  120
GGASEVQLVE SGGGLVQPGG SLRLSCAASG FNIYRYGIHW VRQAPGKGLE WVAVLYPYGY  180
STSYADSVKG RFTISADTSK NTAYLQMNSL RAEDTAVYYC SRSYAYGYFA YWGQGTLVTV  240
SS                                                                 242

SEQ ID NO: 347         moltype = AA  length = 243
FEATURE                Location/Qualifiers
source                 1..243
                       mol_type = protein
                       organism = synthetic construct
SEQUENCE: 347
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SGYIPFTFGQ GTKVEIKRTG GGSGGGGSGG  120
GASEVQLVES GGGLVQPGGS LRLSCAASGF NIYGTMMHWV RQAPGKGLEW VAQFKPDSYN  180
TYYADSVKGR FTISADTSKN TAYLQMNSLR AEDTAVYYCS RGEVYHYYAF DYWGQGTLVT  240
VSS                                                                243

SEQ ID NO: 348         moltype = AA  length = 241
FEATURE                Location/Qualifiers
source                 1..241
                       mol_type = protein
                       organism = synthetic construct
SEQUENCE: 348
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GAYYRPFTFG QGTKVEIKRT GGGSGGGGSG  120
GGASEVQLVE SGGGLVQPGG SLRLSCAASG FNISYSYMHW VRQAPGKGLE WVATLLPYDG  180
NTYYADSVKG RFTISADTSK NTAYLQMNSL RAEDTAVYYC SRAAYSSMDV WGQGTLVTVS  240
```

```
S                                                                   241

SEQ ID NO: 349          moltype = AA  length = 242
FEATURE                 Location/Qualifiers
source                  1..242
                        mol_type = protein
                        organism = synthetic construct
SEQUENCE: 349
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YMYSPVTFGQ GTKVEIKRTG GGSGGGGSGG  120
GASEVQLVES GGGLVQPGGS LRLSCAASGF NVSAYWMHWV RQAPGKGLEW VAQIYGGSGY  180
TMYADSVKGR FTISADTSKN TAYLQMNSLR AEDTAVYYCS RTHSYWSAFD YWGQGTLVTV  240
SS                                                                  242

SEQ ID NO: 350          moltype = AA  length = 240
FEATURE                 Location/Qualifiers
source                  1..240
                        mol_type = protein
                        organism = synthetic construct
SEQUENCE: 350
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SSSSPITFGQ GTKVEIKRTG GGSGGGGSGG  120
GASEVQLVES GGGLVQPGGS LRLSCAASGF NISGYGMHWV RQAPGKGLEW VAYLYGGSDY  180
TNYADSVKGR FTISADTSKN TAYLQMNSLR AEDTAVYYCS RTVRYAFDYW GQGTLVTVSS  240

SEQ ID NO: 351          moltype = AA  length = 240
FEATURE                 Location/Qualifiers
source                  1..240
                        mol_type = protein
                        organism = synthetic construct
SEQUENCE: 351
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SSASPLTFGQ GTKVEIKRTG GGSGGGGSGG  120
GASEVQLVES GGGLVQPGGS LRLSCAASGF NVSSVGMHWV RQAPGKGLEW VAYIYGTSDY  180
TYYADSVKGR FTISADTSKN TAYLQMNSLR AEDTAVYYCS RSSRYSMDYW GQGTLVTVSS  240

SEQ ID NO: 352          moltype = AA  length = 240
FEATURE                 Location/Qualifiers
source                  1..240
                        mol_type = protein
                        organism = synthetic construct
SEQUENCE: 352
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YAYSPLTFGQ GTKVEIKRTG GGSGGGGSGG  120
GASEVQLVES GGGLVQPGGS LRLSCAASGF NVSSYGMHWV RQAPGKGLEW VAFIAPRRDY  180
TSYADSVKGR FTISADTSKN TAYLQMNSLR AEDTAVYYCS RKSSYYFDYW GQGTLVTVSS  240

SEQ ID NO: 353          moltype = AA  length = 246
FEATURE                 Location/Qualifiers
source                  1..246
                        mol_type = protein
                        organism = synthetic construct
SEQUENCE: 353
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYYPITFGQ GTKVEIKRTG GGSGGGGSGG  120
GASEVQLVES GGGLVQPGGS LRLSCAASGF NFSYGYMHWV RQAPGKGLEW VAWISGYTGN  180
TYYADSVKGR FTISADTSKN TAYLQMNSLR AEDTAVYYCS RAASLSSSYY SAFDVWGQGT  240
LVTVSS                                                              246

SEQ ID NO: 354          moltype = AA  length = 241
FEATURE                 Location/Qualifiers
source                  1..241
                        mol_type = protein
                        organism = synthetic construct
SEQUENCE: 354
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYTPVTFGQ GTKVEIKRTG GGSGGGGSGG  120
GASEVQLVES GGGLVQPGGS LRLSCAASGF NVWGPGMHWV RQAPGKGLEW VARIHPFSGN  180
TYYADSVKGR FTISADTSKN TAYLQMNSLR AEDTAVYYCS RGYSYSAMDY WGQGTLVTVS  240
S                                                                   241

SEQ ID NO: 355          moltype = AA  length = 241
FEATURE                 Location/Qualifiers
source                  1..241
                        mol_type = protein
                        organism = synthetic construct
SEQUENCE: 355
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYEPVTFGQ GTKVEIKRTG GGSGGGGSGG  120
```

```
GASEVQLVES GGGLVQPGGS LRLSCAASGF NVSGSQMHWV RQAPGKGLEW VARIPGWSGY  180
TYYADSVKGR FTISADTSKN TAYLQMNSLR AEDTAVYYCS RGYSYFAMDY WGQGTLVTVS  240
S                                                                 241

SEQ ID NO: 356         moltype = AA  length = 245
FEATURE                Location/Qualifiers
source                 1..245
                       mol_type = protein
                       organism = synthetic construct
SEQUENCE: 356
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YAYYSPVTFG QGTKVEIKRT GGGSGGGGSG  120
GGASEVQLVE SGGGLVQPGG SLRLSCAASG FNIYGQMMHW VRQAPGKGLE WVAFLSPFSG  180
NTYYADSVKG RFTISADTSK NTAYLQMNSL RAEDTAVYYC SRNISYEQSS AFDYWGQGTL  240
VTVSS                                                             245

SEQ ID NO: 357         moltype = AA  length = 241
FEATURE                Location/Qualifiers
source                 1..241
                       mol_type = protein
                       organism = synthetic construct
SEQUENCE: 357
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YEYYPMTFGQ GTKVEIKRTG GGSGGGGSGG  120
GASEVQLVES GGGLVQPGGS LRLSCAASGF NVMYSTMHWV RQAPGKGLEW VASIYSWSDY  180
TYYADSVKGR FTISADTSKN TAYLQMNSLR AEDTAVYYCS RGYAHNSFDY WGQGTLVTVS  240
S                                                                 241

SEQ ID NO: 358         moltype = AA  length = 242
FEATURE                Location/Qualifiers
source                 1..242
                       mol_type = protein
                       organism = synthetic construct
SEQUENCE: 358
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSFYPFTFGQ GTKVEIKRTG GGSGGGGSGG  120
GASEVQLVES GGGLVQPGGS LRLSCAASGF NFGSYIHWVR QAPGKGLEWV AIISGYSGNT  180
YYADSVKGRF TISADTSKNT AYLQMNSLRA EDTAVYYCSR SNQSAYSYMD YWGQGTLVTV  240
SS                                                                242

SEQ ID NO: 359         moltype = AA  length = 243
FEATURE                Location/Qualifiers
source                 1..243
                       mol_type = protein
                       organism = synthetic construct
SEQUENCE: 359
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYSPITFGQ GTKVEIKRTG GGSGGGGSGG  120
GASEVQLVES GGGLVQPGGS LRLSCAASGF NISDSYMHWV RQAPGKGLEW VATFSPYSSN  180
TWYADSVKGR FTISADTSKN TAYLQMNSLR AEDTAVYYCS RSQFTFYQYF DYWGQGTLVT  240
VSS                                                               243

SEQ ID NO: 360         moltype = AA  length = 244
FEATURE                Location/Qualifiers
source                 1..244
                       mol_type = protein
                       organism = synthetic construct
SEQUENCE: 360
DIQMTQSPSS LSASVGDRVT ITCRASQDVN TAVAWYQQKP GKAPKLLIYS AYFLYSGVPS  60
RFSGSRSGTD FTLTISSLQP EDFATYYCQQ YSAYYQPITF GQGTKVEIKR TGGGSGGGGS  120
GGGASEVQLV ESGGGLVQPG GSLRLSCAAS GFNIFSDQMH WVRQAPGKGL EWVAGFMPYD  180
SYYTNYADSV KGRFTISADT SKNTAYLQMN SLRAEDTAVY YCSRMSVRNA FDYWGQGTLV  240
TVSS                                                              244

SEQ ID NO: 361         moltype = AA  length = 242
FEATURE                Location/Qualifiers
source                 1..242
                       mol_type = protein
                       organism = synthetic construct
SEQUENCE: 361
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYYPITFGQ GTKVEIKRTG GGSGGGGSGG  120
GASEVQLVES GGGLVQPGGS LRLSCAASGF NLSYSYMHWV RQAPGKGLEW VAVISGFSGN  180
TYYADSVKGR FTISADTSKN TAYLQMNSLR AEDTAVYYCS RSDSYYTAMD YWGQGTLVTV  240
SS                                                                242

SEQ ID NO: 362         moltype = AA  length = 240
FEATURE                Location/Qualifiers
source                 1..240
```

```
                        mol_type = protein
                        organism = synthetic construct
SEQUENCE: 362
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YEYVPHTFGQ GTKVEIKRTG GGSGGGGSGG  120
GASEVQLVES GGGLVQPGGS LRLSCAASGF NISYGYMHWV RQAPGKGLEW VAKFHYGSGN  180
TYYADSVKGR FTISADTSKN TAYLQMNSLR AEDTAVYYCS RSNYYYLDYW GQGTLVTVSS  240

SEQ ID NO: 363          moltype = AA  length = 244
FEATURE                 Location/Qualifiers
source                  1..244
                        mol_type = protein
                        organism = synthetic construct
SEQUENCE: 363
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYMPITFGQ GTKVEIKRTG GGSGGGGSGG  120
GASEVQLVES GGGLVQPGGS LRLSCAASGF NISYQHIHWV RQAPGKGLEW VAVFMPYQGS  180
TYYADSVKGR FTISADTSKN TAYLQMNSLR AEDTAVYYCS RANIYSSHSF FDYWGQGTLV  240
TVSS                                                               244

SEQ ID NO: 364          moltype = AA  length = 243
FEATURE                 Location/Qualifiers
source                  1..243
                        mol_type = protein
                        organism = synthetic construct
SEQUENCE: 364
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YAYYPVTFGQ GTKVEIKRTG GGSGGGGSGG  120
GASEVQLVES GGGLVQPGGS LRLSCAASGF NLSGYYMHWV RQAPGKGLEW VAWFSPYSGY  180
TYYADSVKGR FTISADTSKN TAYLQMNSLR AEDTAVYYCS RTHSSIYHSF DYWGQGTLVT  240
VSS                                                                243

SEQ ID NO: 365          moltype = AA  length = 244
FEATURE                 Location/Qualifiers
source                  1..244
                        mol_type = protein
                        organism = synthetic construct
SEQUENCE: 365
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYMPITFGQ GTKVEIKRTG GGSGGGGSGG  120
GASEVQLVES GGGLVQPGGS LRLSCAASGF NVSGQYMHWV RQAPGKGLEW VAVISPVSGN  180
TYYADSVKGR FTISADTSKN TAYLQMNSLR AEDTAVYYCS RPMKTSYYGA FDYWGQGTLV  240
TVSS                                                               244

SEQ ID NO: 366          moltype = AA  length = 244
FEATURE                 Location/Qualifiers
source                  1..244
                        mol_type = protein
                        organism = synthetic construct
SEQUENCE: 366
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YDYRPVTFGQ GTKVEIKRTG GGSGGGGSGG  120
GASEVQLVES GGGLVQPGGS LRLSCAASGF NVSTSGMHWV RQAPGKGLEW VAFIYGAYSG  180
TYYADSVKGR FTISADTSKN TAYLQMNSLR AEDTAVYYCS RSQSYTYWSA MDYWGQGTLV  240
TVSS                                                               244

SEQ ID NO: 367          moltype = AA  length = 241
FEATURE                 Location/Qualifiers
source                  1..241
                        mol_type = protein
                        organism = synthetic construct
SEQUENCE: 367
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YDFTPMTFGQ GTKVEIKRTG GGSGGGGSGG  120
GASEVQLVES GGGLVQPGGS LRLSCAASGF NISYAKMHWV RQAPGKGLEW VAYLTYWGGY  180
TNYADSVKGR FTISADTSKN TAYLQMNSLR AEDTAVYYCS RGEYGTYMDY WGQGTLVTVS  240
S                                                                  241

SEQ ID NO: 368          moltype = AA  length = 242
FEATURE                 Location/Qualifiers
source                  1..242
                        mol_type = protein
                        organism = synthetic construct
SEQUENCE: 368
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSSSSPVTFG QGTKVEIKRT GGGSGGGGSG  120
GGASEVQLVE SGGGLVQPGG SLRLSCAASG FNFSSYVMHW VRQAPGKGLE WVAVVYPDSG  180
GTYYADSVKG RFTISADTSK NTAYLQMNSL RAEDTAVYYC SRTSSYYAFD YWGQGTLVTV  240
SS                                                                 242
```

```
SEQ ID NO: 369          moltype = AA  length = 241
FEATURE                 Location/Qualifiers
source                  1..241
                        mol_type = protein
                        organism = synthetic construct
SEQUENCE: 369
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SSYTPITFGQ GTKVEIKRTG GGSGGGGSGG  120
GASEVQLVES GGGLVQPGGS LRLSCAASGF NISQGGIHWV RQAPGKGLEW VAYVYPGGGQ  180
TNYADSVKGR FTISADTSKN TAYLQMNSLR AEDTAVYYCS RGYDYSAFDY WGQGTLVTVS  240
S                                                                  241

SEQ ID NO: 370          moltype = AA  length = 241
FEATURE                 Location/Qualifiers
source                  1..241
                        mol_type = protein
                        organism = synthetic construct
SEQUENCE: 370
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YAYYPITFGQ GTKVEIKRTG GGSGGGGSGG  120
GASEVQLVES GGGLVQPGGS LRLSCAASGF NISSTGMHWV RQAPGKGLEW VAELLGGSGN  180
TNYADSVKGR FTISADTSKN TAYLQMNSLR AEDTAVYYCS RGLQYSAMDY WGQGTLVTVS  240
S                                                                  241

SEQ ID NO: 371          moltype = AA  length = 242
FEATURE                 Location/Qualifiers
source                  1..242
                        mol_type = protein
                        organism = synthetic construct
SEQUENCE: 371
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YEYYPITFGQ GTKVEIKRTG GGSGGGGSGG  120
GASEVQLVES GGGLVQPGGS LRLSCAASGF NFFSTVIHWV RQAPGKGLEW VAEIYPWSGS  180
TYYADSVKGR FTISADTSKN TAYLQMNSLR AEDTAVYYCS RSRSSNYYFD VWGQGTLVTV  240
SS                                                                 242

SEQ ID NO: 372          moltype = AA  length = 241
FEATURE                 Location/Qualifiers
source                  1..241
                        mol_type = protein
                        organism = synthetic construct
SEQUENCE: 372
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YTYYPITFGQ GTKVEIKRTG GGSGGGGSGG  120
GASEVQLVES GGGLVQPGGS LRLSCAASGF NLHGYLMHWV RQAPGKGLEW VAFIYPPNGY  180
TYYADSVKGR FTISADTSKN TAYLQMNSLR AEDTAVYYCS RGVDYAYLDY WGQGTLVTVS  240
S                                                                  241

SEQ ID NO: 373          moltype = AA  length = 241
FEATURE                 Location/Qualifiers
source                  1..241
                        mol_type = protein
                        organism = synthetic construct
SEQUENCE: 373
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YSYYPITFGQ GTKVEIKRTG GGSGGGGSGG  120
GASEVQLVES GGGLVQPGGS LRLSCAASGF NLSTHVMHWV RQAPGKGLEW VAEFYPYVGY  180
TYYADSVKGR FTISADTSKN TAYLQMNSLR AEDTAVYYCS RGYRYQYMDV WGQGTLVTVS  240
S                                                                  241

SEQ ID NO: 374          moltype = AA  length = 240
FEATURE                 Location/Qualifiers
source                  1..240
                        mol_type = protein
                        organism = synthetic construct
SEQUENCE: 374
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SSVEPWTFGQ GTKVEIKRTG GGSGGGGSGG  120
GASEVQLVES GGGLVQPGGS LRLSCAASGF NVSYYSIHWV RQAPGKGLEW VAYIYPWNDY  180
TYYADSVKGR FTISADTSKN TAYLQMNSLR AEDTAVYYCS RGSYYSFDYW GQGTLVTVSS  240

SEQ ID NO: 375          moltype = AA  length = 238
FEATURE                 Location/Qualifiers
source                  1..238
                        mol_type = protein
                        organism = synthetic construct
SEQUENCE: 375
DIQMTQSPSS LSASVGDRVT ITCRASQDVN TAVAWYQQKP GKAPKLLIYS ASFLYSGVPS  60
```

```
RFSGSRSGTD FTLTISSLQP EDFATYYCQQ SYYSPPTFGQ GTKVEIKRTG GGSGGGASEV  120
QLVESGGGLV QPGGSLRLSC AASGFNINNT YIHWVRQAPG KGLEWVASIY PTDGYTRYAD  180
SVKGRFTISA DTSKNTAYLQ MNSLRAEDTA VYYCSRTYYS YYSAMDVWGQ GTLVTVSS    238

SEQ ID NO: 376         moltype = AA  length = 241
FEATURE                Location/Qualifiers
source                 1..241
                       mol_type = protein
                       organism = synthetic construct
SEQUENCE: 376
DIQMTQSPSS LSASVGDRVT ITCRASQDVN TAVAWYQQKP GKAPKLLIYS AYFLYSGVPS  60
RFSGSRSGTD FTLTISSLQP EDFATYYCQQ IYTSPITFGQ GTKVEIKRTG GGSGGGGSGG  120
GASEVQLVES GGGLVQPGGS LRLSCAASGF NFITTGMHWV RQAPGKGLEW VARIGPGSDY  180
TNYADSVKGR FTISADTSKN TAYLQMNSLR AEDTAVYYCS RYYYASALDY WGQGTLVTVS  240
S                                                                  241

SEQ ID NO: 377         moltype = AA  length = 240
FEATURE                Location/Qualifiers
source                 1..240
                       mol_type = protein
                       organism = synthetic construct
SEQUENCE: 377
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ RAYFPITFGQ GTKVEIKRTG GGSGGGGSGG  120
GASEVQLVES GGGLVQPGGS LRLSCAASGF NFSDYGMHWV RQAPGKGLEW VAMLIPASGY  180
TNYADSVKGR FTISADTSKN TAYLQMNSLR AEDTAVYYCS RGWSYYMDYW GQGTLVTVSS  240

SEQ ID NO: 378         moltype = AA  length = 241
FEATURE                Location/Qualifiers
source                 1..241
                       mol_type = protein
                       organism = synthetic construct
SEQUENCE: 378
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ QYAYTPITFG QGTKVEIKRT GGGSGGGGSG  120
GGASEVQLVE SGGGLVQPGG SLRLSCAASG FNVWSYGIHW VRQAPGKGLE WVAGVTPDGS  180
YTYYADSVKG RFTISADTSK NTAYLQMNSL RAEDTAVYYC SRSYGWAMDY WGQGTLVTVS  240
S                                                                  241

SEQ ID NO: 379         moltype = AA  length = 241
FEATURE                Location/Qualifiers
source                 1..241
                       mol_type = protein
                       organism = synthetic construct
SEQUENCE: 379
DIQMTQSPSS LSASVGDRVT ITCRASQDVN TAVAWYQQKP GKAPKLLIYS AYFLYSGVPS  60
RFSGSRSGTD FTLTISSLQP EDFATYYCQQ IHYKPLTFGQ GTKVEIKRTG GGSGGGGSGG  120
GASEVQLVES GGGLVQPGGS LRLSCAASGF NVAWYSIHWV RQAPGKGLEW VAQVYGGSSY  180
TYYADSVKGR FTISADTSKN TAYLQMNSLR AEDTAVYYCS RDFYSSGMDY WGQGTLVTVS  240
S                                                                  241

SEQ ID NO: 380         moltype = AA  length = 243
FEATURE                Location/Qualifiers
source                 1..243
                       mol_type = protein
                       organism = synthetic construct
SEQUENCE: 380
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ EWRLPITFGQ GTKVEIKRTG GGSGGGGSGG  120
GASEVQLVES GGGLVQPGGS LRLSCAASGF NVYGNQIHWV RQAPGKGLEW VARIYPYSGS  180
TYYADSVKGR FTISADTSKN TAYLQMNSLR AEDTAVYYCS RSAYVAYSYF DYWGQGTLVT  240
VSS                                                                243

SEQ ID NO: 381         moltype =   length =
SEQUENCE: 381
000

SEQ ID NO: 382         moltype =   length =
SEQUENCE: 382
000

SEQ ID NO: 383         moltype =   length =
SEQUENCE: 383
000

SEQ ID NO: 384         moltype =   length =
SEQUENCE: 384
000
```

-continued

```
SEQ ID NO: 385         moltype =   length =
SEQUENCE: 385
000

SEQ ID NO: 386         moltype =   length =
SEQUENCE: 386
000

SEQ ID NO: 387         moltype =   length =
SEQUENCE: 387
000

SEQ ID NO: 388         moltype =   length =
SEQUENCE: 388
000

SEQ ID NO: 389         moltype =   length =
SEQUENCE: 389
000

SEQ ID NO: 390         moltype = AA  length = 241
FEATURE                Location/Qualifiers
source                 1..241
                       mol_type = protein
                       organism = synthetic construct
SEQUENCE: 390
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GTSTPFTFGQ GTKVEIKRTG GGSGGGGSGG  120
GASEVQLVES GGGLVQPGGS LRLSCAASGF NLSYYGMHWV RQAPGKGLEW VATIYPDSGY  180
TKYADSVKGR FTISADTSKN TAYLQMNSLR AEDTAVYYCS RAYLYYYLAY WGQGTLVTVS  240
S                                                                 241

SEQ ID NO: 391         moltype = AA  length = 240
FEATURE                Location/Qualifiers
source                 1..240
                       mol_type = protein
                       organism = synthetic construct
SEQUENCE: 391
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SWRYPMTFGQ GTKVEIKRTG GGSGGGGSGG  120
GASEVQLVES GGGLVQPGGS LRLSCAASGF NISRYGMHWV RQAPGKGLEW VAVFYPSSSY  180
TYYADSVKGR FTISADTSKN TAYLQMNSLR AEDTAVYYCS RKYYEAMDYW GQGTLVTVSS  240

SEQ ID NO: 392         moltype = AA  length = 240
FEATURE                Location/Qualifiers
source                 1..240
                       mol_type = protein
                       organism = synthetic construct
SEQUENCE: 392
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SYSYPVTFGH GTKVEIKRTG GGSGGGGSGG  120
GASEVQLVES GGGLVQPGGS LRLSCAASGF NIYSSWMHWV RQAPGKGLEW VAYFQPYSGY  180
TKYADSVKGR FTISADTSKN TAYLQMNSLR AEDTAVYYCS REYTYYFDYW GQGTLVTVSS  240

SEQ ID NO: 393         moltype = AA  length = 242
FEATURE                Location/Qualifiers
source                 1..242
                       mol_type = protein
                       organism = synthetic construct
SEQUENCE: 393
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GWLYSPFTFG QGTKVEIKRT GGGSGGGGSG  120
GGASEVQLVE SGGGLVQPGG SLRLSCAASG FNISGYGMHW VRQAPGKGLE WVARVYGGSG  180
YTYYADSVKG RFTISADTSK NTAYLQMNSL RAEDTAVYYC SRAHSSYYVD YWGQGTLVTV  240
SS                                                                242

SEQ ID NO: 394         moltype = AA  length = 241
FEATURE                Location/Qualifiers
source                 1..241
                       mol_type = protein
                       organism = synthetic construct
SEQUENCE: 394
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GYFYYPNTFG QGTKVEIKRT GGGSGGGGSG  120
GGASEVQLVE SGGGLVQPGG SLRLSCAASG FNIGYYGMHW VRQAPGKGLE WVATVYPGGG  180
YTSYADSVKG RFTISADTSK NTAYLQMNSL RAEDTAVYYC SRYYYYGFDY WGQGTLVTVS  240
S                                                                 241

SEQ ID NO: 395         moltype = AA  length = 240
```

```
FEATURE                 Location/Qualifiers
source                  1..240
                        mol_type = protein
                        organism = synthetic construct
SEQUENCE: 395
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYYSPVTFGQ GTKVEIKRTG GGSGGGGSGG  120
GASEVQLVES GGGLVQPGGS LRLSCAASGF NIFYQDMHWV RQAPGKGLEW VAMIYPDYDY  180
TYYADSVKGR FTISADTSKN TAYLQMNSLR AEDTAVYYCS RTYSVYMDYW GQGTLVTVSS  240

SEQ ID NO: 396          moltype = AA  length = 240
FEATURE                 Location/Qualifiers
source                  1..240
                        mol_type = protein
                        organism = synthetic construct
SEQUENCE: 396
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YAYAPFTFGQ GTKVEIKRTG GGSGGGGSGG  120
GASEVQLVES GGGLVQPGGS LRLSCAASGF NVSYSMIHWV RQAPGKGLEW VARVWGDGGV  180
TYYADSVKGR FTISADTSKN TAYLQMNSLR AEDTAVYYCS RGSYYAFDYW GQGTLVTVSS  240

SEQ ID NO: 397          moltype = AA  length = 241
FEATURE                 Location/Qualifiers
source                  1..241
                        mol_type = protein
                        organism = synthetic construct
SEQUENCE: 397
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ AHMIPITFGQ GTKVEIKRTG GGSGGGGSGG  120
GASEVQLVES GGGLVQPGGS LRLSCAASGF NFSFPGMHWV RQAPGKGLEW VAWFVGYDGY  180
TYYADSVKGR FTISADTSKN TAYLQMNSLR AEDTAVYYCS RDYYSFSMDY WGQGTLVTVS  240
S                                                                  241

SEQ ID NO: 398          moltype = AA  length = 240
FEATURE                 Location/Qualifiers
source                  1..240
                        mol_type = protein
                        organism = synthetic construct
SEQUENCE: 398
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SVYDPITFGQ GTKVEIKRTG GGSGGGGSGG  120
GASEVQLVES GGGLVQPGGS LRLSCAASGF NISGSWIHWV RQAPGKGLEW VAWLYPDSDY  180
TYYADSVKGR FTISADTSKN TAYLQMNSLR AEDTAVYYCS RAHTYAFDYW GQGTLVTVSS  240

SEQ ID NO: 399          moltype = AA  length = 249
FEATURE                 Location/Qualifiers
source                  1..249
                        mol_type = protein
                        organism = synthetic construct
SEQUENCE: 399
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ SYTSPLTFGQ GTKVEIKRTG GGSGGGGSGG  120
GASEVQLVES GGGLVQPGGS LRLSCAASGF NIYYGVMHWV RQAPGKGLEW VAMIYPDSSW  180
TYYADSVKGR FTISADTSKN TAYLQMNSLR AEDTAVYYCS RDQDFHYMNY YLSYALDYWG  240
QGTLVTVSS                                                          249

SEQ ID NO: 400          moltype = AA  length = 240
FEATURE                 Location/Qualifiers
source                  1..240
                        mol_type = protein
                        organism = synthetic construct
SEQUENCE: 400
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ GQYSPFTFGQ GTKVEIKRTG GGSGGGGSGG  120
GASEVQLVES GGGLVQPGGS LRLSCAASGF NVSYEYMHWV RQAPGKGLEW VAEIYGGSDN  180
TYYADSVKGR FTISADTSKN TAYLQMNSLR AEDTAVYYCS RPLGSYFDYW GQGTLVTVSS  240

SEQ ID NO: 401          moltype = AA  length = 241
FEATURE                 Location/Qualifiers
source                  1..241
                        mol_type = protein
                        organism = synthetic construct
SEQUENCE: 401
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ YWYLPTTFGQ GTKVEIKRTG GGSGGGGSGG  120
GASEVQLVES GGGLVQPGGS LRLSCAASGF NISWYDIHWV RQAPGKGLEW VADIEPSVGY  180
TYYADSVKGR FTISADTSKN TAYLQMNSLR AEDTAVYYCS RSYPYYYFDY WGQGTLVTVS  240
S                                                                  241
```

```
SEQ ID NO: 402          moltype = AA  length = 8
FEATURE                 Location/Qualifiers
source                  1..8
                        mol_type = protein
                        organism = synthetic construct
SEQUENCE: 402
GFNLSYYG                                                        8

SEQ ID NO: 403          moltype = AA  length = 10
FEATURE                 Location/Qualifiers
source                  1..10
                        mol_type = protein
                        organism = synthetic construct
SEQUENCE: 403
ELAGIGILTV                                                      10

SEQ ID NO: 404          moltype = AA  length = 244
FEATURE                 Location/Qualifiers
source                  1..244
                        mol_type = protein
                        organism = synthetic construct
SEQUENCE: 404
DIQMTQSPSS LSASVGDRVT ITCRASQDIR NYLNWYQQKP GKAPKLLIYY TSRLESGVPS  60
RFSGSGSGTD YTLTISSLQP EDFATYYCQQ GNTLPWTFGQ GTKVEIKGGG GSGGGGSGGG  120
GSEVQLVESG GGLVQPGGSL RLSCAASGYS FTGYTMNWVR QAPGKGLEWV ALINPYKGVS  180
TYNQKFKDRF TISVDKSKNT AYLQMNSLRA EDTAVYYCAR SGYYGDSDWY FDVWGQGTLV  240
TVSS                                                            244

SEQ ID NO: 405          moltype = AA  length = 244
FEATURE                 Location/Qualifiers
source                  1..244
                        mol_type = protein
                        organism = synthetic construct
SEQUENCE: 405
DIQMTQTTSS LSASLGDRVT ISCRASQDIR NYLNWYQQKP DGTVKLLIYY TSRLHSGVPS  60
KFSGSGSGTD YSLTISNLEQ EDIATYFCQQ GNTLPWTFAG GTKLEIKGGG GSGGGGSGGG  120
GSEVQLQQSG PELVKPGASM KISCKASGYS FTGYTMNWVK QSHGKNLEWM GLINPYKGVS  180
TYNQKFKDKA TLTVDKSSST AYMELLSLTS EDSAVYYCAR SGYYGDSDWY FDVWGAGTTV  240
TVSS                                                            244

SEQ ID NO: 406          moltype = AA  length = 240
FEATURE                 Location/Qualifiers
source                  1..240
                        mol_type = protein
                        organism = synthetic construct
SEQUENCE: 406
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKGGGG SGGGGSGGGG  120
SDVQLVQSGA EVKKPGASVK VSCKASGYTF TRYTMHWVRQ APGQGLEWIG YINPSRGYTN  180
YADSVKGRFT ITTDKSTSTA YMELSSLRSE DTATYYCARY YDDHYCLDYW GQGTTVTVSS  240

SEQ ID NO: 407          moltype = AA  length = 249
FEATURE                 Location/Qualifiers
source                  1..249
                        mol_type = protein
                        organism = synthetic construct
SEQUENCE: 407
QAVVTQEPSL TVSPGGTVTL TCRSSTGAVT TSNYANWVQQ KPGQAPRGLI GGTNKRAPWT  60
PARFSGSLLG GKAALTITGA QAEDEADYYC ALWYSNLWVF GGGTKLTVLG GGGSGGGGSG  120
GGGSEVQLVE SGGGLVQPGG SLRLSCAASG FTFNTYAMNW VRQAPGKGLE WVARIRSKYN  180
NYATYYADSV KDRFTISRDD SKNSLYLQMN SLKTEDTAVY YCVRHGNFGN SYVSWFAYWG  240
QGTLVTVSS                                                       249

SEQ ID NO: 408          moltype = AA  length = 240
FEATURE                 Location/Qualifiers
source                  1..240
                        mol_type = protein
                        organism = synthetic construct
SEQUENCE: 408
DIQLTQSPAI MSASPGEKVT MTCRASSSVS YMNWYQQKSG TSPKRWIYDT SKVASGVPYR  60
FSGSGSGTSY SLTISSMEAE DAATYYCQQW SSNPLTFGAG TKLELKGGGG SGGGGSGGGG  120
SDIKLQQSGA ELARPGASVK MSCKTSGYTF TRYTMHWVKQ RPGQGLEWIG YINPSRGYTN  180
YNQKFKDKAT LTTDKSSSTA YMQLSSLTSE DSAVYYCARY YDDHYCLDYW GQGTTLTVSS  240

SEQ ID NO: 409          moltype = AA  length = 240
FEATURE                 Location/Qualifiers
source                  1..240
                        mol_type = protein
                        organism = synthetic construct
```

```
SEQUENCE: 409
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINGGGG SGGGGSGGGG  120
SQVQLQQSGA ELARPGASVK MSCKASGYTF TRYTMHWVKQ RPGQGLEWIG YINPSRGYTN  180
YNQKFKDKAT LTTDKSSSTA YMQLSSLTSE DSAVYYCARY YDDHYCLDYW GQGTTLTVSS  240

SEQ ID NO: 410          moltype = AA  length = 249
FEATURE                 Location/Qualifiers
source                  1..249
                        mol_type = protein
                        organism = synthetic construct
SEQUENCE: 410
QTVVTQEPSL TVSPGGTVTL TCGSSTGAVT SGNYPNWVQQ KPGQAPRGLI GGTKFLAPGT  60
PARFSGSLLG GKAALTLSGV QPEDEAEYYC VLWYSNRWVF GGGTKLTVLG GGGSGGGGSG  120
GGGSEVQLVE SGGGLVQPGG SLKLSCAASG FTFNKYAMNW VRQAPGKGLE WVARIRSKYN  180
NYATYYADSV KDRFTISRDD SKNTAYLQMN NLKTEDTAVY YCVRHGNFGN SYISYWAYWG  240
QGTLVTVSS                                                     249

SEQ ID NO: 411          moltype = AA  length = 241
FEATURE                 Location/Qualifiers
source                  1..241
                        mol_type = protein
                        organism = synthetic construct
SEQUENCE: 411
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPLTFG GGTKVEIKGG GGSGGGGSGG  120
GGSQVQLVES GGGVVQPGRS LRLSCAASGF KFSGYGMHWV RQAPGKGLEW VAVIWYDGSK  180
KYYVDSVKGR FTISRDNSKN TLYLQMNSLR AEDTAVYYCA RQMGYWHFDL WGRGTLVTVS  240
S                                                             241

SEQ ID NO: 412          moltype = AA  length = 241
FEATURE                 Location/Qualifiers
source                  1..241
                        mol_type = protein
                        organism = synthetic construct
SEQUENCE: 412
EIVLTQSPRT LSLSPGERAT LSCRASQSVS SSYLAWYQQK PGQAPRLLIY GASSRATGIP  60
DRFSGSGSGT DFTLTISRLD PEDFAVYYCQ QYGSSPITFG QGTRLEIKGG GGSGGGGSGG  120
GGSQVQLVES GGGVVQPGRS LRLSCAASGF TFRSYGMHWV RQAPGKGLEW VAIIWYDGSK  180
KNYADSVKGR FTISRDNSKN TLYLQMNSLR AEDTAVYYCA RGTGYNWFDP WGQGTLVTVS  240
S                                                             241

SEQ ID NO: 413          moltype = AA  length = 239
FEATURE                 Location/Qualifiers
source                  1..239
                        mol_type = protein
                        organism = synthetic construct
SEQUENCE: 413
DILMTQSPSS LSASVGDRVT ITCRASQGIS SALAWYQQKP GKAPKLLIYY ASSLQSGVPS  60
RFSGSGSGTD YTLTISSLQP EDFATYYCQQ YYSTLTFGGG TKVEIKGGGG SGGGGSGGGG  120
SQVQLVESGG GVVQPGRSLR LSCAASGFTF RSYGMHWVRQ APGKGLEWVA IIWYDGSKKN  180
YADSVKGRFT ISRDNSKNTL YLQMNSLRAE DTAVYYCARG TGYNWFDPWG QGTLVTVSS   239

SEQ ID NO: 414          moltype = AA  length = 241
FEATURE                 Location/Qualifiers
source                  1..241
                        mol_type = protein
                        organism = synthetic construct
SEQUENCE: 414
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPLTFG GGTKVEIKGG GGSGGGGSGG  120
GGSQVQLVQS GGGVVQSGRS LRLSCAASGF KFSGYGMHWV RQAPGKGLEW VAVIWYDGSK  180
KYYVDSVKGR FTISRDNSKN TLYLQMNSLR GEDTAVYYCA RQMGYWHFDL WGRGTLVTVS  240
S                                                             241

SEQ ID NO: 415          moltype = AA  length = 240
FEATURE                 Location/Qualifiers
source                  1..240
                        mol_type = protein
                        organism = synthetic construct
SEQUENCE: 415
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPWTFGQ GTKVEIKGGG GSGGGGSGGG  120
GSQVQLVQSG GGVVQPGRSL RLSCVASGFT FSSYGMHWVR QAPGKGLEWV AAIWYNGRKQ  180
DYADSVKGRF TISRDNSKNT LYLQMNSLRA EDTAVYYCTR GTGYNWFDPW GQGTLVTVSS  240

SEQ ID NO: 416          moltype = AA  length = 240
FEATURE                 Location/Qualifiers
source                  1..240
```

-continued

```
                         mol_type = protein
                         organism = synthetic construct
SEQUENCE: 416
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPITFGQ GTRLEIKGGG GSGGGGSGGG  120
GSQVQLVQSG GGVVQPGRSL RLSCVASGFT FSSYGMHWVR QAPGKGLEWV AAIWYNGRKQ  180
DYADSVKGRF TISRDNSKNT LYLQMNSLRA EDTAVYYCTR GTGYNWFDPW GQGTLVTVSS  240

SEQ ID NO: 417           moltype = AA  length = 241
FEATURE                  Location/Qualifiers
source                   1..241
                         mol_type = protein
                         organism = synthetic construct
SEQUENCE: 417
QIVLSQSPAI LSASPGEKVT MTCRASSSVS YMHWYQQKPG SSPKPWIYAT SNLASGVPAR  60
FSGSGSGTSY SLTISRVEAE DAATYYCQQW SSNPPTFGGG TKLETKRGGG GSGGGGSGGG  120
GSQVQLQQSG AELARPGASV KMSCKASGYT FTSYTMHWVK QRPGQGLEWI GYINPSSGYT  180
KYNQKFKDKA TLTADKSSST AYMQLSSLTS EDSAVYYCAR WQDYDVYFDY WGQGTTLTVS  240
S                                                                 241

SEQ ID NO: 418           moltype = AA  length = 10
FEATURE                  Location/Qualifiers
source                   1..10
                         mol_type = protein
                         organism = synthetic construct
SEQUENCE: 418
SPGAANKRPI                                                        10

SEQ ID NO: 419           moltype = AA  length = 9
FEATURE                  Location/Qualifiers
source                   1..9
                         mol_type = protein
                         organism = synthetic construct
SEQUENCE: 419
VVGACGVGK                                                         9

SEQ ID NO: 420           moltype = AA  length = 9
FEATURE                  Location/Qualifiers
source                   1..9
                         mol_type = protein
                         organism = synthetic construct
SEQUENCE: 420
VVGADGVGK                                                         9
```

What is claimed is:

1. A molecule comprising an antigen-binding domain that can bind to a peptide-human leukocyte antigen (HLA)-beta-2 microglobulin complex, wherein said antigen-binding domain is selected from the group consisting of:

(i) an antigen-binding domain comprising a complementarity determining region (CDR)-VL1 comprising the amino acid sequence QDVNTA (SEQ ID NO:33), a CDR-VL2 comprising the amino acid sequence SAS, a CDR-VL3 comprising the amino acid sequence QQSYGSGSPWT (SEQ ID NO:121), a CDR-VH1 comprising the amino acid sequence GFNIVGGG (SEQ ID NO:124), a CDR-VH2 comprising the amino acid sequence IYPQGDYT (SEQ ID NO:127), and a CDR-VH3 comprising the amino acid sequence SRDSSYLAFDY (SEQ ID NO: 129);

(ii) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQTYYSPWT (SEQ ID NO:122), a CDR-VH1 comprising the amino acid sequence GFNIRSYA (SEQ ID NO:125), a CDR-VH2 comprising the amino acid sequence VGPGKGYT (SEQ ID NO:128), and a CDR-VH3 comprising the amino acid sequence SRNFQSTSHAFDY (SEQ ID NO: 130);

(iii) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQYYYPPIT (SEQ ID NO:123), a CDR-VH1 comprising the amino acid sequence GFNVSHTG (SEQ ID NO:126), a CDR-VH2 comprising the amino acid sequence VGPGKGYT (SEQ ID NO:128), and a CDR-VH3 comprising the amino acid sequence SRKTYYAFDY (SEQ ID NO: 131);

(iv) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQSYYYFRPIT (SEQ ID NO:132), a CDR-VH1 comprising the amino acid sequence GFNLSYSD (SEQ ID NO:137), a CDR-VH2 comprising the amino acid sequence VMPDSGHT (SEQ ID NO:142), and a CDR-VH3 comprising the amino acid sequence SRATNIPVYAFDY (SEQ ID NO: 147);

(v) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQASYYYPLT (SEQ ID NO:133), a CDR-VH1 comprising the amino acid sequence GFNISASG (SEQ ID NO:138), a CDR-VH2 comprising the amino acid sequence IHPLKPYT (SEQ ID NO:143), and a CDR-VH3 comprising the amino acid sequence SRYSSMYYYYFDY (SEQ ID NO: 148);

(vi) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQKSEYSPWT (SEQ ID NO:134), a CDR-VH1 comprising the amino acid sequence GFNIYRYG (SEQ ID NO:139), a CDR-VH2 comprising the amino acid sequence LYPYGYST (SEQ ID NO:144), and a CDR-VH3 comprising the amino acid sequence SRSYAYGYFAY (SEQ ID NO: 149);

(vii) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQSGYIPFT (SEQ ID NO:135), a CDR-VH1 comprising the amino acid sequence GFNIYGTM (SEQ ID NO:140), a CDR VH2 comprising the amino acid sequence FKPDSYNT (SEQ ID NO:145), and a CDR-VH3 comprising the amino acid sequence SRGEVYHYYAFDY (SEQ ID NO: 150);

(viii) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQGAYYRPFT (SEQ ID NO:136), a CDR-VH1 comprising the amino acid sequence GENISYSY (SEQ ID NO:141), a CDR-VH2 comprising the amino acid sequence LLPYDGNT (SEQ ID NO:146), and a CDR-VH3 comprising the amino acid sequence SRAAYSSMDV (SEQ ID NO: 151);

(ix) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQSSYTPIT (SEQ ID NO:229), a CDR-VH1 comprising the amino acid sequence GFNISQGG (SEQ ID NO:234), a CDR-VH2 comprising the amino acid sequence VYPGGGQT (SEQ ID NO:240), and a CDR-VH3 comprising the amino acid sequence SRGYDYSAFDY (SEQ ID NO: 246);

(x) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQYAYYPIT (SEQ ID NO:230), a CDR-VH1 comprising the amino acid sequence GFNISSTG (SEQ ID NO:235), a CDR-VH2 comprising the amino acid sequence LLGGSGNT (SEQ ID NO:241), and a CDR-VH3 comprising the amino acid sequence SRGLQYSAMDY (SEQ ID NO: 247);

(xi) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQYEYYPIT (SEQ ID NO:231), a CDR-VH1 comprising the amino acid sequence GFNFFSTV (SEQ ID NO:236), a CDR-VH2 comprising the amino acid sequence IYPWSGST (SEQ ID NO:242), and a CDR-VH3 comprising the amino acid sequence SRSRSSNYYFDV (SEQ ID NO: 248);

(xii) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQYTYYPIT (SEQ ID NO:232), a CDR-VH1 comprising the amino acid sequence GFNLHGYL (SEQ ID NO:237), a CDR-VH2 comprising the amino acid sequence IYPPNGYT (SEQ ID NO:243), and a CDR-VH3 comprising the amino acid sequence SRGVDYAYLDY (SEQ ID NO: 249);

(xiii) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQYSYYPIT (SEQ ID NO:168), a CDR-VH1 comprising the amino acid sequence GFNLSTHV (SEQ ID NO:238), a CDR-VH2 comprising the amino acid sequence FYPYVGYT (SEQ ID NO:244), and a CDR-VH3 comprising the amino acid sequence SRGYRYQYMDV (SEQ ID NO: 250); or (xiv) an antigen-binding domain comprising a CDR-VL1 comprising the amino acid sequence QDVNTA (SEQ ID NO:33), a CDR-VL2 comprising the amino acid sequence SAS, a CDR-VL3 comprising the amino acid sequence QQSSVEPWT (SEQ ID NO:233), a CDR-VH1 comprising the amino acid sequence GFNVSYYS (SEQ ID NO:239), a CDR-VH2 comprising the amino acid sequence IYPWNDYT (SEQ ID NO:245), and a CDR-VH3 comprising the amino acid sequence SRGSYYSFDY (SEQ ID NO: 251);

wherein said peptide comprises a modified peptide derived from a modified KRAS polypeptide, wherein said HLA is a class I HLA, and wherein said antigen-binding domain does not bind to a complex that includes a wild-type version of the modified peptide, and wherein said modified peptide comprises the amino acid sequence selected from the group consisting of SEQ ID NO:20, SEQ ID NO:21 and SEQ ID NO:22.

2. The molecule of claim 1, wherein said modified peptide comprises SEQ ID NO:20, wherein said class I HLA is an HLA-A3, and wherein said antigen binding fragment comprises an amino acid sequence selected from the group consisting of SEQ ID NO:341, SEQ ID NO:342, and SEQ ID NO:343.

3. The molecule of claim 1, wherein said modified peptide comprises SEQ ID NO:21, wherein said class I HLA is an HLA-A3, and wherein said antigen binding fragment comprises an amino acid sequence selected from the group consisting of SEQ ID NO:342, SEQ ID NO:343, SEQ ID NO:349, SEQ ID NO:350, SEQ ID NO:351, SEQ ID NO: 352, SEQ ID NO:353, SEQ ID NO:354, SEQ ID NO:355, SEQ ID NO:356, and SEQ ID NO: 357.

4. The molecule of claim 1, wherein said modified peptide comprises SEQ ID NO:22, wherein said class I HLA is an HLA-A3, and wherein said antigen-binding domain comprises an amino acid sequence selected from the group consisting of SEQ ID NO:341, SEQ ID NO:342, SEQ ID NO: 343, SEQ ID NO:344, SEQ ID NO:345, SEQ ID NO:346, SEQ ID NO:347, SEQ ID NO: 348, SEQ ID NO:369, SEQ ID NO:370, SEQ ID NO:371, SEQ ID NO:372, SEQ ID NO: 373, SEQ ID NO:374.

5. The molecule of claim 1, wherein said molecule is selected from the group consisting of an antibody, an antibody fragment, a single chain variable fragment (scFv), a chimeric antigen receptor (CAR), a tandem scFv, a bispecific T cell engager, a diabody, a single-chain diabody, an scFv-Fc, a bispecific antibody, and a dual-affinity re-targeting antibody (DART).

6. The molecule of claim 1, wherein said molecule is a single-chain diabody.

7. The molecule of claim 1, wherein said molecule further comprises an antigen-binding domain that can bind to an effector cell receptor selected from the group consisting of CD3, CD28, CD4, CD8, CD16a, NKG2D, PD-1, CTLA-4, 4-1BB, OX40, ICOS, and CD27.

8. The molecule of claim 7, wherein the antigen-binding domain that can bind to an effector cell receptor comprises an amino acid sequence selected from the group consisting of SEQ ID NO:404, SEQ ID NO:405, SEQ ID NO:406, SEQ ID NO: 407, SEQ ID NO:408, SEQ ID NO:409, SEQ ID NO:410, SEQ ID NO:411, SEQ ID NO: 412, SEQ ID NO:413, SEQ ID NO:414, SEQ ID NO:415, SEQ ID NO:416, and SEQ ID NO: 417.

9. The molecule of claim 7, wherein said antigen-binding domain that can bind to an effector cell receptor can bind to CD16a.

10. The molecule of claim 7, wherein said antigen-binding domain that can bind to an effector cell receptor can bind to NKG2D.

* * * * *